(12) United States Patent
Spriggs et al.

(10) Patent No.: US 9,169,328 B2
(45) Date of Patent: Oct. 27, 2015

(54) ANTIBODIES TO MUC16 AND METHODS OF USE THEREOF

(75) Inventors: David Spriggs, New York, NY (US); Dharmarao Thapi, Bayside Hills, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 190 days.

(21) Appl. No.: 13/635,090

(22) PCT Filed: Mar. 25, 2011

(86) PCT No.: PCT/US2011/030025
§ 371 (c)(1),
(2), (4) Date: Feb. 27, 2013

(87) PCT Pub. No.: WO2011/119979
PCT Pub. Date: Sep. 29, 2011

(65) Prior Publication Data
US 2013/0171152 A1 Jul. 4, 2013

Related U.S. Application Data

(60) Provisional application No. 61/317,964, filed on Mar. 26, 2010.

(51) Int. Cl.
*A61K 39/395* (2006.01)
*C07K 16/30* (2006.01)
*A61K 39/00* (2006.01)

(52) U.S. Cl.
CPC ....... *C07K 16/3092* (2013.01); *A61K 2039/505* (2013.01); *A61K 2039/5156* (2013.01); *C07K 2317/33* (2013.01); *C07K 2317/34* (2013.01); *C07K 2317/622* (2013.01); *C07K 2317/77* (2013.01); *C07K 2317/92* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | 435/69.6 |
| 4,816,567 A | 3/1989 | Cabilly et al. | 530/387.3 |
| 4,946,778 A | 8/1990 | Ladner et al. | 435/69.6 |
| 4,975,369 A | 12/1990 | Beavers et al. | 435/69.1 |
| 4,978,745 A | 12/1990 | Schoemaker et al. | 530/387.3 |
| 5,057,313 A | 10/1991 | Shih et al. | 424/1.53 |
| 5,225,539 A | 7/1993 | Winter | 530/387.3 |
| 5,475,092 A | 12/1995 | Chari et al. | 530/391.7 |
| 5,545,806 A | 8/1996 | Lonberg et al. | 800/8 |
| 5,569,825 A | 10/1996 | Lonberg et al. | 800/18 |
| 5,585,499 A | 12/1996 | Chari et al. | 548/420 |
| 5,625,126 A | 4/1997 | Lonberg et al. | 800/18 |
| 5,736,137 A | 4/1998 | Anderson et al. | 424/133.1 |
| 5,846,545 A | 12/1998 | Chari et al. | 424/195.11 |
| 5,976,818 A | 11/1999 | O'Brien | 435/7.23 |
| 6,333,410 B1 | 12/2001 | Chari et al. | 540/456 |
| 6,340,701 B1 | 1/2002 | Chari et al. | 514/449 |
| 6,372,738 B2 | 4/2002 | Chari et al. | 514/232.5 |
| 6,429,295 B1 | 8/2002 | Carr Perez et al. | 530/387.3 |
| 7,202,346 B2 | 4/2007 | Payne et al. | 530/388.1 |
| 7,227,002 B1 | 6/2007 | Kufer et al. | 530/387.3 |
| 7,501,123 B2 | 3/2009 | Roschke et al. | 424/143.1 |
| 7,585,952 B2 | 9/2009 | D'Alessio et al. | 530/387.3 |
| 7,632,925 B2 | 12/2009 | Kufer et al. | 530/387.3 |
| 7,662,387 B2 | 2/2010 | Law et al. | 424/178.1 |
| 7,666,425 B1 | 2/2010 | Bander | 424/181.1 |
| 2004/0057952 A1 | 3/2004 | Payne et al. | 424/144.1 |
| 2004/0162413 A1 | 8/2004 | Watkins et al. | 530/387.3 |
| 2006/0094069 A1 | 5/2006 | Robertson et al. | 435/7.23 |

FOREIGN PATENT DOCUMENTS

| | | |
|---|---|---|
| JP | 2006/502110 A | 1/2006 |
| WO | PCT/US90/02545 | 11/1990 |
| WO | WO/92/22653 | 12/1992 |
| WO | WO 2004/005470 A2 | 1/2004 |
| WO | WO/2008/141044 | 11/2008 |

OTHER PUBLICATIONS

Davies et al, International Journal of Biochemistry and Cell Biology vol. 39 p. 1943 (2007).*
Strome et al., The Oncologist, 2007; 12:1084-95.*
Brand et al., Anticancer Res. 2006; 26:463-70.*
Badgwell and Bast, "Early detection of ovarian cancer." *Dis Markers*, 23(5-6):397-410 (2007).
Bafna, et al., "MUC4, a multifunctional transmembrane glycoprotein, induces oncogenic transformation of NIH3T3 mouse fibroblast cells." *Cancer Res.*, 68(22):9231-9238 (2008).
Barber, et al., "Chimeric NKG2D receptor-bearing T cells as immunotherapy for ovarian cancer." *Cancer Res.*, 67(10):5003-5008 (2007).
Barber, et al., "Immunotherapy with chimeric NKG2D receptors leads to long-term tumor-free survival and development of host antitumor immunity in murine ovarian cancer." *J Immunol.*, 180(1):72-78 (2008).
Bast, et al., "Reactivity of a monoclonal antibody with human ovarian carcinoma." *J Clin Invest.*, 68(5):1331-1337 (1981).
Bast, et al., "A radioimmunoassay using a monoclonal antibody to monitor the course of epithelial ovarian cancer." *N Engl J Med.*, 309(15):883-887 (1983).
Bast, et al., "New tumor markers: CA125 and beyond." *Int J Gynecol Cancer*, 15 Suppl 3:274-281 (2005).

(Continued)

*Primary Examiner* — Sheela J Huff
(74) *Attorney, Agent, or Firm* — Jones Day

(57) ABSTRACT

The invention provides antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

75 Claims, 64 Drawing Sheets

(56) References Cited

OTHER PUBLICATIONS

Bellone, et al., "Generation of CA125-specific cytotoxic T lymphocytes in human leukocyte antigen-A2.1-positive healthy donors and patients with advanced ovarian cancer." *Am J Obstet Gynecol.*, 200(1):75 e71-10 (2009).
Berek, "Immunotherapy of ovarian cancer with antibodies: a focus on oregovomab." *Expert Opin Biol Ther.*,4(7):1159-1165 (2004).
Bernsel and Von Heijne, "Improved membrane protein topology prediction by domain assignments." *Protein Sci.*, 14(7):1723-1728 (2005).
Borghouts, et al., "Current strategies for the development of peptide-based anti-cancer therapeutics." *J Pept Sci.*, 11(11):713-726 (2005).
Brentjens, et al., "Eradication of systemic B-cell tumors by genetically targeted human T lymphocytes co-stimulated by CD80 and interleukin-15." *Nat Med.*, 9(3):279-286 (2003).
Brentjens and Sadelain, "Somatic cell engineering and the immunotherapy of leukemias and lymphomas." *Adv Pharmacol*, 51:347-370 (2004).
Brentjens, et al., "Genetically targeted T cells eradicate systemic acute lymphoblastic leukemia xenografts." *Clin Cancer Res.*, 13(18 Pt 1):5426-5435 (2007).
Brentjens, "A Phase I trial for the treatment of chemo-refractory chronic lymphocytic leukemia with CD19-targeted autologous T cells." *Molecular Therapy* 16:S15 (2008).
Carpenito, et al., "Control of large, established tumor xenografts with genetically retargeted human T cells containing CD28 and CD137 domains." *Proc Natl Acad Sci., USA*, 106(9):3360-3365 (2009).
Chang, et al., "A novel peptide enhances therapeutic efficacy of liposomal anti-cancer drugs in mice models of human lung cancer." *PLoS One*, 4(1):e4171 (2009).
Cole, et al., "The EBV-hybridoma technique and its application to human lung cancer." in *Monoclonal Antibodies and Cancer Therapy* (Sell, Ed.), pp. 77-96, Alan R. Liss, Inc. (1985).
Cote, et al., "Generation of human monoclonal antibodies reactive with cellular antigens." *Proc Natl Acad Sci., USA*, 80(7):2026-2030 (1983).
Curiel, et al., "Specific recruitment of regulatory T cells in ovarian carcinoma fosters immune privilege and predicts reduced survival." *Nat Med.*, 10(9):942-949 (2004).
Daly, et al., "Recognition of human colon cancer by T cells transduced with a chimeric receptor gene." *Cancer Gene Ther.*, 7(2):284-291 (2000).
David and Reisfeld, "Protein iodination with solid state lactoperoxidase." *Biochemistry*, 13(5):1014-1021 (1974).
Doenecke, et al., "Rapid amplification of cDNA ends (RACE) improves the PCR-based isolation of immunoglobulin variable region genes from murine and human lymphoma cells and cell lines." *Leukemia*, 11(10):1787-1792 (1997).
Elofsson and von Heijne, "Membrane protein structure: prediction versus reality." *Annu Rev BioCheml.*, 76:125-140 (2007).
Faisal, et al., "Leptosome-entrapped leptospiral antigens conferred significant higher levels of protection than those entrapped with PC-liposomes in a hamster model." *Vaccine*, 27(47):6537-6545 (2009).
Fendrick, et al., "Characterization of CA 125 synthesized by the human epithelial amnion WISH cell line." *Tumour Biol.*, 14(5):310-318 (1993).
Fendrick, et al., "CA125 phosphorylation is associated with its secretion from the WISH human amnion cell line." *Tumour Biol.*, 18(5):278-289 (1997).
Finney, et al., "Activation of resting human primary T cells with chimeric receptors: costimulation from CD28, inducible costimulator, CD134, and CD137 in series with signals from the TCR zeta chain." *J Immunol.*, 172(1):104-113 (2004).
Fritsche and Bast, "CA 125 in ovarian cancer: advances and controversy." *Clin Cheml.*, 44(7):1379-1380 (1998).
Gong, et al., "Cancer patient T cells genetically targeted to prostate-specific membrane antigen specifically lyse prostate cancer cells and release cytokines in response to prostate-specific membrane antigen." *Neoplasia*, 1(2):123-127 (1999).
Greenwood and Hunter, "Preparation of iodine-131 labelled human growth hormone of high specific activity." *Nature*, 194:495-496 (1962).
Habib-Agahi, et al., "Co-stimulation with 4-1BB ligand allows extended T-cell proliferation, synergizes with CD80/CD86 and can reactivate anergic T cells." *Int Immunol.*, 19(12):1383-1394 (2007).
Habib-Agahi, et al., "Co-stimulation with 4-1BB ligand allows extended T-cell proliferation, synergizes with CD80/CD86 and can reactivate anergic T cells." *Int Immunol.*, 19(12):1383-1394, Sup. List (2007).
Habib-Agahi, et al., "Co-stimulation with 4-1BB ligand allows extended T-cell proliferation, synergizes with CD80/CD86 and can reactivate anergic T cells." *Int Immunol.*, 19(12):1383-1394, Sup. Fig. 1 (2007).
Habib-Agahi, et al., "Co-stimulation with 4-1BB ligand allows extended T-cell proliferation, synergizes with CD80/CD86 and can reactivate anergic T cells." Int Immunol 19(12):1383-1394, Sup. Fig. 2 (2007).
Habib-Agahi, et al., "4-1BBL costimulation retrieves CD28 expression in activated T cells." *Cell Immunol.*, 256(1-2):39-46 (2009).
Hamanishi, et al., "Programmed cell death 1 ligand 1 and tumor-infiltrating CD8+ T lymphocytes are prognostic factors of human ovarian cancer." *Proc Natl Acad Sci., USA*, 104(9):3360-3365 (2007).
Harris, et al., "A comparison of the metastatic pattern of infiltrating lobular carcinoma and infiltrating duct carcinoma of the breast." *Br J Cancer*, 50(1):23-30 (1984).
Hedvat, et al., "Application of tissue microarray technology to the study of non-Hodgkin's and Hodgkin's lymphoma." *Hum Pathol.*, 33(10):968-974 (2002).
High, et al., "Sec61p is adjacent to nascent type I and type II signal-anchor proteins during their membrane insertion." *J Cell Biol.*, 121(4):743-750 (1993).
Hollingsworth and Swanson, "Mucins in cancer: protection and control of the cell surface." *Nat Rev Cancer*, 4(1):45-60 (2004).
Hollyman, et al., "Manufacturing validation of biologically functional T cells targeted to CD19 antigen for autologous adoptive cell therapy." *J ImmunoTher.*, 32(2):169-180 (2009).
Huang, et al., "MUC1 cytoplasmic domain coactivates Wnt target gene transcription and confers transformation." *Cancer Biol Ther.*, 2(6):702-706 (2003).
Hung, et al., "Antigen-specific immunotherapy of cervical and ovarian cancer." *Immunol Rev.*, 222:43-69 (2008).
Huse, et al., "Generation of a large combinatorial library of the immunoglobulin repertoire in phage lambda." *Science*, 246(4935):1275-1281 (1989).
Huwyler, et al., "Tumor targeting using liposomal antineoplastic drugs." *Int J Nanomedicine*, 3(1):21-29 (2008).
Hwu, et al., "In vivo antitumor activity of T cells redirected with chimeric antibody/T-cell receptor genes." *Cancer Res.*, 55(15):3369-3373 (1995).
Imai, et al., "Chimeric receptors with 4-1BB signaling capacity provoke potent cytotoxicity against acute lymphoblastic leukemia." *Leukemia*, 18(4):676-684 (2004).
Jensen, et al., "Engineered CD20-specific primary human cytotoxic T lymphocytes for targeting B-cell malignancy." *Cytotherapy*, 5(2):131-138 (2003).
Kaneko, et al., "A binding domain on mesothelin for CA125/MUC16." *J Biol Cheml.*, 284(6):3739-3749 (2009).
Kershaw, et al., "Dual-specific T cells combine proliferation and antitumor activity." *Nat Biotechnol.*, 20(12):1221-1227 (2002).
Kershaw, et al., "A phase I study on adoptive immunotherapy using gene-modified T cells for ovarian cancer." *Clin Cancer Res.*, 12(20 Pt 1):6106-6115 (2006).
Kochenderfer, et al., "Construction and preclinical evaluation of an anti-CD19 chimeric antigen receptor." *J ImmunoTher.*, 32(7):689-702 (2009).
Kohler and Milstein, "Continuous cultures of fused cells secreting antibody of predefined specificity." *Nature*, 256(5517):495-497 (1975).
Kononen, et al., "Tissue microarrays for high-throughput molecular profiling of tumor specimens." *Nat Med.*, 4(7):844-847 (1998).

(56) References Cited

OTHER PUBLICATIONS

Kozbor and Roder, "Comparison of the specific IgM and IgG antibody response in humans induced by antigen (tetanus toxoid) or a polyclonal activator (EBV) in vitro." *Int Arch Allergy Appl Immunol.*, 72(3):260-266 (1983).

Krivak, et al., "A Gynecologic Oncology Group Study of serum CA-125 levels in patients with stage III optimally debulked ovarian cancer treated with intraperitoneal compared to intravenous chemotherapy: an analysis of patients enrolled in GOG 172." *Gynecol Oncol.*, 115(1):81-85 (2009).

Lamers, et al., "Gene-modified T cells for adoptive immunotherapy of renal cell cancer maintain transgene-specific immune functions in vivo." *Cancer Immunol ImmunoTher.*, 56(12):1875-1883 (2007).

Lamers, et al., "Treatment of metastatic renal cell carcinoma with autologous T-lymphocytes genetically retargeted against carbonic anhydrase IX: first clinical experience." *J Clin Oncol.*, 24(13):e20-22 (2006).

Latouche and Sadelain, "Induction of human cytotoxic T lymphocytes by artificial antigen-presenting cells." *Nat Biotechnol.*, 18(4):405-409 (2000).

Leffers, et al., "Survival of ovarian cancer patients overexpressing the tumour antigen p53 is diminished in case of MHC class I downregulation." *Gynecol Oncol.*, 110(3):365-373 (2008).

Leffers, et al., "Prognostic significance of tumor-infiltrating T-lymphocytes in primary and metastatic lesions of advanced stage ovarian cancer." *Cancer Immunol ImmunoTher.*, 58(3):449-459 (2009).

Li, et al., "Interaction of human MUC1 and beta-catenin is regulated by Lck and ZAP-70 in activated Jurkat T cells." *Biochem Biophys Res Commun.*, 315(2):471-476 (2004).

Li, et al., "4-1BB (CD137) ligand enhanced anti-tumor immune response against mouse forestomach carcinoma in vivo." *Cell Mol Immunol.*, 5(5):379-384 (2008).

Loskog, et al., "Addition of the CD28 signaling domain to chimeric T-cell receptors enhances chimeric T-cell resistance to T regulatory cells." *Leukemia*, 20(10):1819-1828 (2006).

Maher, et al., "Human T-lymphocyte cytotoxicity and proliferation directed by a single chimeric TCRzeta/CD28 receptor." *Nat Biotechnol.*, 20(1):70-75 (2002).

Markwell and Fox, "Surface-specific iodination of membrane proteins of viruses and eucaryotic cells using 1,3,4,6-tetrachloro-3alpha,6alpha-diphenylglycoluril." *Biochemistry*, 17(22):4807-4817 (1978).

Moeller, et al., "A functional role for CD28 costimulation in tumor recognition by single-chain receptor-modified T cells." *Cancer Gene Ther.*, 11(5):371-379 (2004).

Moore, et al., "Current state of biomarker development for clinical application in epithelial ovarian cancer." *Gynecol Oncol.*, 116(2):240-245 (2010).

Nap, et al., "Immunohistochemical characterization of 22 monoclonal antibodies against the CA125 antigen: 2nd report from the ISOBM TD-1 Workshop." *Tumour Biol.*, 17(6):325-331 (1996).

Nelson, "The impact of T-cell immunity on ovarian cancer outcomes." *Immunol Rev.*, 222:101-116 (2008).

Nustad, et al., "Epitopes on CA 125 from cervical mucus and ascites fluid and characterization of six new antibodies. Third report from the ISOBM TD-1 workshop." *Tumour Biol.*, 23(5):303-314 (2002).

Nygren, "Conjugation of horseradish peroxidase to $F_{ab}$ fragments with different homobifunctional and heterobifunctional cross-linking reagents. A comparative study." *Journal of Histochemistry & Cytochemistry*, 30(5):407-412 (1982).

O'Brien, et al., "More than 15 years of CA 125: what is known about the antigen, its structure and its function." *Int J Biol Markers*, 13(4):188-195 (1998).

O'Brien, et al., "The CA 125 gene: an extracellular superstructure dominated by repeat sequences." *Tumour Biol.*, 22(6):348-366 (2001).

O'Brien, et al., "The CA 125 gene: a newly discovered extension of the glycosylated N-terminal domain doubles the size of this extracellular superstructure." *Tumour Biol.*, 23(3):154-169 (2002).

Orlandi, et al., "Cloning immunoglobulin variable domains for expression by the polymerase chain reaction." *Proc Natl Acad Sci., USA*, 86(10):3833-3837 (1989).

Pain and Surolia, "Preparation of protein A-peroxidase monoconjugate using a heterobifunctional reagent, and its use in enzyme immunoassays." *J Immunol Methods*, 40(2):219-230 (1981).

Park, "The extracellular portion of the MUC16 cytoplasmic domain is detectable in ovarian carcinoma using a novel monoclonal antibody, 4H11." *Modern pathology*, 0893-3952 (21 (suppl. 1)):217A-218A (Jan. 1, 2008).

Parker, et al., "Expansion and characterization of T cells transduced with a chimeric receptor against ovarian cancer." *Hum Gene Ther.*, 11(17):2377-2387 (2000).

Ponnusamy, et al., "MUC4 activates HER2 signalling and enhances the motility of human ovarian cancer cells." *Br J Cancer*, 99(3):520-526 (2008).

Pule, et al., "Virus-specific T cells engineered to coexpress tumor-specific receptors: persistence and antitumor activity in individuals with neuroblastoma." *Nat Med.*, 14(11):1264-1270 (2008).

Quintas-Cardama, et al., "Multifactorial optimization of gammaretroviral gene transfer into human T lymphocytes for clinical application." *Hum Gene Ther.*, 18(12):1253-1260 (2007).

Ramsauer, et al., "MUC4-ErbB2 complex formation and signaling in polarized CACO-2 epithelial cells indicate that Muc4 acts as an unorthodox ligand for ErbB2." *Mol Biol Cell*, 17(7):2931-2941 (2006).

Raspollini, et al., "Tumour-infiltrating gamma/delta T-lymphocytes are correlated with a brief disease-free interval in advanced ovarian serous carcinoma." *Ann Oncol.*, 16(4):590-596 (2005).

Ren, et al., "Human MUC1 carcinoma-associated protein confers resistance to genotoxic anticancer agents." *Cancer Cell*, 5(2):163-175 (2004).

Ren, et al., "MUC1 oncoprotein is targeted to mitochondria by heregulin-induced activation of c-Src and the molecular chaperone HSP90." *Oncogene*, 25(1):20-31 (2006).

Riviere, et al., "Effects of retroviral vector design on expression of human adenosine deaminase in murine bone marrow transplant recipients engrafted with genetically modified cells." *Proc Natl Acad Sci., USA*, 92(15):6733-6737 (1995).

Rosen, et al., "Potential markers that complement expression of CA125 in epithelial ovarian cancer." *Gynecol Oncol.*, 99(2):267-277 (2005).

Rustin, et al., "Use of CA-125 in clinical trial evaluation of new therapeutic drugs for ovarian cancer." *Clin Cancer Res.*, 10(11):3919-3926 (2004).

Sadelain, et al., "Targeting tumours with genetically enhanced T lymphocytes." *Nat Rev Cancer*, 3(1):35-45 (2003).

Sadelain, et al., "The promise and potential pitfalls of chimeric antigen receptors." *Curr Opin Immunol.*, 21(2):215-223 (2009).

Salih, et al., "Constitutive expression of functional 4-1BB (CD137) ligand on carcinoma cells." *J Immunol.*, 165(5):2903-2910 (2000).

Santos, et al., "Sensitive in vivo imaging of T cells using a membrane-bound *Gaussia princeps* luciferase." *Nat Med.*, 15(3):338-344 (2009).

Sato, et al., "Intraepithelial CD8+ tumor-infiltrating lymphocytes and a high CD8+/regulatory T cell ratio are associated with favorable prognosis in ovarian cancer." *Proc Natl Acad Sci., USA*, 102(51):18538-18543 (2005).

Savoldo, et al., "Epstein Barr virus specific cytotoxic T lymphocytes expressing the anti-CD30zeta artificial chimeric T-cell receptor for immunotherapy of Hodgkin disease." *Blood*, 110(7):2620-2630 (2007).

Singer, "The structure and insertion of integral proteins in membranes." *Annu Rev Cell Biol.*, 6:247-296, A: pp. 247-268 (1990).

Singer, "The structure and insertion of integral proteins in membranes." *Annu Rev Cell Biol.*, 6:247-296, B: pp. 269:296 (1990).

Singh, et al., "Clinical potential of mucins in diagnosis, prognosis, and therapy of ovarian cancer." *Lancet Oncol.*, 9(11):1076-1085 (2008).

Song, et al., "Peptide ligand-mediated liposome distribution and targeting to EGFR expressing tumor in vivo." *Int J Pharm.*, 363(1-2):155-161 (2008).

(56) References Cited

OTHER PUBLICATIONS

Soslow, "Histologic subtypes of ovarian carcinoma: an overview." *Int J Gynecol Pathol.*, 27(2):161-174 (2008).
Stephan, et al., "T cell-encoded CD80 and 4-1BBL induce auto- and transcostimulation, resulting in potent tumor rejection." *Nat Med.*, 13(12):1440-1449 (2007).
Sun, et al., "Quality of life for patients with epithelial ovarian cancer." *Nat Clin Pract Oncol.*, 4(1):18-29 (2007).
Till, et al., "Adoptive immunotherapy for indolent non-Hodgkin lymphoma and mantle cell lymphoma using genetically modified autologous CD20-specific T cells." *Blood*, 112(6):2261-2271 (2008).
Tomsova, et al., "Prognostic significance of CD3+ tumor-infiltrating lymphocytes in ovarian carcinoma." *Gynecol Oncol.*, 108(2):415-420 (2008).
Voinea and Simionescu, "Designing of 'intelligent' liposomes for efficient delivery of drugs." *J Cell Mol Med.*, 6(4):465-474 (2002).
Wan, et al., "Expression of co-stimulator 4-1BB molecule in hepatocellular carcinoma and adjacent non-tumor liver tissue, and its possible role in tumor immunity." *World J Gastroenterol.*, 10(2):195-199 (2004).
Wang, et al., "A T cell-independent antitumor response in mice with bone marrow cells retrovirally transduced with an antibody/Fc-gamma chain chimeric receptor gene recognizing a human ovarian cancer antigen." *Nat Med.*, 4(2):168-172 (1998).
Wang, et al., "Universal PCR amplification of mouse immunoglobulin gene variable regions: the design of degenerate primers and an assessment of the effect of DNA polymerase 3' to 5' exonuclease activity." *J Immunol Methods*, 233(1-2):167-177 (2000).
Westwood, et al., "Adoptive transfer of T cells modified with a humanized chimeric receptor gene inhibits growth of Lewis-Y-expressing tumors in mice." *Proc Natl Acad Sci., USA*, 102(52):19051-19056 (2005).
Wilkie, et al., "Retargeting of human T cells to tumor-associated MUC1: the evolution of a chimeric antigen receptor." *J Immunol.*, 180(7):4901-4909 (2008).
Wolf, et al., "The expression of the regulatory T cell-specific forkhead box transcription factor FoxP3 is associated with poor prognosis in ovarian cancer." *Clin Cancer Res.*, 11(23):8326-8331 (2005).
Woo, et al., "Regulatory CD4(+)CD25(+) T cells in tumors from patients with early-stage non-small cell lung cancer and late-stage ovarian cancer." *Cancer Res.*, 61(12):4766-4772 (2001).
Yin, et al., "Ovarian cancer antigen CA125 is encoded by the MUC16 mucin gene." *Int J Cancer*, 98(5):737-740 (2002).
Yin and Lloyd, "Molecular cloning of the CA125 ovarian cancer antigen: identification as a new mucin, MUC16." *J Biol Cheml.*, 276(29):27371-27375 (2001).
Zhang, et al., "Intratumoral T cells, recurrence, and survival in epithelial ovarian cancer." *N Engl J Med.*, 348(3):203-213 (2003).
ISR PCT/US2011/030025, (2011).
Davies, et al., "MUC16 is produced in tracheal surface epithelium and submucosal glands and is present in secretions from normal human airway and cultured bronchial epithelial cells." *Int J Biochem Cell Biol.*, 39(10):1943-1954 (2007).
Rao, et al., "Novel Monoclonal Antibodies Against the Proximal (Carboxy-Terminal) Portions of MUC16." *Applied Immunohistochemistry & Molecular Morphology*, 18(5):462-472 (2010).
Blalock et al., 2008, "Release of Membrane-Associated Mucins from Ocular Surface Epithelia", Investigative Ophthalmology & Visual Science, vol. 49, No. 5, pp. 1864-1871.
Blalock et al., 2007, "Functions of MUC16 in Corneal Epithelial Cells", Investigative Ophthalmology & Visual Science, vol. 48, No. 10, pp. 4509-4518.

\* cited by examiner

Peptide 1 near Cleavage Site:
NFSPLARRVDRVAIYEE (SEQ ID NO:01)

Peptide 2 before Transmembrane:
TLDRSSVLVDGYSPNRNE (SEQ ID NO:02)

Peptide 3 inside Transmembrane:
CGVLVTTRRRKKEGEYNVQQQ (SEQ ID NO:03)

FIGURE 1

FIG. 8A
4A5 VH (SEQ ID NO:04)
gtgaagctggaggagtcaggggggaggcttcgtgaagcctggagggtccctcaaaatctcctgtgcagcctctggattcac
tttcagaaactatgccatgtcctgggttcgcctgagtccggagatgaggctggagtgggtcgcaaccattagcagtgctg
gtggttacatcttctattctgacagtgtgcagggacgattcaccatttccagagacaatgccaagaacaccctccacttg
caaatgggcagtctgaggtctggggacacggccatgtattactgtgcaaggcaggatttggtaactacggtgattacta
tgctatggactactggggccaagggaccacggtcaccgtctcctca

FIG. 8B
4A5 VL (SEQ ID NO:05)
gacattgagctcacccagtctccatcctccctggctgtgtcagcaggagagaaggtcactatgagctgcaaatccagtca
gagtctgctcaacagtagaacccgaaagaaccagttggcttggtaccagcaaaaaccaggacagtctcctgaactgctga
tctactgggcatccactctggcaatctggggtccctgatcgcttcacaggcagtggatctgggacagatttcactctcacc
atcagcagtgtgcaggctgaagacctggcagtttattactgccagcaatcttataatctactcacgttcggtcctgggac
caagctggagatcaaacgg

FIG. 8C
4H11 VH (SEQ ID NO:06)
gtgaagctgcaggagtcaggggggaggcttcgtgaagcctggagggtccctcaaagtctcctgtgcagcctctggattcac
tttcagtagctatgccatgtcctgggttcgcctgagtccggagatgaggctggagtgggtcgcaaccattagcagtgctg
gtggttacatcttctattctgacagtgtgcagggacgattcaccatttccagagacaatgccaagaacaccctgcacctg
caaatgggcagtctgaggtctggggacacggccatgtattactgtgcaaggcagggatttggtaactacggtgattacta
tgctatggactactggggccaagggaccacggtcaccgtctcctca

FIG. 8D
4H11 VL (SEQ ID NO:07)
gacattgagctcacccagtctccatcctccctggctgtgtcagcaggagagaaggtcactatgagctgcaaatccagtca
gagtctgctcaacagtagaacccgaaagaaccagttggcttggtaccagcaaaaaccaggacagtctcctgaactgctga
tctactgggcatccactaggcaatctggagtccctgatcgcttcacaggcagtggatctgggacagatttcactctcacc
atcagcagtgtgcaggctgaagacctggcagtttattactgccagcaatcttataatctactcacgttcggtcctgggac
caagctggaggtcaaacgg

FIG. 8E
9B11 VH (SEQ ID NO:08)
gtgaagctggaggagtcaggggggagacttggtgaagcctggagggtccctgaaactctcctgtgcagtctctggattcac
tttcagtagccattccatgtcttggattcgtcagactccagagaagaggctagagtgggtcgcatccgtgagtagtggtg
gtaggatctactattggacagtgtgaagggcgattcaccgtcaccagagaaaatgacaggaacaccctgtatttgtta
atgagtagtctgaggtctgaggacacggccatgtattattgtggaagaggacaggtatttatgcttggacaattgggg
ccaagggaccacggtcaccgtctcctca

FIG. 8F
9B11 VL.A (SEQ ID NO:09)
gacattgagctcacccagtctccatcctccctggctgtgtcagcaggagagaaggtcactatgagctgcaaatccagtca
gagtctgctcaacagtagaacccgaaagaaccagttggcttggtaccagcaaaaaccaggacagtctcctgaactgctga
tctactgggcatccactaggcaatctggagtccctgatcgcttcacaggcagtggatctgggacagatttcactctcacc
atcagcagtgtgcaggctgaagacctggcagtttattactgccagcaatcttataatctactcacgttcggtcctgggac
caagctggagatcaaacgg

FIG. 8G
9B11 VL.B (SEQ ID NO:10)
gacattgagctcacccagtctccaaagctcctgatctacaaggtttccaaccgattttctggggtcccagacaggttcag
tggcagtggatcagggacagatttcacactcaagatcagcagagtggaggctgaggatctgggagtttattactgtttc
aaggttcacatgttccgtggacgttcggtggagggaccaagctggagatcaaacgg

(H) 24B3-VH (SEQ ID NO:11)
GAGGTGAAGCTGGAGGAGTCAGGACCTGAACTGGTGAAGCCTGGGGCTTCAGTGAAGATATCCTGCAAGGCTTCTGGTTA
CTCATTTACTGGCTACTTTATGAACTGGGTGAAGCAGACCCATGGAAAGAGCCTTGAGTGGATTGGACGTATTAATCCTT
ACAATGGTGCTACTTTCTACAATCAGAAGTTCACGGGCAAGGCCACAATGACTGTAGACAAATCCTCTACCACAGCCCAC
ATGGAGCTCCTGAGCCTGACATCTGAGGACTCTGCAGTCTATTATTGTGGAAAGGGGAATTACTACGGCCCCTTTGATTA
CTGGGGCCAAGGGACCACGGTCACCGTCTCCTCA

(I) 24B3-VL (SEQ ID NO:12)
GACATTGAGCTCACCCAGTCTCCATCTTATCTTGCTGCATCTCCTGAAGAAACCATTACTATTAATTGCAGGGCAAGTAA
GAGCATTAGCAAATATTTAGCCTGGTATCAAAAGAAACCTGGGAAAACTAATAAGCTTCTTATCTACTCTGGATCCACTT
TGCAATCTGGAATTCCATCAAGGTTCAGTGGCAGTGGATCTGGTACAGATTTCACTCTCACCATCAGTAGCCTGGAGCCT
GAAGATTTTGCAATGTATTACTGTCAACAGCATAATGAATACCCGTGGACGTTCGGTGGAGGGACCAAGCTGGAGATCAA
ACGGGCGGCCGCA

FIGURE 8

FIG. 9A
Homo sapiens MUCIN-16 (GenBank NP_078966) (SEQ ID NO:13)

```
   1 mlkpsglpgs saptrslmtg srstkatpem dsgltgatls pktstgaivv tehtlpfts
  61 dktlasptss vvgrttqslg vmssalpest srgmthseqr tspslspqvn gtpsrnypa
 121 smvsglsspr trtsstegnf tkeastytlt vettsgpvte kytvptetst tegdstetp
 181 dtryipvkit spmktfadst askenapvsm tpaettvtds htpgrtnpsf qtlyssfld
 241 spkgtpnsrg etslelilst tgypfsspep gssghsrist saplsssaev ldnkisets
 301 fsgqsltspl spgvpearas tmpnsaipfs mtlsnsetes ervrstissl gtpsistkq
 361 aetiltfhaf aetmdipsth iaktlasewl gspgtlggts tsaltttsps ttlvseetn
 421 hhstsgkete gtlntsmtpl etsapgeese mtatlvptlg fttldskirs psqvssshp
 481 relrttgsts grqssstaah gssdilratt sstskasswt sestaqqfse pqhtqwvet
 541 psmkterppa stsvaapitt svpsvvsgft tlktsetkgi wleetsadtl igestagpt
 601 hqfavptgis mtggsstrgs qgtthlltra tassetssdl tlatnqvpvs vspavskta
 661 gsppggtkp sytmvssvip eteslqesaf regtslgltp lntrhpfssp spdssghtk
 721 stsipllssa svledkvsat stfshhkats sittgtpeis tktkpssavl ssmtlsnas
 781 spervrnats plthpspsge etagsvltls tsaettdspn ihptgtltss ssespstls
 841 psvsgvkttf ssstpsthlf tsgeeteets npsvsqpets vervrttlas tsvptpvfp
 901 mdtwptrssq fssshlvsel ratsstsvtn stgsalpkis hltgtatmsq tnrdtfnds
 961 apqsttwpet sprfktglps atttvstsat elsatvmvsk ftspatssms atsirepst
1021 ilttettngp gsmavastni pigkgyiteg rldtshlpig ttassetsmd ftmskesvs
1081 svspsqsmda agsstpgrts qfvdtfsddv yhltsreiti prdgtssalt pqmtathpp
1141 pdpgsarstw lgilssspss ptpkvtmest fstqrvttsm imdtvetsrw nmpnlpstt
1201 ltpsniptsg aigkstlvpl dtpspatsle asegglptls typestntps ihlgahass
1261 spstiklmta svvkpgsytp ltfpsiethi hvstarmays sgssepemtap getntgstw
1321 pttyittdp kdtssaqvst phsvrtlrtt enhpktesat paaysgspki ssspnltsp
1381 tkawtitdtt ehstqlhytk laekssgfst qsapgpvsvv iptsptigss tleltsdvp
1441 eplvlapseq ttitlpmatw lstelteema stdldissps spmstfalfp pmstpshel
1501 kseadtsair ntdsttldqh lgirslgrtg dlttvpitpl tttwtsvieh stqaqdtls
1561 tmspthvtqs lkdqtsipas aspshltevy pelgtqgrss seattfwkps tdtlsreie
1621 gptniqstpp mdnttgsss sgvtlgiahl pigtsspaet stnmalerrs statvsmag
1681 mgllvtsapg rsisqslgrv ssvlsestte gvtdsskgss prlntqgnta lssslepsy
1741 egsqmstsip ltssptpdv efiggstfwt kevttvmtsd iskssartes ssatlmsta
1801 gstentgkek lrtsasmdlps ptpsmevtpw isltlsnapn ttdsldlshg vhtssagtl
1861 tdrslntgvt rasrlenqsd tsskelsmgn sthtsmtyte ksevsssihp rpetsapga
1921 ttltstpgnr aisltlpfss ipveevistg itsgpdinss pmthspitpp tivwtstgt
1981 eqstqplhav ssekvsvqtq stpyvnsvav ssapthensv ssgsstsspy ssaslesld
2041 tisrrnaits wlwdlttslp tttwpstsls ealssghasv snpssttef plfssasts
2101 akqrnpetet hgpqntaast lntdassvtg lsetpvgasi sssevplpmai tsradvsgl
2161 sestanpslg tassagtklt rtislptses lvsfrmnkdp wtvsiplgah pttntetsi
2221 vnsagppgls tvasdvidtp sdgaesiptv sfspspdtev ttishfpekt thsfrtiss
2281 theltsrvtp lpgdwmssam stkptgasps itlgerrtit ssaapttspiv ltasftets
2341 vsldnettvk tsdildarkt nelpsdssss sdlintsiss stmdvtktas isptsisgm
2401 asssspslfss drpqvptstt etntstspsv ssntysldgg snvqgtpstl ppftithpv
2461 tssallawsr pvrtfstmvs tdtassgenpt ssnsvvtsvp apgtwtsvgs ttdlpangf
2521 ktspageshs llastiepat aftphlsaav vtgssatsea sllttseska ihsspqgtpt
```

FIG. 9B

```
2581 ptsganwets atpesllvvt stsdttltsk ilvtdtilfs tvstppskfp stgtlsgas
2641 ptllpdtpai pltateptss latsfdstpl vtiasdslgt vpettltmss tsngdalvl
2701 tvsnpdrsip gitiqgvtes plhpssteps kivaprntty egsitvalst lpagttgsl
2761 fsqssenset talvdssagl erasvmpltt gsqgmassgg irsgsthstg tktfsslpl
2821 mnpgevtams eittnrltat qstapkglpv kptsaesgll tpvsassspa kafasltta
2881 ptwglpqstl tfefsevpsl dtksaslptp gqslntipds dastasssls kspeknpra
2941 mmtstkaisa ssfqstgfts tpegsaspsm agheprvpts gtgdpryase smsypdpsk
3001 ssamtstsla sklttlfstg qaarsgssss pislsteket sflsptaste rktslflgp
3061 marqpnilvh lqtsaltlsp tstlnmsqee ppeltssqti aessgttast qtltftpse
3121 ptsllpvssp teptarrkss petwassslsv paktslvett dqtlvttikm ssqsaqgns
3181 vpapasetgs spagtspgsp emsttlkims skepsispsi ratvrnspwk tpettvpme
3241 tvepvtlqst algsgstsis hlptgttspt ksptenmlat ervslspspp eawtnlysg
3301 pggtrqslat mssvslsspt arsitgtgqq sspelvsktt gmefsmwhgs tggttgdth
3361 slstssnile dpvtspnsvs sltdkskhkt etwvsttaip stvlnnkima asqqtsrsv
3421 eayssstssws dqtsgsditl qaspdvtntl yitstaqtts lvslpsqdqg italtnpsg
3481 ktssassvts psigletlra nvssvksdia ptaghlsqts spaevsildv ttaptpgis
3541 tittmgtnsi stttpnpevg metmdstpat errttstehp stwsstaasd swtvtdmts
3601 lkvarspgti stmhttsfla ssteldsmst phgritvigt slvtpssdas avktetsts
3661 rtlepsdtta stpistfsrv qrmsisvpdi lstswtpsst esedvpvsmv stdhastkt
3721 pntplstilf dslstldwdt grslssatat tsapggattp qeltlstmis patsqlpfs
3781 qhitssavtpa amarssgvtf srpdptskka eqtstqlptt tsahpgqvpr esattldvi
3841 htaktpdatf qrqgqtaltt ssratsdswn ekekstpsap witemmnsvs sdtikevts
3901 ssvlrtlntl dinlesgtts spswksspye riapssesttd keaihpstnt vettgwvts
3961 ehashstipa hsasskltsp vvttstreqa ivsmstttwp estrartepn sfltielrd
4021 spymdtsett qtsllsspgs taitkgprte itsskrises flaqsmrssd spseaitrl
4081 nfpamtesgg milamqtspp gatslsaptl dtsatsswtg tplattqrft yseekttlfs
4141 gpedtsqpsp paveetssss slvpihatts psnilltsqg hspsstppvt svflsetsg
4201 gkttdmsris lepgtslppn lsstaqssls tyessrdtka ihhssdtavt nmesatssey
4261 pipghtkpsk atsplvtshi mgditsstsv fgsssettels tvssvnqqlq erstsqvas
4321 atststvith vssgdatthv tktqatfssg tslssphqfi tststntftdvs tnpstslim
4381 essgvtittq tgptgaatqg pylldtstmp yltstplavt pdfmqsektt liskgpkdv
4441 wtsppsvaet sypssltpfl vttippstst lqgqhtsspv satsvltsgl vkttdmlnt
4501 mepvtnspqn lnnpsneilla tlssttdiet ihpsinkavt mmgtssssahv lhstlpvss
4561 patstspmvp sssmgdalss isipgssttd iegeptsslt agrkenstlq emnsttssn
4621 ilsnvsvgai teatkmevps fdatfiptps qetkfpdifs vsserlsnsp pmtisthmt
4681 tqtgsssgats klplaldtst letsaqtpsv vtegfahski ttammndvkd vsqtnppfq
4741 easspasqap vlvttlpssv aftpqwhsts spvsmssvlt sslvktagkv dtslstvts
4801 pqsmentldd isvtsaattd ietthpsint vvtnvgttgs afeshstvsa ypepskvts
4861 nvttstmedt tisrsipkss kttrtstett ssltpklret sisqeitsst stsvpyke
4921 tgattsvart dvtsssstsf pgpdqstvsl distetntrl stspimtsss eitittqtg
4981 hgatsqdtft mdpanttpqa gihsamthgf sqldvttlms ripqdvswts ppsvdktss
5041 ssflsspamt tpslisstlp edklsspmte lltsglvkit dilrtrlepv taslpnfss
5101 sdkilatskd skdtkeifps inteetnvka nnsgheshsp aladsetpka ttqmvittt
5161 gdpapstsmp vhgssettnl kreptyfltp rlretstsqs ssfptdtsfl lskvptgti
```

FIG. 9C

```
5221 evsstgvnss skistpdhdk stvppdtftg eiprvftssi ktksaemtit tqasppesa
5281 hstlpldtst tlsqggthst vtqgfpysev ttlmgmgpgn vswmttppve etssvsslm
5341 spamtsepv  astspqsips splpvtalpt svlvtttdvl gttspesvts sppnlssit
5401 erpatykdta hteaamhhst ntavtnvgts gsghksqssv ladsetskat plmsttatl
5461 dtsvststpn isqtnqiqte ptsslsprlr esstsektss ttetntafsy vptgaitqa
5521 rteissesrts isdldrptis pdistgmitr lftspimtks aemtvttqtt tpgatsqgi
5581 pwdtettlfq ggthstvsqg fphseittlr srtpgdvswm tppveetss  gfslmspsm
5641 spspvsstsp esipssplpv talltsvlvt ttnvlgttsp epvtsspnl  ssptqerlt
5701 ykdtahteam hasmhtntav anvgtsisgh esqssvpads htskatspmg itfamgdts
5761 ststpaffet riqteestssl ipglrdtrts eeintvtets tvlsevpttt ttevsrtev
5821 tssrttisgp dhskmspyis tetitrlstf pfvtgstema itnqtgpigt isqatltld
5881 sstaswegth spvtqrfphs setttmsrst kgvswqsppss veetsspssp vplpaitsh
5941 slysavegss ptssalpvtsl ltsgrrktid mldthselvt ssalpssssfs geiltssss
6001 ntetihfsen taetnmgttn smhklhssvs ihsqpsghtp pkvtgsmmed aivststpg
6061 petknvdrds tspltpelke dstalvmnst tesntvfssv sldaatevsr aevtyydpt
6121 mpasaqstks pdispessss hsnsppltis thktiatqtg psgvtslgql tldtstiat
6181 agtpsartqd fvdsettsvm nndlndvlkt spfssseesans lsssqapllvt tspspvtst
6241 qehstsslvs vtsvptptla kitdmdtnls pvtrspqnlr ntlatseatt dthtmhpsi
6301 tavanvgtts spnefyftvs pdsdpykats avvitststgd sivstsmprs samkkiese
6361 tfslifrlre tstsqkigss sdtstvfdka ftaattevsr teltsssrts iqgtekptm
6421 pdtstrsvtm lstfsgltks eertiatqtg phratsqgtl twdtsittsq agthsamth
6481 fsqldlstlt srvpeyisgt sppsvektss ssllalpai  tspspvpttl pesrpsspv
6541 ltslptsglv kttdmlasva slppnlgsts hkipttsedi kdtekmypst nlavtnvgt
6601 tsekesysav payseppkvt spmvtsfnir dtivststmpg sseitrieme stfalahgl
6661 gtstsqdpiv steksavlhk lttgstetsr tevassrrts ipgpdhstes pdistevip
6721 lpislgites snmtiitrtg pplgststsqgt ftldtpttss ragthsmatq efphsemtt
6781 mnkdpeilaw tippsiekts fssslmpspa mtsppvsstl pktihttpsp mtslltpsl
6841 mttdtlgtsp epttsppnl asstsheiltt dedttaieam hpststaatn vettsghg
6901 qssvladsek tkatspmdtt stmghttvst smsvssettk ikrestyslt pglretsis
6961 nasfstdtsi vlsevptgtt aevsrtevts sgrtsipgps qstvlpsist rtmtrlfss
7021 tmtssaemti ptqtgpsgst sqdtltldts ttksqakths tltqrfphse mttlmsrgp
7081 dmswqsspsl enpsslpsll slpattsppp isstlpvtis ssplpvtsll tsspvtttd
7141 lhtspelvts sppklshtsd erlttgkdtt nteavhpstn taasnveips sghespssa
7201 adsetskats pmfitstqed ttvaistphf letsriqkss isslspklre tgssvetss
7261 ietsavlsev sigatteisr tevtssesrts isgeaestml peisttrkii kfptspila
7321 ssemtiktqt sppgstsest ftldtsttps lvithstmtq rlphseittl vargagdvp
7381 pasIpvseta ppssqlslss mispspvsst lpasshsssa svtslltpgq vkttevlda
7441 aepetsspps lsstsveila tsevttdtek ihpfsntavt kvgtsssghe spssvlpds
7501 ttkatssamgt isimgdtavs tltpalsntr kiqsepsssl ttrlretsts eetslatea
7561 tvlskvstga ttevsrteai sfsrtsmsgp eqstmsqdis igtiprisss svltessakm
7621 ittqtgpsess tlsestlnlnt attpswveth siviqgfphp emttsmgrgp ggvswpsspp
7681 vketsppssp lslpavtsph pvsttflahi ppsplpvtsl ltsgpatttd ilgtstepg
7741 sssslstts  herlttykdt ahteavhpst ntggtnvstt ssgyksqssv ladsspmct
7801 stmgdtsvlt stpafletrr iqtelasslt pglressgsse gtssgtkmst vlskvptga
```

FIG. 9D

```
 7861 teiskedvts ipgpaqstis pdistrtvsw fstspvmtes aeitmnthts plgattqgt
 7921 tldtssttsl tmthstisqg fshsqmstlm rrgpedvswm sppllektrp sfslmsspa
 7981 tspspvsstl pesissspip vtslltsgla kttdmlhkss spvtnspanl satsveila
 8041 sevttdtekt hpssnrtvtd vgtsssghes tsfvladsqt skvtspmvit stmedtsvs
 8101 stpgffetsr iqteptsslt lglrktssse gtslatemst vlsgvptgat aevsrtevt
 8161 sartslsgfa qltvspetst etitrlptss imtesaemmi ktqtdppgst pesthtvdi
 8221 ttpnwveths tvtqrfshse mttlvsrspg dmlwpsqssv eetssaassll slpattsps
 8281 vsstlvedfp saslpvtsll npglvittdr mgisrepgts stsnlsstsh erlttledt
 8341 dtedmqpsth tavtnvrtsi sghesqssvl sdsetpkats pmgttytmgs tsvsistsd
 8401 fetsriqiep tssltsglre tssserissa tegstvlsev psgattsvsr tevissrgt
 8461 msgpdqftis pdistsaitr lstspimtss aesaitietg spgatsegtl tldtstttf
 8521 sgthstaspg fshsemttlm srtpgdvpwp slpsveeass vsaslsspam tstsffstl
 8581 esissspbpv talltlgpvk ttdmlrtsse petsspnls stsseilats evtkdreki
 8641 pssntpvvnv gtviykhlsp ssvladlvtt kptspmatts tlgntsvsts tpafpetmm
 8701 qptsoltsgl reistsqets satersssls gmptgattkv srtealslgr tstpgpaqs
 8761 ispeisteti tristplttt gsaemtitpk tghsgassqg tftldtssra swpgthssa
 8821 hrsphsgmtt pmsrgpedvs wpsrpsvekt sppsslvsls avtspsplys tpsssshss
 8881 lrvtslftpv mmkttdmldt slepvttspp smmitsdesl atsskatmete aiqlssnta
 8941 tqmgtisarq efysaypglp epskvtspvv tsstikdivs ttipassseit riemsstst
 9001 tptpretsts qeihsstkps tvpykaltsa tiedsmtqvm sssrgpspdq stmsqdist
 9061 vitrlstspi kteestemtit tqtgspgats rgtltldtst tfmsgthsta sqgfshsqm
 9121 almsrtpgdv pwlshpsvee asssstslss pvmtessspvs stlpdsihss slpvtsllt
 9181 glvkttellg tsssepetssp pnlsstsaei laitevttdt eklemtnvvt sgythssps
 9241 vladsvttka tssmgitypt gdtnvltstp afsdtsriqt ksklsltpgl metsiseet
 9301 satekstvls svptgattev srtsaissssr tsipgpaqst mssdtsmeti tristpltr
 9361 estdmaitpk tgpsgatsqg tftldsssta swpgthsatt qrfpqsvvtt pmsrgpedv
 9421 wpsplsvekn sppsslvsss svtspsplys tpsgsshssp vpvtslftsi mmkatdmld
 9481 slepettssp nmmitsdesl asskattete aihvfentss shvettsste elyssspgf
 9541 eptkvispyv tsssirdnmv sttmpgssgi trieiesmss ltpglretrt sqditsste
 9601 stvlykmpeg atpevsrtev mpssrtsipg paqstmsldi sdevvtrlst spimtesse
 9661 tittqtgysl atsqvtlplg tsmtflsgth stmsqglshs emtnlmsrgp sslswtspr
 9721 vettrsssssl tslplttsls pvsstlldes pssplpvtsl ilpglvktte vldtssepk
 9781 ssspnlssts veipatseim tdtekihpss ntavakvrts ssvhsshssv ladsettit
 9841 psmgitsavd dttvftsnpa fsetrripts ptfsltpgfr etstsseetts itetsavly
 9901 vptsattevs mteimssnri hipdsdqstm spdiitevit rlsssssmmss stqmtittq
 9961 sspgatsqst ltlatttapl arthstvppr flhsemttlm srspenpswk sslfvekts
10021 ssslslpvt tspsvsstlp qsipsssfsv tslltpgmvk ttdtstepgt slspnlsgt
10081 veilaasevt tdtekihpss smavtnvgtt seghslyssv sihsspskat ypvgtpssm
10141 etsistsmpa nfettgfeae pfshltsgfr ktnmsldtss vtptntpssp gsthllqssl
10201 tdftssakts spdwppasqy teipvdiitp fnaspsites tgitsfpssr ftmsvtestl
10261 hlstdllpss etistgtvmp slssemtsfa ttgvpraisg sgspfsrtes gpgdatlst
10321 aeslpsstpv pfssstfttt dsstipalhe itsssatpyr vdtslgtsss ttegrlvmv
10381 tldtssqpgr tssspildtr mtesvelgtv tssayqvpsls trlrtrtdgim ehitkipns
10441 ahrgtirpvk gpqtstspas pkylhtggtk rmsetttalk ttttalktts ratlttsvy
```

FIG. 9E

```
10501 ptlgtltpln asmqmastip temmittpyv fpdvpettss latslgaets talprttps
10561 fnresettas lvsrsgaers pvigtldvss sepdttaswv ihpaetiptv skttpnffh
10621 eldtvsstat shgadvssai ptnispsseld altplvtisg tdtsttfptl tksphetet
10681 ttwlthpaet sstiprtipn fshhesdatp siatspgaet ssaipimtvs pgaedlvts
10741 vtssgtdrnm tiptltlspg epktiaslvt hpeaqtssai ptstispavs rlvtsmvts
10801 aaktsttnra ltnspgepat tvslvthpaq tsptvpwtts iffhsksdtt psmttshga
10861 sssavptptv stevpgvvtp lvtssravis ttipiltlsp gepettpsma tshgseass
10921 iptptvspgv pgvvtslvts sravtsttip iltfslgepe ttpsmatshg teagsavpt
10981 lpevpgmvts lvassravts ttlptltlsp gepettpsma tshgaeasst vptvspevp
11041 vvtslvtssg gvnstsiptl ilspgelett psmatshgae assavptptv spgvsgvvt
11101 lvtssravts ttipiltlss sepettpsma tshgveassa vltvspevpg mvtslvtss
11161 avtsttiptl tissdepett tslvthseak misaiptlav sptvqglvts lvtssgset
11221 afsnltvass qpetidswva hpgteassvv ptlcvstgep ftnislvthp aessstlpr
11281 tsrfshseld tmpstvtspe aesssaistt ispgipgvlt slvtssqrdi satfptvpe
11341 pheseatasw vthpavtett vprttpnysh sepdttpsia tspgaeatsd fptitvspd
11401 pdmvtsqvts sgtdtsitip tltlssgepe ttsfityse thtssaiptl pvspgaskm
11461 tslvissgtd stttfptlte tpyepettai qlihpaetnt mvprttpkfs hsksdttlp
11521 altspgpeas savstttisp dmsdlvtslv pssgtdtstt fptlsetpye pettatwlt
11581 paetsttvsg tipnfshrgs dtapsmvtsp gvdtrsgvpt ttippsipgv vtsqvtssa
11641 dtstaipclt pspgepetta ssathpgtqt gftvpirtvp ssepdtmasw vthppqtst
11701 vsrttssfsh sspdatpvma tsprteassa vlttispgap emvtsqitss gaatsttvp
11761 lthspgmpet tallsthprt etsktfpast vfpqvsetta sltirpgaet stalptqtt
11821 slftllvtgt srvdlsptas pgvsaktapl sthpgtetst mdptstlslg llettglla
11881 sssaetstst ltltvspavs glssasittd kpqtvtswnt etspavtsvg ppefsrtvt
11941 ttmtlipsem ptppktshge gvsepttilrt tmveatnlat tgssptvakt tttfntlag
12001 lftplttpgm stlasesvts rtsynhrswi sttssynrry wtpatstpvt stfspgist
12061 sipsstaatv pfmvpftlnf titnlqyeed mrhpgsrkfn aterelqgll kplfrnssl
12121 ylysgcrlas lrpekdssat avdaicthrp dpedlgldre rlywelsnlt ngiqelgpy
12181 ldrnslyvng fthrssmptt stpgtstvdv gtsgtpsssp spttagpllm pftlnftit
12241 lqyeedmrrt gsrkfntmes vlqgllkplf kntsvgplys gcrltllrpe kdgaatgvd
12301 icthrldpks pglnreqlyw elskltndie elgpytldrn slyvngfthq ssvsttstp
12361 tstvdlrtsg tpsslssspti maaqpllvpf tlnftitnlq ygedmghpgs rkfntterv
12421 qgllgpifkn tsvgplysgc rltslrsekd gaatgvdaic ihhldpkspg lnrerlywe
12481 sqltngikel gpytldmsl yvngfthrts vptsstpgts tvdlgtsgtp fslpspata
12541 pllvlftlnf titnlkyeed mhrpgsrkfn ttervlqtll gpmfkntsvg llysgcrlt
12601 lrsekdgaat gvdaicthrl dpkspgvdre qlywelsqlt ngikelgpyt ldrnslyvn
12661 fthwipvpts stpgtstvdl gsgtpsslps pttagpllvp ftlnftitnl kyeedmhcp
12721 srkfntterv lqsllgpmfk ntsvgplysg crltllrsek dgaatgvdai cthrldpks
12781 gvdreqlywe lsqltngike lgpytldrns lyvngfthqt sapntstpgt stvdlgtsg
12841 psslpsptsa gpllvpftln ftitnlqyee dmhhpgsrkf ntteervlqgl lgpmfknts
12901 gllysgcrlt llrpskngaa tgmdaicshr ldpkspglnr eqlywelsql thgikelgp
12961 tldrnslyvn gfthrssvap tstpgtstvd lgtsgtpssl pspttavpll vpftlnfti
13021 nlqygedmrh pgsrkfntte rvlqgllgpl fknssvgply sgcrlislrs ekdgaatgv
13081 aicthhlnpq spgldreqly wqlsqmtngi kelgpytldr nslyvngfth rssgltsstp
```

FIG. 9F

```
13141 wtstvdlgts gtpspvpspt ttgpllvpft lnftitnlqy eenmghpgsr kfnitesvl
13201 gllkplfkst svgplysgcr ltllrpekdg vatrvdaict hrpdpkipgl drqqlywel
13261 qlthsitelg pytldrdsly vngftqrssv pttstpgtft vqpetsetps slpgptatg
13321 vllpftlnft itnlqyeedm rrpgsrkfnt tervlqgllm plfkntsvss lysgcrltl
13381 rpekdgaatr vdavcthrpd pkspgldrer lywklsqlth gitelgpytl drhslyvng
13441 thqssmtttr tpdtstmhla tartpaslsg pmtaspllvl ftinftitnl ryeenmhhp
13501 srkfntterv lqgllrpvfk ntsvgplysg crltllrpkk dgaastkvdai ctyrpdpks
13561 gldreqlywe lsqlthsite lgpytldrds lyvngftqrs svpttsipgt ptvdlgtsg
13621 pvskpgpsaa spllvlftln ftitnlryee nmqhpgsrkf nttervlqgl lrslfksts
13681 gplysgcrlt llrpekdgta tgvdaicthh pdpksprldr eqlywelsql thnitelgp
13741 aldndslfvn gfthrssvst tstpgtptvy lgasktpasi fgpssashll ilftlnfti
13801 nlryeenmwp gsrkfntter vlqgllrplf kntsvgplys gcrltllrpe kdgsatgvd
13861 icthrpdptg pgldreqlyl elsqlthsit elgpytldrd slyvngfthr ssvpttstg
13921 vseepftlnf tinnlrymad mgqpgslkfn itdnvmqhll splfqrsslg arytgcrvi
13981 lrsvkngaet rvdllctylq plsgpglpik qvfhelsqgt hgitrlgpys ldkdslyln
14041 ynepgpdepp ttpkpattfl pplseattam gyhlktltln ftisnlqysp dmgkgsatf
14101 stegvlqhll rplfqkssmg pfylgcqlis lrpekdgaat gvdttctyhp dpvgpgldi
14161 qlywelsqlt hgvtqlgfyv ldrdslfing yapqnlsirg eyqinfhivn wnlsnpdpt
14221 seyitllrdi qdkvttlykg sqlhdtfrfc lvtnltmdsv lvtvkalfss nldpslveq
14291 fldktlnasf hwlgstyqlv dihvtemess vyqptsssst qhfylnftit nlpysqdka
14341 pgttnyqrnk rniedalnql frnssiksyf sdcqvstfrs vpnrhhtgvd slcnfspla
14401 rvdrvaiyes flrmtrngtq lqnftldrss vlvdgyspnr nepltqnsdl pfwavilig
14461 agllgvitcl icgvlvttrr rkkegeynvq qqcpgyyqsh ldledlq
```

FIG. 9G
    Peptide 1
14394              14410
    nfsplar rvdrvaiyes (SEQ ID NO:01)

FIG. 9H
    Peptide 2
14425              14442
    tldrss vlvdgyspnr ne (SEQ ID NO:02)

FIG. 9I
    Peptide 3
14472              14492
    cgvlvttrr rkkegeynvq qq (SEQ ID NO:03)

FIG. 9J
    Transmembrane Region:
14452              14475
    fwaviligl agllgvitcl icgvl (SEQ ID NO:14)

FIG. 9K
    Peptide containing the cysteine loop peptide:
14367                      14398
    ksyf sdcqvstfrs vpnrhhtgvd slcnfspl (SEQ ID NO:15)

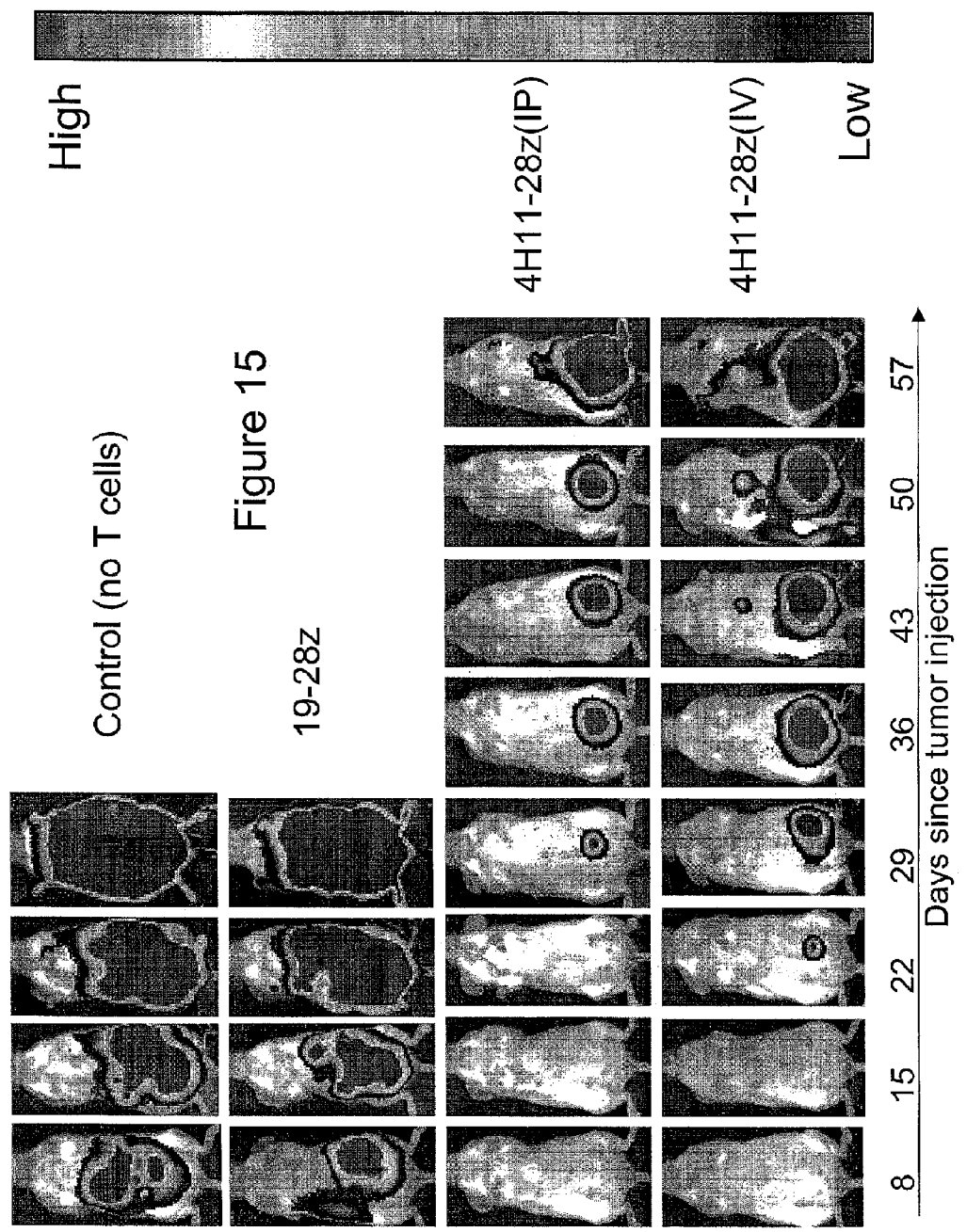

CD8 leader sequence
ATGGCTC TCCCAGTGAC TGCCCTACTG CTTCCCCTAG CGCTTCTCCT GCATGCAGAG (SEQ ID NO:32)

CD3 zeta chain intracellular domain
AGAGT GAAGTTCAGC AGGAGCGCAG AGCCCCCCGC GTACCAGCAG GGCCAGAACC AGCTCTATAA
CGAGCTCAAT CTAGGACGAA GAGAGGAGTA CGATGTTTTG GACAAGAGAC GTGGCCGGGA CCCTGAGATG
GGGGGAAAGC CGAGAAGGAA GAACCCTCAG GAAGGCCTGT ACAATGAACT GCAGAAAGAT AAGATGGCGG
AGGCCTACAG TGAGATTGGG ATGAAAGGCG AGCGCCGGAG GGGCAAGGGG CACGATGGCC TTTACCAGGG
TCTCAGTACA GCCACCAAGG ACACCTACGA CGCCCTTCAC ATGCAGGCCC TGCCCCCTCG
(SEQ ID NO:33)

(G4S)3 serine-glycine linker
GGTG GAGGTGGATC AGGTGGAGGT GGATCTGGTGGAGGTGGATC T (SEQ ID NO:34)

CD8 transmembrane domain
GCGGCCGCAC CCACCACGAC GCCAGCGCCG CGACCACCAA CCCCGGCGCC CACGATCGCG TCGCAGCCCC
TGTCCCTGCG CCCAGAGGCG TGCCGGCCAG CGGCGGGGGG CGCAGTGCAC ACGAGGGGGC TGGACTTCGC
CTGTGATATC TACATCTGGG CGCCCTTGGC CGGGACTTGT GGGGTCCTTC TCCTGTCACT GGTTATCACC
CTTTACTGCA ACCAC (SEQ ID NO:35)

CD28 transmembrane + intracellular domains (-STOP)
CAA TTGAAGTTAT GTATCCTCCT CCTTACCTAG ACAATGAGAA GAGCAATGGA ACCATTATCC
ATGTGAAAGG GAAACACCTT TGTCCAAGTC CCTATTTCC CGGACCTTCT AAGCCCTTTT GGGTGCTGGT
GGTGGTTGGT GGAGTCCTGG CTTGCTATAG CTTGCTAGTA ACAGTGGCCT TTATTATTTT CTGGGTGAGG
AGTAAGAGGA GCAGGCTCCT (SEQ ID NO:36)

```
6001  TRTTAAACTT CCCTGACCCT GACATGACAA GAGTTACTAA CAGCCCCTCT CTCCAAGCTC ACTTACAGGC TCTCTACTTA GTCCAGCACG AAGTCTGGAG
      AACATTTGAA GGGACTGGGA CTGTACTGTT CTCAATGATT GTCGGGGAGA CAGGTTCGAG TGAATGTCCG ACAGATGAAT CAGGTCGTGC TTCAGACCTC
6101  ACCTCTGACG GCAGCCTACC AAGAACACT GGACCGACCG GTGGTACCTC ACCCTTACCG AGTCGGCGAC ACAGTGTGGG TCCGCCGACA CCAAGACTAAG
      TGGAGACCGC CGTCGGATGG TTCTGTTGA CCTGGCTGGC CACCATGGGA TGGGAATGGC TCAAGCCGTG TGTCACACCG AGGCGGCTGT GGTCTGATTC
                                                                                                          PmlI
6201  AACCTAGAAC CTCGCTGAA AGGACCTTAC ACAGTCCTGC TGACCACCCC TGAACGTAC GATCGCAGC TTGGATACAG GCCGGCCACG
      TTGGATCTTG GAGGCGACTT TCCTGGAAGT TGTCAGGAGG ACTGGTGGGG GTGGGCGGGAG TTTCATCTGC CGTAGCGTCG AACCTATCTG CGGCCGGTGC
                                                                         CD8-Leader
                         PmlI                                  NcoI
6301  TGAAGGCTGC CGACCCCGGG GGTGACCAT CCCTCTAGAC GCCATGGCTC TCCCAGTGAC TGCCCCTACTG CTCCCCCTAG CGCTTCTCCT GCATGCAGAG
      ACTTCCGACG GCTGGGGCCC CCACCTGGTA GGAGATCTGA CGGTACCGAG AGGGTCACTG ACGGGGATGAC GAGGGGATCA GCGAAGAGGA CGTACGTCTC
                                                                                          VH
6401  GTGAAGCTGC AGGAGTCAGG GGGAGGCTTC GTGAAGCCTG GAGGGTCCCT CAAAGTCTCC TGTGCAGCCT CTGGATTCAC TTTCAGTAGC TATGCCATGT
      CACTTCGACG TCCTCAGTCC CCCTCCGAAG CACTTCGGAC CTCCCAGGGA GTTTCAGAGG ACACGTCGGA GACCTAAGTG AAAGTCATCG ATACGGTACA
                                                                                          VH
6501  CCTGGGTTCG CCTGAGTCCG GAGATGAGGC TGGAGTCGGT CGCAACCATT AGCAGTGCTG GTGGTTACAT CACCAATGTA TCGTCACGAC AGGGACGATT
      GGACCCAAGC GGACTCAGGC CTCTACTCCG ACCTCAGCCA GCGTTGGTAA TCGTCACGAC CACCAATGTA GTGGTTACAT AGCAGTGCTG TCCCTGCTAA
                                                                                          VH
6601  CACCATTTCC AGAGACAACG CCAAGAACAC CCTGTACCTG CAAATGGGCA GTCTGAGGTC TGGGGACACG GCCATGTATT ACTGTGCAAG GCAGGGATTT
      GTGTAAAGG TCTCTGTTGC GGTTCTTGTG GGACATGGAC GTTTACCCGT CAGACTCCAG ACCCCTGTGC CGGTACATAA TGACACGTTC CGTCCCTAAA
                                                                                          VH
6701  GGTAACTACG GTGATTACTA TGCTATGGAC TACTGGGGGC AAGGGACCAC GGTCACCGTC TCCTCAGGTG TCCTCAGGTG GAGGTGGAGGT GGATCTGGTG
      CCAATTGATG CACTACGTCA ACGATACCTG ATGACCCCCG TTCCCTGGTG CCAGTGGCAG AGGAGTCCAC CTCCACCTCCA CCTAGACCAC
(G4S)3 Serine-glycine linker
6801  GAGGTGGATC TGACATTGAG CTCACCCAGT CCCTGGCTGT TCAGCAGGAG AGAGGGTCAC AATCCCAGTC AGAGTCTGCT
      CTCCACCTAG ACTGTAACTC GAGTGGGTCA GGGACCGACA GTCGTCCTC TCTTCCAGTG TTTAGTGAGG TCTCAGACGA
                                     VL                                 VL
6901  CAACAGTAGA ACCGGAAAGA TGGCTTTGCC TTGGTACCAG ACCAGAAACAG GACAGTCTCC TGAACTGCTG CATCCACTAG GCAATCTGGA
      GTTGTCATCT TGGCTTTCT TGGCTTTCTT GTTTGGTC AACCATGGTC GTTTTGTC CTGTCAGAGG ACTTGACGAC TAGATGACCC GTTAGACCT
                                                VL                                 VL
```

FIG. 18D

```
7001  GTCCCTGATC GCTTCACAGG CACTCGGATCT GGGACAGAGATT TCACTCTCAC CATCAGCACT GTGCAGGCTG AAGACCTGGC AGTTTATTAC TGCCAGCAAT
      CAGGGACTAG CGAAGTGTCC GTGAGTCTAGA CCCTGTCTAA AGTGAGAGTG GTAGTCGTCA CACGTCCGAC TTCTGGACCG TCAAATAATG ACGGTCGTTA
                                           VL                                                    CD8 transmembrane domain 7101  CTTTATAAATCT ACTCACGTTC GGTCCTGGGA CCAAGCTGGA GATCAAACGG GCGGCCGCAC CCACCACGAC GCCAGCGCCG CGACCACCAA CCCCGGCGCC
      GAATATTTAGA TGAGTGCAAG CCAGGACCCT GGTTCGACCT CTAGTTTGCC CGCCGGCGTG CGGCCGGCTG CGGTCGCGGC GCTGGTGGTT GGGGCCGCGG
                                                                    NotI
                                                                                   Cd8 transmembrane domain 7201  CACGGATCGCG TCGCAGCCCC CCCAGAGGGG TGCCTCCTGCG CCCGGCCCAG TGCCGGCCAC CGCAGTGCAC ACGAGGGGGC TGGACTTCGC CTGTGATATC
      GTGCTAGCGC AGCGTCGGGG AGGGAGAGCG ACGGAGGACGC GGGCCGGGTC ACGGCCGGTG GCGTCACGTG TGCTCCCCCG ACCTGAAGCG GACACTATAG
                     Cd8 transmembrane domain                                                   CD3 zeta chain intracellular domain 7301  TACATCTGGG CGGGCCTTGT GGGGTCCTTC TCCTGTGTCACT GGTTATCACC CTTTACTGCA ACCACAGAGT GAAGTTCAGC AGGAGCGCAG
      ATGTAGACCC GCCCGGAACCG CCCCAGGACAA CCCCAGGACAA AGGAGGAGAA CCAATAGTGG GAAATGACGT TGGTGTCTCA CTTCAAGTCG TCCTCGCGTC
                                                       CD3 zeta chain intracellular domain 7401  AGCCCCCCGC GTACCAGCAG GGCCAGAACC AGTCTCTATAA CGAGCTCAAT CTAGGACGAA GAGAGGAGTA CGATGTTTTG GACAAGAGAC GTGCCGGGA
      TCGGGGGGCG CATGGTCGTC CCGGTCTTGG TCGAGATATT GCTCGAGTTA GATCCTGCTT CTCTCCTCAT GCTACAAAAC CTGTTCTCTG CACCGGCCCT
                                                     CD3 zeta chain intracellular domain 7501  CCCTGAGATG GGGGGAAAGC CGAGAAGGAA GAACCCTCAG GAAGGCCTGT ACAATGAACT TGTTACTTGA CGTCTTTCTA AGCCTACAAG TGAGATTGGG
      GGGACTCTAC CCCCCTTTCG GCTCTTCCTT CTTGGGAGTC CTTCCGGACA TGTTACTTGA CGTCTTTCTA AGCCTACAAG TCCGATGTC ACTCTAACCC 7601  ATGAAAGCG AGCGCCGGAG GGGCAAGGGG CCCGTTCCCC CACGATGGCC CACGACCGGA GCGGAGTGCT CGGTGGTTCC AGACCCTTCAC ATGCAGGCCCC
      TACTTTTCGC TCGCGGCCTC CCCGTTCCCC GGGCAAGGGG GTGCTACCGG AAATGGTCCC AGAGTCATGT CGCCACCAAGG ACACCCTACGA TACGTCCGGG
                             CD3 zeta chain intracellular domain
                                                                    XhoI

7701  TGGCCCCCTCG CTAACAGCCA CTCGAG
      ACGGGGGAGC GATTGTCGGT GAGCTC
```

Figure 18 top strand: SEQ ID NO:37
Figure 18 bottom strand: SEQ ID NO:38

```
6101  ACCTCTGGCG GCAGCCTACC AAGAACAACT GGACCGACCG GTGGTACCTC ACCCTTACCG AGTCGGCGAC ACAGTGTGGG TCCGCCGACA CCAGACTAAG
      TGGAGACCGC CGTCGGATGG TTCTTGTTGA CCTGGCTGGC CACCATGGAG TGGGAATGGC TCAGCCGCTG TGTCACACCC AGGCGGCTGT GGTCTGATTC
                                                                                                          PmlI
                                                                                                          ────
                                                                                                            VH
                                                                                                            ══

6201  AACCTAGAAC CTCGCTGGAA AGGACCCTTAC ACAGTCCTGC TGACCACCCC CACCGCCCTC AAAGTAGACG GCATCGCAGC TTGGATACAC GCCGCCCACG
      TTGGATCTTG GAGCGACCTT TCCTGGAATG TGTCAGGACG ACTGGTGGGG GTGGCGGGAG TTTCATCTGC CGTAGCGTCG AACCTATGTG CGGCGGGTGC
                                                                                    ┌───────────────────────────
                                                                                                           VH
                                                                                                           ══
              ┌──────
               PmlI                                            CD8-Leader 6301  TGAAGGCTGC CGACCCCGGG GGTGGACCAT CCTCTAGACT GCCATGGCTC TCCCAGTGAC TGCCCTACTG CTTCCCCTAG CGCTTCTCCT GCATGCAGAG
      ACTTCCGACG GCTGGGGCCC CCACCTGGTA GGAGATCTGA CGGTACCGAG AGGGTCACTG ACGGGATGAC GAAGGGGATC GCGAAGAGGA CGTACGTCTC
                                              ─────────────                                    ────────────────
                                                 NcoI                                                   VH
                                                                                                        ══

6401  GTGAAGCTGC AGGAGTCAGG GGGAGGCTTC GTGAAGCCTG GGGAGTCTCC CAAAGTCTCC TGTGCAGCCT CTGGATTCAC TTTCAGTAGC TATGCCATGT
      CACTTCGACG TCCTCAGTCC CCCTCCGAAG CACTTCGGAC CCCTCAGAGG GTTTCAGAGG ACACGTCGGA GACCTAAGTG AAAGTCATCG ATACGGTACA
      ─────────────────────────────────────────────────────────────────────────────────────────────────────────
                                                             VH
                                                             ══

6501  CCTGGGTTCG CCTGAGTCCG GAGATGAGGC TGGAGTGGGT CGCAACCATT AGCAGTGGTG GTGGTTACAT CACCAATGTA GAAGATAAGA TCCCTGCTAA
      GGACCCAAGC GGACTCAGGC CTCTACTCCG ACCTCACCCA GCGTTGGTAA TCGTCACCAC CACCAATGTA GTGGTTACAT CTTCTATTCT AGGGACGATT
      ─────────────────────────────────────────────────────────────────────────────────────────────────────────
                                                             VH
                                                             ══

6601  CACCATTTCC AGAGACAATG CCAAGAACAC CCTGCACCTG GTCTGAGGTC TGGGGACACG GCCATGTATT ACTGTGCAAG GCAGGGATTT
      GTGGTAAAGG TCTCTGTTAC GGTTCTTGTG GGACGTGGAC CAGACTCCAG ACCCCCTGTG CGGTACATAA TGACACGTTC CGTCCCTAAA
      ─────────────────────────────────────────────────────────────────────────────────────────────────
                                                             VH                                                (G4S)3 Glycine-Serine Linker
                                                             ══

6701  GGTAACTACG GTGATTACTA TGCTATGGAC TACTGGGGCC AAGGGACCAC GGTCACCGTC TCCTCAGGTG GAGGTGGATC AGGTGGAGGT GGATCTGGTG
      CCATTGATGC CACTAATGAT ACGATACCTG ATGACCCCGG TTCCCTGGTG CCAGTGGCAG AGGAGTCCAC CTCCACCTAG TCCACCTCCA CCTAGACCAC
                                                             ─────────
                                                                VL
                                                                ══
```

FIG. 19D

```
      (G4S)3 Glycine-Serine linker
      ─────────────────────────────
6801  GAGGTGGATC TGACATTGAG CTCACCCAGT CTCCATCCTC GCTGGCTGTG TCAGCAGGAG AGAAGGTCAC TATGAGCTGC AAATCCAGTC AGAGTCTGCT
      CTCCACCTAG ACTGTAACTC GAGTGGGTCA GAGGTAGGAG GGACCGACAC AGTCGTCCTC TCTTCCAGTG ATACTCGACG TTTAGGTCAG TCTCAGACGA
                                                                                     VL
6901  CAACAGTAGA ACCCGAAAGA ACCAGTTGGC TTGGTACCAG CAAAAACCAG GACAGTCTCC TGAACTGCTG ATCTACTGGG CATCCACTAG GCAATCTGGA
      GTTGTCATCT TGGGCTTTCT TGGTCAACCG AACCATGGTC GTTTTTGGTC CTGTCAGAGG ACTTGACGAC TAGATGACCC GTAGGTGATC CGTTAGACCT
                                                                                     VL
7001  GTCCCTGATC GCTTCACAGG CAGTGGATCT GGGACAGAAT TCACTCTCAC CATCAGCAGT GTGCAGGCTG AAGACCTTGC AGTTTATTAC TGCCAGCAAT
      CAGGGACTAG CGAAGTGTCC GTCACCTAGA CCCTGTCTTA AGTGAGAGTG GTAGTCGTCA CACGTCCGAC TTCTGGAACG TCAAATAATG ACGGTCGTTA
                                                                                              CD28 transmembrane + intracellular domains (-STOP)
              VL                                                                              ──────────────────────────────────────────────────
      ───────────────                                 NotI
                                                     ─────
7101  CTTATAAATCT ACTCACGTTC GGTCCTGGGA CCAAGCTGGA GATCAAACGG GCGGCCGCAA TTGAAGTTAT GTATCCTCCT CCTTACCTAG ACAATGAGAA
      GAATATTAGA TGAGTGCAAG CCAGGACCCT GGTTCGACCT CTAGTTTGCC CGCCGGCGTT AACTTCAATA CATAGGAGGA GGAATGGATC TGTTACTCTT
      CD28 transmembrane + intracellular domains (-STOP)
      ──────────────────────────────────────────────────
7201  GAGCAATGGA ACCATTATCC ATGTGAAAGG GAAACACCTT TGTCCAAGTC CCCTATTTCC CGGACCTTCT AAGCCCTTTT GGGTGCTGGT GGTGGTTGGT
      CTCGTTACCT TGGTAATAGG TACACTTTCC CTTTGTGGAA ACAGGTTCAG GGGATAAAGG GCCTGGAAGA TTCGGGAAAA CCCACGACCA CCACCAACCA
      CD28 transmembrane + intracellular domains (-STOP)
      ──────────────────────────────────────────────────
7301  GGAGTCCTGG CTTGCTATAG CTTGCTAGTA ACAGTGGGCT TGTCACCCGA AATAATAAAA GACCCACTCC TCATTCTCCT CGTCCGAAGA GCAGGCTCCT GCACAGTGAC TACATGAACA
      CCTCAGGACC GAACGATATC GAACGATCAT TGTCACCCGA TTATTATTTT CTGGGTGAGG AGTAAGAGGA GCAGGCTCCT CGTCCGAAGA CGTGTCACTG ATGTACTTGT
      CD28 transmembrane + intracellular domains (-STOP)                              CD3 zeta chain intracellular domain
      ──────────────────────────────────────────────────                              ───────────────────────────────────
7401  TGACTCCCCG CCGCCCCCGG CCCGGCCCGG AGCATTACCA GCCCTATGCC CCACCACCCG ACTTCGCAGC CTATGCTCCC AGAGTGAAGT TCAGCAGGAG
      ACTGAGGGGC GGCGGGGGCC GGGTGGGGCC TCGTAATGGT CGGGATACGG GGTGGTGGGC TGAAGCGTCG GATAGCGAGG TCTCACTTCA AGTCGTCCTC
      CD3 zeta chain intracellular domain
      ───────────────────────────────────
7501  CGCAGAGCCC CCCGGCTACC AGCAGGGCCA GAACCAGCTC TATAACGAGC TCAATCTAGG ACGAAGAGAG GAGTACGATG TTTTGGACAA GAGACGTGGC
      GCGTCTCGGG GGGCCGATGG TCGTCCCGGT CTTGGTCGAG AGTTAGATCC TGCTTCTCTC CTCATGCTAC AAAACCTGTT CTCTGCACCG
      CD3 zeta chain intracellular domain
      ───────────────────────────────────
7601  CGGGACCCTG AGATGGGGGG AAAGCCGAGA AGGAAGAACC CTCAGGAAGG CCTGTACAAT GAACTGCAGA AAGATAAGAT GGCGGAGGCC TACAGTGAGA
      GCCCTGGGAC TCTACCCCCC TTTCGGCTCT TCCTTCTTGG GAGTCCTTCC GGACATGTTA CTTGACGTCT TTCTATTCTA CCGCCTCCGG ATGTCACTCT
      CD3 zeta chain intracellular domain
      ───────────────────────────────────
```

FIG. 19E

```
7701  TTGGGATGAA AGGCGAGCGC CGGAGGGGCA AGGGCCACGA TGGCCTTTAC CAGGGTCTCA GTACAGCCAC CAAGGACACC TACGACGCCC TTCACATGCA
      AACCCTACTT TCCGCTCGCG GCCTCCCCGT TCCCGGTGCT ACCGGAAATG GTCCCAGAGT CATGTCGGTG GTTCCTGGTG ATGCTGCGGG AAGTGTACGT
      CD3 zeta chain intracellular domain
                                                                    XhoI
                                                                  -------
7801  GGCCCTGCCC CCTCGCTAAC AGCCACTCGA G
      CCGGGACGGG GGAGCGATTG TCGGTGAGCT C Figure 19 top strand: SEQ ID NO:39
Figure 19 bottom strand: SEQ ID NO:40
```

1. Mouse MUC16-CD Peptide 1 (SEQ ID NO:21):

TLDRKSVFVDGYSQNRDD                                    19 AA

2. Mouse 1st Cysteine Loop peptide 2 (SEQ ID NO:22):

KSYFSDCQVLAFRSVSNNNNHTGVDSLCNFSPL                     33 AA

3. Mouse 2nd Cysteine Loop peptide 3 (SEQ ID NO:23):

SLYSNCRLASLRPKKNGTATGVNAICSYHQN                       32 AA

Figure 20B
Alignment of mouse MUC16 (SEQ ID NO:24) and human MUC16 (SEQ ID NO:25) amino acid sequences

```
                           Peptide 3 (2nd cysteine loop)
mouse complete    HLIRPLVQNE---SLYSNGRLASLRPKKNGTATGVNAICSYHQNPDHPELDTQELYTKLT
8244
human complete    HLLRPLFQKSSMCPFYLCQQLISLRPEKDCAATGVDTTQTYHPDPVGPGLDIQQLYWELS
14167
                  **:***.*:    .:* .*:* ****:*:*:****::  *:**  :*   *  ** *:**  :*:

mouse complete    QLTQGVTQLGSYMLDQNSIYVNGYVPLNITIQGKYQLNFQIINWNLNNTDPTSSEYITLE
8304
human complete    QLTHGVTQLGFYVLDRDSLFINGYAPQNLSIRGEYQINFHIVNWNLSNPDPTSSEYITLL
14227
                  *:**** *:**:*::***.* *:::*:*:: *:****.*.********** mouse complete    RDIEDKVTTLYTGSQLKEVFQSQLVTNMTSGSTVVTLEALFSSHLDPNLVKQVFLNKTLN
8364
human complete    RDIQDKVTTLYKGSQLHDTFRFQLVTNLTMDSVLVTVKALFSSNLDPSLVEQVFLDKTLN
14287
                  ***:******* ****::.*: *****:* .*.:**::*****:***.**:****:****

mouse complete    ASSHWLGATYQLKDLHVIDMKTSILLPAEIPTTSSSSQHFNLNFTITNLPYSQDIAQPST
8424
human complete    ASFHWLGSTYQLVDIHVTEMESSVYQ----PTSSSSTQHFYLNFTITNLPYSQDKAQPGT
14343
                  ** ****:**** *:** :*::*:         **:***:*** ************ ***.*

Peptide 3 (1st cysteine loop)
mouse complete    TKYQQTKRSIENAINQLFRNSSIKSYFSQQVLAFRSVSNNNQTNVDSLQNFSPLARRV
8484
human complete    TNYQRNKRNIEDALNQLFRNSSIKSYFSDQQVSTFRSVPN-RHETGVDSLQNFSPLARRV
14402
                  *:**:.**.**:******************* :****.*  .:.****************

Peptide 4
mouse complete    DRVAIYEEFLRMTHNGTQLLNF          DVMKNSGLPFWAIILICLAV
8544
human complete    DRVAIYEEFLRMTRNGTQLQNFTLDRSSVLVDGYSPNRNEPLTGNSDLPFWAVILIGLAG
14462
                  ***********:**            *:*  ** mouse complete    LLVLITCLMCQFLVTVCRRKKEGDYQVQRHRLAYYLSHLDLRKLQ  8589
human complete    LLGVITCLICGVLVTTRRRKKEGEYNVQQQPGYYQSHLDLEDLQ  14507
                  ** :****:*  ***. ****** :***:.   .** ***** .**
```

Figure 21
Mouse MUC16 CD Peptide 1
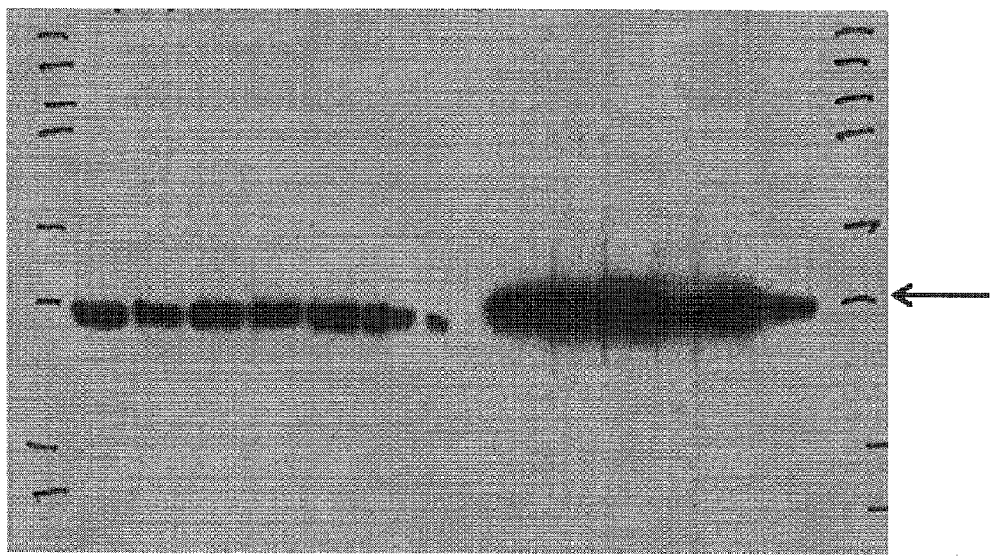
Mouse MUC16 CL Peptide 3
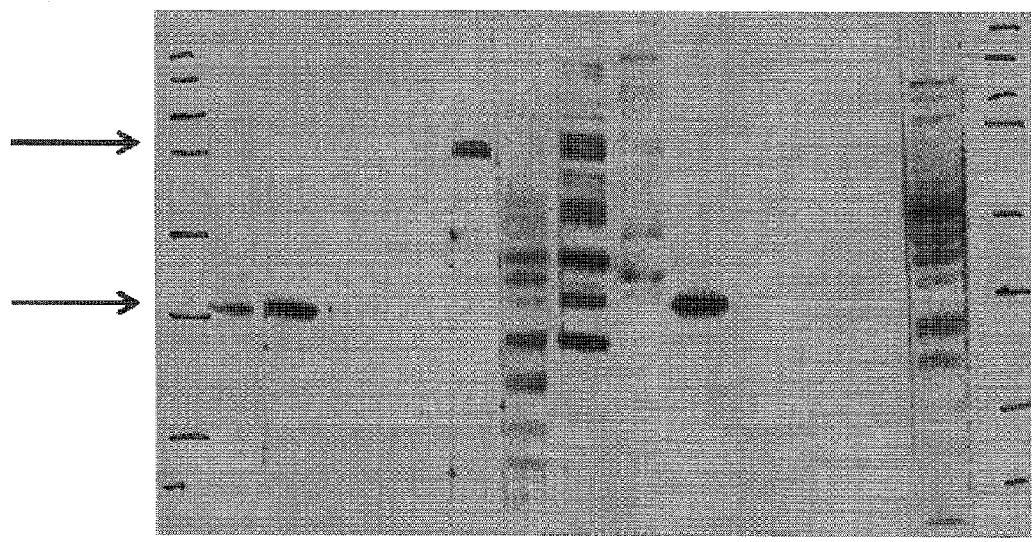

A. Nucleotide sequence encoding 12B10.3G10-V$_H$ (SEQ ID NO:26)

GAGGTGAAGCTGGAGGAGTCAGGTGGAGGATTGGTGCAGCCTAAAGGATCATTGAAACTCTCATGTGCCGCCTCT
GGTTTCACCTTCAATACCTATGCCGTGCACTGGGTCCGCCAGGCTCCAGGAAAGGGTATGGAATGGGTTGCTCGC
ATAAGAAGTAAAAGTGGAAATTATGCAACATATTATGCCGATTCAGTGAAAGACAGATTCACCATCTCCAGAAAT
GATTCACAGAGCATGCTCTATCTGCAAATGAACAACCTGAAAACTGAGGACACAGCCATATATTACTGTGTGAGA
GCGGGTAACAACGGGGCCTTTCCTTACTGGGGCCAAGGGACCACGGTCACCGTCTCCTCA

B. 12B10.3G10-V$_H$ Amino Acid sequence (SEQ ID NO:27)

EVKLEESGGGLVQPKGSLKLSCAASGFTFNTYAVHWVRQAPGKGMEWVARIRSKSGNYAT
YYADSVKDRFTISRNDSQSMLYLQMNNLKTEDTAIYYCVRAGNNGAFPYWGQGTTVTVSS

C. Nucleotide sequence encoding 12B10.3G10-V$_L$ (SEQ ID NO:28)

Note the VL has an optional NotI site added by the primer for
cloning.

GACATTGAGCTCACCCAGTCTCCATCCTCACTGTCTGCATCTCTGGGAGGCAGAGTCACCATCACTTGCAAGGCT
AGCCAAGATATTAAGAAGTATATAGCTTGGTACCAACACAAGCCTGGAAAAACTCCTCGACTACTCATACATTTC
ACATCTACATTACAGACAGGCATCCATCAAGGTTCAGTGGACGTGGGTCTGGAGAGACTATTCCTTCAGCATC
AGCAACCTGGAGTCTGAAGATATTGCAACTTATTATTGTCTACAGTATGATAGTCTGTACACGTTCGGAGGGGGG
ACCAAGCTGGAGATCAAACGGGCGGCCGCA

D. 12B10.3G10-V$_L$ Amino Acid sequence (SEQ ID NO:29)

DIELTQSPSSLSASLGGRVTITCKASQDIKKYIAWYQHKPGKTPRLLIHFTSTLQTGIPS
RFSGRGSGRDYSFSISNLESEDIATYYCLQYDSLYTFGGGTKLEIKRAAA

Figure 24

SEQUENCE LISTING

<160> NUMBER OF SEQ ID NOS: 40

<210> SEQ ID NO 1
<211> LENGTH: 17
<212> TYPE: PRT

```
<213> ORGANISM: Artificial Sequence
<220> FEATURE:
<223> OTHER INFORMATION: Synthetic

<400> SEQUENCE: 1

Asn Phe Ser Pro Leu Ala Arg Arg Val Asp Arg Val Ala Ile Tyr Glu
1               5                   10                  15

Glu

<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

Thr Leu Asp Arg Ser Ser Val Leu Val Asp Gly Tyr Ser Pro Asn Arg
1               5                   10                  15

Asn Glu

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Cys Gly Val Leu Val Thr Thr Arg Arg Arg Lys Lys Glu Gly Glu Tyr
1               5                   10                  15

Asn Val Gln Gln Gln
            20

<210> SEQ ID NO 4
<211> LENGTH: 366
<212> TYPE: DNA
<213> ORGANISM: Artificial Sequence
<220> FEATURE:
<223> OTHER INFORMATION: Synthetic

<400> SEQUENCE: 4
gtgaagctgg aggagtcagg gggaggcttc gtgaagcctg agggtccct caaaatctcc      60 tgtgcagcct ctggattcac tttcagaaac tatgccatgt cctgggttcg cctgagtccg     120
gagatgaggc tggagtgggt cgcaaccatt agcagtgctg gtggttacat cttctattct    180
gacagtgtgc agggacgatt caccatttcc agagacaatg ccaagaacac cctccacttg     240
caaatgggca gtctgaggtc tggggacacg gccatgtatt actgtgcaag cagggatttt     300
ggtaactacg gtgattacta tgctatggac tactggggcc aagggaccac ggtcaccgtc     360
tcctca                                                                366

<210> SEQ ID NO 5
<211> LENGTH: 339
<212> TYPE: DNA
<213> ORGANISM: Artificial Sequence
<220> FEATURE:
<223> OTHER INFORMATION: Synthetic

<400> SEQUENCE: 5
gacattgagc tcacccagtc tccatcctcc ctggctgtgt cagcaggaga gaaggtcact      60
atgagctgca aatccagtca gagtctgctc aacagtagaa cccgaaagaa ccagttggct     120
```

```
tggtaccagc aaaaaacagg acagtctcct gaactgctga tctactgggc atccactcgg    180
caatctgggg tccctgatcg cttcacaggc agtggatctg ggacagattt cactctcacc    240
atcagcagtg tgcaggctga agacctggca gtttattact gccagcaatc ttataatcta    300
ctcacgttcg gtcctgggac caagctggag atcaaacgg                           339

<210> SEQ ID NO 6
<211> LENGTH: 366
<212> TYPE: DNA
<213> ORGANISM: Artificial Sequence
<220> FEATURE:
<223> OTHER INFORMATION: Synthetic

<400> SEQUENCE: 6
gtgaagctgc aggagtcagg gggaggcttc gtgaagcctg gagggtccct caaagtctcc     60
tgtgcagcct ctggattcac tttcagtagc tatgccatgt cctgggttcg cctgagtccg    120
gagatgaggc tggagtgggt cgcaaccatt agcagtgctg gtggttacat cttctattct    180
gacagtgtgc agggacgatt caccatttcc agagacaatg ccaagaacac cctgcacctg    240
caaatgggca gtctgagggtc tggggacacg gccatgtatt actgtgcaag cagggatttt   300
ggtaactacg gtgattacta tgctatggac tactggggcc aagggaccac ggtcaccgtc    360
tcctca                                                               366

<210> SEQ ID NO 7
<211> LENGTH: 339
<212> TYPE: DNA
<213> ORGANISM: Artificial Sequence
<220> FEATURE:
<223> OTHER INFORMATION: Synthetic

<400> SEQUENCE: 7
gacattgagc tcacccagtc tccatcctcc ctggctgtgt cagcaggaga gaaggtcact     60
atgagctgca atccagtca gagtctgctc aacagtagaa cccgaaagaa ccagttggct    120
tggtaccagc aaaaaccagg acagtctcct gaactgctga tctactgggc atccactagg    180
caatctggag tccctgatcg cttcacaggc agtggatctg ggacagattt cactctcacc    240
atcagcagtg tgcaggctga agacctggca gtttattact gccagcaatc ttataatcta    300
ctcacgttcg gtcctgggac caagctggag gtcaaacgg                           339

<210> SEQ ID NO 8
<211> LENGTH: 348
<212> TYPE: DNA
<213> ORGANISM: Artificial Sequence
<220> FEATURE:
<223> OTHER INFORMATION: Synthetic

<400> SEQUENCE: 8
gtgaagctgg aggagtcagg gggagacttg gtgaagcctg gagggtccct gaaactctcc     60
tgtgcagtct ctggattcac tttcagtagc cattccatgt cttggattcg tcagactcca    120
gagaagaggc tagagtgggt cgcatccgtg agtagtggtg gtaggatcta ctattcggac    180
agtgtgaagg gccgattcac cgtcaccaga gaaaatgaca ggaacaccct gtatttgtta    240
atgagtagtc tgaggtctga ggacacggcc atgtattatt gtggaagagg acaggtattt    300
tatgctttgg acaattgggg ccaagggacc acggtcaccg tctcctca                 348

<210> SEQ ID NO 9
```

```
<211> LENGTH: 339
<212> TYPE: DNA
<213> ORGANISM: Artificial Sequence
<220> FEATURE:
<223> OTHER INFORMATION: Synthetic

<400> SEQUENCE: 9
gacattgagc tcacccagtc tccatcctcc ctggctgtgt cagcaggaga gaaggtcact      60
atgagctgca atccagtca gagtctgctc aacagtagaa cccgaaagaa ccagttggct     120
tggtaccagc aaaaaccagg acagtctcct gaactgctga tctactgggc atccactagg    180
caatctggag tccctgatcg cttcacaggc agtggatctg ggacagattt cactctcacc    240
atcagcagtg tgcaggctga agacctggca gtttattact gccagcaatc ttataatcta    300
ctcacgttcg gtcctgggac caagctggag gtcaaacgg                           339

<210> SEQ ID NO 10
<211> LENGTH: 216
<212> TYPE: DNA
<213> ORGANISM: Artificial Sequence
<220> FEATURE:
<223> OTHER INFORMATION: Synthetic

<400> SEQUENCE: 10
gacattgagc tcacccagtc tccaaagctc ctgatctaca aggtttccaa ccgattttct     60
ggggtcccag acaggttcag tggcagtgga tcagggacag atttcacact caagatcagc    120
agagtggagg ctgaggatct ggagttttat tactgctttc aaggttcaca tgttccgtgg    180
acgttcggtg agggaccaa gctggagatc aaacgg                               216

<210> SEQ ID NO 11
<211> LENGTH: 354
<212> TYPE: DNA
<213> ORGANISM: Artificial Sequence
<220> FEATURE:
<223> OTHER INFORMATION: Synthetic

<400> SEQUENCE: 11
gaggtgaagc tggaggagtc aggacctgaa ctggtgaagc ctggggcttc agtgaagata     60
tcctgcaagg cttctggtta ctcatttact ggctacttta tgaactgggt gaagcagacc    120
catggaaaga gccttgagtg gattggacgt attaatcctt acaatggtgc tactttctac    180
aatcagaagt tcacgggcaa ggccacaatg actgtagaca atcctctac cacagcccac     240 atggagctcc tgagcctgac atctgaggac tctgcagtct attattgtgg aaagggggaat   300 tactacggcc cctttgatta ctggggccaa gggaccacgg tcaccgtctc ctca          354

<210> SEQ ID NO 12
<211> LENGTH: 333
<212> TYPE: DNA
<213> ORGANISM: Artificial Sequence
<220> FEATURE:
<223> OTHER INFORMATION: Synthetic

<400> SEQUENCE: 12
gacattgagc tcacccagtc tccatcttat cttgctgcat ctcctgaaga aaccattact     60
attaattgca gggcaagtaa gagcattagc aaatatttag cctggtatca aagaaacct    120 gggaaaacta taagcttct tatctactct ggatccactt tgcaatctgg aattccatca     180
aggttcagtg gcagtggatc tggtacagat ttcactctca ccatcagtag cctgagcct    240 gaagattttg caatgtatta ctgtcaacag cataatgaat acccgtggac gttcggtgga    300
```
gggaccaagc tggagatcaa acgggcggcc gca    333

<210> SEQ ID NO 13
<211> LENGTH: 14507
<212> TYPE: PRT
<213> ORGANISM: Homo sapiens

<400> SEQUENCE: 13

| | | | | | | | | | | | | | | |
|---|---|---|---|---|---|---|---|---|---|---|---|---|---|---|
| Met | Leu | Lys | Pro | Ser | Gly | Leu | Pro | Gly | Ser | Ser | Pro | Thr | Arg | Ser |
| 1 | | | | 5 | | | | | 10 | | | | | 15 |
| Leu | Met | Thr | Gly | Ser | Arg | Ser | Thr | Lys | Ala | Thr | Pro | Glu | Met | Asp | Ser |
| | | | 20 | | | | | 25 | | | | | 30 | | |
| Gly | Leu | Thr | Gly | Ala | Thr | Leu | Ser | Pro | Lys | Thr | Ser | Thr | Gly | Ala | Ile |
| | | | | 35 | | | | | 40 | | | | | 45 | |
| Val | Val | Thr | Glu | His | Thr | Leu | Pro | Phe | Thr | Ser | Pro | Asp | Lys | Thr | Leu |
| | | 50 | | | | | 55 | | | | | 60 | | | |
| Ala | Ser | Pro | Thr | Ser | Ser | Val | Val | Gly | Arg | Thr | Thr | Gln | Ser | Leu | Gly |
| 65 | | | | | 70 | | | | | 75 | | | | | 80 |
| Val | Met | Ser | Ser | Ala | Leu | Pro | Glu | Ser | Thr | Ser | Arg | Gly | Met | Thr | His |
| | | | | 85 | | | | | 90 | | | | | 95 | |
| Ser | Glu | Gln | Arg | Thr | Ser | Pro | Ser | Leu | Ser | Pro | Gln | Val | Asn | Gly | Thr |
| | | | 100 | | | | | 105 | | | | | 110 | | |
| Pro | Ser | Arg | Asn | Tyr | Pro | Ala | Thr | Ser | Met | Val | Ser | Gly | Leu | Ser | Ser |
| | | | | 115 | | | | | 120 | | | | | 125 | |
| Pro | Arg | Thr | Arg | Thr | Ser | Ser | Thr | Glu | Gly | Asn | Phe | Thr | Lys | Glu | Ala |
| | | 130 | | | | | 135 | | | | | 140 | | | |
| Ser | Thr | Tyr | Thr | Leu | Thr | Val | Glu | Thr | Thr | Ser | Gly | Pro | Val | Thr | Glu |
| 145 | | | | | 150 | | | | | 155 | | | | | 160 |
| Lys | Tyr | Thr | Val | Pro | Thr | Glu | Thr | Ser | Thr | Thr | Glu | Gly | Asp | Ser | Thr |
| | | | | 165 | | | | | 170 | | | | | 175 | |
| Glu | Thr | Pro | Trp | Asp | Thr | Arg | Tyr | Ile | Pro | Val | Lys | Ile | Thr | Ser | Pro |
| | | | 180 | | | | | 185 | | | | | 190 | | |
| Met | Lys | Thr | Phe | Ala | Asp | Ser | Thr | Ala | Ser | Lys | Glu | Asn | Ala | Pro | Val |
| | | | | 195 | | | | | 200 | | | | | 205 | |
| Ser | Met | Thr | Pro | Ala | Glu | Thr | Thr | Val | Thr | Asp | Ser | His | Thr | Pro | Gly |
| | | 210 | | | | | 215 | | | | | 220 | | | |
| Arg | Thr | Asn | Pro | Ser | Phe | Gly | Thr | Leu | Tyr | Ser | Ser | Phe | Leu | Asp | Leu |
| 225 | | | | | 230 | | | | | 235 | | | | | 240 |
| Ser | Pro | Lys | Gly | Thr | Pro | Asn | Ser | Arg | Gly | Glu | Thr | Ser | Leu | Glu | Leu |
| | | | | 245 | | | | | 250 | | | | | 255 | |
| Ile | Leu | Ser | Thr | Thr | Gly | Tyr | Pro | Phe | Ser | Ser | Pro | Glu | Pro | Gly | Ser |
| | | | 260 | | | | | 265 | | | | | 270 | | |
| Ala | Gly | His | Ser | Arg | Ile | Ser | Thr | Ser | Ala | Pro | Leu | Ser | Ser | Ser | Ala |
| | | | | 275 | | | | | 280 | | | | | 285 | |
| Ser | Val | Leu | Asp | Asn | Lys | Ile | Ser | Glu | Thr | Ser | Ile | Phe | Ser | Gly | Gln |
| | | 290 | | | | | 295 | | | | | 300 | | | |
| Ser | Leu | Thr | Ser | Pro | Leu | Ser | Pro | Gly | Val | Pro | Glu | Ala | Arg | Ala | Ser |
| 305 | | | | | 310 | | | | | 315 | | | | | 320 |
| Thr | Met | Pro | Asn | Ser | Ala | Ile | Pro | Phe | Ser | Met | Thr | Leu | Ser | Asn | Ala |
| | | | | 325 | | | | | 330 | | | | | 335 | |
| Glu | Thr | Ser | Ala | Glu | Arg | Val | Arg | Ser | Thr | Ile | Ser | Ser | Leu | Gly | Thr |
| | | | 340 | | | | | 345 | | | | | 350 | | |
| Pro | Ser | Ile | Ser | Thr | Lys | Gln | Thr | Ala | Glu | Thr | Ile | Leu | Thr | Phe | His |
| | | | | 355 | | | | | 360 | | | | | 365 | |

```
Ala Phe Ala Glu Thr Met Asp Ile Pro Ser Thr His Ile Ala Lys Thr
    370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
            405                 410                 415

Glu Thr Asn Thr His His Ser Thr Ser Gly Lys Glu Thr Glu Gly Thr
                420                 425                 430

Leu Asn Thr Ser Met Thr Pro Leu Glu Thr Ser Ala Pro Gly Glu Glu
            435                 440                 445

Ser Glu Met Thr Ala Thr Leu Val Pro Thr Leu Gly Phe Thr Thr Leu
    450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
            485                 490                 495

Thr Ala Ala His Gly Ser Ser Asp Ile Leu Arg Ala Thr Thr Ser Ser
                500                 505                 510

Thr Ser Lys Ala Ser Ser Trp Thr Ser Glu Ser Thr Ala Gln Gln Phe
            515                 520                 525

Ser Glu Pro Gln His Thr Gln Trp Val Glu Thr Ser Pro Ser Met Lys
    530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
            565                 570                 575

Thr Lys Gly Ile Trp Leu Glu Glu Thr Ser Ala Asp Thr Leu Ile Gly
                580                 585                 590

Glu Ser Thr Ala Gly Pro Thr Thr His Gln Phe Ala Val Pro Thr Gly
            595                 600                 605

Ile Ser Met Thr Gly Gly Ser Ser Thr Arg Gly Ser Gln Gly Thr Thr
    610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
            645                 650                 655

Lys Thr Ala Ala Gly Ser Ser Pro Pro Gly Gly Thr Lys Pro Ser Tyr
                660                 665                 670

Thr Met Val Ser Ser Val Ile Pro Glu Thr Ser Ser Leu Gln Ser Ser
            675                 680                 685

Ala Phe Arg Glu Gly Thr Ser Leu Gly Leu Thr Pro Leu Asn Thr Arg
    690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
            725                 730                 735

Val Ser Ala Thr Ser Thr Phe Ser His His Lys Ala Thr Ser Ser Ile
                740                 745                 750

Thr Thr Gly Thr Pro Glu Ile Ser Thr Lys Thr Lys Pro Ser Ser Ala
            755                 760                 765

Val Leu Ser Ser Met Thr Leu Ser Asn Ala Ala Thr Ser Pro Glu Arg
    770                 775                 780
```

```
Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
        805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
        835                 840                 845

Thr Phe Ser Ser Ser Thr Pro Ser Thr His Leu Phe Thr Ser Gly Glu
    850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
                900                 905                 910

Ser Ser His Leu Val Ser Glu Leu Arg Ala Thr Ser Ser Thr Ser Val
            915                 920                 925

Thr Asn Ser Thr Gly Ser Ala Leu Pro Lys Ile Ser His Leu Thr Gly
    930                 935                 940

Thr Ala Thr Met Ser Gln Thr Asn Arg Asp Thr Phe Asn Asp Ser Ala
945                 950                 955                 960

Ala Pro Gln Ser Thr Thr Trp Pro Glu Thr Ser Pro Arg Phe Lys Thr
                965                 970                 975

Gly Leu Pro Ser Ala Thr Thr Thr Val Ser Thr Ser Ala Thr Ser Leu
                980                 985                 990

Ser Ala Thr Val Met Val Ser Lys Phe Thr Ser Pro Ala Thr Ser Ser
        995                 1000                1005

Met Glu Ala Thr Ser Ile Arg Glu Pro Ser Thr Thr Ile Leu Thr
    1010                1015                1020

Thr Glu Thr Thr Asn Gly Pro Gly Ser Met Ala Val Ala Ser Thr
    1025                1030                1035

Asn Ile Pro Ile Gly Lys Gly Tyr Ile Thr Glu Gly Arg Leu Asp
    1040                1045                1050

Thr Ser His Leu Pro Ile Gly Thr Thr Ala Ser Ser Glu Thr Ser
    1055                1060                1065

Met Asp Phe Thr Met Ala Lys Glu Ser Val Ser Met Ser Val Ser
    1070                1075                1080

Pro Ser Gln Ser Met Asp Ala Ala Gly Ser Ser Thr Pro Gly Arg
    1085                1090                1095

Thr Ser Gln Phe Val Asp Thr Phe Ser Asp Asp Val Tyr His Leu
    1100                1105                1110

Thr Ser Arg Glu Ile Thr Ile Pro Arg Asp Gly Thr Ser Ser Ala
    1115                1120                1125

Leu Thr Pro Gln Met Thr Ala Thr His Pro Pro Ser Pro Asp Pro
    1130                1135                1140

Gly Ser Ala Arg Ser Thr Trp Leu Gly Ile Leu Ser Ser Ser Pro
    1145                1150                1155

Ser Ser Pro Thr Pro Lys Val Thr Met Ser Ser Thr Phe Ser Thr
    1160                1165                1170

Gln Arg Val Thr Thr Ser Met Ile Met Asp Thr Val Glu Thr Ser
    1175                1180                1185

Arg Trp Asn Met Pro Asn Leu Pro Ser Thr Thr Ser Leu Thr Pro
```

```
                1190                1195                1200
Ser Asn Ile Pro Thr Ser Gly Ala Ile Gly Lys Ser Thr Leu Val
    1205                1210                1215

Pro Leu Asp Thr Pro Ser Pro Ala Thr Ser Leu Glu Ala Ser Glu
    1220                1225                1230

Gly Gly Leu Pro Thr Leu Ser Thr Tyr Pro Glu Ser Thr Asn Thr
    1235                1240                1245

Pro Ser Ile His Leu Gly Ala His Ala Ser Ser Glu Ser Pro Ser
    1250                1255                1260

Thr Ile Lys Leu Thr Met Ala Ser Val Val Lys Pro Gly Ser Tyr
    1265                1270                1275

Thr Pro Leu Thr Phe Pro Ser Ile Glu Thr His Ile His Val Ser
    1280                1285                1290

Thr Ala Arg Met Ala Tyr Ser Ser Gly Ser Ser Pro Glu Met Thr
    1295                1300                1305

Ala Pro Gly Glu Thr Asn Thr Gly Ser Thr Trp Asp Pro Thr Thr
    1310                1315                1320

Tyr Ile Thr Thr Thr Asp Pro Lys Asp Thr Ser Ser Ala Gln Val
    1325                1330                1335

Ser Thr Pro His Ser Val Arg Thr Leu Arg Thr Thr Glu Asn His
    1340                1345                1350

Pro Lys Thr Glu Ser Ala Thr Pro Ala Ala Tyr Ser Gly Ser Pro
    1355                1360                1365

Lys Ile Ser Ser Ser Pro Asn Leu Thr Ser Pro Ala Thr Lys Ala
    1370                1375                1380

Trp Thr Ile Thr Asp Thr Thr Glu His Ser Thr Gln Leu His Tyr
    1385                1390                1395

Thr Lys Leu Ala Glu Lys Ser Ser Gly Phe Glu Thr Gln Ser Ala
    1400                1405                1410

Pro Gly Pro Val Ser Val Val Ile Pro Thr Ser Pro Thr Ile Gly
    1415                1420                1425

Ser Ser Thr Leu Glu Leu Thr Ser Asp Val Pro Gly Glu Pro Leu
    1430                1435                1440

Val Leu Ala Pro Ser Glu Gln Thr Thr Ile Thr Leu Pro Met Ala
    1445                1450                1455

Thr Trp Leu Ser Thr Ser Leu Thr Glu Glu Met Ala Ser Thr Asp
    1460                1465                1470

Leu Asp Ile Ser Ser Pro Ser Ser Pro Met Ser Thr Phe Ala Ile
    1475                1480                1485

Phe Pro Pro Met Ser Thr Pro Ser His Glu Leu Ser Lys Ser Glu
    1490                1495                1500

Ala Asp Thr Ser Ala Ile Arg Asn Thr Asp Ser Thr Thr Leu Asp
    1505                1510                1515

Gln His Leu Gly Ile Arg Ser Leu Gly Arg Thr Gly Asp Leu Thr
    1520                1525                1530

Thr Val Pro Ile Thr Pro Leu Thr Thr Thr Trp Thr Ser Val Ile
    1535                1540                1545

Glu His Ser Thr Gln Ala Gln Asp Thr Leu Ser Ala Thr Met Ser
    1550                1555                1560

Pro Thr His Val Thr Gln Ser Leu Lys Asp Gln Thr Ser Ile Pro
    1565                1570                1575

Ala Ser Ala Ser Pro Ser His Leu Thr Glu Val Tyr Pro Glu Leu
    1580                1585                1590
```

-continued

Gly Thr Gln Gly Arg Ser Ser Ser Glu Ala Thr Thr Phe Trp Lys
1595                1600                1605

Pro Ser Thr Asp Thr Leu Ser Arg Glu Ile Glu Thr Gly Pro Thr
1610                1615                1620

Asn Ile Gln Ser Thr Pro Pro Met Asp Asn Thr Thr Thr Gly Ser
1625                1630                1635

Ser Ser Ser Gly Val Thr Leu Gly Ile Ala His Leu Pro Ile Gly
1640                1645                1650

Thr Ser Ser Pro Ala Glu Thr Ser Thr Asn Met Ala Leu Glu Arg
1655                1660                1665

Arg Ser Ser Thr Ala Thr Val Ser Met Ala Gly Thr Met Gly Leu
1670                1675                1680

Leu Val Thr Ser Ala Pro Gly Arg Ser Ile Ser Gln Ser Leu Gly
1685                1690                1695

Arg Val Ser Ser Val Leu Ser Glu Ser Thr Thr Glu Gly Val Thr
1700                1705                1710

Asp Ser Ser Lys Gly Ser Ser Pro Arg Leu Asn Thr Gln Gly Asn
1715                1720                1725

Thr Ala Leu Ser Ser Ser Leu Glu Pro Ser Tyr Ala Glu Gly Ser
1730                1735                1740

Gln Met Ser Thr Ser Ile Pro Leu Thr Ser Ser Pro Thr Thr Pro
1745                1750                1755

Asp Val Glu Phe Ile Gly Gly Ser Thr Phe Trp Thr Lys Glu Val
1760                1765                1770

Thr Thr Val Met Thr Ser Asp Ile Ser Lys Ser Ser Ala Arg Thr
1775                1780                1785

Glu Ser Ser Ala Thr Leu Met Ser Thr Ala Leu Gly Ser Thr
1790                1795                1800

Glu Asn Thr Gly Lys Glu Lys Leu Arg Thr Ala Ser Met Asp Leu
1805                1810                1815

Pro Ser Pro Thr Pro Ser Met Glu Val Thr Pro Trp Ile Ser Leu
1820                1825                1830

Thr Leu Ser Asn Ala Pro Asn Thr Thr Asp Ser Leu Asp Leu Ser
1835                1840                1845

His Gly Val His Thr Ser Ser Ala Gly Thr Leu Ala Thr Asp Arg
1850                1855                1860

Ser Leu Asn Thr Gly Val Thr Arg Ala Ser Arg Leu Glu Asn Gly
1865                1870                1875

Ser Asp Thr Ser Ser Lys Ser Leu Ser Met Gly Asn Ser Thr His
1880                1885                1890

Thr Ser Met Thr Tyr Thr Glu Lys Ser Glu Val Ser Ser Ser Ile
1895                1900                1905

His Pro Arg Pro Glu Thr Ser Ala Pro Gly Ala Glu Thr Thr Leu
1910                1915                1920

Thr Ser Thr Pro Gly Asn Arg Ala Ile Ser Leu Thr Leu Pro Phe
1925                1930                1935

Ser Ser Ile Pro Val Glu Glu Val Ile Ser Thr Gly Ile Thr Ser
1940                1945                1950

Gly Pro Asp Ile Asn Ser Ala Pro Met Thr His Ser Pro Ile Thr
1955                1960                1965

Pro Pro Thr Ile Val Trp Thr Ser Thr Gly Thr Ile Glu Gln Ser
1970                1975                1980

-continued

```
Thr Gln Pro Leu His Ala Val Ser Ser Glu Lys Val Ser Val Gln
    1985                1990                1995
Thr Gln Ser Thr Pro Tyr Val Asn Ser Val Ala Val Ser Ala Ser
    2000                2005                2010
Pro Thr His Glu Asn Ser Val Ser Ser Gly Ser Ser Thr Ser Ser
    2015                2020                2025
Pro Tyr Ser Ser Ala Ser Leu Glu Ser Leu Asp Ser Thr Ile Ser
    2030                2035                2040
Arg Arg Asn Ala Ile Thr Ser Trp Leu Trp Asp Leu Thr Thr Ser
    2045                2050                2055
Leu Pro Thr Thr Thr Trp Pro Ser Thr Ser Leu Ser Glu Ala Leu
    2060                2065                2070
Ser Ser Gly His Ser Gly Val Ser Asn Pro Ser Ser Thr Thr Thr
    2075                2080                2085
Glu Phe Pro Leu Phe Ser Ala Ala Ser Thr Ser Ala Ala Lys Gln
    2090                2095                2100
Arg Asn Pro Glu Thr Glu Thr His Gly Pro Gln Asn Thr Ala Ala
    2105                2110                2115
Ser Thr Leu Asn Thr Asp Ala Ser Ser Val Thr Gly Leu Ser Glu
    2120                2125                2130
Thr Pro Val Gly Ala Ser Ile Ser Ser Glu Val Pro Leu Pro Met
    2135                2140                2145
Ala Ile Thr Ser Arg Ser Asp Val Ser Gly Leu Thr Ser Glu Ser
    2150                2155                2160
Thr Ala Asn Pro Ser Leu Gly Thr Ala Ser Ser Ala Gly Thr Lys
    2165                2170                2175
Leu Thr Arg Thr Ile Ser Leu Pro Thr Ser Glu Ser Leu Val Ser
    2180                2185                2190
Phe Arg Met Asn Lys Asp Pro Trp Thr Val Ser Ile Pro Leu Gly
    2195                2200                2205
Ser His Pro Thr Thr Asn Thr Glu Thr Ser Ile Pro Val Asn Ser
    2210                2215                2220
Ala Gly Pro Pro Gly Leu Ser Thr Val Ala Ser Asp Val Ile Asp
    2225                2230                2235
Thr Pro Ser Asp Gly Ala Glu Ser Ile Pro Thr Val Ser Phe Ser
    2240                2245                2250
Pro Ser Pro Asp Thr Glu Val Thr Thr Ile Ser His Phe Pro Glu
    2255                2260                2265
Lys Thr Thr His Ser Phe Arg Thr Ile Ser Ser Leu Thr His Glu
    2270                2275                2280
Leu Thr Ser Arg Val Thr Pro Ile Pro Gly Asp Trp Met Ser Ser
    2285                2290                2295
Ala Met Ser Thr Lys Pro Thr Gly Ala Ser Pro Ser Ile Thr Leu
    2300                2305                2310
Gly Glu Arg Arg Thr Ile Thr Ser Ala Ala Pro Thr Thr Ser Pro
    2315                2320                2325
Ile Val Leu Thr Ala Ser Phe Thr Glu Thr Ser Thr Val Ser Leu
    2330                2335                2340
Asp Asn Glu Thr Thr Val Lys Thr Ser Asp Ile Leu Asp Ala Arg
    2345                2350                2355
Lys Thr Asn Glu Leu Pro Ser Asp Ser Ser Ser Ser Asp Leu
    2360                2365                2370
Ile Asn Thr Ser Ile Ala Ser Ser Thr Met Asp Val Thr Lys Thr
```

-continued

```
                2375                2380                2385

Ala Ser Ile Ser Pro Thr Ser Ile Ser Gly Met Thr Ala Ser Ser
        2390                2395                2400

Ser Pro Ser Leu Phe Ser Ser Asp Arg Pro Gln Val Pro Thr Ser
        2405                2410                2415

Thr Thr Glu Thr Asn Thr Ala Thr Ser Pro Ser Val Ser Ser Asn
        2420                2425                2430

Thr Tyr Ser Leu Asp Gly Gly Ser Asn Val Gly Gly Thr Pro Ser
        2435                2440                2445

Thr Leu Pro Pro Phe Thr Ile Thr His Pro Val Glu Thr Ser Ser
        2450                2455                2460

Ala Leu Leu Ala Trp Ser Arg Pro Val Arg Thr Phe Ser Thr Met
        2465                2470                2475

Val Ser Thr Asp Thr Ala Ser Gly Glu Asn Pro Thr Ser Ser Asn
        2480                2485                2490

Ser Val Val Thr Ser Val Pro Ala Pro Gly Thr Trp Thr Ser Val
        2495                2500                2505

Gly Ser Thr Thr Asp Leu Pro Ala Met Gly Phe Leu Lys Thr Ser
        2510                2515                2520

Pro Ala Gly Glu Ala His Ser Leu Leu Ala Ser Thr Ile Glu Pro
        2525                2530                2535

Ala Thr Ala Phe Thr Pro His Leu Ser Ala Ala Val Val Thr Gly
        2540                2545                2550

Ser Ser Ala Thr Ser Glu Ala Ser Leu Leu Thr Thr Ser Glu Ser
        2555                2560                2565

Lys Ala Ile His Ser Ser Pro Gln Thr Pro Thr Thr Pro Thr Ser
        2570                2575                2580

Gly Ala Asn Trp Glu Thr Ser Ala Thr Pro Glu Ser Leu Leu Val
        2585                2590                2595

Val Thr Glu Thr Ser Asp Thr Thr Leu Thr Ser Lys Ile Leu Val
        2600                2605                2610

Thr Asp Thr Ile Leu Phe Ser Thr Val Ser Thr Pro Pro Ser Lys
        2615                2620                2625

Phe Pro Ser Thr Gly Thr Leu Ser Gly Ala Ser Phe Pro Thr Leu
        2630                2635                2640

Leu Pro Asp Thr Pro Ala Ile Pro Leu Thr Ala Thr Glu Pro Thr
        2645                2650                2655

Ser Ser Leu Ala Thr Ser Phe Asp Ser Thr Pro Leu Val Thr Ile
        2660                2665                2670

Ala Ser Asp Ser Leu Gly Thr Val Pro Glu Thr Thr Leu Thr Met
        2675                2680                2685

Ser Glu Thr Ser Asn Gly Asp Ala Leu Val Leu Lys Thr Val Ser
        2690                2695                2700

Asn Pro Asp Arg Ser Ile Pro Gly Ile Thr Ile Gln Gly Val Thr
        2705                2710                2715

Glu Ser Pro Leu His Pro Ser Ser Thr Ser Pro Ser Lys Ile Val
        2720                2725                2730

Ala Pro Arg Asn Thr Thr Tyr Glu Gly Ser Ile Thr Val Ala Leu
        2735                2740                2745

Ser Thr Leu Pro Ala Gly Thr Gly Ser Leu Val Phe Ser Gln
        2750                2755                2760

Ser Ser Glu Asn Ser Glu Thr Thr Ala Leu Val Asp Ser Ser Ala
        2765                2770                2775
```

-continued

Gly Leu Glu Arg Ala Ser Val Met Pro Leu Thr Thr Gly Ser Gln
            2780                    2785                2790

Gly Met Ala Ser Ser Gly Gly Ile Arg Ser Gly Ser Thr His Ser
            2795                    2800                2805

Thr Gly Thr Lys Thr Phe Ser Ser Leu Pro Leu Thr Met Asn Pro
            2810                    2815                2820

Gly Glu Val Thr Ala Met Ser Glu Ile Thr Thr Asn Arg Leu Thr
            2825                    2830                2835

Ala Thr Gln Ser Thr Ala Pro Lys Gly Ile Pro Val Lys Pro Thr
            2840                    2845                2850

Ser Ala Glu Ser Gly Leu Leu Thr Pro Val Ser Ala Ser Ser Ser
            2855                    2860                2865

Pro Ser Lys Ala Phe Ala Ser Leu Thr Thr Ala Pro Pro Thr Trp
            2870                    2875                2880

Gly Ile Pro Gln Ser Thr Leu Thr Phe Glu Phe Ser Glu Val Pro
            2885                    2890                2895

Ser Leu Asp Thr Lys Ser Ala Ser Leu Pro Thr Pro Gly Gln Ser
            2900                    2905                2910

Leu Asn Thr Ile Pro Asp Ser Asp Ala Ser Thr Ala Ser Ser Ser
            2915                    2920                2925

Leu Ser Lys Ser Pro Glu Lys Asn Pro Arg Ala Arg Met Met Thr
            2930                    2935                2940

Ser Thr Lys Ala Ile Ser Ala Ser Ser Phe Gln Ser Thr Gly Phe
            2945                    2950                2955

Thr Glu Thr Pro Glu Gly Ser Ala Ser Pro Ser Met Ala Gly His
            2960                    2965                2970

Glu Pro Arg Val Pro Thr Ser Gly Thr Gly Asp Pro Arg Tyr Ala
            2975                    2980                2985

Ser Glu Ser Met Ser Tyr Pro Asp Pro Ser Lys Ala Ser Ser Ala
            2990                    2995                3000

Met Thr Ser Thr Ser Leu Ala Ser Lys Leu Thr Thr Leu Phe Ser
            3005                    3010                3015

Thr Gly Gln Ala Ala Arg Ser Gly Ser Ser Ser Pro Ile Ser
            3020                    3025                3030

Leu Ser Thr Glu Lys Glu Thr Ser Phe Leu Ser Pro Thr Ala Ser
            3035                    3040                3045

Thr Ser Arg Lys Thr Ser Leu Phe Leu Gly Pro Ser Met Ala Arg
            3050                    3055                3060

Gln Pro Asn Ile Leu Val His Leu Gln Thr Ser Ala Leu Thr Leu
            3065                    3070                3075

Ser Pro Thr Ser Thr Leu Asn Met Ser Gln Glu Glu Pro Pro Glu
            3080                    3085                3090

Leu Thr Ser Ser Gln Thr Ile Ala Glu Glu Glu Gly Thr Thr Ala
            3095                    3100                3105

Glu Thr Gln Thr Leu Thr Phe Thr Pro Ser Glu Thr Pro Thr Ser
            3110                    3115                3120

Leu Leu Pro Val Ser Ser Pro Thr Glu Pro Thr Ala Arg Arg Lys
            3125                    3130                3135

Ser Ser Pro Glu Thr Trp Ala Ser Ser Ile Ser Val Pro Ala Lys
            3140                    3145                3150

Thr Ser Leu Val Glu Thr Thr Asp Gly Thr Leu Val Thr Thr Ile
            3155                    3160                3165

```
Lys Met Ser Ser Gln Ala Ala Gln Gly Asn Ser Thr Trp Pro Ala
    3170            3175                3180

Pro Ala Glu Glu Thr Gly Ser Ser Pro Ala Gly Thr Ser Pro Gly
    3185            3190                3195

Ser Pro Glu Met Ser Thr Thr Leu Lys Ile Met Ser Ser Lys Glu
    3200            3205                3210

Pro Ser Ile Ser Pro Glu Ile Arg Ser Thr Val Arg Asn Ser Pro
    3215            3220                3225

Trp Lys Thr Pro Glu Thr Thr Val Pro Met Glu Thr Thr Val Glu
    3230            3235                3240

Pro Val Thr Leu Gln Ser Thr Ala Leu Gly Ser Gly Ser Thr Ser
    3245            3250                3255

Ile Ser His Leu Pro Thr Gly Thr Thr Ser Pro Thr Lys Ser Pro
    3260            3265                3270

Thr Glu Asn Met Leu Ala Thr Glu Arg Val Ser Leu Ser Pro Ser
    3275            3280                3285

Pro Pro Glu Ala Trp Thr Asn Leu Tyr Ser Gly Thr Pro Gly Gly
    3290            3295                3300

Thr Arg Gln Ser Leu Ala Thr Met Ser Ser Val Ser Leu Glu Ser
    3305            3310                3315

Pro Thr Ala Arg Ser Ile Thr Gly Thr Gly Gln Gln Ser Ser Pro
    3320            3325                3330

Glu Leu Val Ser Lys Thr Thr Gly Met Glu Phe Ser Met Trp His
    3335            3340                3345

Gly Ser Thr Gly Gly Thr Thr Gly Asp Thr His Val Ser Leu Ser
    3350            3355                3360

Thr Ser Ser Asn Ile Leu Glu Asp Pro Val Thr Ser Pro Asn Ser
    3365            3370                3375

Val Ser Ser Leu Thr Asp Lys Ser Lys His Lys Thr Glu Thr Trp
    3380            3385                3390

Val Ser Thr Thr Ala Ile Pro Ser Thr Val Leu Asn Asn Lys Ile
    3395            3400                3405

Met Ala Ala Glu Gln Gln Thr Ser Arg Ser Val Asp Glu Ala Tyr
    3410            3415                3420

Ser Ser Thr Ser Ser Trp Ser Asp Gln Thr Ser Gly Ser Asp Ile
    3425            3430                3435

Thr Leu Gly Ala Ser Pro Asp Val Thr Asn Thr Leu Tyr Ile Thr
    3440            3445                3450

Ser Thr Ala Gln Thr Thr Ser Leu Val Ser Leu Pro Ser Gly Asp
    3455            3460                3465

Gln Gly Ile Thr Ser Leu Thr Asn Pro Ser Gly Gly Lys Thr Ser
    3470            3475                3480

Ser Ala Ser Ser Val Thr Ser Pro Ser Ile Gly Leu Glu Thr Leu
    3485            3490                3495

Arg Ala Asn Val Ser Ala Val Lys Ser Asp Ile Ala Pro Thr Ala
    3500            3505                3510

Gly His Leu Ser Gln Thr Ser Ser Pro Ala Glu Val Ser Ile Leu
    3515            3520                3525

Asp Val Thr Thr Ala Pro Thr Pro Gly Ile Ser Thr Thr Ile Thr
    3530            3535                3540

Thr Met Gly Thr Asn Ser Ile Ser Thr Thr Thr Pro Asn Pro Glu
    3545            3550                3555

Val Gly Met Ser Thr Met Asp Ser Thr Pro Ala Thr Glu Arg Arg
```

```
                3560                3565                3570
Thr Thr Ser Thr Glu His Pro Ser Thr Trp Ser Ser Thr Ala Ala
    3575            3580            3585
Ser Asp Ser Trp Thr Val Thr Asp Met Thr Ser Asn Leu Lys Val
    3590            3595            3600
Ala Arg Ser Pro Gly Thr Ile Ser Thr Met His Thr Thr Ser Phe
    3605            3610            3615
Leu Ala Ser Ser Thr Glu Leu Asp Ser Met Ser Thr Pro His Gly
    3620            3625            3630
Arg Ile Thr Val Ile Gly Thr Ser Leu Val Thr Pro Ser Ser Asp
    3635            3640            3645
Ala Ser Ala Val Lys Thr Glu Thr Ser Thr Ser Glu Arg Thr Leu
    3650            3655            3660
Ser Pro Ser Asp Thr Thr Ala Ser Thr Pro Ile Ser Thr Phe Ser
    3665            3670            3675
Arg Val Gln Arg Met Ser Ile Ser Val Pro Asp Ile Leu Ser Thr
    3680            3685            3690
Ser Trp Thr Pro Ser Ser Thr Glu Ala Glu Asp Val Pro Val Ser
    3695            3700            3705
Met Val Ser Thr Asp His Ala Ser Thr Lys Thr Asp Pro Asn Thr
    3710            3715            3720
Pro Leu Ser Thr Phe Leu Phe Asp Ser Leu Ser Thr Leu Asp Trp
    3725            3730            3735
Asp Thr Gly Arg Ser Leu Ser Ser Ala Thr Ala Thr Thr Ser Ala
    3740            3745            3750
Pro Gln Gly Ala Thr Thr Pro Gln Glu Leu Thr Leu Glu Thr Met
    3755            3760            3765
Ile Ser Pro Ala Thr Ser Gln Leu Pro Phe Ser Ile Gly His Ile
    3770            3775            3780
Thr Ser Ala Val Thr Pro Ala Ala Met Ala Arg Ser Ser Gly Val
    3785            3790            3795
Thr Phe Ser Arg Pro Asp Pro Thr Ser Lys Lys Ala Glu Gln Thr
    3800            3805            3810
Ser Thr Gln Leu Pro Thr Thr Thr Ser Ala His Pro Gly Gln Val
    3815            3820            3825
Pro Arg Ser Ala Ala Thr Thr Leu Asp Val Ile Pro His Thr Ala
    3830            3835            3840
Lys Thr Pro Asp Ala Thr Phe Gln Arg Gln Gly Gln Thr Ala Leu
    3845            3850            3855
Thr Thr Glu Ala Arg Ala Thr Ser Asp Ser Trp Asn Glu Lys Glu
    3860            3865            3870
Lys Ser Thr Pro Ser Ala Pro Trp Ile Thr Glu Met Met Asn Ser
    3875            3880            3885
Val Ser Glu Asp Thr Ile Lys Glu Val Thr Ser Ser Ser Ser Val
    3890            3895            3900
Leu Arg Thr Leu Asn Thr Leu Asp Ile Asn Leu Glu Ser Gly Thr
    3905            3910            3915
Thr Ser Ser Pro Ser Trp Lys Ser Ser Pro Tyr Glu Arg Ile Ala
    3920            3925            3930
Pro Ser Glu Ser Thr Thr Asp Lys Glu Ala Ile His Pro Ser Thr
    3935            3940            3945
Asn Thr Val Glu Thr Thr Gly Trp Val Thr Ser Ser Glu His Ala
    3950            3955            3960
```

```
Ser His Ser Thr Ile Pro Ala His Ser Ala Ser Ser Lys Leu Thr
    3965                3970                3975

Ser Pro Val Val Thr Thr Ser Thr Arg Glu Gln Ala Ile Val Ser
    3980                3985                3990

Met Ser Thr Thr Thr Trp Pro Glu Ser Thr Arg Ala Arg Thr Glu
    3995                4000                4005

Pro Asn Ser Phe Leu Thr Ile Glu Leu Arg Asp Val Ser Pro Tyr
    4010                4015                4020

Met Asp Thr Ser Ser Thr Thr Gln Thr Ser Ile Ile Ser Ser Pro
    4025                4030                4035

Gly Ser Thr Ala Ile Thr Lys Gly Pro Arg Thr Glu Ile Thr Ser
    4040                4045                4050

Ser Lys Arg Ile Ser Ser Ser Phe Leu Ala Gln Ser Met Arg Ser
    4055                4060                4065

Ser Asp Ser Pro Ser Glu Ala Ile Thr Arg Leu Ser Asn Phe Pro
    4070                4075                4080

Ala Met Thr Glu Ser Gly Gly Met Ile Leu Ala Met Gln Thr Ser
    4085                4090                4095

Pro Pro Gly Ala Thr Ser Leu Ser Ala Pro Thr Leu Asp Thr Ser
    4100                4105                4110

Ala Thr Ala Ser Trp Thr Gly Thr Pro Leu Ala Thr Thr Gln Arg
    4115                4120                4125

Phe Thr Tyr Ser Glu Lys Thr Thr Leu Phe Ser Lys Gly Pro Glu
    4130                4135                4140

Asp Thr Ser Gln Pro Ser Pro Pro Ser Val Glu Glu Thr Ser Ser
    4145                4150                4155

Ser Ser Ser Leu Val Pro Ile His Ala Thr Thr Ser Pro Ser Asn
    4160                4165                4170

Ile Leu Leu Thr Ser Gln Gly His Ser Pro Ser Ser Thr Pro Pro
    4175                4180                4185

Val Thr Ser Val Phe Leu Ser Glu Thr Ser Gly Leu Gly Lys Thr
    4190                4195                4200

Thr Asp Met Ser Arg Ile Ser Leu Glu Pro Gly Thr Ser Leu Pro
    4205                4210                4215

Pro Asn Leu Ser Ser Thr Ala Gly Glu Ala Leu Ser Thr Tyr Glu
    4220                4225                4230

Ala Ser Arg Asp Thr Lys Ala Ile His His Ser Ala Asp Thr Ala
    4235                4240                4245

Val Thr Asn Met Glu Ala Thr Ser Ser Glu Tyr Ser Pro Ile Pro
    4250                4255                4260

Gly His Thr Lys Pro Ser Lys Ala Thr Ser Pro Leu Val Thr Ser
    4265                4270                4275

His Ile Met Gly Asp Ile Thr Ser Ser Thr Ser Val Phe Gly Ser
    4280                4285                4290

Ser Glu Thr Thr Glu Ile Glu Thr Val Ser Ser Val Asn Gln Gly
    4295                4300                4305

Leu Gln Glu Arg Ser Thr Ser Gln Val Ala Ser Ser Ala Thr Glu
    4310                4315                4320

Thr Ser Thr Val Ile Thr His Val Ser Ser Gly Asp Ala Thr Thr
    4325                4330                4335

His Val Thr Lys Thr Gln Ala Thr Phe Ser Ser Gly Thr Ser Ile
    4340                4345                4350
```

```
Ser Ser Pro His Gln Phe Ile Thr Ser Thr Asn Thr Phe Thr Asp
4355                4360                4365

Val Ser Thr Asn Pro Ser Ser Leu Ile Met Thr Glu Ser Ser
4370                4375                4380

Gly Val Thr Ile Thr Thr Gln Thr Gly Pro Thr Gly Ala Ala Thr
4385                4390                4395

Gln Gly Pro Tyr Leu Leu Asp Thr Ser Thr Met Pro Tyr Leu Thr
4400                4405                4410

Glu Thr Pro Leu Ala Val Thr Pro Asp Phe Met Gln Ser Glu Lys
4415                4420                4425

Thr Thr Leu Ile Ser Lys Gly Pro Lys Asp Val Ser Trp Thr Ser
4430                4435                4440

Pro Pro Ser Val Ala Glu Thr Ser Tyr Pro Ser Ser Leu Thr Pro
4445                4450                4455

Phe Leu Val Thr Thr Ile Pro Pro Ala Thr Ser Thr Leu Gln Gly
4460                4465                4470

Gln His Thr Ser Ser Pro Val Ser Ala Thr Ser Val Leu Thr Ser
4475                4480                4485

Gly Leu Val Lys Thr Thr Asp Met Leu Asn Thr Ser Met Glu Pro
4490                4495                4500

Val Thr Asn Ser Pro Gln Asn Leu Asn Asn Pro Ser Asn Glu Ile
4505                4510                4515

Leu Ala Thr Leu Ala Ala Thr Thr Asp Ile Glu Thr Ile His Pro
4520                4525                4530

Ser Ile Asn Lys Ala Val Thr Asn Met Gly Thr Ala Ser Ser Ala
4535                4540                4545

His Val Leu His Ser Thr Leu Pro Val Ser Ser Glu Pro Ser Thr
4550                4555                4560

Ala Thr Ser Pro Met Val Pro Ala Ser Ser Met Gly Asp Ala Leu
4565                4570                4575

Ala Ser Ile Ser Ile Pro Gly Ser Glu Thr Thr Asp Ile Glu Gly
4580                4585                4590

Glu Pro Thr Ser Ser Leu Thr Ala Gly Arg Lys Glu Asn Ser Thr
4595                4600                4605

Leu Gln Glu Met Asn Ser Thr Thr Glu Ser Asn Ile Ile Leu Ser
4610                4615                4620

Asn Val Ser Val Gly Ala Ile Thr Glu Ala Thr Lys Met Glu Val
4625                4630                4635

Pro Ser Phe Asp Ala Thr Phe Ile Pro Thr Pro Ala Gln Ser Thr
4640                4645                4650

Lys Phe Pro Asp Ile Phe Ser Val Ala Ser Ser Arg Leu Ser Asn
4655                4660                4665

Ser Pro Pro Met Thr Ile Ser Thr His Met Thr Thr Thr Gln Thr
4670                4675                4680

Gly Ser Ser Gly Ala Thr Ser Lys Ile Pro Leu Ala Leu Asp Thr
4685                4690                4695

Ser Thr Leu Glu Thr Ser Ala Gly Thr Pro Ser Val Val Thr Glu
4700                4705                4710

Gly Phe Ala His Ser Lys Ile Thr Thr Ala Met Asn Asn Asp Val
4715                4720                4725

Lys Asp Val Ser Gln Thr Asn Pro Pro Phe Gln Asp Glu Ala Ser
4730                4735                4740

Ser Pro Ser Ser Gln Ala Pro Val Leu Val Thr Thr Leu Pro Ser
```

```
                    4745                4750                4755
Ser  Val  Ala  Phe  Thr  Pro  Gln  Trp  His  Ser  Thr  Ser  Ser  Pro  Val
     4760                4765                4770

Ser  Met  Ser  Ser  Val  Leu  Thr  Ser  Ser  Leu  Val  Lys  Thr  Ala  Gly
     4775                4780                4785

Lys  Val  Asp  Thr  Ser  Leu  Glu  Thr  Val  Thr  Ser  Ser  Pro  Gln  Ser
     4790                4795                4800

Met  Ser  Asn  Thr  Leu  Asp  Asp  Ile  Ser  Val  Thr  Ser  Ala  Ala  Thr
     4805                4810                4815

Thr  Asp  Ile  Glu  Thr  Thr  His  Pro  Ser  Ile  Asn  Thr  Val  Val  Thr
     4820                4825                4830

Asn  Val  Gly  Thr  Thr  Gly  Ser  Ala  Phe  Glu  Ser  His  Ser  Thr  Val
     4835                4840                4845

Ser  Ala  Tyr  Pro  Glu  Pro  Ser  Lys  Val  Thr  Ser  Pro  Asn  Val  Thr
     4850                4855                4860

Thr  Ser  Thr  Met  Glu  Asp  Thr  Thr  Ile  Ser  Arg  Ser  Ile  Pro  Lys
     4865                4870                4875

Ser  Ser  Lys  Thr  Thr  Arg  Thr  Glu  Thr  Glu  Thr  Thr  Ser  Ser  Leu
     4880                4885                4890

Thr  Pro  Lys  Leu  Arg  Glu  Thr  Ser  Ile  Ser  Gln  Glu  Ile  Thr  Ser
     4895                4900                4905

Ser  Thr  Glu  Thr  Ser  Thr  Val  Pro  Tyr  Lys  Glu  Leu  Thr  Gly  Ala
     4910                4915                4920

Thr  Thr  Glu  Val  Ser  Arg  Thr  Asp  Val  Thr  Ser  Ser  Ser  Ser  Thr
     4925                4930                4935

Ser  Phe  Pro  Gly  Pro  Asp  Gln  Ser  Thr  Val  Ser  Leu  Asp  Ile  Ser
     4940                4945                4950

Thr  Glu  Thr  Asn  Thr  Arg  Leu  Ser  Thr  Ser  Pro  Ile  Met  Thr  Glu
     4955                4960                4965

Ser  Ala  Glu  Ile  Thr  Ile  Thr  Thr  Gln  Thr  Gly  Pro  His  Gly  Ala
     4970                4975                4980

Thr  Ser  Gln  Asp  Thr  Phe  Thr  Met  Asp  Pro  Ser  Asn  Thr  Thr  Pro
     4985                4990                4995

Gln  Ala  Gly  Ile  His  Ser  Ala  Met  Thr  His  Gly  Phe  Ser  Gln  Leu
     5000                5005                5010

Asp  Val  Thr  Thr  Leu  Met  Ser  Arg  Ile  Pro  Gln  Asp  Val  Ser  Trp
     5015                5020                5025

Thr  Ser  Pro  Pro  Ser  Val  Asp  Lys  Thr  Ser  Ser  Pro  Ser  Ser  Phe
     5030                5035                5040

Leu  Ser  Ser  Pro  Ala  Met  Thr  Thr  Pro  Ser  Leu  Ile  Ser  Ser  Thr
     5045                5050                5055

Leu  Pro  Glu  Asp  Lys  Leu  Ser  Ser  Pro  Met  Thr  Ser  Leu  Leu  Thr
     5060                5065                5070

Ser  Gly  Leu  Val  Lys  Ile  Thr  Asp  Ile  Leu  Arg  Thr  Arg  Leu  Glu
     5075                5080                5085

Pro  Val  Thr  Ser  Ser  Leu  Pro  Asn  Phe  Ser  Ser  Thr  Ser  Asp  Lys
     5090                5095                5100

Ile  Leu  Ala  Thr  Ser  Lys  Asp  Ser  Lys  Asp  Thr  Lys  Glu  Ile  Phe
     5105                5110                5115

Pro  Ser  Ile  Asn  Thr  Glu  Glu  Thr  Asn  Val  Lys  Ala  Asn  Asn  Ser
     5120                5125                5130

Gly  His  Glu  Ser  His  Ser  Pro  Ala  Leu  Ala  Asp  Ser  Glu  Thr  Pro
     5135                5140                5145
```

-continued

```
Lys Ala Thr Thr Gln Met Val Ile Thr Thr Val Gly Asp Pro
5150                5155                5160

Ala Pro Ser Thr Ser Met Pro Val His Gly Ser Ser Glu Thr Thr
5165                5170                5175

Asn Ile Lys Arg Glu Pro Thr Tyr Phe Leu Thr Pro Arg Leu Arg
5180                5185                5190

Glu Thr Ser Thr Ser Gln Glu Ser Ser Phe Pro Thr Asp Thr Ser
5195                5200                5205

Phe Leu Leu Ser Lys Val Pro Thr Gly Thr Ile Thr Glu Val Ser
5210                5215                5220

Ser Thr Gly Val Asn Ser Ser Ser Lys Ile Ser Thr Pro Asp His
5225                5230                5235

Asp Lys Ser Thr Val Pro Pro Asp Thr Phe Thr Gly Glu Ile Pro
5240                5245                5250

Arg Val Phe Thr Ser Ser Ile Lys Thr Lys Ser Ala Glu Met Thr
5255                5260                5265

Ile Thr Thr Gln Ala Ser Pro Pro Glu Ser Ala Ser His Ser Thr
5270                5275                5280

Leu Pro Leu Asp Thr Ser Thr Thr Leu Ser Gln Gly Gly Thr His
5285                5290                5295

Ser Thr Val Thr Gln Gly Phe Pro Tyr Ser Glu Val Thr Thr Leu
5300                5305                5310

Met Gly Met Gly Pro Gly Asn Val Ser Trp Met Thr Thr Pro Pro
5315                5320                5325

Val Glu Glu Thr Ser Ser Val Ser Ser Leu Met Ser Ser Pro Ala
5330                5335                5340

Met Thr Ser Pro Ser Pro Val Ser Ser Thr Ser Pro Gln Ser Ile
5345                5350                5355

Pro Ser Ser Pro Leu Pro Val Thr Ala Leu Pro Thr Ser Val Leu
5360                5365                5370

Val Thr Thr Thr Asp Val Leu Gly Thr Thr Ser Pro Glu Ser Val
5375                5380                5385

Thr Ser Ser Pro Pro Asn Leu Ser Ser Ile Thr His Glu Arg Pro
5390                5395                5400

Ala Thr Tyr Lys Asp Thr Ala His Thr Glu Ala Ala Met His His
5405                5410                5415

Ser Thr Asn Thr Ala Val Thr Asn Val Gly Thr Ser Gly Ser Gly
5420                5425                5430

His Lys Ser Gln Ser Ser Val Leu Ala Asp Ser Glu Thr Ser Lys
5435                5440                5445

Ala Thr Pro Leu Met Ser Thr Thr Ser Thr Leu Gly Asp Thr Ser
5450                5455                5460

Val Ser Thr Ser Thr Pro Asn Ile Ser Gln Thr Asn Gln Ile Gln
5465                5470                5475

Thr Glu Pro Thr Ala Ser Leu Ser Pro Arg Leu Arg Glu Ser Ser
5480                5485                5490

Thr Ser Glu Lys Thr Ser Ser Thr Thr Glu Thr Asn Thr Ala Phe
5495                5500                5505

Ser Tyr Val Pro Thr Gly Ala Ile Thr Gln Ala Ser Arg Thr Glu
5510                5515                5520

Ile Ser Ser Ser Arg Thr Ser Ile Ser Asp Leu Asp Arg Pro Thr
5525                5530                5535
```

-continued

```
Ile Ala Pro Asp Ile Ser Thr Gly Met Ile Thr Arg Leu Phe Thr
    5540                5545                5550

Ser Pro Ile Met Thr Lys Ser Ala Glu Met Thr Val Thr Thr Gln
    5555                5560                5565

Thr Thr Thr Pro Gly Ala Thr Ser Gln Gly Ile Leu Pro Trp Asp
    5570                5575                5580

Thr Ser Thr Thr Leu Phe Gln Gly Gly Thr His Ser Thr Val Ser
    5585                5590                5595

Gln Gly Phe Pro His Ser Glu Ile Thr Thr Leu Arg Ser Arg Thr
    5600                5605                5610

Pro Gly Asp Val Ser Trp Met Thr Thr Pro Val Glu Glu Thr
    5615                5620                5625

Ser Ser Gly Phe Ser Leu Met Ser Pro Ser Met Thr Ser Pro Ser
    5630                5635                5640

Pro Val Ser Ser Thr Ser Pro Glu Ser Ile Pro Ser Ser Pro Leu
    5645                5650                5655

Pro Val Thr Ala Leu Leu Thr Ser Val Leu Val Thr Thr Thr Asn
    5660                5665                5670

Val Leu Gly Thr Thr Ser Pro Glu Pro Val Thr Ser Ser Pro Pro
    5675                5680                5685

Asn Leu Ser Ser Pro Thr Gln Glu Arg Leu Thr Thr Tyr Lys Asp
    5690                5695                5700

Thr Ala His Thr Glu Ala Met His Ala Ser Met His Thr Asn Thr
    5705                5710                5715

Ala Val Ala Asn Val Gly Thr Ser Ile Ser Gly His Glu Ser Gln
    5720                5725                5730

Ser Ser Val Pro Ala Asp Ser His Thr Ser Lys Ala Thr Ser Pro
    5735                5740                5745

Met Gly Ile Thr Phe Ala Met Gly Asp Thr Ser Val Ser Thr Ser
    5750                5755                5760

Thr Pro Ala Phe Phe Glu Thr Arg Ile Gln Thr Glu Ser Thr Ser
    5765                5770                5775

Ser Leu Ile Pro Gly Leu Arg Asp Thr Arg Thr Ser Glu Glu Ile
    5780                5785                5790

Asn Thr Val Thr Glu Thr Ser Thr Val Leu Ser Glu Val Pro Thr
    5795                5800                5805

Thr Thr Thr Thr Glu Val Ser Arg Thr Glu Val Ile Thr Ser Ser
    5810                5815                5820

Arg Thr Thr Ile Ser Gly Pro Asp His Ser Lys Met Ser Pro Tyr
    5825                5830                5835

Ile Ser Thr Glu Thr Ile Thr Arg Leu Ser Thr Phe Pro Phe Val
    5840                5845                5850

Thr Gly Ser Thr Glu Met Ala Ile Thr Asn Gln Thr Gly Pro Ile
    5855                5860                5865

Gly Thr Ile Ser Gln Ala Thr Leu Thr Leu Asp Thr Ser Ser Thr
    5870                5875                5880

Ala Ser Trp Glu Gly Thr His Ser Pro Val Thr Gln Arg Phe Pro
    5885                5890                5895

His Ser Glu Glu Thr Thr Thr Met Ser Arg Ser Thr Lys Gly Val
    5900                5905                5910

Ser Trp Gln Ser Pro Pro Ser Val Glu Glu Thr Ser Ser Pro Ser
    5915                5920                5925

Ser Pro Val Pro Leu Pro Ala Ile Thr Ser His Ser Ser Leu Tyr
```

-continued

```
              5930            5935            5940
Ser Ala Val Ser Gly Ser Ser Pro Thr Ser Ala Leu Pro Val Thr
              5945            5950            5955
Ser Leu Leu Thr Ser Gly Arg Arg Lys Thr Ile Asp Met Leu Asp
              5960            5965            5970
Thr His Ser Glu Leu Val Thr Ser Ser Leu Pro Ser Ala Ser Ser
              5975            5980            5985
Phe Ser Gly Glu Ile Leu Thr Ser Glu Ala Ser Thr Asn Thr Glu
              5990            5995            6000
Thr Ile His Phe Ser Glu Asn Thr Ala Glu Thr Asn Met Gly Thr
              6005            6010            6015
Thr Asn Ser Met His Lys Leu His Ser Ser Val Ser Ile His Ser
              6020            6025            6030
Gln Pro Ser Gly His Thr Pro Pro Lys Val Thr Gly Ser Met Met
              6035            6040            6045
Glu Asp Ala Ile Val Ser Thr Ser Thr Pro Gly Ser Pro Glu Thr
              6050            6055            6060
Lys Asn Val Asp Arg Asp Ser Thr Ser Pro Leu Thr Pro Glu Leu
              6065            6070            6075
Lys Glu Asp Ser Thr Ala Leu Val Met Asn Ser Thr Thr Glu Ser
              6080            6085            6090
Asn Thr Val Phe Ser Ser Val Ser Leu Asp Ala Ala Thr Glu Val
              6095            6100            6105
Ser Arg Ala Glu Val Thr Tyr Tyr Asp Pro Thr Phe Met Pro Ala
              6110            6115            6120
Ser Ala Gln Ser Thr Lys Ser Pro Asp Ile Ser Pro Glu Ala Ser
              6125            6130            6135
Ser Ser His Ser Asn Ser Pro Pro Leu Thr Ile Ser Thr His Lys
              6140            6145            6150
Thr Ile Ala Thr Gln Thr Gly Pro Ser Gly Val Thr Ser Leu Gly
              6155            6160            6165
Gln Leu Thr Leu Asp Thr Ser Thr Ile Ala Thr Ser Ala Gly Thr
              6170            6175            6180
Pro Ser Ala Arg Thr Gln Asp Phe Val Asp Ser Glu Thr Thr Ser
              6185            6190            6195
Val Met Asn Asn Asp Leu Asn Asp Val Leu Lys Thr Ser Pro Phe
              6200            6205            6210
Ser Ala Glu Glu Ala Asn Ser Leu Ser Ser Gln Ala Pro Leu Leu
              6215            6220            6225
Val Thr Thr Ser Pro Ser Pro Val Thr Ser Thr Leu Gln Glu His
              6230            6235            6240
Ser Thr Ser Ser Leu Val Ser Val Thr Ser Val Pro Thr Pro Thr
              6245            6250            6255
Leu Ala Lys Ile Thr Asp Met Asp Thr Asn Leu Glu Pro Val Thr
              6260            6265            6270
Arg Ser Pro Gln Asn Leu Arg Asn Thr Leu Ala Thr Ser Glu Ala
              6275            6280            6285
Thr Thr Asp Thr His Thr Met His Pro Ser Ile Asn Thr Ala Val
              6290            6295            6300
Ala Asn Val Gly Thr Thr Ser Ser Pro Asn Glu Phe Tyr Phe Thr
              6305            6310            6315
Val Ser Pro Asp Ser Asp Pro Tyr Lys Ala Thr Ser Ala Val Val
              6320            6325            6330
```

-continued

Ile Thr Ser Thr Ser Gly Asp Ser Ile Val Ser Thr Ser Met Pro
6335                6340                6345

Arg Ser Ser Ala Met Lys Lys Ile Glu Ser Glu Thr Thr Phe Ser
6350                6355                6360

Leu Ile Phe Arg Leu Arg Glu Thr Ser Thr Ser Gln Lys Ile Gly
6365                6370                6375

Ser Ser Ser Asp Thr Ser Thr Val Phe Asp Lys Ala Phe Thr Ala
6380                6385                6390

Ala Thr Thr Glu Val Ser Arg Thr Glu Leu Thr Ser Ser Ser Arg
6395                6400                6405

Thr Ser Ile Gln Gly Thr Glu Lys Pro Thr Met Ser Pro Asp Thr
6410                6415                6420

Ser Thr Arg Ser Val Thr Met Leu Ser Thr Phe Ala Gly Leu Thr
6425                6430                6435

Lys Ser Glu Glu Arg Thr Ile Ala Thr Gln Thr Gly Pro His Arg
6440                6445                6450

Ala Thr Ser Gln Gly Thr Leu Thr Trp Asp Thr Ser Ile Thr Thr
6455                6460                6465

Ser Gln Ala Gly Thr His Ser Ala Met Thr His Gly Phe Ser Gln
6470                6475                6480

Leu Asp Leu Ser Thr Leu Thr Ser Arg Val Pro Glu Tyr Ile Ser
6485                6490                6495

Gly Thr Ser Pro Pro Ser Val Glu Lys Thr Ser Ser Ser Ser Ser
6500                6505                6510

Leu Leu Ser Leu Pro Ala Ile Thr Ser Pro Ser Pro Val Pro Thr
6515                6520                6525

Thr Leu Pro Glu Ser Arg Pro Ser Ser Pro Val His Leu Thr Ser
6530                6535                6540

Leu Pro Thr Ser Gly Leu Val Lys Thr Thr Asp Met Leu Ala Ser
6545                6550                6555

Val Ala Ser Leu Pro Pro Asn Leu Gly Ser Thr Ser His Lys Ile
6560                6565                6570

Pro Thr Thr Ser Glu Asp Ile Lys Asp Thr Glu Lys Met Tyr Pro
6575                6580                6585

Ser Thr Asn Ile Ala Val Thr Asn Val Gly Thr Thr Thr Ser Glu
6590                6595                6600

Lys Glu Ser Tyr Ser Ser Val Pro Ala Tyr Ser Glu Pro Pro Lys
6605                6610                6615

Val Thr Ser Pro Met Val Thr Ser Phe Asn Ile Arg Asp Thr Ile
6620                6625                6630

Val Ser Thr Ser Met Pro Gly Ser Ser Glu Ile Thr Arg Ile Glu
6635                6640                6645

Met Glu Ser Thr Phe Ser Leu Ala His Gly Leu Lys Gly Thr Ser
6650                6655                6660

Thr Ser Gln Asp Pro Ile Val Ser Thr Glu Lys Ser Ala Val Leu
6665                6670                6675

His Lys Leu Thr Thr Gly Ala Thr Glu Thr Ser Arg Thr Glu Val
6680                6685                6690

Ala Ser Ser Arg Arg Thr Ser Ile Pro Gly Pro Asp His Ser Thr
6695                6700                6705

Glu Ser Pro Asp Ile Ser Thr Glu Val Ile Pro Ser Leu Pro Ile
6710                6715                6720

```
Ser Leu Gly Ile Thr Glu Ser  Ser Asn Met Thr Ile  Ile Thr Arg
    6725            6730              6735

Thr Gly Pro Pro Leu Gly Ser  Thr Ser Gln Gly Thr  Phe Thr Leu
    6740            6745              6750

Asp Thr Pro Thr Thr Ser Ser  Arg Ala Gly Thr His  Ser Met Ala
    6755            6760              6765

Thr Gln Glu Phe Pro His Ser  Glu Met Thr Thr Val  Met Asn Lys
    6770            6775              6780

Asp Pro Glu Ile Leu Ser Trp  Thr Ile Pro Pro Ser  Ile Glu Lys
    6785            6790              6795

Thr Ser Phe Ser Ser Ser Leu  Met Pro Ser Pro Ala  Met Thr Ser
    6800            6805              6810

Pro Pro Val Ser Ser Thr Leu  Pro Lys Thr Ile His  Thr Thr Pro
    6815            6820              6825

Ser Pro Met Thr Ser Leu Leu  Thr Pro Ser Leu Val  Met Thr Thr
    6830            6835              6840

Asp Thr Leu Gly Thr Ser Pro  Glu Pro Thr Thr Ser  Ser Pro Pro
    6845            6850              6855

Asn Leu Ser Ser Thr Ser His  Glu Ile Leu Thr Thr  Asp Glu Asp
    6860            6865              6870

Thr Thr Ala Ile Glu Ala Met  His Pro Ser Thr Ser  Thr Ala Ala
    6875            6880              6885

Thr Asn Val Glu Thr Thr Ser  Ser Gly His Gly Ser  Gln Ser Ser
    6890            6895              6900

Val Leu Ala Asp Ser Glu Lys  Thr Lys Ala Thr Ala  Pro Met Asp
    6905            6910              6915

Thr Thr Ser Thr Met Gly His  Thr Thr Val Ser Thr  Ser Met Ser
    6920            6925              6930

Val Ser Ser Glu Thr Thr Lys  Ile Lys Arg Glu Ser  Thr Tyr Ser
    6935            6940              6945

Leu Thr Pro Gly Leu Arg Glu  Thr Ser Ile Ser Gln  Asn Ala Ser
    6950            6955              6960

Phe Ser Thr Asp Thr Ser Ile  Val Leu Ser Glu Val  Pro Thr Gly
    6965            6970              6975

Thr Thr Ala Glu Val Ser Arg  Thr Glu Val Thr Ser  Ser Gly Arg
    6980            6985              6990

Thr Ser Ile Pro Gly Pro Ser  Gln Ser Thr Val Leu  Pro Glu Ile
    6995            7000              7005

Ser Thr Arg Thr Met Thr Arg  Leu Phe Ala Ser Pro  Thr Met Thr
    7010            7015              7020

Glu Ser Ala Glu Met Thr Ile  Pro Thr Gln Thr Gly  Pro Ser Gly
    7025            7030              7035

Ser Thr Ser Gln Asp Thr Leu  Thr Leu Asp Thr Ser  Thr Thr Lys
    7040            7045              7050

Ser Gln Ala Lys Thr His Ser  Thr Leu Thr Gln Arg  Phe Pro His
    7055            7060              7065

Ser Glu Met Thr Thr Leu Met  Ser Arg Gly Pro Gly  Asp Met Ser
    7070            7075              7080

Trp Gln Ser Ser Pro Ser Leu  Glu Asn Pro Ser Ser  Leu Pro Ser
    7085            7090              7095

Leu Leu Ser Leu Pro Ala Thr  Thr Ser Pro Pro Pro  Ile Ser Ser
    7100            7105              7110

Thr Leu Pro Val Thr Ile Ser  Ser Ser Pro Leu Pro  Val Thr Ser
```

-continued

```
              7115                7120                7125
Leu Leu Thr Ser Ser Pro Val Thr Thr Thr Asp Met Leu His Thr
              7130                7135                7140

Ser Pro Glu Leu Val Thr Ser Ser Pro Pro Lys Leu Ser His Thr
              7145                7150                7155

Ser Asp Glu Arg Leu Thr Thr Gly Lys Asp Thr Thr Asn Thr Glu
              7160                7165                7170

Ala Val His Pro Ser Thr Asn Thr Ala Ala Ser Asn Val Glu Ile
              7175                7180                7185

Pro Ser Ser Gly His Glu Ser Pro Ser Ser Ala Leu Ala Asp Ser
              7190                7195                7200

Glu Thr Ser Lys Ala Thr Ser Pro Met Phe Ile Thr Ser Thr Gln
              7205                7210                7215

Glu Asp Thr Thr Val Ala Ile Ser Thr Pro His Phe Leu Glu Thr
              7220                7225                7230

Ser Arg Ile Gln Lys Glu Ser Ile Ser Ser Leu Ser Pro Lys Leu
              7235                7240                7245

Arg Glu Thr Gly Ser Ser Val Glu Thr Ser Ser Ala Ile Glu Thr
              7250                7255                7260

Ser Ala Val Leu Ser Glu Val Ser Ile Gly Ala Thr Thr Glu Ile
              7265                7270                7275

Ser Arg Thr Glu Val Thr Ser Ser Ser Arg Thr Ser Ile Ser Gly
              7280                7285                7290

Ser Ala Glu Ser Thr Met Leu Pro Glu Ile Ser Thr Thr Arg Lys
              7295                7300                7305

Ile Ile Lys Phe Pro Thr Ser Pro Ile Leu Ala Glu Ser Ser Glu
              7310                7315                7320

Met Thr Ile Lys Thr Gln Thr Ser Pro Pro Gly Ser Thr Ser Glu
              7325                7330                7335

Ser Thr Phe Thr Leu Asp Thr Ser Thr Thr Pro Ser Leu Val Ile
              7340                7345                7350

Thr His Ser Thr Met Thr Gln Arg Leu Pro His Ser Glu Ile Thr
              7355                7360                7365

Thr Leu Val Ser Arg Gly Ala Gly Asp Val Pro Arg Pro Ser Ser
              7370                7375                7380

Leu Pro Val Glu Glu Thr Ser Pro Pro Ser Ser Gln Leu Ser Leu
              7385                7390                7395

Ser Ala Met Ile Ser Pro Pro Val Ser Ser Thr Leu Pro Ala
              7400                7405                7410

Ser Ser His Ser Ser Ser Ala Ser Val Thr Ser Leu Leu Thr Pro
              7415                7420                7425

Gly Gln Val Lys Thr Thr Glu Val Leu Asp Ala Ser Ala Glu Pro
              7430                7435                7440

Glu Thr Ser Ser Pro Pro Ser Leu Ser Ser Thr Ser Val Glu Ile
              7445                7450                7455

Leu Ala Thr Ser Glu Val Thr Thr Asp Thr Glu Lys Ile His Pro
              7460                7465                7470

Phe Ser Asn Thr Ala Val Thr Lys Val Gly Thr Ser Ser Ser Gly
              7475                7480                7485

His Glu Ser Pro Ser Ser Val Leu Pro Asp Ser Glu Thr Thr Lys
              7490                7495                7500

Ala Thr Ser Ala Met Gly Thr Ile Ser Ile Met Gly Asp Thr Ser
              7505                7510                7515
```

-continued

```
Val Ser Thr Leu Thr Pro Ala Leu Ser Asn Thr Arg Lys Ile Gln
7520                7525                7530

Ser Glu Pro Ala Ser Ser Leu Thr Thr Arg Leu Arg Glu Thr Ser
7535                7540                7545

Thr Ser Glu Glu Thr Ser Leu Ala Thr Glu Ala Asn Thr Val Leu
7550                7555                7560

Ser Lys Val Ser Thr Gly Ala Thr Thr Glu Val Ser Arg Thr Glu
7565                7570                7575

Ala Ile Ser Phe Ser Arg Thr Ser Met Ser Gly Pro Glu Gln Ser
7580                7585                7590

Thr Met Ser Gln Asp Ile Ser Ile Gly Thr Ile Pro Arg Ile Ser
7595                7600                7605

Ala Ser Ser Val Leu Thr Glu Ser Ala Lys Met Thr Ile Thr Thr
7610                7615                7620

Gln Thr Gly Pro Ser Glu Ser Thr Leu Glu Ser Thr Leu Asn Leu
7625                7630                7635

Asn Thr Ala Thr Thr Pro Ser Trp Val Glu Thr His Ser Ile Val
7640                7645                7650

Ile Gln Gly Phe Pro His Pro Glu Met Thr Thr Ser Met Gly Arg
7655                7660                7665

Gly Pro Gly Gly Val Ser Trp Pro Ser Pro Pro Phe Val Lys Glu
7670                7675                7680

Thr Ser Pro Pro Ser Ser Pro Leu Ser Leu Pro Ala Val Thr Ser
7685                7690                7695

Pro His Pro Val Ser Thr Thr Phe Leu Ala His Ile Pro Pro Ser
7700                7705                7710

Pro Leu Pro Val Thr Ser Leu Leu Thr Ser Gly Pro Ala Thr Thr
7715                7720                7725

Thr Asp Ile Leu Gly Thr Ser Thr Glu Pro Gly Thr Ser Ser Ser
7730                7735                7740

Ser Ser Leu Ser Thr Thr Ser His Glu Arg Leu Thr Thr Tyr Lys
7745                7750                7755

Asp Thr Ala His Thr Glu Ala Val His Pro Ser Thr Asn Thr Gly
7760                7765                7770

Gly Thr Asn Val Ala Thr Ser Ser Gly Tyr Lys Ser Gln Ser
7775                7780                7785

Ser Val Leu Ala Asp Ser Ser Pro Met Cys Thr Thr Ser Thr Met
7790                7795                7800

Gly Asp Thr Ser Val Leu Thr Ser Thr Pro Ala Phe Leu Glu Thr
7805                7810                7815

Arg Arg Ile Gln Thr Glu Leu Ala Ser Ser Leu Thr Pro Gly Leu
7820                7825                7830

Arg Glu Ser Ser Gly Ser Glu Gly Thr Ser Ser Gly Thr Lys Met
7835                7840                7845

Ser Thr Val Leu Ser Lys Val Pro Thr Gly Ala Thr Thr Glu Ile
7850                7855                7860

Ser Lys Glu Asp Val Thr Ser Ile Pro Gly Pro Ala Gln Ser Thr
7865                7870                7875

Ile Ser Pro Asp Ile Ser Thr Arg Thr Val Ser Trp Phe Ser Thr
7880                7885                7890

Ser Pro Val Met Thr Glu Ser Ala Glu Ile Thr Met Asn Thr His
7895                7900                7905
```

```
Thr Ser Pro Leu Gly Ala Thr  Thr Gln Gly Thr Ser  Thr Leu Asp
    7910                7915                7920

Thr Ser Ser Thr Thr Ser Leu  Thr Met Thr His Ser  Thr Ile Ser
    7925                7930                7935

Gln Gly Phe Ser His Ser Gln  Met Ser Thr Leu Met  Arg Arg Gly
    7940                7945                7950

Pro Glu Asp Val Ser Trp Met  Ser Pro Pro Leu Leu  Glu Lys Thr
    7955                7960                7965

Arg Pro Ser Phe Ser Leu Met  Ser Ser Pro Ala Thr  Thr Ser Pro
    7970                7975                7980

Ser Pro Val Ser Ser Thr Leu  Pro Glu Ser Ile Ser  Ser Ser Pro
    7985                7990                7995

Leu Pro Val Thr Ser Leu Leu  Thr Ser Gly Leu Ala  Lys Thr Thr
    8000                8005                8010

Asp Met Leu His Lys Ser Ser  Glu Pro Val Thr Asn  Ser Pro Ala
    8015                8020                8025

Asn Leu Ser Ser Thr Ser Val  Glu Ile Leu Ala Thr  Ser Glu Val
    8030                8035                8040

Thr Thr Asp Thr Glu Lys Thr  His Pro Ser Ser Asn  Arg Thr Val
    8045                8050                8055

Thr Asp Val Gly Thr Ser Ser  Ser Gly His Glu Ser  Thr Ser Phe
    8060                8065                8070

Val Leu Ala Asp Ser Gln Thr  Ser Lys Val Thr Ser  Pro Met Val
    8075                8080                8085

Ile Thr Ser Thr Met Glu Asp  Thr Ser Val Ser Thr  Ser Thr Pro
    8090                8095                8100

Gly Phe Phe Glu Thr Ser Arg  Ile Gln Thr Glu Pro  Thr Ser Ser
    8105                8110                8115

Leu Thr Leu Gly Leu Arg Lys  Thr Ser Ser Ser Glu  Gly Thr Ser
    8120                8125                8130

Leu Ala Thr Glu Met Ser Thr  Val Leu Ser Gly Val  Pro Thr Gly
    8135                8140                8145

Ala Thr Ala Glu Val Ser Arg  Thr Glu Val Thr Ser  Ser Ser Arg
    8150                8155                8160

Thr Ser Ile Ser Gly Phe Ala  Gln Leu Thr Val Ser  Pro Glu Thr
    8165                8170                8175

Ser Thr Glu Thr Ile Thr Arg  Leu Pro Thr Ser Ser  Ile Met Thr
    8180                8185                8190

Glu Ser Ala Glu Met Met Ile  Lys Thr Gln Thr Asp  Pro Pro Gly
    8195                8200                8205

Ser Thr Pro Glu Ser Thr His  Thr Val Asp Ile Ser  Thr Thr Pro
    8210                8215                8220

Asn Trp Val Glu Thr His Ser  Thr Val Thr Gln Arg  Phe Ser His
    8225                8230                8235

Ser Glu Met Thr Thr Leu Val  Ser Arg Ser Pro Gly  Asp Met Leu
    8240                8245                8250

Trp Pro Ser Gln Ser Ser Val  Glu Glu Thr Ser Ser  Ala Ser Ser
    8255                8260                8265

Leu Leu Ser Leu Pro Ala Thr  Thr Ser Pro Ser Pro  Val Ser Ser
    8270                8275                8280

Thr Leu Val Glu Asp Phe Pro  Ser Ala Ser Leu Pro  Val Thr Ser
    8285                8290                8295

Leu Leu Asn Pro Gly Leu Val  Ile Thr Thr Asp Arg  Met Gly Ile
```

-continued

|  | 8300 |  |  | 8305 |  |  | 8310 |  |  |  |
| Ser | Arg | Glu | Pro | Gly | Thr | Ser | Ser | Thr | Ser | Asn | Leu | Ser | Ser | Thr |
|  | 8315 |  |  |  | 8320 |  |  |  | 8325 |  |
| Ser | His | Glu | Arg | Leu | Thr | Thr | Leu | Glu | Asp | Thr | Val | Asp | Thr | Glu |
|  | 8330 |  |  |  | 8335 |  |  |  | 8340 |  |
| Asp | Met | Gln | Pro | Ser | Thr | His | Thr | Ala | Val | Thr | Asn | Val | Arg | Thr |
|  | 8345 |  |  |  | 8350 |  |  |  | 8355 |  |
| Ser | Ile | Ser | Gly | His | Glu | Ser | Gln | Ser | Val | Leu | Ser | Asp | Ser |
|  | 8360 |  |  |  | 8365 |  |  |  | 8370 |  |
| Glu | Thr | Pro | Lys | Ala | Thr | Ser | Pro | Met | Gly | Thr | Thr | Tyr | Thr | Met |
|  | 8375 |  |  |  | 8380 |  |  |  | 8385 |  |
| Gly | Glu | Thr | Ser | Val | Ser | Ile | Ser | Thr | Ser | Asp | Phe | Phe | Glu | Thr |
|  | 8390 |  |  |  | 8395 |  |  |  | 8400 |  |
| Ser | Arg | Ile | Gln | Ile | Glu | Pro | Thr | Ser | Ser | Leu | Thr | Ser | Gly | Leu |
|  | 8405 |  |  |  | 8410 |  |  |  | 8415 |  |
| Arg | Glu | Thr | Ser | Ser | Ser | Glu | Arg | Ile | Ser | Ser | Ala | Thr | Glu | Gly |
|  | 8420 |  |  |  | 8425 |  |  |  | 8430 |  |
| Ser | Thr | Val | Leu | Ser | Glu | Val | Pro | Ser | Gly | Ala | Thr | Thr | Glu | Val |
|  | 8435 |  |  |  | 8440 |  |  |  | 8445 |  |
| Ser | Arg | Thr | Glu | Val | Ile | Ser | Ser | Arg | Gly | Thr | Ser | Met | Ser | Gly |
|  | 8450 |  |  |  | 8455 |  |  |  | 8460 |  |
| Pro | Asp | Gln | Phe | Thr | Ile | Ser | Pro | Asp | Ile | Ser | Thr | Glu | Ala | Ile |
|  | 8465 |  |  |  | 8470 |  |  |  | 8475 |  |
| Thr | Arg | Leu | Ser | Thr | Ser | Pro | Ile | Met | Thr | Glu | Ser | Ala | Glu | Ser |
|  | 8480 |  |  |  | 8485 |  |  |  | 8490 |  |
| Ala | Ile | Thr | Ile | Glu | Thr | Gly | Ser | Pro | Gly | Ala | Thr | Ser | Glu | Gly |
|  | 8495 |  |  |  | 8500 |  |  |  | 8505 |  |
| Thr | Leu | Thr | Leu | Asp | Thr | Ser | Thr | Thr | Thr | Phe | Trp | Ser | Gly | Thr |
|  | 8510 |  |  |  | 8515 |  |  |  | 8520 |  |
| His | Ser | Thr | Ala | Ser | Pro | Gly | Phe | Ser | His | Ser | Glu | Met | Thr | Thr |
|  | 8525 |  |  |  | 8530 |  |  |  | 8535 |  |
| Leu | Met | Ser | Arg | Thr | Pro | Gly | Asp | Val | Pro | Trp | Pro | Ser | Leu | Pro |
|  | 8540 |  |  |  | 8545 |  |  |  | 8550 |  |
| Ser | Val | Glu | Glu | Ala | Ser | Ser | Val | Ser | Ser | Leu | Ser | Ser | Pro |
|  | 8555 |  |  |  | 8560 |  |  |  | 8565 |  |
| Ala | Met | Thr | Ser | Thr | Ser | Phe | Phe | Ser | Thr | Leu | Pro | Glu | Ser | Ile |
|  | 8570 |  |  |  | 8575 |  |  |  | 8580 |  |
| Ser | Ser | Ser | Pro | His | Pro | Val | Thr | Ala | Leu | Leu | Thr | Leu | Gly | Pro |
|  | 8585 |  |  |  | 8590 |  |  |  | 8595 |  |
| Val | Lys | Thr | Thr | Asp | Met | Leu | Arg | Thr | Ser | Ser | Glu | Pro | Glu | Thr |
|  | 8600 |  |  |  | 8605 |  |  |  | 8610 |  |
| Ser | Ser | Pro | Pro | Asn | Leu | Ser | Ser | Thr | Ser | Ala | Glu | Ile | Leu | Ala |
|  | 8615 |  |  |  | 8620 |  |  |  | 8625 |  |
| Thr | Ser | Glu | Val | Thr | Lys | Asp | Arg | Glu | Lys | Ile | His | Pro | Ser | Ser |
|  | 8630 |  |  |  | 8635 |  |  |  | 8640 |  |
| Asn | Thr | Pro | Val | Val | Asn | Val | Gly | Thr | Val | Ile | Tyr | Lys | His | Leu |
|  | 8645 |  |  |  | 8650 |  |  |  | 8655 |  |
| Ser | Pro | Ser | Ser | Val | Leu | Ala | Asp | Leu | Val | Thr | Thr | Lys | Pro | Thr |
|  | 8660 |  |  |  | 8665 |  |  |  | 8670 |  |
| Ser | Pro | Met | Ala | Thr | Thr | Ser | Thr | Leu | Gly | Asn | Thr | Ser | Val | Ser |
|  | 8675 |  |  |  | 8680 |  |  |  | 8685 |  |
| Thr | Ser | Thr | Pro | Ala | Phe | Pro | Glu | Thr | Met | Met | Thr | Gln | Pro | Thr |
|  | 8690 |  |  |  | 8695 |  |  |  | 8700 |  |

-continued

```
Ser Ser Leu Thr Ser Gly Leu Arg Glu Ile Ser Thr Ser Gln Glu
    8705            8710                8715

Thr Ser Ser Ala Thr Glu Arg Ser Ala Ser Leu Ser Gly Met Pro
    8720            8725                8730

Thr Gly Ala Thr Thr Lys Val Ser Arg Thr Glu Ala Leu Ser Leu
    8735            8740                8745

Gly Arg Thr Ser Thr Pro Gly Pro Ala Gln Ser Thr Ile Ser Pro
    8750            8755                8760

Glu Ile Ser Thr Glu Thr Ile Thr Arg Ile Ser Thr Pro Leu Thr
    8765            8770                8775

Thr Thr Gly Ser Ala Glu Met Thr Ile Thr Pro Lys Thr Gly His
    8780            8785                8790

Ser Gly Ala Ser Ser Gln Gly Thr Phe Thr Leu Asp Thr Ser Ser
    8795            8800                8805

Arg Ala Ser Trp Pro Gly Thr His Ser Ala Ala Thr His Arg Ser
    8810            8815                8820

Pro His Ser Gly Met Thr Thr Pro Met Ser Arg Gly Pro Glu Asp
    8825            8830                8835

Val Ser Trp Pro Ser Arg Pro Ser Val Glu Lys Thr Ser Pro Pro
    8840            8845                8850

Ser Ser Leu Val Ser Leu Ser Ala Val Thr Ser Pro Ser Pro Leu
    8855            8860                8865

Tyr Ser Thr Pro Ser Glu Ser Ser His Ser Ser Pro Leu Arg Val
    8870            8875                8880

Thr Ser Leu Phe Thr Pro Val Met Met Lys Thr Thr Asp Met Leu
    8885            8890                8895

Asp Thr Ser Leu Glu Pro Val Thr Thr Ser Pro Pro Ser Met Asn
    8900            8905                8910

Ile Thr Ser Asp Glu Ser Leu Ala Thr Ser Lys Ala Thr Met Glu
    8915            8920                8925

Thr Glu Ala Ile Gln Leu Ser Glu Asn Thr Ala Val Thr Gln Met
    8930            8935                8940

Gly Thr Ile Ser Ala Arg Gln Glu Phe Tyr Ser Ser Tyr Pro Gly
    8945            8950                8955

Leu Pro Glu Pro Ser Lys Val Thr Ser Pro Val Val Thr Ser Ser
    8960            8965                8970

Thr Ile Lys Asp Ile Val Ser Thr Thr Ile Pro Ala Ser Ser Glu
    8975            8980                8985

Ile Thr Arg Ile Glu Met Glu Ser Thr Ser Thr Leu Thr Pro Thr
    8990            8995                9000

Pro Arg Glu Thr Ser Thr Ser Gln Glu Ile His Ser Ala Thr Lys
    9005            9010                9015

Pro Ser Thr Val Pro Tyr Lys Ala Leu Thr Ser Ala Thr Ile Glu
    9020            9025                9030

Asp Ser Met Thr Gln Val Met Ser Ser Ser Arg Gly Pro Ser Pro
    9035            9040                9045

Asp Gln Ser Thr Met Ser Gln Asp Ile Ser Thr Glu Val Ile Thr
    9050            9055                9060

Arg Leu Ser Thr Ser Pro Ile Lys Thr Glu Ser Thr Glu Met Thr
    9065            9070                9075

Ile Thr Thr Gln Thr Gly Ser Pro Gly Ala Thr Ser Arg Gly Thr
    9080            9085                9090
```

-continued

```
Leu Thr Leu Asp Thr Ser Thr Thr Phe Met Ser Gly Thr His Ser
    9095            9100                9105
Thr Ala Ser Gln Gly Phe Ser His Ser Gln Met Thr Ala Leu Met
    9110            9115                9120
Ser Arg Thr Pro Gly Asp Val Pro Trp Leu Ser His Pro Ser Val
    9125            9130                9135
Glu Glu Ala Ser Ser Ala Ser Phe Ser Leu Ser Ser Pro Val Met
    9140            9145                9150
Thr Ser Ser Ser Pro Val Ser Ser Thr Leu Pro Asp Ser Ile His
    9155            9160                9165
Ser Ser Ser Leu Pro Val Thr Ser Leu Leu Thr Ser Gly Leu Val
    9170            9175                9180
Lys Thr Thr Glu Leu Leu Gly Thr Ser Ser Glu Pro Glu Thr Ser
    9185            9190                9195
Ser Pro Pro Asn Leu Ser Ser Thr Ser Ala Glu Ile Leu Ala Ile
    9200            9205                9210
Thr Glu Val Thr Thr Asp Thr Glu Lys Leu Glu Met Thr Asn Val
    9215            9220                9225
Val Thr Ser Gly Tyr Thr His Glu Ser Pro Ser Ser Val Leu Ala
    9230            9235                9240
Asp Ser Val Thr Thr Lys Ala Thr Ser Ser Met Gly Ile Thr Tyr
    9245            9250                9255
Pro Thr Gly Asp Thr Asn Val Leu Thr Ser Thr Pro Ala Phe Ser
    9260            9265                9270
Asp Thr Ser Arg Ile Gln Thr Lys Ser Lys Leu Ser Leu Thr Pro
    9275            9280                9285
Gly Leu Met Glu Thr Ser Ile Ser Glu Glu Thr Ser Ser Ala Thr
    9290            9295                9300
Glu Lys Ser Thr Val Leu Ser Ser Val Pro Thr Gly Ala Thr Thr
    9305            9310                9315
Glu Val Ser Arg Thr Glu Ala Ile Ser Ser Ser Arg Thr Ser Ile
    9320            9325                9330
Pro Gly Pro Ala Gln Ser Thr Met Ser Ser Asp Thr Ser Met Glu
    9335            9340                9345
Thr Ile Thr Arg Ile Ser Thr Pro Leu Thr Arg Lys Glu Ser Thr
    9350            9355                9360
Asp Met Ala Ile Thr Pro Lys Thr Gly Pro Ser Gly Ala Thr Ser
    9365            9370                9375
Gln Gly Thr Phe Thr Leu Asp Ser Ser Ser Thr Ala Ser Trp Pro
    9380            9385                9390
Gly Thr His Ser Ala Thr Thr Gln Arg Phe Pro Gln Ser Val Val
    9395            9400                9405
Thr Thr Pro Met Ser Arg Gly Pro Glu Asp Val Ser Trp Pro Ser
    9410            9415                9420
Pro Leu Ser Val Glu Lys Asn Ser Pro Pro Ser Ser Leu Val Ser
    9425            9430                9435
Ser Ser Ser Val Thr Ser Pro Ser Pro Leu Tyr Ser Thr Pro Ser
    9440            9445                9450
Gly Ser Ser His Ser Ser Pro Val Pro Val Thr Ser Leu Phe Thr
    9455            9460                9465
Ser Ile Met Met Lys Ala Thr Asp Met Leu Asp Ala Ser Leu Glu
    9470            9475                9480
Pro Glu Thr Thr Ser Ala Pro Asn Met Asn Ile Thr Ser Asp Glu
```

-continued

```
                9485                9490                9495

Ser Leu Ala Ala Ser Lys Ala Thr Thr Glu Thr Glu Ala Ile His
    9500                9505                9510

Val Phe Glu Asn Thr Ala Ala Ser His Val Glu Thr Thr Ser Ala
    9515                9520                9525

Thr Glu Glu Leu Tyr Ser Ser Ser Pro Gly Phe Ser Glu Pro Thr
    9530                9535                9540

Lys Val Ile Ser Pro Val Val Thr Ser Ser Ser Ile Arg Asp Asn
    9545                9550                9555

Met Val Ser Thr Thr Met Pro Gly Ser Ser Gly Ile Thr Arg Ile
    9560                9565                9570

Glu Ile Glu Ser Met Ser Ser Leu Thr Pro Gly Leu Arg Glu Thr
    9575                9580                9585

Arg Thr Ser Gln Asp Ile Thr Ser Ser Thr Glu Thr Ser Thr Val
    9590                9595                9600

Leu Tyr Lys Met Pro Ser Gly Ala Thr Pro Glu Val Ser Arg Thr
    9605                9610                9615

Glu Val Met Pro Ser Ser Arg Thr Ser Ile Pro Gly Pro Ala Gln
    9620                9625                9630

Ser Thr Met Ser Leu Asp Ile Ser Asp Glu Val Val Thr Arg Leu
    9635                9640                9645

Ser Thr Ser Pro Ile Met Thr Glu Ser Ala Glu Ile Thr Ile Thr
    9650                9655                9660

Thr Gln Thr Gly Tyr Ser Leu Ala Thr Ser Gln Val Thr Leu Pro
    9665                9670                9675

Leu Gly Thr Ser Met Thr Phe Leu Ser Gly Thr His Ser Thr Met
    9680                9685                9690

Ser Gln Gly Leu Ser His Ser Glu Met Thr Asn Leu Met Ser Arg
    9695                9700                9705

Gly Pro Glu Ser Leu Ser Trp Thr Ser Pro Arg Phe Val Glu Thr
    9710                9715                9720

Thr Arg Ser Ser Ser Ser Leu Thr Ser Leu Pro Leu Thr Thr Ser
    9725                9730                9735

Leu Ser Pro Val Ser Ser Thr Leu Leu Asp Ser Ser Pro Ser Ser
    9740                9745                9750

Pro Leu Pro Val Thr Ser Leu Ile Leu Pro Gly Leu Val Lys Thr
    9755                9760                9765

Thr Glu Val Leu Asp Thr Ser Ser Glu Pro Lys Thr Ser Ser Ser
    9770                9775                9780

Pro Asn Leu Ser Ser Thr Ser Val Glu Ile Pro Ala Thr Ser Glu
    9785                9790                9795

Ile Met Thr Asp Thr Glu Lys Ile His Pro Ser Ser Asn Thr Ala
    9800                9805                9810

Val Ala Lys Val Arg Thr Ser Ser Ser Val His Glu Ser His Ser
    9815                9820                9825

Ser Val Leu Ala Asp Ser Glu Thr Thr Ile Thr Ile Pro Ser Met
    9830                9835                9840

Gly Ile Thr Ser Ala Val Asp Asp Thr Thr Val Phe Thr Ser Asn
    9845                9850                9855

Pro Ala Phe Ser Glu Thr Arg Arg Ile Pro Thr Glu Pro Thr Phe
    9860                9865                9870

Ser Leu Thr Pro Gly Phe Arg Glu Thr Ser Thr Ser Glu Glu Thr
    9875                9880                9885
```

```
Thr  Ser  Ile  Thr  Glu  Thr  Ser  Ala  Val  Leu  Tyr  Gly  Val  Pro  Thr
     9890                9895                     9900

Ser  Ala  Thr  Thr  Glu  Val  Ser  Met  Thr  Glu  Ile  Met  Ser  Ser  Asn
     9905                9910                     9915

Arg  Ile  His  Ile  Pro  Asp  Ser  Asp  Gln  Ser  Thr  Met  Ser  Pro  Asp
     9920                9925                     9930

Ile  Ile  Thr  Glu  Val  Ile  Thr  Arg  Leu  Ser  Ser  Ser  Ser  Met  Met
     9935                9940                     9945

Ser  Glu  Ser  Thr  Gln  Met  Thr  Ile  Thr  Thr  Gln  Lys  Ser  Ser  Pro
     9950                9955                     9960

Gly  Ala  Thr  Ala  Gln  Ser  Thr  Leu  Thr  Leu  Ala  Thr  Thr  Thr  Ala
     9965                9970                     9975

Pro  Leu  Ala  Arg  Thr  His  Ser  Thr  Val  Pro  Pro  Arg  Phe  Leu  His
     9980                9985                     9990

Ser  Glu  Met  Thr  Thr  Leu  Met  Ser  Arg  Ser  Pro  Glu  Asn  Pro  Ser
     9995                10000                    10005

Trp  Lys  Ser  Ser  Leu  Phe  Val  Glu  Lys  Thr  Ser  Ser  Ser  Ser  Ser
     10010               10015                    10020

Leu  Leu  Ser  Leu  Pro  Val  Thr  Thr  Ser  Pro  Ser  Val  Ser  Ser  Thr
     10025               10030                    10035

Leu  Pro  Gln  Ser  Ile  Pro  Ser  Ser  Ser  Phe  Ser  Val  Thr  Ser  Leu
     10040               10045                    10050

Leu  Thr  Pro  Gly  Met  Val  Lys  Thr  Thr  Asp  Thr  Ser  Thr  Glu  Pro
     10055               10060                    10065

Gly  Thr  Ser  Leu  Ser  Pro  Asn  Leu  Ser  Gly  Thr  Ser  Val  Glu  Ile
     10070               10075                    10080

Leu  Ala  Ala  Ser  Glu  Val  Thr  Thr  Asp  Thr  Glu  Lys  Ile  His  Pro
     10085               10090                    10095

Ser  Ser  Ser  Met  Ala  Val  Thr  Asn  Val  Gly  Thr  Thr  Ser  Ser  Gly
     10100               10105                    10110

His  Glu  Leu  Tyr  Ser  Ser  Val  Ser  Ile  His  Ser  Glu  Pro  Ser  Lys
     10115               10120                    10125

Ala  Thr  Tyr  Pro  Val  Gly  Thr  Pro  Ser  Ser  Met  Ala  Glu  Thr  Ser
     10130               10135                    10140

Ile  Ser  Thr  Ser  Met  Pro  Ala  Asn  Phe  Glu  Thr  Thr  Gly  Phe  Glu
     10145               10150                    10155

Ala  Glu  Pro  Phe  Ser  His  Leu  Thr  Ser  Gly  Phe  Arg  Lys  Thr  Asn
     10160               10165                    10170

Met  Ser  Leu  Asp  Thr  Ser  Ser  Val  Thr  Pro  Thr  Asn  Thr  Pro  Ser
     10175               10180                    10185

Ser  Pro  Gly  Ser  Thr  His  Leu  Leu  Gln  Ser  Ser  Lys  Thr  Asp  Phe
     10190               10195                    10200

Thr  Ser  Ser  Ala  Lys  Thr  Ser  Ser  Pro  Asp  Trp  Pro  Pro  Ala  Ser
     10205               10210                    10215

Gln  Tyr  Thr  Glu  Ile  Pro  Val  Asp  Ile  Ile  Thr  Pro  Phe  Asn  Ala
     10220               10225                    10230

Ser  Pro  Ser  Ile  Thr  Glu  Ser  Thr  Gly  Ile  Thr  Ser  Phe  Pro  Glu
     10235               10240                    10245

Ser  Arg  Phe  Thr  Met  Ser  Val  Thr  Glu  Ser  Thr  His  His  Leu  Ser
     10250               10255                    10260

Thr  Asp  Leu  Leu  Pro  Ser  Ala  Glu  Thr  Ile  Ser  Thr  Gly  Thr  Val
     10265               10270                    10275
```

-continued

| | | | | | | | | | |
|---|---|---|---|---|---|---|---|---|---|
| Met Pro | Ser | Leu | Ser | Glu | Ala | Met | Thr Ser | Phe | Ala Thr Thr Gly |
| 10280 | | | | | 10285 | | | | 10290 |

Val Pro Arg Ala Ile Ser Gly Ser Gly Ser Pro Phe Ser Arg Thr
10295            10300            10305

Glu Ser Gly Pro Gly Asp Ala Thr Leu Ser Thr Ile Ala Glu Ser
10310            10315            10320

Leu Pro Ser Ser Thr Pro Val Pro Phe Ser Ser Ser Thr Phe Thr
10325            10330            10335

Thr Thr Asp Ser Ser Thr Ile Pro Ala Leu His Glu Ile Thr Ser
10340            10345            10350

Ser Ser Ala Thr Pro Tyr Arg Val Asp Thr Ser Leu Gly Thr Glu
10355            10360            10365

Ser Ser Thr Thr Glu Gly Arg Leu Val Met Val Ser Thr Leu Asp
10370            10375            10380

Thr Ser Ser Gln Pro Gly Arg Thr Ser Ser Ser Pro Ile Leu Asp
10385            10390            10395

Thr Arg Met Thr Glu Ser Val Glu Leu Gly Thr Val Thr Ser Ala
10400            10405            10410

Tyr Gln Val Pro Ser Leu Ser Thr Arg Leu Thr Arg Thr Asp Gly
10415            10420            10425

Ile Met Glu His Ile Thr Lys Ile Pro Asn Glu Ala Ala His Arg
10430            10435            10440

Gly Thr Ile Arg Pro Val Lys Gly Pro Gln Thr Ser Thr Ser Pro
10445            10450            10455

Ala Ser Pro Lys Gly Leu His Thr Gly Gly Thr Lys Arg Met Glu
10460            10465            10470

Thr Thr Thr Thr Ala Leu Lys Thr Thr Thr Thr Ala Leu Lys Thr
10475            10480            10485

Thr Ser Arg Ala Thr Leu Thr Thr Ser Val Tyr Thr Pro Thr Leu
10490            10495            10500

Gly Thr Leu Thr Pro Leu Asn Ala Ser Met Gln Met Ala Ser Thr
10505            10510            10515

Ile Pro Thr Glu Met Met Ile Thr Thr Pro Tyr Val Phe Pro Asp
10520            10525            10530

Val Pro Glu Thr Thr Ser Ser Leu Ala Thr Ser Leu Gly Ala Glu
10535            10540            10545

Thr Ser Thr Ala Leu Pro Arg Thr Thr Pro Ser Val Phe Asn Arg
10550            10555            10560

Glu Ser Glu Thr Thr Ala Ser Leu Val Ser Arg Ser Gly Ala Glu
10565            10570            10575

Arg Ser Pro Val Ile Gln Thr Leu Asp Val Ser Ser Ser Glu Pro
10580            10585            10590

Asp Thr Ala Ser Trp Val Ile His Pro Ala Glu Thr Ile Pro
10595            10600            10605

Thr Val Ser Lys Thr Thr Pro Asn Phe Phe His Ser Glu Leu Asp
10610            10615            10620

Thr Val Ser Ser Thr Ala Thr Ser His Gly Ala Asp Val Ser Ser
10625            10630            10635

Ala Ile Pro Thr Asn Ile Ser Pro Ser Glu Leu Asp Ala Leu Thr
10640            10645            10650

Pro Leu Val Thr Ile Ser Gly Thr Asp Thr Ser Thr Thr Phe Pro
10655            10660            10665

Thr Leu Thr Lys Ser Pro His Glu Thr Glu Thr Arg Thr Thr Trp

```
              10670               10675               10680

Leu Thr His Pro Ala Glu Thr     Ser Ser Thr Ile Pro     Arg Thr Ile
        10685               10690                   10695

Pro Asn Phe Ser His His Glu     Ser Asp Ala Thr Pro     Ser Ile Ala
        10700               10705                   10710

Thr Ser Pro Gly Ala Glu Thr     Ser Ser Ala Ile Pro     Ile Met Thr
        10715               10720                   10725

Val Ser Pro Gly Ala Glu Asp     Leu Val Thr Ser Gln     Val Thr Ser
        10730               10735                   10740

Ser Gly Thr Asp Arg Asn Met     Thr Ile Pro Thr Leu     Thr Leu Ser
        10745               10750                   10755

Pro Gly Glu Pro Lys Thr Ile     Ala Ser Leu Val Thr     His Pro Glu
        10760               10765                   10770

Ala Gln Thr Ser Ser Ala Ile     Pro Thr Ser Thr Ile     Ser Pro Ala
        10775               10780                   10785

Val Ser Arg Leu Val Thr Ser     Met Val Thr Ser Leu     Ala Ala Lys
        10790               10795                   10800

Thr Ser Thr Thr Asn Arg Ala     Leu Thr Asn Ser Pro     Gly Glu Pro
        10805               10810                   10815

Ala Thr Thr Val Ser Leu Val     Thr His Pro Ala Gln     Thr Ser Pro
        10820               10825                   10830

Thr Val Pro Trp Thr Thr Ser     Ile Phe Phe His Ser     Lys Ser Asp
        10835               10840                   10845

Thr Thr Pro Ser Met Thr Thr     Ser His Gly Ala Glu     Ser Ser Ser
        10850               10855                   10860

Ala Val Pro Thr Pro Thr Val     Ser Thr Glu Val Pro     Gly Val Val
        10865               10870                   10875

Thr Pro Leu Val Thr Ser Ser     Arg Ala Val Ile Ser     Thr Thr Ile
        10880               10885                   10890

Pro Ile Leu Thr Leu Ser Pro     Gly Glu Pro Glu Thr     Thr Pro Ser
        10895               10900                   10905

Met Ala Thr Ser His Gly Glu     Glu Ala Ser Ser Ala     Ile Pro Thr
        10910               10915                   10920

Pro Thr Val Ser Pro Gly Val     Pro Gly Val Val Thr     Ser Leu Val
        10925               10930                   10935

Thr Ser Ser Arg Ala Val Thr     Ser Thr Thr Ile Pro     Ile Leu Thr
        10940               10945                   10950

Phe Ser Leu Gly Glu Pro Glu     Thr Thr Pro Ser Met     Ala Thr Ser
        10955               10960                   10965

His Gly Thr Glu Ala Gly Ser     Ala Val Pro Thr Val     Leu Pro Glu
        10970               10975                   10980

Val Pro Gly Met Val Thr Ser     Leu Val Ala Ser Ser     Arg Ala Val
        10985               10990                   10995

Thr Ser Thr Thr Leu Pro Thr     Leu Thr Leu Ser Pro     Gly Glu Pro
        11000               11005                   11010

Glu Thr Thr Pro Ser Met Ala     Thr Ser His Gly Ala     Glu Ala Ser
        11015               11020                   11025

Ser Thr Val Pro Thr Val Ser     Pro Glu Val Pro Gly     Val Val Thr
        11030               11035                   11040

Ser Leu Val Thr Ser Ser Ser     Gly Val Asn Ser Thr     Ser Ile Pro
        11045               11050                   11055

Thr Leu Ile Leu Ser Pro Gly     Glu Leu Glu Thr Thr     Pro Ser Met
        11060               11065                   11070
```

```
Ala Thr Ser His Gly Ala Glu  Ala Ser Ser Ala Val  Pro Thr Pro
    11075           11080              11085

Thr Val Ser Pro Gly Val Ser  Gly Val Val Thr Pro  Leu Val Thr
    11090           11095              11100

Ser Ser Arg Ala Val Thr Ser  Thr Thr Ile Pro Ile  Leu Thr Leu
    11105           11110              11115

Ser Ser Ser Glu Pro Glu Thr  Thr Pro Ser Met Ala  Thr Ser His
    11120           11125              11130

Gly Val Glu Ala Ser Ser Ala  Val Leu Thr Val Ser  Pro Glu Val
    11135           11140              11145

Pro Gly Met Val Thr Ser Leu  Val Thr Ser Ser Arg  Ala Val Thr
    11150           11155              11160

Ser Thr Thr Ile Pro Thr Leu  Thr Ile Ser Ser Asp  Glu Pro Glu
    11165           11170              11175

Thr Thr Thr Ser Leu Val Thr  His Ser Glu Ala Lys  Met Ile Ser
    11180           11185              11190

Ala Ile Pro Thr Leu Ala Val  Ser Pro Thr Val Gln  Gly Leu Val
    11195           11200              11205

Thr Ser Leu Val Thr Ser Ser  Gly Ser Glu Thr Ser  Ala Phe Ser
    11210           11215              11220

Asn Leu Thr Val Ala Ser Ser  Gln Pro Glu Thr Ile  Asp Ser Trp
    11225           11230              11235

Val Ala His Pro Gly Thr Glu  Ala Ser Ser Val Val  Pro Thr Leu
    11240           11245              11250

Thr Val Ser Thr Gly Glu Pro  Phe Thr Asn Ile Ser  Leu Val Thr
    11255           11260              11265

His Pro Ala Glu Ser Ser Ser  Thr Leu Pro Arg Thr  Thr Ser Arg
    11270           11275              11280

Phe Ser His Ser Glu Leu Asp  Thr Met Pro Ser Thr  Val Thr Ser
    11285           11290              11295

Pro Glu Ala Glu Ser Ser Ser  Ala Ile Ser Thr Thr  Ile Ser Pro
    11300           11305              11310

Gly Ile Pro Gly Val Leu Thr  Ser Leu Val Thr Ser  Ser Gly Arg
    11315           11320              11325

Asp Ile Ser Ala Thr Phe Pro  Thr Val Pro Glu Ser  Pro His Glu
    11330           11335              11340

Ser Glu Ala Thr Ala Ser Trp  Val Thr His Pro Ala  Val Thr Ser
    11345           11350              11355

Thr Thr Val Pro Arg Thr Thr  Pro Asn Tyr Ser His  Ser Glu Pro
    11360           11365              11370

Asp Thr Thr Pro Ser Ile Ala  Thr Ser Pro Gly Ala  Glu Ala Thr
    11375           11380              11385

Ser Asp Phe Pro Thr Ile Thr  Val Ser Pro Asp Val  Pro Asp Met
    11390           11395              11400

Val Thr Ser Gln Val Thr Ser  Ser Gly Thr Asp Thr  Ser Ile Thr
    11405           11410              11415

Ile Pro Thr Leu Thr Leu Ser  Ser Gly Glu Pro Glu  Thr Thr Thr
    11420           11425              11430

Ser Phe Ile Thr Tyr Ser Glu  Thr His Thr Ser Ser  Ala Ile Pro
    11435           11440              11445

Thr Leu Pro Val Ser Pro Gly  Ala Ser Lys Met Leu  Thr Ser Leu
    11450           11455              11460
```

```
Val Ile Ser Ser Gly Thr Asp  Ser Thr Thr Thr Phe  Pro Thr Leu
    11465            11470                11475

Thr Glu Thr Pro Tyr Glu Pro  Glu Thr Thr Ala Ile  Gln Leu Ile
    11480            11485                11490

His Pro Ala Glu Thr Asn Thr  Met Val Pro Arg Thr  Thr Pro Lys
    11495            11500                11505

Phe Ser His Ser Lys Ser Asp  Thr Thr Leu Pro Val  Ala Ile Thr
    11510            11515                11520

Ser Pro Gly Pro Glu Ala Ser  Ser Ala Val Ser Thr  Thr Thr Ile
    11525            11530                11535

Ser Pro Asp Met Ser Asp Leu  Val Thr Ser Leu Val  Pro Ser Ser
    11540            11545                11550

Gly Thr Asp Thr Ser Thr Thr  Phe Pro Thr Leu Ser  Glu Thr Pro
    11555            11560                11565

Tyr Glu Pro Glu Thr Thr Ala  Thr Trp Leu Thr His  Pro Ala Glu
    11570            11575                11580

Thr Ser Thr Thr Val Ser Gly  Thr Ile Pro Asn Phe  Ser His Arg
    11585            11590                11595

Gly Ser Asp Thr Ala Pro Ser  Met Val Thr Ser Pro  Gly Val Asp
    11600            11605                11610

Thr Arg Ser Gly Val Pro Thr  Thr Thr Ile Pro Pro  Ser Ile Pro
    11615            11620                11625

Gly Val Val Thr Ser Gln Val  Thr Ser Ser Ala Thr  Asp Thr Ser
    11630            11635                11640

Thr Ala Ile Pro Thr Leu Thr  Pro Ser Pro Gly Glu  Pro Glu Thr
    11645            11650                11655

Thr Ala Ser Ser Ala Thr His  Pro Gly Thr Gln Thr  Gly Phe Thr
    11660            11665                11670

Val Pro Ile Arg Thr Val Pro  Ser Ser Glu Pro Asp  Thr Met Ala
    11675            11680                11685

Ser Trp Val Thr His Pro Pro  Gln Thr Ser Thr Pro  Val Ser Arg
    11690            11695                11700

Thr Thr Ser Ser Phe Ser His  Ser Ser Pro Asp Ala  Thr Pro Val
    11705            11710                11715

Met Ala Thr Ser Pro Arg Thr  Glu Ala Ser Ser Ala  Val Leu Thr
    11720            11725                11730

Thr Ile Ser Pro Gly Ala Pro  Glu Met Val Thr Ser  Gln Ile Thr
    11735            11740                11745

Ser Ser Gly Ala Ala Thr Ser  Thr Thr Val Pro Thr  Leu Thr His
    11750            11755                11760

Ser Pro Gly Met Pro Glu Thr  Thr Ala Leu Leu Ser  Thr His Pro
    11765            11770                11775

Arg Thr Glu Thr Ser Lys Thr  Phe Pro Ala Ser Thr  Val Phe Pro
    11780            11785                11790

Gln Val Ser Glu Thr Thr Ala  Ser Leu Thr Ile Arg  Pro Gly Ala
    11795            11800                11805

Glu Thr Ser Thr Ala Leu Pro  Thr Gln Thr Thr Ser  Ser Leu Phe
    11810            11815                11820

Thr Leu Leu Val Thr Gly Thr  Ser Arg Val Asp Leu  Ser Pro Thr
    11825            11830                11835

Ala Ser Pro Gly Val Ser Ala  Lys Thr Ala Pro Leu  Ser Thr His
    11840            11845                11850

Pro Gly Thr Glu Thr Ser Thr  Met Ile Pro Thr Ser  Thr Leu Ser
```

-continued

```
                    11855               11860               11865
Leu Gly Leu Leu Glu Thr Thr Gly Leu Leu Ala Thr Ser Ser Ser
    11870               11875               11880
Ala Glu Thr Ser Thr Ser Thr Leu Thr Leu Thr Val Ser Pro Ala
    11885               11890               11895
Val Ser Gly Leu Ser Ser Ala Ser Ile Thr Thr Asp Lys Pro Gln
    11900               11905               11910
Thr Val Thr Ser Trp Asn Thr Glu Thr Ser Pro Ser Val Thr Ser
    11915               11920               11925
Val Gly Pro Pro Glu Phe Ser Arg Thr Val Thr Gly Thr Thr Met
    11930               11935               11940
Thr Leu Ile Pro Ser Glu Met Pro Thr Pro Pro Lys Thr Ser His
    11945               11950               11955
Gly Glu Gly Val Ser Pro Thr Thr Ile Leu Arg Thr Thr Met Val
    11960               11965               11970
Glu Ala Thr Asn Leu Ala Thr Thr Gly Ser Ser Pro Thr Val Ala
    11975               11980               11985
Lys Thr Thr Thr Thr Phe Asn Thr Leu Ala Gly Ser Leu Phe Thr
    11990               11995               12000
Pro Leu Thr Thr Pro Gly Met Ser Thr Leu Ala Ser Glu Ser Val
    12005               12010               12015
Thr Ser Arg Thr Ser Tyr Asn His Arg Ser Trp Ile Ser Thr Thr
    12020               12025               12030
Ser Ser Tyr Asn Arg Arg Tyr Trp Thr Pro Ala Thr Ser Thr Pro
    12035               12040               12045
Val Thr Ser Thr Phe Ser Pro Gly Ile Ser Thr Ser Ser Ile Pro
    12050               12055               12060
Ser Ser Thr Ala Ala Thr Val Pro Phe Met Val Pro Phe Thr Leu
    12065               12070               12075
Asn Phe Thr Ile Thr Asn Leu Gln Tyr Glu Glu Asp Met Arg His
    12080               12085               12090
Pro Gly Ser Arg Lys Phe Asn Ala Thr Glu Arg Glu Leu Gln Gly
    12095               12100               12105
Leu Leu Lys Pro Leu Phe Arg Asn Ser Ser Leu Glu Tyr Leu Tyr
    12110               12115               12120
Ser Gly Cys Arg Leu Ala Ser Leu Arg Pro Glu Lys Asp Ser Ser
    12125               12130               12135
Ala Thr Ala Val Asp Ala Ile Cys Thr His Arg Pro Asp Pro Glu
    12140               12145               12150
Asp Leu Gly Leu Asp Arg Glu Arg Leu Tyr Trp Glu Leu Ser Asn
    12155               12160               12165
Leu Thr Asn Gly Ile Gln Glu Leu Gly Pro Tyr Thr Leu Asp Arg
    12170               12175               12180
Asn Ser Leu Tyr Val Asn Gly Phe Thr His Arg Ser Ser Met Pro
    12185               12190               12195
Thr Thr Ser Thr Pro Gly Thr Ser Thr Val Asp Val Gly Thr Ser
    12200               12205               12210
Gly Thr Pro Ser Ser Ser Pro Ser Pro Thr Thr Ala Gly Pro Leu
    12215               12220               12225
Leu Met Pro Phe Thr Leu Asn Phe Thr Ile Thr Asn Leu Gln Tyr
    12230               12235               12240
Glu Glu Asp Met Arg Arg Thr Gly Ser Arg Lys Phe Asn Thr Met
    12245               12250               12255
```

```
Glu Ser Val Leu Gln Gly Leu  Leu Lys Pro Leu Phe  Lys Asn Thr
    12260           12265            12270

Ser Val Gly Pro Leu Tyr Ser  Gly Cys Arg Leu Thr  Leu Leu Arg
    12275           12280            12285

Pro Glu Lys Asp Gly Ala Ala  Thr Gly Val Asp Ala  Ile Cys Thr
    12290           12295            12300

His Arg Leu Asp Pro Lys Ser  Pro Gly Leu Asn Arg  Glu Gln Leu
    12305           12310            12315

Tyr Trp Glu Leu Ser Lys Leu  Thr Asn Asp Ile Glu  Glu Leu Gly
    12320           12325            12330

Pro Tyr Thr Leu Asp Arg Asn  Ser Leu Tyr Val Asn  Gly Phe Thr
    12335           12340            12345

His Gln Ser Ser Val Ser Thr  Thr Ser Thr Pro Gly  Thr Ser Thr
    12350           12355            12360

Val Asp Leu Arg Thr Ser Gly  Thr Pro Ser Ser Leu  Ser Ser Pro
    12365           12370            12375

Thr Ile Met Ala Ala Gly Pro  Leu Leu Val Pro Phe  Thr Leu Asn
    12380           12385            12390

Phe Thr Ile Thr Asn Leu Gln  Tyr Gly Glu Asp Met  Gly His Pro
    12395           12400            12405

Gly Ser Arg Lys Phe Asn Thr  Thr Glu Arg Val Leu  Gln Gly Leu
    12410           12415            12420

Leu Gly Pro Ile Phe Lys Asn  Thr Ser Val Gly Pro  Leu Tyr Ser
    12425           12430            12435

Gly Cys Arg Leu Thr Ser Leu  Arg Ser Glu Lys Asp  Gly Ala Ala
    12440           12445            12450

Thr Gly Val Asp Ala Ile Cys  Ile His His Leu Asp  Pro Lys Ser
    12455           12460            12465

Pro Gly Leu Asn Arg Glu Arg  Leu Tyr Trp Glu Leu  Ser Gln Leu
    12470           12475            12480

Thr Asn Gly Ile Lys Glu Leu  Gly Pro Tyr Thr Leu  Asp Arg Asn
    12485           12490            12495

Ser Leu Tyr Val Asn Gly Phe  Thr His Arg Thr Ser  Val Pro Thr
    12500           12505            12510

Ser Ser Thr Pro Gly Thr Ser  Thr Val Asp Leu Gly  Thr Ser Gly
    12515           12520            12525

Thr Pro Phe Ser Leu Pro Ser  Pro Ala Thr Ala Gly  Pro Leu Leu
    12530           12535            12540

Val Leu Phe Thr Leu Asn Phe  Thr Ile Thr Asn Leu  Lys Tyr Glu
    12545           12550            12555

Glu Asp Met His Arg Pro Gly  Ser Arg Lys Phe Asn  Thr Thr Glu
    12560           12565            12570

Arg Val Leu Gln Thr Leu Leu  Gly Pro Met Phe Lys  Asn Thr Ser
    12575           12580            12585

Val Gly Leu Leu Tyr Ser Gly  Cys Arg Leu Thr Leu  Leu Arg Ser
    12590           12595            12600

Glu Lys Asp Gly Ala Ala Thr  Gly Val Asp Ala Ile  Cys Thr His
    12605           12610            12615

Arg Leu Asp Pro Lys Ser Pro  Gly Val Asp Arg Glu  Gln Leu Tyr
    12620           12625            12630

Trp Glu Leu Ser Gln Leu Thr  Asn Gly Ile Lys Glu  Leu Gly Pro
    12635           12640            12645
```

```
Tyr Thr Leu Asp Arg Asn Ser   Leu Tyr Val Asn Gly   Phe Thr His
    12650             12655                 12660

Trp Ile Pro Val Pro Thr Ser   Ser Thr Pro Gly Thr   Ser Thr Val
    12665             12670                 12675

Asp Leu Gly Ser Gly Thr Pro   Ser Ser Leu Pro Ser   Pro Thr Thr
    12680             12685                 12690

Ala Gly Pro Leu Leu Val Pro   Phe Thr Leu Asn Phe   Thr Ile Thr
    12695             12700                 12705

Asn Leu Lys Tyr Glu Glu Asp   Met His Cys Pro Gly   Ser Arg Lys
    12710             12715                 12720

Phe Asn Thr Thr Glu Arg Val   Leu Gln Ser Leu Leu   Gly Pro Met
    12725             12730                 12735

Phe Lys Asn Thr Ser Val Gly   Pro Leu Tyr Ser Gly   Cys Arg Leu
    12740             12745                 12750

Thr Leu Leu Arg Ser Glu Lys   Asp Gly Ala Ala Thr   Gly Val Asp
    12755             12760                 12765

Ala Ile Cys Thr His Arg Leu   Asp Pro Lys Ser Pro   Gly Val Asp
    12770             12775                 12780

Arg Glu Gln Leu Tyr Trp Glu   Leu Ser Gln Leu Thr   Asn Gly Ile
    12785             12790                 12795

Lys Glu Leu Gly Pro Tyr Thr   Leu Asp Arg Asn Ser   Leu Tyr Val
    12800             12805                 12810

Asn Gly Phe Thr His Gln Thr   Ser Ala Pro Asn Thr   Ser Thr Pro
    12815             12820                 12825

Gly Thr Ser Thr Val Asp Leu   Gly Thr Ser Gly Thr   Pro Ser Ser
    12830             12835                 12840

Leu Pro Ser Pro Thr Ser Ala   Gly Pro Leu Leu Val   Pro Phe Thr
    12845             12850                 12855

Leu Asn Phe Thr Ile Thr Asn   Leu Gln Tyr Glu Glu   Asp Met His
    12860             12865                 12870

His Pro Gly Ser Arg Lys Phe   Asn Thr Thr Glu Arg   Val Leu Gln
    12875             12880                 12885

Gly Leu Leu Gly Pro Met Phe   Lys Asn Thr Ser Val   Gly Leu Leu
    12890             12895                 12900

Tyr Ser Gly Cys Arg Leu Thr   Leu Leu Arg Pro Glu   Lys Asn Gly
    12905             12910                 12915

Ala Ala Thr Gly Met Asp Ala   Ile Cys Ser His Arg   Leu Asp Pro
    12920             12925                 12930

Lys Ser Pro Gly Leu Asn Arg   Glu Gln Leu Tyr Trp   Glu Leu Ser
    12935             12940                 12945

Gln Leu Thr His Gly Ile Lys   Glu Leu Gly Pro Tyr   Thr Leu Asp
    12950             12955                 12960

Arg Asn Ser Leu Tyr Val Asn   Gly Phe Thr His Arg   Ser Ser Val
    12965             12970                 12975

Ala Pro Thr Ser Thr Pro Gly   Thr Ser Thr Val Asp   Leu Gly Thr
    12980             12985                 12990

Ser Gly Thr Pro Ser Ser Leu   Pro Ser Pro Thr Thr   Ala Val Pro
    12995             13000                 13005

Leu Leu Val Pro Phe Thr Leu   Asn Phe Thr Ile Thr   Asn Leu Gln
    13010             13015                 13020

Tyr Gly Glu Asp Met Arg His   Pro Gly Ser Arg Lys   Phe Asn Thr
    13025             13030                 13035

Thr Glu Arg Val Leu Gln Gly   Leu Leu Gly Pro Leu   Phe Lys Asn
```

|       |     |     |     |     |     |       |     |     |     |     |     |       |     |     |     |
|-------|-----|-----|-----|-----|-----|-------|-----|-----|-----|-----|-----|-------|-----|-----|-----|
| 13040 |     |     |     |     |     | 13045 |     |     |     |     |     | 13050 |     |     |     |
| Ser   | Ser | Val | Gly | Pro | Leu | Tyr   | Ser | Gly | Cys | Arg | Leu | Ile   | Ser | Leu |     |
| 13055 |     |     |     |     |     | 13060 |     |     |     |     |     | 13065 |     |     |     |
| Arg   | Ser | Glu | Lys | Asp | Gly | Ala   | Ala | Thr | Gly | Val | Asp | Ala   | Ile | Cys |     |
| 13070 |     |     |     |     |     | 13075 |     |     |     |     |     | 13080 |     |     |     |
| Thr   | His | His | Leu | Asn | Pro | Gln   | Ser | Pro | Gly | Leu | Asp | Arg   | Glu | Gln |     |
| 13085 |     |     |     |     |     | 13090 |     |     |     |     |     | 13095 |     |     |     |
| Leu   | Tyr | Trp | Gln | Leu | Ser | Gln   | Met | Thr | Asn | Gly | Ile | Lys   | Glu | Leu |     |
| 13100 |     |     |     |     |     | 13105 |     |     |     |     |     | 13110 |     |     |     |
| Gly   | Pro | Tyr | Thr | Leu | Asp | Arg   | Asn | Ser | Leu | Tyr | Val | Asn   | Gly | Phe |     |
| 13115 |     |     |     |     |     | 13120 |     |     |     |     |     | 13125 |     |     |     |
| Thr   | His | Arg | Ser | Ser | Gly | Leu   | Thr | Thr | Ser | Thr | Pro | Trp   | Thr | Ser |     |
| 13130 |     |     |     |     |     | 13135 |     |     |     |     |     | 13140 |     |     |     |
| Thr   | Val | Asp | Leu | Gly | Thr | Ser   | Gly | Thr | Pro | Ser | Pro | Val   | Pro | Ser |     |
| 13145 |     |     |     |     |     | 13150 |     |     |     |     |     | 13155 |     |     |     |
| Pro   | Thr | Thr | Thr | Gly | Pro | Leu   | Leu | Val | Pro | Phe | Thr | Leu   | Asn | Phe |     |
| 13160 |     |     |     |     |     | 13165 |     |     |     |     |     | 13170 |     |     |     |
| Thr   | Ile | Thr | Asn | Leu | Gln | Tyr   | Glu | Glu | Asn | Met | Gly | His   | Pro | Gly |     |
| 13175 |     |     |     |     |     | 13180 |     |     |     |     |     | 13185 |     |     |     |
| Ser   | Arg | Lys | Phe | Asn | Ile | Thr   | Glu | Ser | Val | Leu | Gln | Gly   | Leu | Leu |     |
| 13190 |     |     |     |     |     | 13195 |     |     |     |     |     | 13200 |     |     |     |
| Lys   | Pro | Leu | Phe | Lys | Ser | Thr   | Ser | Val | Gly | Pro | Leu | Tyr   | Ser | Gly |     |
| 13205 |     |     |     |     |     | 13210 |     |     |     |     |     | 13215 |     |     |     |
| Cys   | Arg | Leu | Thr | Leu | Leu | Arg   | Pro | Glu | Lys | Asp | Gly | Val   | Ala | Thr |     |
| 13220 |     |     |     |     |     | 13225 |     |     |     |     |     | 13230 |     |     |     |
| Arg   | Val | Asp | Ala | Ile | Cys | Thr   | His | Arg | Pro | Asp | Pro | Lys   | Ile | Pro |     |
| 13235 |     |     |     |     |     | 13240 |     |     |     |     |     | 13245 |     |     |     |
| Gly   | Leu | Asp | Arg | Gln | Gln | Leu   | Tyr | Trp | Glu | Leu | Ser | Gln   | Leu | Thr |     |
| 13250 |     |     |     |     |     | 13255 |     |     |     |     |     | 13260 |     |     |     |
| His   | Ser | Ile | Thr | Glu | Leu | Gly   | Pro | Tyr | Thr | Leu | Asp | Arg   | Asp | Ser |     |
| 13265 |     |     |     |     |     | 13270 |     |     |     |     |     | 13275 |     |     |     |
| Leu   | Tyr | Val | Asn | Gly | Phe | Thr   | Gln | Arg | Ser | Ser | Val | Pro   | Thr | Thr |     |
| 13280 |     |     |     |     |     | 13285 |     |     |     |     |     | 13290 |     |     |     |
| Ser   | Thr | Pro | Gly | Thr | Phe | Thr   | Val | Gln | Pro | Glu | Thr | Ser   | Glu | Thr |     |
| 13295 |     |     |     |     |     | 13300 |     |     |     |     |     | 13305 |     |     |     |
| Pro   | Ser | Ser | Leu | Pro | Gly | Pro   | Thr | Ala | Thr | Gly | Pro | Val   | Leu | Leu |     |
| 13310 |     |     |     |     |     | 13315 |     |     |     |     |     | 13320 |     |     |     |
| Pro   | Phe | Thr | Leu | Asn | Phe | Thr   | Ile | Thr | Asn | Leu | Gln | Tyr   | Glu | Glu |     |
| 13325 |     |     |     |     |     | 13330 |     |     |     |     |     | 13335 |     |     |     |
| Asp   | Met | Arg | Arg | Pro | Gly | Ser   | Arg | Lys | Phe | Asn | Thr | Thr   | Glu | Arg |     |
| 13340 |     |     |     |     |     | 13345 |     |     |     |     |     | 13350 |     |     |     |
| Val   | Leu | Gln | Gly | Leu | Leu | Met   | Pro | Leu | Phe | Lys | Asn | Thr   | Ser | Val |     |
| 13355 |     |     |     |     |     | 13360 |     |     |     |     |     | 13365 |     |     |     |
| Ser   | Ser | Leu | Tyr | Ser | Gly | Cys   | Arg | Leu | Thr | Leu | Leu | Arg   | Pro | Glu |     |
| 13370 |     |     |     |     |     | 13375 |     |     |     |     |     | 13380 |     |     |     |
| Lys   | Asp | Gly | Ala | Ala | Thr | Arg   | Val | Asp | Ala | Val | Cys | Thr   | His | Arg |     |
| 13385 |     |     |     |     |     | 13390 |     |     |     |     |     | 13395 |     |     |     |
| Pro   | Asp | Pro | Lys | Ser | Pro | Gly   | Leu | Asp | Arg | Glu | Arg | Leu   | Tyr | Trp |     |
| 13400 |     |     |     |     |     | 13405 |     |     |     |     |     | 13410 |     |     |     |
| Lys   | Leu | Ser | Gln | Leu | Thr | His   | Gly | Ile | Thr | Glu | Leu | Gly   | Pro | Tyr |     |
| 13415 |     |     |     |     |     | 13420 |     |     |     |     |     | 13425 |     |     |     |
| Thr   | Leu | Asp | Arg | His | Ser | Leu   | Tyr | Val | Asn | Gly | Phe | Thr   | His | Gln |     |
| 13430 |     |     |     |     |     | 13435 |     |     |     |     |     | 13440 |     |     |     |

```
Ser Ser Met Thr Thr Thr Arg   Thr Pro Asp Thr Ser   Thr Met His
    13445                 13450             13455

Leu Ala Thr Ser Arg Thr Pro   Ala Ser Leu Ser Gly   Pro Met Thr
    13460                 13465             13470

Ala Ser Pro Leu Leu Val Leu   Phe Thr Ile Asn Phe   Thr Ile Thr
    13475                 13480             13485

Asn Leu Arg Tyr Glu Glu Asn   Met His His Pro Gly   Ser Arg Lys
    13490                 13495             13500

Phe Asn Thr Thr Glu Arg Val   Leu Gln Gly Leu Leu   Arg Pro Val
    13505                 13510             13515

Phe Lys Asn Thr Ser Val Gly   Pro Leu Tyr Ser Gly   Cys Arg Leu
    13520                 13525             13530

Thr Leu Leu Arg Pro Lys Lys   Asp Gly Ala Ala Thr   Lys Val Asp
    13535                 13540             13545

Ala Ile Cys Thr Tyr Arg Pro   Asp Pro Lys Ser Pro   Gly Leu Asp
    13550                 13555             13560

Arg Glu Gln Leu Tyr Trp Glu   Leu Ser Gln Leu Thr   His Ser Ile
    13565                 13570             13575

Thr Glu Leu Gly Pro Tyr Thr   Leu Asp Arg Asp Ser   Leu Tyr Val
    13580                 13585             13590

Asn Gly Phe Thr Gln Arg Ser   Ser Val Pro Thr Thr   Ser Ile Pro
    13595                 13600             13605

Gly Thr Pro Thr Val Asp Leu   Gly Thr Ser Gly Thr   Pro Val Ser
    13610                 13615             13620

Lys Pro Gly Pro Ser Ala Ala   Ser Pro Leu Leu Val   Leu Phe Thr
    13625                 13630             13635

Leu Asn Phe Thr Ile Thr Asn   Leu Arg Tyr Glu Glu   Asn Met Gln
    13640                 13645             13650

His Pro Gly Ser Arg Lys Phe   Asn Thr Thr Glu Arg   Val Leu Gln
    13655                 13660             13665

Gly Leu Leu Arg Ser Leu Phe   Lys Ser Thr Ser Val   Gly Pro Leu
    13670                 13675             13680

Tyr Ser Gly Cys Arg Leu Thr   Leu Leu Arg Pro Glu   Lys Asp Gly
    13685                 13690             13695

Thr Ala Thr Gly Val Asp Ala   Ile Cys Thr His His   Pro Asp Pro
    13700                 13705             13710

Lys Ser Pro Arg Leu Asp Arg   Glu Gln Leu Tyr Trp   Glu Leu Ser
    13715                 13720             13725

Gln Leu Thr His Asn Ile Thr   Glu Leu Gly Pro Tyr   Ala Leu Asp
    13730                 13735             13740

Asn Asp Ser Leu Phe Val Asn   Gly Phe Thr His Arg   Ser Ser Val
    13745                 13750             13755

Ser Thr Thr Ser Thr Pro Gly   Thr Pro Thr Val Tyr   Leu Gly Ala
    13760                 13765             13770

Ser Lys Thr Pro Ala Ser Ile   Phe Gly Pro Ser Ala   Ala Ser His
    13775                 13780             13785

Leu Leu Ile Leu Phe Thr Leu   Asn Phe Thr Ile Thr   Asn Leu Arg
    13790                 13795             13800

Tyr Glu Glu Asn Met Trp Pro   Gly Ser Arg Lys Phe   Asn Thr Thr
    13805                 13810             13815

Glu Arg Val Leu Gln Gly Leu   Leu Arg Pro Leu Phe   Lys Asn Thr
    13820                 13825             13830
```

```
Ser Val Gly Pro Leu Tyr Ser   Gly Cys Arg Leu Thr   Leu Leu Arg
    13835                 13840                 13845

Pro Glu Lys Asp Gly Glu Ala   Thr Gly Val Asp Ala   Ile Cys Thr
    13850                 13855                 13860

His Arg Pro Asp Pro Thr Gly   Pro Gly Leu Asp Arg   Glu Gln Leu
    13865                 13870                 13875

Tyr Leu Glu Leu Ser Gln Leu   Thr His Ser Ile Thr   Glu Leu Gly
    13880                 13885                 13890

Pro Tyr Thr Leu Asp Arg Asp   Ser Leu Tyr Val Asn   Gly Phe Thr
    13895                 13900                 13905

His Arg Ser Ser Val Pro Thr   Thr Ser Thr Gly Val   Val Ser Glu
    13910                 13915                 13920

Glu Pro Phe Thr Leu Asn Phe   Thr Ile Asn Asn Leu   Arg Tyr Met
    13925                 13930                 13935

Ala Asp Met Gly Gln Pro Gly   Ser Leu Lys Phe Asn   Ile Thr Asp
    13940                 13945                 13950

Asn Val Met Gln His Leu Leu   Ser Pro Leu Phe Gln   Arg Ser Ser
    13955                 13960                 13965

Leu Gly Ala Arg Tyr Thr Gly   Cys Arg Val Ile Ala   Leu Arg Ser
    13970                 13975                 13980

Val Lys Asn Gly Ala Glu Thr   Arg Val Asp Leu Leu   Cys Thr Tyr
    13985                 13990                 13995

Leu Gln Pro Leu Ser Gly Pro   Gly Leu Pro Ile Lys   Gln Val Phe
    14000                 14005                 14010

His Glu Leu Ser Gln Gln Thr   His Gly Ile Thr Arg   Leu Gly Pro
    14015                 14020                 14025

Tyr Ser Leu Asp Lys Asp Ser   Leu Tyr Leu Asn Gly   Tyr Asn Glu
    14030                 14035                 14040

Pro Gly Pro Asp Glu Pro Pro   Thr Thr Pro Lys Pro   Ala Thr Thr
    14045                 14050                 14055

Phe Leu Pro Pro Leu Ser Glu   Ala Thr Thr Ala Met   Gly Tyr His
    14060                 14065                 14070

Leu Lys Thr Leu Thr Leu Asn   Phe Thr Ile Ser Asn   Leu Gln Tyr
    14075                 14080                 14085

Ser Pro Asp Met Gly Lys Gly   Ser Ala Thr Phe Asn   Ser Thr Glu
    14090                 14095                 14100

Gly Val Leu Gln His Leu Leu   Arg Pro Leu Phe Gln   Lys Ser Ser
    14105                 14110                 14115

Met Gly Pro Phe Tyr Leu Gly   Cys Gln Leu Ile Ser   Leu Arg Pro
    14120                 14125                 14130

Glu Lys Asp Gly Ala Ala Thr   Gly Val Asp Thr Thr   Cys Thr Tyr
    14135                 14140                 14145

His Pro Asp Pro Val Gly Pro   Gly Leu Asp Ile Gln   Gln Leu Tyr
    14150                 14155                 14160

Trp Glu Leu Ser Gln Leu Thr   His Gly Val Thr Gln   Leu Gly Phe
    14165                 14170                 14175

Tyr Val Leu Asp Arg Asp Ser   Leu Phe Ile Asn Gly   Tyr Ala Pro
    14180                 14185                 14190

Gln Asn Leu Ser Ile Arg Gly   Glu Tyr Gln Ile Asn   Phe His Ile
    14195                 14200                 14205

Val Asn Trp Asn Leu Ser Asn   Pro Asp Pro Thr Ser   Ser Glu Tyr
    14210                 14215                 14220

Ile Thr Leu Leu Arg Asp Ile   Gln Asp Lys Val Thr   Thr Leu Tyr
```

```
                 14225                   14230                   14235
Lys Gly   Ser Gln Leu His Asp    Thr Phe Arg Phe Cys    Leu Val Thr
                 14240                   14245                   14250
Asn Leu   Thr Met Asp Ser Val    Leu Val Thr Val Lys    Ala Leu Phe
                 14255                   14260                   14265
Ser Ser   Asn Leu Asp Pro Ser    Leu Val Glu Gln Val    Phe Leu Asp
                 14270                   14275                   14280
Lys Thr   Leu Asn Ala Ser Phe    His Trp Leu Gly Ser    Thr Tyr Gln
                 14285                   14290                   14295
Leu Val   Asp Ile His Val Thr    Glu Met Glu Ser Ser    Val Tyr Gln
                 14300                   14305                   14310
Pro Thr   Ser Ser Ser Thr Gln    His Phe Tyr Leu        Asn Phe Thr
                 14315                   14320                   14325
Ile Thr   Asn Leu Pro Tyr Ser    Gln Asp Lys Ala Gln    Pro Gly Thr
                 14330                   14335                   14340
Thr Asn   Tyr Gln Arg Asn Lys    Arg Asn Ile Glu Asp    Ala Leu Asn
                 14345                   14350                   14355
Gln Leu   Phe Arg Asn Ser Ser    Ile Lys Ser Tyr Phe    Ser Asp Cys
                 14360                   14365                   14370
Gln Val   Ser Thr Phe Arg Ser    Val Pro Asn Arg His    His Thr Gly
                 14375                   14380                   14385
Val Asp   Ser Leu Cys Asn Phe    Ser Pro Leu Ala Arg    Arg Val Asp
                 14390                   14395                   14400
Arg Val   Ala Ile Tyr Glu Glu    Phe Leu Arg Met Thr    Arg Asn Gly
                 14405                   14410                   14415
Thr Gln   Leu Gln Asn Phe Thr    Leu Asp Arg Ser Ser    Val Leu Val
                 14420                   14425                   14430
Asp Gly   Tyr Ser Pro Asn Arg    Asn Glu Pro Leu Thr    Gly Asn Ser
                 14435                   14440                   14445
Asp Leu   Pro Phe Trp Ala Val    Ile Leu Ile Gly Leu    Ala Gly Leu
                 14450                   14455                   14460
Leu Gly   Val Ile Thr Cys Leu    Ile Cys Gly Val Leu    Val Thr Thr
                 14465                   14470                   14475
Arg Arg   Arg Lys Lys Glu Gly    Glu Tyr Asn Val Gln    Gln Gln Cys
                 14480                   14485                   14490
Pro Gly   Tyr Tyr Gln Ser His    Leu Asp Leu Glu Asp    Leu Gln
                 14495                   14500                   14505

<210> SEQ ID NO 14
<211> LENGTH: 24
<212> TYPE: PRT
<213> ORGANISM: Artificial Sequence
<220> FEATURE:
<223> OTHER INFORMATION: Synthetic

<400> SEQUENCE: 14

Phe Trp Ala Val Ile Leu Ile Gly Leu Ala Gly Leu Leu Gly Leu Ile
1               5                   10                  15

Thr Cys Leu Ile Cys Gly Val Leu
            20

<210> SEQ ID NO 15
<211> LENGTH: 32
<212> TYPE: PRT
<213> ORGANISM: Artificial Sequence
<220> FEATURE:
<223> OTHER INFORMATION: Synthetic
```

```
<400> SEQUENCE: 15

Lys Ser Tyr Phe Ser Asp Cys Gln Val Ser Thr Phe Arg Ser Val Pro
1               5                   10                  15

Asn Arg His His Thr Gly Val Asp Ser Leu Cys Asn Phe Ser Pro Leu
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Synthetic

<400> SEQUENCE: 16

Val Thr Thr Arg Arg Arg Lys Lys Glu Gly Glu Tyr Asn Val Gln Gln
1               5                   10                  15

Gln Cys Pro Gly Tyr Tyr Gln Ser His Leu Asp Leu Glu Asp Leu Gln
            20                  25                  30

<210> SEQ ID NO 17
<211> LENGTH: 58
<212> TYPE: PRT
<213> ORGANISM: Artificial Sequence
<220> FEATURE:
<223> OTHER INFORMATION: Synthetic

<400> SEQUENCE: 17

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro
    50                  55

<210> SEQ ID NO 18
<211> LENGTH: 17
<212> TYPE: PRT
<213> ORGANISM: Artificial Sequence
<220> FEATURE:
<223> OTHER INFORMATION: Synthetic

<400> SEQUENCE: 18

Val Thr Thr Arg Arg Arg Lys Lys Glu Gly Glu Tyr Asn Val Gln Gln
1               5                   10                  15

Gln

<210> SEQ ID NO 19
<211> LENGTH: 21
<212> TYPE: PRT
<213> ORGANISM: Artificial Sequence
<220> FEATURE:
<223> OTHER INFORMATION: Synthetic

<400> SEQUENCE: 19

Cys Gln Val Ser Thr Phe Arg Ser Val Pro Asn Arg His His Thr Gly
1               5                   10                  15

Val Asp Ser Leu Cys
            20
```

```
<210> SEQ ID NO 20
<211> LENGTH: 18
<212> TYPE: PRT
<213> ORGANISM: Artificial Sequence
<220> FEATURE:
<223> OTHER INFORMATION: Synthetic

<400> SEQUENCE: 20

Leu Val Thr Thr Arg Arg Lys Lys Glu Gly Glu Tyr Asn Val Gln
1               5                   10                  15

Gln Gln

<210> SEQ ID NO 21
<211> LENGTH: 18
<212> TYPE: PRT
<213> ORGANISM: Mus musculus

<400> SEQUENCE: 21

Thr Leu Asp Arg Lys Ser Val Phe Val Asp Gly Tyr Ser Gln Asn Arg
1               5                   10                  15

Asp Asp

<210> SEQ ID NO 22
<211> LENGTH: 33
<212> TYPE: PRT
<213> ORGANISM: Mus musculus

<400> SEQUENCE: 22

Lys Ser Tyr Phe Ser Asp Cys Gln Val Leu Ala Phe Arg Ser Val Ser
1               5                   10                  15

Asn Asn Asn Asn His Thr Gly Val Asp Ser Leu Cys Asn Phe Ser Pro
                20                  25                  30

Leu

<210> SEQ ID NO 23
<211> LENGTH: 31
<212> TYPE: PRT
<213> ORGANISM: Mus musculus

<400> SEQUENCE: 23

Ser Leu Tyr Ser Asn Cys Arg Leu Ala Ser Leu Arg Pro Lys Lys Asn
1               5                   10                  15

Gly Thr Ala Thr Gly Val Asn Ala Ile Cys Ser Tyr His Gln Asn
                20                  25                  30

<210> SEQ ID NO 24
<211> LENGTH: 402
<212> TYPE: PRT
<213> ORGANISM: Mus musculus

<400> SEQUENCE: 24

His Leu Ile Arg Pro Leu Val Gln Asn Glu Ser Leu Tyr Ser Asn Cys
1               5                   10                  15

Arg Leu Ala Ser Leu Arg Pro Lys Lys Asn Gly Thr Ala Thr Gly Val
                20                  25                  30

Asn Ala Ile Cys Ser Tyr His Gln Asn Pro Asp His Pro Glu Leu Asp
                35                  40                  45

Thr Gln Glu Leu Tyr Thr Lys Leu Thr Gln Leu Thr Gln Gly Val Thr
        50                  55                  60

Gln Leu Gly Ser Tyr Met Leu Asp Gln Asn Ser Ile Tyr Val Asn Gly
65              70                  75                  80
```

```
Tyr Val Pro Leu Asn Ile Thr Ile Gln Gly Lys Tyr Gln Leu Asn Phe
                85                  90                  95

Cys Ile Ile Asn Trp Asn Leu Asn Thr Asp Pro Thr Ser Ser Glu
            100                 105                 110

Tyr Ile Thr Leu Glu Arg Asp Ile Glu Asp Lys Val Thr Thr Leu Tyr
            115                 120                 125

Thr Gly Ser Gln Leu Lys Glu Val Phe Gln Ser Cys Leu Val Thr Asn
        130                 135                 140

Met Thr Ser Gly Ser Thr Val Val Thr Leu Glu Ala Leu Phe Ser Ser
145                 150                 155                 160

His Leu Asp Pro Asn Leu Val Lys Gln Val Phe Leu Asn Lys Thr Leu
                165                 170                 175

Asn Ala Ser Ser His Trp Leu Gly Ala Thr Tyr Gln Leu Lys Asp Leu
            180                 185                 190

His Val Ile Asp Met Lys Thr Ser Ile Leu Leu Pro Ala Glu Ile Pro
        195                 200                 205

Thr Thr Ser Ser Ser Ser Gln His Phe Asn Leu Asn Phe Thr Ile Thr
    210                 215                 220

Asn Leu Pro Tyr Ser Gln Asp Ile Ala Gln Pro Ser Thr Thr Lys Tyr
225                 230                 235                 240

Gln Gln Thr Lys Arg Ser Ile Glu Asn Ala Leu Asn Gln Leu Phe Arg
                245                 250                 255

Asn Ser Ser Ile Lys Ser Tyr Phe Ser Asp Cys Gln Val Leu Ala Phe
            260                 265                 270

Arg Ser Val Ser Asn Asn Asn His Thr Gly Val Asp Ser Leu Cys
        275                 280                 285

Asn Phe Ser Pro Leu Ala Arg Arg Val Asp Arg Val Ala Ile Tyr Glu
        290                 295                 300

Glu Phe Leu Arg Met Thr His Asn Gly Thr Gln Leu Leu Asn Phe Thr
305                 310                 315                 320

Leu Asp Arg Lys Ser Val Phe Val Asp Gly Tyr Ser Gln Asn Arg Asp
                325                 330                 335

Asp Asp Val Met Lys Asn Ser Gly Leu Pro Phe Trp Ala Ile Ile Leu
            340                 345                 350

Ile Cys Leu Ala Val Leu Leu Val Leu Ile Thr Cys Leu Met Cys Cys
        355                 360                 365

Phe Leu Val Thr Val Cys Arg Arg Lys Lys Glu Gly Asp Tyr Gln Val
370                 375                 380

Gln Arg His Arg Leu Ala Tyr Tyr Leu Ser His Leu Asp Leu Arg Lys
385                 390                 395                 400

Leu Gln

<210> SEQ ID NO 25
<211> LENGTH: 400
<212> TYPE: PRT
<213> ORGANISM: Homo sapiens

<400> SEQUENCE: 25

His Leu Leu Arg Pro Leu Phe Gln Lys Ser Ser Met Gly Pro Phe Tyr
1               5                   10                  15

Leu Gly Cys Gln Leu Ile Ser Leu Arg Pro Glu Lys Asp Gly Ala Ala
            20                  25                  30

Thr Gly Val Asp Thr Thr Cys Thr Tyr His Pro Asp Pro Val Gly Pro
        35                  40                  45
```

```
Gly Leu Asp Ile Gln Gln Leu Tyr Trp Glu Leu Ser Gln Leu Thr His
 50                  55                  60
Gly Val Thr Gln Leu Gly Phe Tyr Val Leu Asp Arg Asp Ser Leu Phe
 65                  70                  75                  80
Ile Asn Gly Tyr Ala Pro Gln Asn Leu Ser Ile Arg Gly Glu Tyr Gln
                 85                  90                  95
Ile Asn Phe His Ile Val Asn Trp Asn Leu Ser Asn Pro Asp Pro Thr
            100                 105                 110
Ser Ser Glu Tyr Ile Thr Leu Leu Arg Asp Ile Gln Asp Lys Val Thr
        115                 120                 125
Thr Leu Tyr Lys Gly Ser Gln Leu His Asp Thr Phe Arg Phe Cys Leu
130                 135                 140
Val Thr Asn Leu Thr Met Asp Ser Val Leu Val Thr Val Lys Ala Leu
145                 150                 155                 160
Phe Ser Ser Asn Leu Asp Pro Ser Leu Val Glu Gln Val Phe Leu Asp
                165                 170                 175
Lys Thr Leu Asn Ala Ser Phe His Trp Leu Gly Ser Thr Tyr Gln Leu
            180                 185                 190
Val Asp Ile His Val Thr Glu Met Glu Ser Ser Val Tyr Gln Pro Thr
        195                 200                 205
Ser Ser Ser Ser Thr Gln His Phe Tyr Leu Asn Phe Thr Ile Thr Asn
210                 215                 220
Leu Pro Tyr Ser Gln Asp Lys Ala Gln Pro Gly Thr Thr Asn Tyr Gln
225                 230                 235                 240
Arg Asn Lys Arg Asn Ile Glu Asp Ala Leu Asn Gln Leu Phe Arg Asn
                245                 250                 255
Ser Ser Ile Lys Ser Tyr Phe Ser Asp Cys Gln Val Ser Thr Phe Arg
            260                 265                 270
Ser Val Pro Asn Arg His His Thr Gly Val Asp Ser Leu Cys Asn Phe
        275                 280                 285
Ser Pro Leu Ala Arg Arg Val Asp Arg Val Ala Ile Tyr Glu Glu Phe
290                 295                 300
Leu Arg Met Thr Arg Asn Gly Thr Gln Leu Gln Asn Phe Thr Leu Asp
305                 310                 315                 320
Arg Ser Ser Val Leu Val Asp Gly Tyr Ser Pro Asn Arg Asn Glu Pro
                325                 330                 335
Leu Thr Gly Asn Ser Asp Leu Pro Phe Trp Ala Val Ile Leu Ile Gly
            340                 345                 350
Leu Ala Gly Leu Leu Gly Val Ile Thr Cys Leu Ile Cys Gly Val Leu
        355                 360                 365
Val Thr Thr Arg Arg Arg Lys Lys Glu Gly Glu Tyr Asn Val Gln Gln
370                 375                 380
Gln Cys Pro Gly Tyr Tyr Gln Ser His Leu Asp Leu Glu Asp Leu Gln
385                 390                 395                 400

<210> SEQ ID NO 26
<211> LENGTH: 360
<212> TYPE: DNA
<213> ORGANISM: Artificial Sequence
<220> FEATURE:
<223> OTHER INFORMATION: Synthetic

<400> SEQUENCE: 26
gaggtgaagc tggaggagtc aggtggagga ttggtgcagc ctaaaggatc attgaaactc      60
```

```
tcatgtgccg cctctggttt caccttcaat acctatgccg tgcactgggt ccgccaggct     120
ccaggaaagg gtatggaatg ggttgctcgc ataagaagta aaagtggaaa ttatgcaaca     180
tattatgccg attcagtgaa agacagattc accatctcca gaaatgattc acagagcatg     240
ctctatctgc aaatgaacaa cctgaaaact gaggacacag ccatatatta ctgtgtgaga     300
gcgggtaaca acggggcctt tccttactgg ggccaaggga ccacggtcac cgtctcctca     360
```

<210> SEQ ID NO 27
<211> LENGTH: 120
<212> TYPE: PRT
<213> ORGANISM: Artificial Sequence
<220> FEATURE:
<223> OTHER INFORMATION: Synthetic

<400> SEQUENCE: 27

```
Glu Val Lys Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Val His Trp Val Arg Gln Ala Pro Gly Lys Gly Met Glu Trp Val
        35                  40                  45

Ala Arg Ile Arg Ser Lys Ser Gly Asn Tyr Ala Thr Tyr Tyr Ala Asp
    50                  55                  60

Ser Val Lys Asp Arg Phe Thr Ile Ser Arg Asn Asp Ser Gln Ser Met
65                  70                  75                  80

Leu Tyr Leu Gln Met Asn Asn Leu Lys Thr Glu Asp Thr Ala Ile Tyr
                85                  90                  95

Tyr Cys Val Arg Ala Gly Asn Asn Gly Ala Phe Pro Tyr Trp Gly Gln
            100                 105                 110

Gly Thr Thr Val Thr Val Ser Ser
        115                 120
```

<210> SEQ ID NO 28
<211> LENGTH: 330
<212> TYPE: DNA
<213> ORGANISM: Artificial Sequence
<220> FEATURE:
<223> OTHER INFORMATION: Synthetic

<400> SEQUENCE: 28

```
gacattgagc tcacccagtc tccatcctca ctgtctgcat ctctgggagg cagagtcacc      60
atcacttgca aggctagcca agatattaag aagtatatag cttggtacca acacaagcct     120
ggaaaaactc ctcgactact catacatttc acatctacat tacagacagg catcccatca     180
aggttcagtg gacgtgggtc tgggagagac tattccttca gcatcagcaa cctggagtct     240
gaagatattg caacttatta ttgtctacag tatgatagtc tgtacacgtt cggagggggg     300
accaagctgg agatcaaacg ggcggccgca                                      330
```

<210> SEQ ID NO 29
<211> LENGTH: 110
<212> TYPE: PRT
<213> ORGANISM: Artificial Sequence
<220> FEATURE:
<223> OTHER INFORMATION: Synthetic

<400> SEQUENCE: 29

```
Asp Ile Glu Leu Thr Gln Ser Pro Ser Ser Leu Ser Ala Ser Leu Gly
1               5                   10                  15
```

Gly Arg Val Thr Ile Thr Cys Lys Ala Ser Gln Asp Ile Lys Lys Tyr
            20                  25                  30

Ile Ala Trp Tyr Gln His Lys Pro Gly Lys Thr Pro Arg Leu Leu Ile
            35                  40                  45

His Phe Thr Ser Thr Leu Gln Thr Gly Ile Pro Ser Arg Phe Ser Gly
        50                  55                  60

Arg Gly Ser Gly Arg Asp Tyr Ser Phe Ser Ile Ser Asn Leu Glu Ser
65                  70                  75                  80

Glu Asp Ile Ala Thr Tyr Tyr Cys Leu Gln Tyr Asp Ser Leu Tyr Thr
                85                  90                  95

Phe Gly Gly Gly Thr Lys Leu Glu Ile Lys Arg Ala Ala Ala
            100                 105                 110

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Lys Ser Tyr Phe Ser Asp Cys Gln Val Asn Asn Phe Arg Ser
1               5                   10

<210> SEQ ID NO 31
<211> LENGTH: 18
<212> TYPE: PRT
<213> ORGANISM: Artificial Sequence
<220> FEATURE:
<223> OTHER INFORMATION: Synthetic

<400> SEQUENCE: 31

Thr Leu Asp Arg Ser Ser Val Leu Val Asp Gly Tyr Ser Gln Asn Arg
1               5                   10                  15

Asp Asp

<210> SEQ ID NO 32
<211> LENGTH: 57
<212> TYPE: DNA
<213> ORGANISM: Artificial Sequence
<220> FEATURE:
<223> OTHER INFORMATION: CD8 leader sequence

<400> SEQUENCE: 32
atggctctcc cagtgactgc cctactgctt ccCctagcgc ttctcctgca tgcagag         57

<210> SEQ ID NO 33
<211> LENGTH: 335
<212> TYPE: DNA
<213> ORGANISM: Artificial Sequence
<220> FEATURE:
<223> OTHER INFORMATION: CD3 zeta chain intracellular domain

<400> SEQUENCE: 33
agagtgaagt tcagcaggag cgcagagccc ccgcgtacc agcagggcca gaaccagctc         60
tataacgagc tcaatctagg acgaagagag gagtacgatg ttttggacaa gagacgtggc        120
cgggaccctg agatgggggg aaagccgaga aggaagaacc ctcaggaagg cctgtacaat        180
gaactgcaga agataagat ggcggaggcc tacagtgaga ttgggatgaa aggcgagcgc        240
cggaggggca aggggcacga tggcctttac cagggtctca gtacagccac caaggacacc        300
tacgacgccc ttcacatgca ggccctgccc cctcg                                   335

<210> SEQ ID NO 34
<211> LENGTH: 45
<212> TYPE: DNA
<213> ORGANISM: Artificial Sequence
<220> FEATURE:
<223> OTHER INFORMATION: (G4S)3 serine-glycine linker

<400> SEQUENCE: 34

```
ggtggaggtg gatcaggtgg aggtggatct ggtggaggtg gatct              45
```

<210> SEQ ID NO 35
<211> LENGTH: 225
<212> TYPE: DNA
<213> ORGANISM: Artificial Sequence
<220> FEATURE:
<223> OTHER INFORMATION: CD8 transmembrane domain

<400> SEQUENCE: 35

```
gcggccgcac ccaccacgac gccagcgccg cgaccaccaa ccccggcgcc cacgatcgcg    60
tcgcagcccc tgtccctgcg cccagaggcg tgccggccag cggcgggggg cgcagtgcac   120
acgaggggc tggacttcgc ctgtgatatc tacatctggg cgcccttggc cgggacttgt    180
ggggtccttc tcctgtcact ggttatcacc ctttactgca accac                   225
```

<210> SEQ ID NO 36
<211> LENGTH: 223
<212> TYPE: DNA
<213> ORGANISM: Artificial Sequence
<220> FEATURE:
<223> OTHER INFORMATION: CD28 transmembrane + intracellular domains
      (-STOP)

<400> SEQUENCE: 36

```
caattgaagt tatgtatcct cctccttacc tagacaatga agagcaat ggaaccatta      60
tccatgtgaa agggaaacac ctttgtccaa gtccccatt tcccggacct tctaagccct    120
tttgggtgct ggtggtggtt ggtggagtcc tggcttgcta tagcttgcta gtaacagtgg   180
cctttattat tttctgggtg aggagtaaga ggagcaggct cct                     223
```

<210> SEQ ID NO 37
<211> LENGTH: 7726
<212> TYPE: DNA
<213> ORGANISM: Artificial Sequence
<220> FEATURE:
<223> OTHER INFORMATION: SFG_4H11z forward sequence

<400> SEQUENCE: 37

```
ggatccggat tagtccaatt tgttaaagac aggatatcag tggtccaggc tctagttttg    60
actcaacaat atcaccagct gaagcctata gagtacgagc catagataaa ataaaagatt   120
ttatttagtc tccagaaaaa ggggggaatg aaagacccca cctgtaggtt tggcaagcta   180
gcttaagtaa cgccatttg caaggcatgg aaaaatacat aactgagaat agagaagttc    240
agatcaaggt caggaacaga tggaacagct gaatatgggc caaacaggat atctgtggta   300
agcagttcct gccccggctc agggccaaga acagatggaa cagctgaata tgggccaaac   360
aggatatctg tggtaagcag ttcctgcccc ggctcagggc caagaacaga tggtccccag   420
atgcggtcca gccctcagca gtttctagag aaccatcaga tgtttccagg gtgccccaag   480
gacctgaaat gaccctgtgc cttatttgaa ctaaccaatc agttcgcttc tcgcttctgt   540
tcgcgcgctt ctgctccccg agctcaataa aagagcccac aacccctcac tcggggcgcc   600
```

```
agtcctccga ttgactgagt cgcccgggta cccgtgtatc caataaaccc tcttgcagtt    660
gcatccgact tgtggtctcg ctgttccttg ggagggtctc ctctgagtga ttgactaccc    720
gtcagcgggg gtcttccaca catgcagcat gtatcaaaat taatttggtt ttttttctta    780
agtatttaca ttaaatggcc atagtactta aagttacatt ggcttccttg aaataaacat    840
ggagtattca gaatgtgtca taaatatttc taattttaag atagtatctc cattggcttt    900 ctacttttc ttttattttt ttttgtcctc tgtcttccat ttgttgttgt tgttgtttgt    960
ttgtttgttt gttggttggt tggttaattt tttttttaaag atcctacact atagttcaag   1020
ctagactatt agctactctg taacccaggg tgaccttgaa gtcatgggta gcctgctgtt   1080
ttagccttcc cacatctaag attacaggta tgagctatca tttttggtat attgattgat   1140
tgattgattg atgtgtgtgt gtgtgattgt gtttgtgtgt gtgactgtga aaatgtgtgt   1200
atgggtgtgt gtgaatgtgt gtatgtatgt gtgtgtgtga gtgtgtgtgt gtgtgtgtgc   1260
atgtgtgtgt gtgtgactgt gtctatgtgt atgactgtgt gtgtgtgtgt gtgtgtgtgt   1320
gtgtgtgtgt gtgtgtgtgt gttgtgaaaa aatattctat ggtagtgaga gccaacgctc   1380
cggctcaggt gtcaggttgg tttttgagac agagtctttc acttagcttg gaattcactg   1440
gccgtcgttt tacaacgtcg tgactgggaa acccctggcg ttacccaact taatcgcctt   1500
gcagcacatc ccccttttcgc cagctggcgt aatagcgaag aggcccgcac cgatcgccct   1560
tcccaacagt tgcgcagcct gaatggcgaa tggcgcctga tgcggtattt tctccttacg   1620
catctgtgcg gtatttcaca ccgcatatgg tgcactctca gtacaatctg ctctgatgcc   1680
gcatagttaa gccagccccg acacccgcca acacccgctg acgcgccctg acgggcttgt   1740
ctgctcccgg catccgctta cagacaagct gtgaccgtct ccgggagctg catgtgtcag   1800
aggttttcac cgtcatcacc gaaacgcgcg atgacgaaag ggcctcgtga tacgcctatt   1860
tttataggtt aatgtcatga taataatggt ttcttagacg tcaggtggca cttttcgggg   1920
aaatgtgcgc ggaacccta tttgtttatt tttctaaata cattcaaata tgtatccgct   1980
catgagacaa taaccctgat aaatgcttca ataatattga aaaggaaga gtatgagtat   2040 tcaacatttc cgtgtcgccc ttattccctt ttttgcggca ttttgccttc ctgttttgc    2100 tcacccagaa acgctggtga agtaaaaga tgctgaagat cagttgggtg cacgagtggg   2160
ttacatcgaa ctggatctca acagcggtaa gatccttgag agttttcgcc ccgaagaacg   2220
ttttccaatg atgagcactt ttaaagttct gctatgtggc gcggtattat cccgtattga   2280
cgccgggcaa gagcaactcg gtcgccgcat acactattct cagaatgact tggttgagta   2340
ctcaccagtc acagaaaagc atcttacgga tggcatgaca gtaagagaat tatgcagtgc   2400
tgccataacc atgagtgata acactgcggc caacttactt ctgacaacga tcggaggacc   2460
gaaggagcta accgcttttt tgcacaacat ggggatcat gtaactcgcc ttgatcgttg   2520
ggaaccggag ctgaatgaag ccataccaaa cgacgagcgt gacaccacga tgcctgtagc   2580
aatggcaaca acgttgcgca aactattaac tggcgaacta cttactctag cttcccggca   2640
acaattaata gactgatgg aggcggataa agttgcagga ccacttctgc gctcggccct   2700
tccggctggc tggtttattg ctgataaatc tggagccggt gagcgtgggt ctcgcggtat   2760
cattgcagca ctggggccag atggtaagcc ctcccgtatc gtagttatct acacgacggg   2820
gagtcaggca actatggatg aacgaaatag acagatcgct gagataggtg cctcactgat   2880
taagcattgg taactgtcag accaagttta ctcatatata ctttagattg atttaaaact   2940
```

```
tcattttta  tttaaaagga  tctaggtgaa  gatccttttt  gataatctca  tgaccaaaat    3000
cccttaacgt  gagttttcgt  tccactgagc  gtcagacccc  gtagaaaaga  tcaaaggatc    3060
ttcttgagat  cctttttttc  tgcgcgtaat  ctgctgcttg  caaacaaaaa  aaccaccgct    3120
accagcggtg  gtttgtttgc  cggatcaaga  gctaccaact  cttttttccga  aggtaactgg    3180 cttcagcaga  gcgcagatac  caaatactgt  ccttctagtg  tagccgtagt  taggccacca    3240
cttcaagaac  tctgtagcac  cgcctacata  cctcgctctg  ctaatcctgt  taccagtggc    3300
tgctgccagt  ggcgataagt  cgtgtcttac  cgggttggac  tcaagacgat  agttaccgga    3360
taaggcgcag  cggtcgggct  gaacggggggg  ttcgtgcaca  cagcccagct  tggagcgaac    3420
gacctacacc  gaactgagat  acctacagcg  tgagcattga  gaaagcgcca  cgcttcccga    3480
agggagaaag  gcggacaggt  atccggtaag  cggcagggtc  ggaacaggag  agcgcacgag    3540
ggagcttcca  gggggaaacg  cctggtatct  ttatagtcct  gtcgggtttc  gccacctctg    3600
acttgagcgt  cgatttttgt  gatgctcgtc  aggggggcgg  agcctatgga  aaaacgccag    3660
caacgcggcc  ttttacggt  tcctggcctt  ttgctggcct  tttgctcaca  tgttctttcc    3720
tgcgttatcc  cctgattctg  tggataaccg  tattaccgcc  tttgagtgag  ctgataccgc    3780
tcgccgcagc  cgaacgaccg  agcgcagcga  gtcagtgagc  gaggaagcgg  aagagcgccc    3840
aatacgcaaa  ccgcctctcc  ccgcgcgttg  gccgattcat  taatgcagct  ggcacgacag    3900
gtttcccgac  tggaaagcgg  gcagtgagcg  caacgcaatt  aatgtgagtt  agctcactca    3960
ttaggcaccc  caggctttac  actttatgct  tccggctcgt  atgttgtgtg  gaattgtgag    4020
cggataacaa  tttcacacag  gaaacagcta  tgaccatgat  tacgccaagc  tttgctctta    4080
ggagtttcct  aatacatccc  aaactcaaat  atataaagca  tttgacttgt  tctatgccct    4140
agggggcggg  gggaagctaa  gccagctttt  tttaacatt  aaaatgttaa  ttccatttta    4200
aatgcacaga  tgttttatt  tcataagggt  ttcaatgtgc  atgaatgctg  caatattcct    4260
gttaccaaag  ctagtataaa  taaaaataga  taaacgtgga  aattacttag  agtttctgtc    4320
attaacgttt  ccttcctcag  ttgacaacat  aaatgcgctg  ctgagcaagc  cagtttgcat    4380
ctgtcaggat  caatttccca  ttatgccagt  catattaatt  actagtcaat  tagttgattt    4440 ttattttga  catatacatg  tgaatgaaag  accccacctg  taggtttggc  aagctagctt    4500
aagtaacgcc  atttttgcaag  gcatggaaaa  atacataact  gagaatagaa  aagttcagat    4560
caaggtcagg  aacagatgga  acagctgaat  atgggccaaa  caggatatct  gtggtaagca    4620
gttcctgccc  cggctcaggg  ccaagaacag  atggaacagc  tgaatatggg  ccaaacagga    4680
tatctgtggt  aagcagttcc  tgccccggct  cagggccaag  aacagatggt  ccccagatgc    4740
ggtccagccc  tcagcagttt  ctagagaacc  atcagatgtt  tccagggtgc  cccaaggacc    4800
tgaaatgacc  ctgtgcctta  tttgaactaa  ccaatcagtt  cgcttctcgc  ttctgttcgc    4860
gcgcttatgc  tccccgagct  caataaaaga  gcccacaacc  cctcactcgg  ggcgccagtc    4920
ctccgattga  ctgagtcgcc  cgggtacccg  tgtatccaat  aaaccctctt  gcagttgcat    4980
ccgacttgtg  gtctcgctgt  tccttgggag  ggtctcctct  gagtgattga  ctacccgtca    5040 gcggggggtct  ttcatttggg  ggctcgtccg  ggatcgggag  acccctgccc  agggaccacc    5100
gacccaccac  cgggaggtaa  gctggccagc  aacttatctg  tgtctgtccg  attgtctagt    5160
gtctatgact  gatttatgc  gcctgcgtcg  gtactagtta  gctaactagc  tctgtatctg    5220
gcggacccgt  ggtggaactg  acgagttcgg  aacacccggc  cgcaaccctg  ggagacgtcc    5280
cagggacttc  gggggccgtt  tttgtggccc  gacctgagtc  ctaaaatccc  gatcgtttag    5340
```

-continued

```
gactctttgg tgcacccccc ttagaggagg gatatgtggt tctggtagga gacgagaacc    5400
taaaacagtt cccgcctccg tctgaatttt tgctttcggt ttgggaccga agccgcgccg    5460
cgcgtcttgt ctgctgcagc atcgttctgt gttgtctctg tctgactgtg tttctgtatt    5520
tgtctgaaaa tatgggcccg ggctagactg ttaccactcc cttaagtttg accttaggtc    5580
actggaaaga tgtcgagcgg atcgctcaca accagtcggt agatgtcaag aagagacgtt    5640
gggttacctt ctgctctgca gaatggccaa cctttaacgt cggatggccg cgagacggca    5700
cctttaaccg agacctcatc acccaggtta agatcaaggt cttttcacct ggcccgcatg    5760
gacacccaga ccaggtcccc tacatcgtga cctgggaagc cttggctttt gaccccctc     5820
cctgggtcaa gccctttgta cacctaagc ctccgcctcc tcttcctcca tccgccccgt     5880
ctctcccct tgaacctcct cgttcgaccc cgcctcgatc ctccctttat ccagccctca     5940
ctccttctct aggcgccccc atatggccat atgagatctt atatggggca ccccgcccc    6000
ttgtaaactt ccctgaccct gacatgacaa gagttactaa cagcccctct ctccaagctc    6060
acttacaggc tctctactta gtccagcacg aagtctggag acctctggcg gcagcctacc    6120
aagaacaact ggaccgaccg gtggtacctc acccttaccg agtcggcgac acagtgtggg    6180
tccgccgaca ccagactaag aacctagaac ctcgctggaa aggaccttac acagtcctgc    6240
tgaccacccc caccgccctc aaagtagacg gcatcgcagc ttggatacac gccgccacg     6300
tgaaggctgc cgaccccggg ggtggaccat cctctagact gccatggctc tcccagtgac    6360
tgccctactg cttcccctag cgcttctcct gcatgcagag gtgaagctgc aggagtcagg    6420
gggaggcttc gtgaagcctg agggtccct caaagtctcc tgtgcagcct ctggattcac    6480
tttcagtagc tatgccatgt cctgggttcg cctgagtccg gagatgaggc tggagtgggt    6540
cgcaaccatt agcagtgctg gtggttacat cttctattct gacagtgtgc agggacgatt    6600
caccatttcc agagacaatg ccaagaacac cctgcacctg caaatgggca gtctgaggtc    6660
tggggacacg gccatgtatt actgtgcaag gcagggattt ggtaactacg gtgattacta    6720
tgctatggac tactggggcc aagggaccac ggtcaccgtc tcctcaggtg aggtggatc     6780
aggtggaggt ggatctggtg gaggtggatc tgacattgag ctcacccagt ctccatcctc    6840
cctggctgtg tcagcaggag agaaggtcac tatgagctgc aaatccagtc agagtctgct    6900
caacagtaga acccgaaaga accagttggc ttggtaccag caaaaaccag acagtctcc     6960
tgaactgctg atctactggg catccactag gcaatctgga gtccctgatc gcttcacagg    7020
cagtggatct gggacagatt tcactctcac catcagcagt gtgcaggctg aagacctggc    7080
agtttattac tgccagcaat cttataatct actcacgttc ggtcctggga ccaagctgga    7140
gatcaaacgg gcggccgcac ccaccacgac gccagcgccg cgaccaccaa ccccggcgcc    7200
cacgatcgcg tcgcagcccc tgtccctgcg cccagaggcg tgccggccag cggcgggggg    7260
cgcagtgcac acgaggggggc tggacttcgc ctgtgatatc tacatctggg cgcccttggc    7320
cgggacttgt ggggtccttc tcctgtcact ggttatcacc ctttactgca accacagagt    7380
gaagttcagc aggagcgcag agccccccgc gtaccagcag gccagaacc agctctataa     7440
cgagctcaat ctaggacgaa gagaggagta cgatgttttg gacaagagac gtggccggga    7500
ccctgagatg gggggaaagc cgagaaggaa gaaccctcag gaaggcctgt acaatgaact    7560
gcagaaagat aagatggcgg aggcctacag tgagattggg atgaaaggcg agcgccggag    7620
gggcaagggg cacgatggcc tttaccaggg tctcagtaca gccaccaagg acacctacga    7680
```
cgcccttcac atgcaggccc tgcccctcg ctaacagcca ctcgag      7726

<210> SEQ ID NO 38
<211> LENGTH: 7726
<212> TYPE: DNA
<213> ORGANISM: Artificial Sequence
<220> FEATURE:
<223> OTHER INFORMATION: SFG_4H11z reverse sequence

<400> SEQUENCE: 38

```
cctaggccta atcaggttaa acaatttctg tcctatagtc accaggtccg agatcaaaac      60
tgagttgtta tagtggtcga cttcggatat ctcatgctcg gtatctattt tatttttctaa    120
aataaatcag aggtcttttt ccccccttac tttctggggt ggacatccaa accgttcgat    180
cgaattcatt gcggtaaaac gttccgtacc tttttatgta ttgactctta tctcttcaag    240
tctagttcca gtccttgtct accttgtcga cttatacccg gtttgtccta tagacaccat    300
tcgtcaagga cggggccgag tcccggttct tgtctacctt gtcgacttat acccggtttg    360
tcctatagac accattcgtc aaggacgggg ccgagtcccg gttcttgtct accagggtc     420
tacgccaggt cgggagtcgt caaagatctc ttggtagtct acaaaggtcc cacggggttc    480
ctggacttta ctgggacacg gaataaactt gattggttag tcaagcgaag agcgaagaca    540
agcgcgcgaa gacgaggggc tcgagttatt ttctcgggtg ttggggagtg agccccgcgg    600
tcaggaggct aactgactca gcgggccat gggcacatag gttatttggg agaacgtcaa    660
cgtaggctga acaccagagc gacaaggaac cctcccagag gagactcact aactgatggg    720
cagtcgcccc cagaaagtgt gtacgtcgta catagtttta attaaaccaa aaaaaagaat    780
tcataaatgt aatttaccgg tatcatgaat ttcaatgtaa ccgaaggaac tttatttgta    840
cctcataagt cttacacagt atttataaag attaaaattc tatcatagag gtaaccgaaa    900
gatgaaaaag aaaataaaaa aaaacaggag acagaaggta acaacaaca acaacaaaca    960
aacaaacaaa caaccaacca accaattaaa aaaaatttc taggatgtga tatcaagttc    1020
gatctgataa tcgatgagac attgggtccc actggaactt cagtacccat cggacgacaa    1080
aatcggaagg gtgtagattc taatgtccat actcgatagt aaaaaccata taactaacta    1140
actaactaac tacacacaca cacactaaca caaacacaca cactgacact tttacacaca    1200
tacccacaca cacttacaca catacataca cacacacact cacacacaca cacacacacg    1260
tacacacaca cacactgaca cagatacaca tactgacaca cacacacaca cacacacaca    1320
cacacacaca cacacacaca caacactttt ttataagata ccatcactct cggttgcgag    1380
gccgagtcca cagtccaacc aaaaactctg tctcagaaag tgaatcgaac cttaagtgac    1440
cggcagcaaa atgttgcagc actgacccctt ttgggaccgc aatgggttga attagcggaa    1500
cgtcgtgtag ggggaaagcg gtcgaccgca ttatcgcttc tccgggcgtg gctagcggga    1560
agggttgtca acgcgtcgga cttaccgctt accgcggact acgccataaa agaggaatgc    1620
gtagacacgc cataaagtgt ggcgtatacc acgtgagagt catgttagac gagactacgg    1680
cgtatcaatt cggtcggggc tgtgggcggt tgtgggcgac tgcgcgggac tgcccgaaca    1740
gacgagggcc gtaggcgaat gtctgttcga cactggcaga ggccctcgac gtacacagtc    1800
tccaaaagtg gcagtagtgg ctttgcgcgc tactgctttc ccggagcact atgcggataa    1860
aaatatccaa ttacagtact attattacca aagaatctgc agtccaccgt gaaaagcccc    1920
tttacacgcg ccttggggat aaacaaataa aaagatttat gtaagtttat acataggcga    1980
gtactctgtt attgggacta tttacgaagt tattataact ttttccttct catactcata    2040
```

```
agttgtaaag gcacagcggg aataagggaa aaaacgccgt aaaacggaag gacaaaaacg    2100
agtgggtctt tgcgaccact ttcattttct acgacttcta gtcaaccc ac gtgctcaccc    2160 aatgtagctt gacctagagt tgtcgccatt ctaggaactc tcaaaagcgg ggcttcttgc    2220
aaaaggttac tactcgtgaa aatttcaaga cgatacaccg cgccataata gggcataact    2280
gcggcccgtt ctcgttgagc cagcggcgta tgtgataaga gtcttactga accaactcat    2340
gagtggtcag tgtcttttcg tagaatgcct accgtactgt cattctctta atacgtcacg    2400
acggtattgg tactcactat tgtgacgccg gttaatgaa gactgttgct agcctcctgg    2460
cttcctcgat tggcgaaaaa acgtgttgta cccctagta cattgagcgg aactagcaac    2520
ccttggcctc gacttacttc ggtatggttt gctgctcgca ctgtggtgct acggacatcg    2580
ttaccgttgt tgcaacgcgt ttgataattg accgcttgat gaatgagatc gaagggccgt    2640
tgttaattat ctgacctacc tccgcctatt tcaacgtcct ggtgaagacg cgagccggga    2700
aggccgaccg accaaataac gactatttag acctcggcca ctcgcaccca gagcgccata    2760
gtaacgtcgt gaccccggtc taccattcgg gagggcatag catcaataga tgtgctgccc    2820
ctcagtccgt tgatacctac ttgctttatc tgtctagcga ctctatccac ggagtgacta    2880
attcgtaacc attgacagtc tggttcaaat gagtatatat gaaatctaac taaattttga    2940
agtaaaaatt aaattttcct agatccactt ctaggaaaaa ctattagagt actggtttta    3000
gggaattgca ctcaaaagca aggtgactcg cagtctgggg catcttttct agtttcctag    3060
aagaactcta ggaaaaaaag acgcgcatta gacgacgaac gtttgttttt ttggtggcga    3120
tggtcgccac caaacaaacg gcctagttct cgatggttga gaaaaaggct tccattgacc    3180
gaagtcgtct cgcgtctatg gtttatgaca ggaagatcac atcggcatca atccggtggt    3240
gaagttcttg agacatcgtg gcggatgtat ggagcgagac gattaggaca atggtcaccg    3300
acgacggtca ccgctattca gcacagaatg gcccaacctg agttctgcta tcaatggcct    3360
attccgcgtc gccagcccga cttgcccccc aagcacgtgt gtcgggtcga acctcgcttg    3420
ctggatgtgg cttgactcta tggatgtcgc actcgtaact ctttcgcggt gcgaagggct    3480
tccctctttc cgcctgtcca taggccattc gccgtcccag ccttgtcctc tcgcgtgctc    3540
cctcgaaggt cccccttgc ggaccataga aatatcagga cagcccaaag cggtggagac    3600
tgaactcgca gctaaaaaca ctacgagcag tccccccgcc tcggatacct ttttgcggtc    3660
gttgcgccgg aaaatgcca aggaccggaa aacgaccgga aaacgagtgt acaagaaagg    3720
acgcaatagg ggactaagac acctattggc ataatgcgg aaactcactc gactatggcg    3780
agcggcgtcg gcttgctggc tcgcgtcgct cagtcactcg ctccttcgcc ttctcgcggg    3840
ttatgcgttt ggcggagagg ggcgcgcaac cggctaagta attacgtcga ccgtgctgtc    3900
caaagggctg accttcgcc cgtcactcgc gttgcgttaa ttacactcaa tcgagtgagt    3960
aatccgtggg gtccgaaatg tgaaatacga aggccgagca tacaacacac cttaacactc    4020
gcctattgtt aaagtgtgtc ctttgtcgat actggtacta atgcggttcg aaacgagaat    4080
cctcaaagga ttatgtaggg tttgagttta tatttcgt aaactgaaca agatacggga    4140
tcccccgccc cccttcgatt cggtcgaaaa aaattgtaaa ttttacaatt aaggtaaaat    4200
ttacgtgtct acaaaaataa agtattccca aagttacacg tacttacgac gttataagga    4260
caatggtttc gatcatattt attttttatct atttgcacct ttaatgaatc tcaaagacag    4320
taattgcaaa ggaaggagtc aactgttgta tttacgcgac gactcgttcg gtcaaacgta    4380
```

-continued

```
gacagtccta gttaaagggt aatacggtca gtataattaa tgatcagtta atcaactaaa    4440
aataaaaact gtatatgtac acttactttc tggggtggac atccaaaccg ttcgatcgaa    4500
ttcattgcgg taaaacgttc cgtaccttt tatgtattga ctcttatctt ttcaagtcta    4560
gttccagtcc ttgtctacct tgtcgactta tacccggttt gtcctataga caccattcgt    4620
caaggacggg gccgagtccc ggttcttgtc taccttgtcg acttatacc ggtttgtcct    4680 atagacacca ttcgtcaagg acggggccga gtcccggttc ttgtctacca ggggtctacg    4740
ccaggtcggg agtcgtcaaa gatctcttgg tagtctacaa aggtcccacg gggttcctgg    4800
actttactgg gacacggaat aaacttgatt ggttagtcaa gcgaagagcg aagacaagcg    4860
cgcgaatacg aggggctcga gttattttct cgggtgttgg ggagtgagcc ccgcggtcag    4920
gaggctaact gactcagcgg gcccatgggc acataggtta tttgggagaa cgtcaacgta    4980
ggctgaacac cagagcgaca aggaaccctc ccagaggaga ctcactaact gatgggcagt    5040
cgcccccaga agtaaaccc ccgagcaggc cctagccctc tggggacggg tccctggtgg    5100
ctgggtggtg gccctccatt cgaccggtcg ttgaatagac acagcaggc taacagatca    5160 cagatactga ctaaaatacg cggacgcagc catgatcaat cgattgatcg agacatagac    5220
cgcctgggca ccaccttgac tgctcaagcc ttgtgggccg gcgttgggac cctctgcagg    5280
gtccctgaag cccccggcaa aaacaccggg ctggactcag gattttaggg ctagcaaatc    5340
ctgagaaacc acgtggggg aatctcctcc ctatacacca agaccatcct ctgctcttgg    5400
attttgtcaa gggcggaggc agacttaaaa acgaaagcca aaccctggct tcggcgcggc    5460
gcgcagaaca gacgacgtcg tagcaagaca caacagagac agactgacac aaagacataa    5520
acagactttt atacccgggc ccgatctgac aatggtgagg gaattcaaac tggaatccag    5580
tgacctttct acagctcgcc tagcgagtgt tggtcagcca tctacagttc ttctctgcaa    5640
cccaatggaa gacgagacgt cttaccggtt ggaaattgca gcctaccggc gctctgccgt    5700
ggaaattggc tctggagtag tgggtccaat tctagttcca gaaaagtgga ccgggcgtac    5760
ctgtgggtct ggtccagggg atgtagcact ggacccttcg gaaccgaaaa ctgggggag    5820 ggacccagtt cgggaaacat gtgggattcg gagcggagg agaaggaggt aggcggggca    5880
gagaggggga acttggagga gcaagctggg gcggagctag gagggaaata ggtcgggagt    5940
gaggaagaga tccgcggggg tataccggta tactctagaa tatacccgt gggggcgggg    6000 aacatttgaa gggactggga ctgtactgtt ctcaatgatt gtcggggaga gaggttcgag    6060
tgaatgtccg agagatgaat caggtcgtgc ttcagacctc tggagaccgc cgtcggatgg    6120
ttcttgttga cctggctggc caccatggag tgggaatggc tcagccgctg tgtcacaccc    6180
aggcggctgt ggtctgattc ttggatcttg gagcgacctt tcctggaatg tgtcaggacg    6240
actggtgggg gtggcgggag tttcatctgc cgtagcgtcg aacctatgtg cggcgggtgc    6300
acttccgacg gctggggccc ccacctggta ggagatctga cggtaccgag agggtcactg    6360
acgggatgac gaagggatc gcgaagagga cgtacgtctc cacttcgacg tcctcagtcc    6420
ccctccgaag cacttcggac ctcccaggga gtttcagagg acacgtcgga gacctaagtg    6480
aaagtcatcg atacggtaca ggacccaagc ggactcaggc ctctactccg acctcaccca    6540
gcgttggtaa tcgtcacgac caccaatgta gaagataaga ctgtcacacg tccctgctaa    6600
gtggtaaagg tctctgttac ggttcttgtg ggacgtggac gtttaccgt cagactccag    6660 accccgtgc cggtacataa tgacacgttc cgtccctaaa ccattgatgc cactaatgat    6720
acgatacctg atgaccccgg ttccctggtg ccagtggcag aggagtccac ctccacctag    6780
```

```
tccacctcca cctagaccac ctccacctag actgtaactc gagtgggtca gaggtaggag    6840
ggaccgacac agtcgtcctc tcttccagtg atactcgacg tttaggtcag tctcagacga    6900
gttgtcatct tgggctttct tggtcaaccg aaccatggtc gttttggtc ctgtcagagg     6960 acttgacgac tagatgaccc gtaggtgatc cgttagacct cagggactag cgaagtgtcc    7020
gtcacctaga ccctgtctaa agtgagagtg gtagtcgtca cacgtccgac ttctggaccg    7080
tcaaataatg acgtcgtta gaatattaga tgagtgcaag ccaggaccct ggttcgacct     7140
ctagtttgcc cgccggcgtg ggtggtgctg cggtcgcggc gctggtggtt ggggccgcgg    7200
gtgctagcgc agcgtcgggg acagggacgg gggtctccgc acggccggtc gccgcccccc    7260
gcgtcacgtg tgctcccccg acctgaagcg acactatag atgtagaccc gcgggaaccg     7320
gccctgaaca ccccaggaag aggacagtga ccaatagtgg gaaatgacgt tggtgtctca    7380
cttcaagtcg tcctcgcgtc tcgggggcg catggtcgtc ccggtcttgg tcgagatatt      7440
gctcgagtta gatcctgctt ctctcctcat gctacaaaac ctgttctctg caccggccct    7500
gggactctac cccccttcg gctcttcctt cttgggagtc cttccggaca tgttacttga     7560 cgtcttcta ttctaccgcc tccggatgtc actctaaccc tactttccgc tcgcggcctc     7620
cccgttcccc gtgctaccgg aaatggtccc agagtcatgt cggtggttcc tgtggatgct    7680
gcgggaagtg tacgtccggg acggggagc gattgtcggt gagctc                    7726
```

<210> SEQ ID NO 39
<211> LENGTH: 7831
<212> TYPE: DNA
<213> ORGANISM: Artificial Sequence
<220> FEATURE:
<223> OTHER INFORMATION: SFG_4H11-28z forward sequence

<400> SEQUENCE: 39

```
ggatccggat tagtccaatt tgttaaagac aggatatcag tggtccaggc tctagttttg      60
actcaacaat atcaccagct gaagcctata gagtacgagc catagataaa ataaaagatt     120
ttatttagtc tccagaaaaa gggggaatg aaagacccca cctgtaggtt tggcaagcta      180
gcttaagtaa cgccattttg caaggcatgg aaaaatacat aactgagaat agagaagttc     240
agatcaaggt caggaacaga tggaacagct gaatatgggc caaacaggat atctgtggta    300
agcagttcct gccccggctc agggccaaga acagatggaa cagctgaata tgggccaaac    360
aggatatctg tggtaagcag ttcctgcccc ggctcagggc caagaacaga tggtccccag    420
atgcggtcca gccctcagca gtttctagag aaccatcaga tgtttccagg gtgccccaag    480
gacctgaaat gaccctgtgc cttatttgaa ctaaccaatc agttcgcttc tcgcttctgt    540
tcgcgcgctt ctgctccccg agctcaataa aagagcccac aacccctcac tcggggcgcc    600
agtcctccga ttgactgagt cgcccgggta cccgtgtatc caataaaccc tcttgcagtt    660
gcatccgact tgtggtctcg ctgttccttg ggagggtctc ctctgagtga ttgactaccc    720
gtcagcgggg gtcttcaca catgcagcat gtatcaaaat taatttggtt tttttctta      780 agtatttaca ttaaatggcc atagtactta aagttacatt ggcttccttg aaataaacat    840
ggagtattca gaatgtgtca taaatatttc taattttaag atagtatctc cattggcttt     900 ctacttttc ttttattttt tttgtcctc tgtcttccat ttgttgttgt tgttgtttgt      960
ttgtttgttt gttggttggt tggttaattt ttttttaaag atcctacact atagttcaag    1020
ctagactatt agctactctg taacccaggg tgaccttgaa gtcatgggta gcctgctgtt    1080
```

```
ttagccttcc cacatctaag attacaggta tgagctatca ttttggtat attgattgat    1140
tgattgattg atgtgtgtgt gtgtgattgt gtttgtgtgt gtgactgtga aaatgtgtgt    1200
atgggtgtgt gtgaatgtgt gtatgtatgt gtgtgtgtga gtgtgtgtgt gtgtgtgtgc    1260
atgtgtgtgt gtgtgactgt gtctatgtgt atgactgtgt gtgtgtgtgt gtgtgtgtgt    1320
gtgtgtgtgt gtgtgtgtgt gttgtgaaaa aatattctat ggtagtgaga gccaacgctc    1380
cggctcaggt gtcaggttgg ttttgagac agagtctttc acttagcttg gaattcactg     1440
gccgtcgttt tacaacgtcg tgactgggaa accctggcg ttacccaact taatcgcctt    1500
gcagcacatc ccccttcgc cagctggcgt aatagcgaag aggcccgcac cgatcgccct    1560
tcccaacagt tgcgcagcct gaatggcgaa tggcgcctga tgcggtattt tctccttacg    1620
catctgtgcg gtatttcaca ccgcatatgg tgcactctca gtacaatctg ctctgatgcc    1680
gcatagttaa gccagccccg acacccgcca acacccgctg acgcgccctg acgggcttgt    1740
ctgctcccgg catccgctta cagacaagct gtgaccgtct ccgggagctg catgtgtcag    1800
aggttttcac cgtcatcacc gaaacgcgcg atgacgaaag gcctcgtga tacgcctatt     1860
tttataggtt aatgtcatga taataatggt ttcttagacg tcaggtggca cttttcgggg    1920
aaatgtgcgc ggaaccccta ttgtttatt tttctaaata cattcaaata tgtatccgct    1980
catgagacaa taaccctgat aaatgcttca ataatattga aaaggaaga gtatgagtat    2040
tcaacatttc cgtgtcgccc ttattccctt ttttgcggca ttttgccttc ctgtttttgc    2100
tcacccagaa acgctggtga agtaaaaga tgctgaagat cagttgggtg cacgagtggg    2160
ttacatcgaa ctggatctca acagcggtaa gatccttgag agttttcgcc ccgaagaacg    2220
ttttccaatg atgagcactt ttaaagttct gctatgtggc gcggtattat cccgtattga    2280
cgccgggcaa gagcaactcg gtcgccgcat acactattct cagaatgact tggttgagta    2340
ctcaccagtc acagaaaagc atcttacgga tggcatgaca gtaagagaat tatgcagtgc    2400
tgccataacc atgagtgata acactgcggc caacttactt ctgacaacga tcggaggacc    2460
gaaggagcta accgcttttt tgcacaacat ggggatcat gtaactcgcc ttgatcgttg    2520
ggaaccggag ctgaatgaag ccataccaaa cgacagcgt gacaccacga tgcctgtagc    2580
aatggcaaca acgttgcgca aactattaac tggcgaacta cttactctag cttcccggca    2640
acaattaata gactgatgg aggcggataa agttgcagga ccacttctgc gctcggccct    2700
tccggctggc tggtttattg ctgataaatc tggagccggt gagcgtgggt ctcgcggtat    2760
cattgcagca ctggggccag atggtaagcc ctcccgtatc gtagttatct acacgacggg    2820
gagtcaggca actatggatg aacgaaatag acagatcgct gagataggtg cctcactgat    2880
taagcattgg taactgtcag accaagttta ctcatatata ctttagattg atttaaaact    2940
tcatttttaa tttaaaagga tctaggtgaa gatcctttt gataatctca tgaccaaaat    3000
cccttaacgt gagttttcgt tccactgagc gtcagacccc gtagaaaaga tcaaaggatc    3060
ttcttgagat ccttttttc tgcgcgtaat ctgctgcttg caaacaaaaa aaccaccgct    3120
accagcggtg gtttgtttgc cggatcaaga gctaccaact cttttccga aggtaactgg    3180
cttcagcaga gcgcagatac caaatactgt ccttctagtg tagccgtagt taggccacca    3240
cttcaagaac tctgtagcac cgcctacata cctcgctctg ctaatcctgt taccagtggc    3300
tgctgccagt ggcgataagt cgtgtcttac cgggttggac tcaagacgat agttaccgga    3360
taaggcgcag cggtcgggct gaacgggggg ttcgtgcaca cagcccagct tggagcgaac    3420
gacctacacc gaactgagat acctacagcg tgagcattga gaaagcgcca cgcttcccga    3480
```

```
agggagaaag gcggacaggt atccggtaag cggcagggtc ggaacaggag agcgcacgag   3540
ggagcttcca gggggaaacg cctggtatct ttatagtcct gtcgggtttc gccacctctg   3600
acttgagcgt cgattttttgt gatgctcgtc agggggcgg agcctatgga aaaacgccag   3660
caacgcggcc ttttttacggt tcctggcctt ttgctggcct tttgctcaca tgttctttcc   3720
tgcgttatcc cctgattctg tggataaccg tattaccgcc tttgagtgag ctgataccgc   3780
tcgccgcagc cgaacgaccg agcgcagcga gtcagtgagc gaggaagcgg aagagcgccc   3840
aatacgcaaa ccgcctctcc ccgcgcgttg gccgattcat taatgcagct ggcacgacag   3900
gtttcccgac tggaaagcgg gcagtgagcg caacgcaatt aatgtgagtt agctcactca   3960
ttaggcaccc caggctttac actttatgct tccggctcgt atgttgtgtg gaattgtgag   4020
cggataacaa tttcacacag gaaacagcta tgaccatgat tacgccaagc tttgctctta   4080
ggagtttcct aatacatccc aaactcaaat atataaagca tttgacttgt tctatgccct   4140 aggggcggg gggaagctaa gccagctttt tttaacattt aaaatgttaa ttccatttta   4200
aatgcacaga tgtttttatt tcataagggt ttcaatgtgc atgaatgctg caatattcct   4260
gttaccaaag ctagtataaa taaaaataga taaacgtgga aattacttag agtttctgtc   4320
attaacgttt ccttcctcag ttgacaacat aaatgcgctg ctgagcaagc cagtttgcat   4380
ctgtcaggat caatttccca ttatgccagt catattaatt actagtcaat tagttgattt   4440
ttatttttga catatacatg tgaatgaaag accccacctg taggtttggc aagctagctt   4500
aagtaacgcc attttgcaag gcatggaaaa atacataact gagaatagaa aagttcagat   4560
caaggtcagg aacagatgga acagctgaat atgggccaaa caggatatct gtggtaagca   4620
gttcctgccc cggctcaggg ccaagaacag atggaacagc tgaatatggg ccaaacagga   4680
tatctgtggt aagcagttcc tgccccggct cagggccaag aacagatggt ccccagatgc   4740
ggtccagccc tcagcagttt ctagagaacc atcagatgtt tccagggtgc cccaaggacc   4800
tgaaatgacc ctgtgcctta tttgaactaa ccaatcagtt cgcttctcgc ttctgttcgc   4860
gcgcttatgc tccccgagct caataaaaga gcccacaacc cctcactcgg ggcgccagtc   4920
ctccgattga ctgagtcgcc cgggtacccg tgtatccaat aaaccctctt gcagttgcat   4980
ccgacttgtg gtctcgctgt tccttgggag ggtctcctct gagtgattga ctacccgtca   5040 gcggggtct ttcatttggg ggctcgtccg ggatcgggag acccctgccc agggaccacc   5100
gacccaccac cggggaggtaa gctggccagc aacttatctg tgtctgtccg attgtctagt   5160
gtctatgact gattttatgc gcctgcgtcg gtactagtta gctaactagc tctgtatctg   5220
gcggacccgt ggtggaactg acgagttcgg aacacccggc cgcaaccctg ggagacgtcc   5280
cagggacttc gggggccgtt tttgtggccc gacctgagtc ctaaaatccc gatcgtttag   5340
gactctttgg tgcaccccc ttagaggagg gatatgtggt tctggtagga gacgagaacc   5400
taaaacagtt cccgcctccg tctgaattttt gctttcggt ttgggaccga agccgcgccg   5460
cgcgtcttgt ctgctgcagc atcgttctgt gttgtctctg tctgactgtg tttctgtatt   5520
tgtctgaaaa tatgggcccg ggctagactg ttaccactcc cttaagtttg acttaggtc   5580 actgaaagaa tgtcgagcgg atcgctcaca accagtcggt agatgtcaag aagagacgtt   5640
gggttacctt ctgctctgca gaatggccaa cctttaacgt cggatggccg cgagacggca   5700
cctttaaccg agacctcatc acccaggtta agatcaaggt cttttcacct ggcccgcatg   5760
gacacccaga ccaggtcccc tacatcgtga cctgggaagc cttggctttt gacccccctc   5820
```

```
cctgggtcaa gcccttttgta caccctaagc ctccgcctcc tcttcctcca tccgccccgt    5880
ctctccccct tgaacctcct cgttcgaccc cgcctcgatc ctccctttat ccagccctca    5940
ctccttctct aggcgccccc atatggccat atgagatctt atatggggca ccccgcccc    6000 ttgtaaactt ccctgaccct gacatgacaa gagttactaa cagcccctct ctccaagctc    6060
acttacaggc tctctactta gtccagcacg aagtctggag acctctggcg cagcctacc    6120 aagaacaact ggaccgaccg gtggtacctc acccttaccg agtcggcgac acagtgtggg    6180
tccgccgaca ccagactaag aacctagaac ctcgctggaa aggaccttac acagtcctgc    6240
tgaccacccc caccgccctc aaagtagacg gcatcgcagc ttggatacac gccgcccacg    6300
tgaaggctgc cgaccccggg ggtggaccat cctctagact gccatggctc tcccagtgac    6360
tgccctactg cttcccctag cgcttctcct gcatgcagag gtgaagctgc aggagtcagg    6420
gggaggcttc gtgaagcctg agggtccct caaagtctcc tgtgcagcct ctggattcac    6480
tttcagtagc tatgccatgt cctgggttcg cctgagtccg gagatgaggc tggagtgggt    6540
cgcaaccatt agcagtgctg gtggttacat cttctattct gacagtgtgc agggacgatt    6600
caccatttcc agacacaatg ccaagaacac cctgcacctg caaatgggca gtctgaggtc    6660
tggggacacg gccatgtatt actgtgcaag gcagggattt ggtaactacg gtgattacta    6720
tgctatggac tactggggcc aagggaccac ggtcaccgtc tcctcaggtg gaggtggatc    6780
aggtggaggt ggatctggtg gaggtggatc tgacattgag ctcacccagt ctccatcctc    6840
cctggctgtg tcagcaggag agaaggtcac tatgagctgc aaatccagtc agagtctgct    6900
caacagtaga acccgaaaga accagttggc ttggtaccag caaaaaccag acagtctcc    6960 tgaactgctg atctactggg catccactag gcaatctgga gtccctgatc gcttcacagg    7020
cagtggatct gggacagatt tcactctcac catcagcagt gtgcaggctg aagacctggc    7080
agtttattac tgccagcaat cttataatct actcacgttc ggtcctggga ccaagctgga    7140
gatcaaacgg gcgccgcaa ttgaagttat gtatcctcct ccttacctag acaatgagaa    7200
gagcaatgga accattatcc atgtgaaagg gaaacacctt tgtccaagtc cctatttcc    7260 cggaccttct aagccctttt gggtgctggt ggtggttggt ggagtcctgg cttgctatag    7320
cttgctagta acagtggcct ttattatttt ctgggtgagg agtaagagga gcaggctcct    7380
gcacagtgac tacatgaaca tgactccccg ccgccccggg cccacccgca agcattacca    7440 gcccctatgcc ccaccacgcg acttcgcagc ctatcgctcc agagtgaagt tcagcaggag    7500
cgcagagccc cccgcgtacc agcagggcca gaaccagctc tataacgagc tcaatctagg    7560
acgaagagag gagtacgatg ttttggacaa gagacgtggc cgggaccctg agatgggggg    7620
aaagccgaga aggaagaacc ctcaggaagg cctgtacaat gaactgcaga agataagat    7680 ggcggaggcc tacagtgaga ttgggatgaa aggcgagcgc cggaggggca aggggcacga    7740
tggcctttac cagggtctca gtacagccac caaggacacc tacgacgccc ttcacatgca    7800
ggccctgccc cctcgctaac agccactcga g                                    7831
```

<210> SEQ ID NO 40
<211> LENGTH: 7831
<212> TYPE: DNA
<213> ORGANISM: Artificial Sequence
<220> FEATURE:
<223> OTHER INFORMATION: SFG_4H11-28z reverse sequence

<400> SEQUENCE: 40

```
cctaggccta atcaggttaa acaatttctg tcctatagtc accaggtccg agatcaaaac    60
```

```
tgagttgtta tagtggtcga cttcggatat ctcatgctcg gtatctattt tattttctaa    120
aataaatcag aggtcttttt ccccccttac tttctggggt ggacatccaa accgttcgat    180
cgaattcatt gcggtaaaac gttccgtacc tttttatgta ttgactctta tctcttcaag    240
tctagttcca gtccttgtct accttgtcga cttatacccg gtttgtccta tagacaccat    300
tcgtcaagga cggggccgag tcccggttct tgtctacctt gtcgacttat acccggtttg    360
tcctatagac accattcgtc aaggacgggg ccgagtcccg gttcttgtct accaggggtc    420
tacgccaggt cgggagtcgt caaagatctc ttggtagtct acaaaggtcc cacggggttc    480
ctggacttta ctgggacacg gaataaactt gattggttag tcaagcgaag agcgaagaca    540
agcgcgcgaa gacgaggggc tcgagttatt ttctcgggtg ttggggagtg agccccgcgg    600
tcaggaggct aactgactca gcgggcccat gggcacatag gttatttggg agaacgtcaa    660
cgtaggctga acaccagagc gacaaggaac cctcccagag gagactcact aactgatggg    720
cagtcgcccc cagaaagtgt gtacgtcgta catagtttta attaaaccaa aaaaaagaat    780
tcataaatgt aatttaccgg tatcatgaat ttcaatgtaa ccgaaggaac tttatttgta    840
cctcataagt cttacacagt atttataaag attaaaattc tatcatagag gtaaccgaaa    900
gatgaaaaag aaaataaaaa aaaacaggag acagaaggta aacaacaaca acaacaaaca    960
aacaaacaaa caaccaacca accaattaaa aaaaatttc taggatgtga tatcaagttc    1020
gatctgataa tcgatgagac attgggtccc actggaactt cagtacccat cggacgacaa    1080
aatcggaagg gtgtagattc taatgtccat actcgatagt aaaaaccata taactaacta    1140
actaactaac tacacacaca cacactaaca caaacacaca cactgacact tttacacaca    1200
tacccacaca cacttacaca catacataca cacacacact cacacacaca cacacacacg    1260
tacacacaca cacactgaca cagatacaca tactgacaca cacacacaca cacacacaca    1320
cacacacaca cacacacaca caacactttt ttataagata ccatcactct cggttgcgag    1380
gccgagtcca cagtccaacc aaaaactctg tctcagaaag tgaatcgaac cttaagtgac    1440
cggcagcaaa atgttgcagc actgacccct ttgggaccgc aatgggttga attagcggaa    1500
cgtcgtgtag ggggaaagcg gtcgaccgca ttatcgcttc tccgggcgtg gctagcggga    1560
agggttgtca acgcgtcgga cttaccgctt accgcggact acgccataaa agaggaatgc    1620
gtagacacgc cataaagtgt ggcgtatacc acgtgagagt catgttagac gagactacgg    1680
cgtatcaatt cggtcggggc tgtgggcggt tgtgggcgac tgcgcgggac tgcccgaaca    1740
gacgagggcc gtaggcgaat gtctgttcga cactggcaga ggccctcgac gtacacagtc    1800
tccaaaagtg gcagtagtgg ctttgcgcgc tactgctttc ccggagcact atgcggataa    1860
aaatatccaa ttacagtact attattacca aagaatctgc agtccaccgt gaaaagcccc    1920
tttacacgcg ccttggggat aaacaaataa aaagatttat gtaagtttat acataggcga    1980
gtactctgtt attgggacta tttacgaagt tattataact ttttccttct catactcata    2040
agttgtaaag gcacagcggg aataagggaa aaaacgccgt aaaacggaag gacaaaaacg    2100
agtgggtctt tgcgaccact ttcatttttct acgacttcta gtcaacccac gtgctcaccc    2160
aatgtagctt gacctagagt tgtcgccatt ctaggaactc tcaaaagcgg ggcttcttgc    2220
aaaaggttac tactcgtgaa aatttcaaga cgatacaccg cgccataata gggcataact    2280
gcggcccgtt ctcgttgagc cagcggccgta tgtgataaga gtcttactga accaactcat    2340
gagtggtcag tgtcttttcg tagaatgcct accgtactgt cattctctta atacgtcacg    2400
```

```
acggtattgg tactcactat tgtgacgccg gttgaatgaa gactgttgct agcctcctgg    2460
cttcctcgat tggcgaaaaa acgtgttgta cccctagta cattgagcgg aactagcaac    2520
ccttggcctc gacttacttc ggtatggttt gctgctcgca ctgtggtgct acggacatcg    2580
ttaccgttgt tgcaacgcgt ttgataattg accgcttgat gaatgagatc gaagggccgt    2640
tgttaattat ctgacctacc tccgcctatt tcaacgtcct ggtgaagacg cgagccggga    2700
aggccgaccg accaaataac gactatttag acctcggcca ctcgcaccca gagcgccata    2760
gtaacgtcgt gaccccggtc taccattcgg gagggcatag catcaataga tgtgctgccc    2820
ctcagtccgt tgatacctac ttgctttatc tgtctagcga ctctatccac ggagtgacta    2880
attcgtaacc attgacagtc tggttcaaat gagtatatat gaaatctaac taaattttga    2940
agtaaaaatt aaattttcct agatccactt ctaggaaaaa ctattagagt actggtttta    3000
gggaattgca ctcaaaagca aggtgactcg cagtctgggg catcttttct agtttcctag    3060
aagaactcta ggaaaaaaag acgcgcatta gacgacgaac gtttgttttt ttggtggcga    3120
tggtcgccac caaacaaacg gcctagttct cgatggttga gaaaaaggct tccattgacc    3180
gaagtcgtct cgcgtctatg gtttatgaca ggaagatcac atcggcatca atccggtggt    3240
gaagttcttg agacatcgtg gcggatgtat ggagcgagac gattaggaca atggtcaccg    3300
acgacggtca ccgctattca gcacagaatg gcccaacctg agttctgcta tcaatggcct    3360
attccgcgtc gccagcccga cttgccccc aagcacgtgt gtcgggtcga acctcgcttg    3420
ctggatgtgg cttgactcta tggatgtcgc actcgtaact ctttcgcggt gcgaagggct    3480
tccctctttc cgcctgtcca taggccattc gccgtcccag ccttgtcctc tcgcgtgctc    3540
cctcgaaggt ccccctttgc ggaccataga aatatcagga cagcccaaag cggtggagac    3600
tgaactcgca gctaaaaaca ctacgagcag tcccccgcc tcggatacct ttttgcggtc    3660
gttgcgccgg aaaaatgcca aggaccggaa aacgaccgga aaacgagtgt acaagaaagg    3720
acgcaatagg ggactaagac acctattggc ataatgcgg aaactcactc gactatggcg    3780
agcggcgtcg gcttgctggc tcgcgtcgct cagtcactcg ctccttcgcc ttctcgcggg    3840
ttatgcgttt ggcggagagg ggcgcgcaac cggctaagta attacgtcga ccgtgctgtc    3900
caaagggctg acctttcgcc cgtcactcgc gttgcgttaa ttacactcaa tcgagtgagt    3960
aatccgtggg gtccgaaatg tgaaatacga aggccgagca tacaacacac cttaacactc    4020
gcctattgtt aaagtgtgtc ctttgtcgat actggtacta atgcggttcg aaacgagaat    4080
cctcaaagga ttatgtaggg tttgagttta tatatttcgt aaactgaaca agatacggga    4140
tcccccgccc cccttcgatt cggtcgaaaa aaattgtaaa ttttacaatt aaggtaaaat    4200
ttacgtgtct acaaaaataa agtattccca aagttacacg tacttacgac gttataagga    4260
caatggtttc gatcatattt atttttatct atttgcacct ttaatgaatc tcaaagacag    4320
taattgcaaa ggaaggagtc aactgttgta tttacgcgac gactcgttcg gtcaaacgta    4380
gacagtccta gttaaagggt aatacggtca gtataattaa tgatcagtta atcaactaaa    4440
aataaaaact gtatatgtac acttactttc tggggtggac atccaaaccg ttcgatcgaa    4500
ttcattgcgg taaacgttc cgtaccttt tatgtattga ctcttatctt ttcaagtcta    4560
gttccagtcc ttgtctacct tgtcgactta tacccggttt gtcctataga caccattcgt    4620
caaggacggg gccgagtccc ggttcttgtc taccttgtcg acttataccc ggtttgtcct    4680
atagacacca ttcgtcaagg acggggccga gtccggttc ttgtctacca ggggtctacg    4740
ccaggtcggg agtcgtcaaa gatctcttgg tagtctacaa aggtcccacg gggttcctgg    4800
```

```
actttactgg gacacggaat aaacttgatt ggttagtcaa gcgaagagcg aagacaagcg    4860
cgcgaatacg aggggctcga gttattttct cgggtgttgg ggagtgagcc ccgcggtcag    4920
gaggctaact gactcagcgg gcccatgggc acataggtta tttgggagaa cgtcaacgta    4980
ggctgaacac cagagcgaca aggaaccctc ccagaggaga ctcactaact gatgggcagt    5040
cgcccccaga aagtaaaccc ccgagcaggc cctagccctc tggggacggg tccctggtgg    5100
ctgggtggtg gccctccatt cgaccggtcg ttgaatagac acagacaggc taacagatca    5160
cagatactga ctaaaatacg cggacgcagc catgatcaat cgattgatcg agacatagac    5220
cgcctgggca ccaccttgac tgctcaagcc ttgtgggccg cgttgggac cctctgcagg    5280
gtccctgaag cccccggcaa aaacaccggg ctggactcag gattttaggg ctagcaaatc    5340
ctgagaaacc acgtgggggg aatctcctcc ctatacacca agaccatcct ctgctcttgg    5400
attttgtcaa gggcggaggc agacttaaaa acgaaagcca aaccctggct tcggcgcggc    5460
gcgcagaaca gacgacgtcg tagcaagaca caacagagac agactgacac aaagacataa    5520
acagactttt atacccgggc ccgatctgac aatggtgagg gaattcaaac tggaatccag    5580
tgacctttct acagctcgcc tagcgagtgt tggtcagcca tctacagttc ttctctgcaa    5640
cccaatggaa gacgagacgt cttaccggtt ggaaattgca gcctaccggc gctctgccgt    5700
ggaaattggc tctggagtag tgggtccaat tctagttcca gaaagtggaa ccgggcgtac    5760
ctgtgggtct ggtccagggg atgtagcact ggacccttcg gaaccgaaaa ctgggggggag    5820
ggacccagtt cgggaaacat gtgggattcg gaggcggagg agaaggaggt aggcggggca    5880
gagagggga acttggagga gcaagctggg gcggagctag gagggaaata ggtcgggagt    5940
gaggaagaga tccgcggggg tataccggta tactctagaa tataccccgt ggggggcgggg    6000
aacatttgaa gggactggga ctgtactgtt ctcaatgatt gtcggggaga gaggttcgag    6060
tgaatgtccg agagatgaat caggtcgtgc ttcagacctc tggagaccgc cgtcggatgg    6120
ttcttgttga cctggctggc caccatggag tgggaatggc tcagccgctg tgtcacaccc    6180
aggcggctgt ggtctgattc ttggatcttg gagcgacctt tcctggaatg tgtcaggacg    6240
actggtgggg gtggcgggag tttcatctgc cgtagcgtcg aacctatgtg cggcgggtgc    6300
acttccgacg gctggggccc ccacctggta ggagatctga cggtaccgag agggtcactg    6360
acgggatgac gaagggatc gcgaagagga cgtacgtctc cacttcgacg tcctcagtcc    6420
ccctccgaag cacttcggac ctcccaggga gtttcagagg acacgtcgga gacctaagtg    6480
aaagtcatcg atacggtaca ggacccaagc ggactcaggc ctctactccg acctcaccca    6540
gcgttggtaa tcgtcacgac caccaatgta gaagataaga ctgtcacacg tccctgctaa    6600
gtggtaaagg tctctgttac ggttcttgtg ggacgtggac gtttacccgt cagactccag    6660
accctgtgc cggtacataa tgacacgttc cgtccctaaa ccattgatgc cactaatgat    6720
acgatacctg atgaccccgg ttccctggtg ccagtggcag aggagtccac ctccacctag    6780
tccacctcca cctagaccac ctccacctag actgtaactc gagtgggtca gaggtaggag    6840
ggaccgacac agtcgtcctc tcttccagtg atactcgacg tttaggtcag tctcagacga    6900
gttgtcatct tgggctttct tggtcaaccg aaccatggtc gttttggtc ctgtcagagg    6960
acttgacgac tagatgaccc gtaggtgatc cgttagacct cagggactag cgaagtgtcc    7020
gtcacctaga ccctgtctaa agtgagagtg gtagtcgtca cacgtccgac ttctggaccg    7080
tcaaataatg acggtcgtta gaatattaga tgagtgcaag ccaggaccct ggttcgacct    7140
```

-continued

```
ctagtttgcc cgccggcgtt aacttcaata cataggagga ggaatggatc tgttactctt  7200
ctcgttacct tggtaatagg tacactttcc ctttgtggaa acaggttcag gggataaagg  7260
gcctggaaga ttcgggaaaa cccacgacca ccaccaacca cctcaggacc gaacgatatc  7320
gaacgatcat tgtcaccgga aataataaaa gacccactcc tcattctcct cgtccgagga  7380
cgtgtcactg atgtacttgt actgaggggc ggcggggccc gggtgggcgt tcgtaatggt  7440
cgggatacgg ggtggtgcgc tgaagcgtcg gatagcgagg tctcacttca agtcgtcctc  7500
gcgtctcggg gggcgcatgg tcgtcccggt cttggtcgag atattgctcg agttagatcc  7560
tgcttctctc ctcatgctac aaaacctgtt ctctgcaccg gccctgggac tctacccccc  7620
tttcggctct tccttcttgg gagtccttcc ggacatgtta cttgacgtct ttctattcta  7680
ccgcctccgg atgtcactct aaccctactt tccgctcgcg gcctccccgt tccccgtgct  7740
accggaaatg gtcccagagt catgtcggtg gttcctgtgg atgctgcggg aagtgtacgt  7800
ccgggacggg ggagcgattg tcggtgagct c                                 7831
```

ANTIBODIES TO MUC16 AND METHODS OF USE THEREOF

This application claims benefit of U.S. Provisional Application No. 61/317,964, filed on Mar. 26, 2010, which is herein incorporated by reference in its entirety for all purposes.

This invention was made with government support under P01-CA52477-16 awarded by the United States Public Health Service (US PHS). The government has certain rights in the invention.

FIELD OF THE INVENTION

The invention relates to antibodies, and antigen-binding fragments thereof, that specifically bind to a polypeptide, or antigenic portion thereof, wherein the polypeptide is selected from a) MUC 16 ectodomain polypeptide, b) MUC 16 cytoplasmic domain polypeptide, and c) MUC 16 extracellular domain polypeptide that contains a cysteine loop polypeptide. The invention's antibodies and compositions containing them are useful in diagnostic and therapeutic applications for diseases in which MUC16 is overexpressed, such as cancer.

BACKGROUND OF THE INVENTION

Cell surface markers and shed antigens are used in the diagnosis of several cancers. For example, the CA125 antigen, recognized by the OC125 antibody, is a tissue-specific, circulating antigen expressed in ovarian cancer. The CA125 antigen is encoded by the MUC16 gene, cloned by Lloyd and Yin. The full-length gene describes a complex tethered mucin protein present primarily in a variety of gynecologic tissues, especially neoplasms. OC125 and other related antibodies react with glycosylation-dependent antigens present exclusively in the cleaved portion of the molecule.

A serum assay can detect elevated levels of the circulating CA125 antigen in many epithelial ovarian cancer patients, and this antigen, derived using the ovarian cell line OVCA433, is recognized by the OC125 antibody (1-2). The detection of circulating CA125 in serum has proven to be a useful tool for the management of ovarian cancer patients and clinical trials (3-4). However, CA125 is neither sufficiently sensitive nor specific for general cancer screening (5-6). A variety of CA125 linked antibodies including VK8 and M11 have subsequently been defined as present on ovarian cancer cells (7-9). Although these antibodies have been used to develop serum assays and various other studies in ovarian cancer, they have significant shortcomings for clinical use in screening or tissue delivery. These antibodies are not useful as screening tools, nor can they detect the proximal residual MUC16 protein fragment after cleavage. This has limited their diagnostic and therapeutic applications.

For example, OC125, M11, and most other antibodies prepared against ovarian cancer cell extracts are directed at complex, glycosylation-dependent antigens. These antigens are exclusively present in the shed portion of MUC16 and cannot be employed to follow the biology of the proximal portion of MUC 16 and may not accurately reflect tissue distribution since the glycosylation patterns can vary substantially among tissues. Because the vast majority of MUC16-reactive antibodies, including OC125, react with the glycosylation-dependent antigen present exclusively in the cleaved portion of the molecule, the true distribution of MUC16 expression is not known (21). There is currently no antibody available to track the fate of the remaining MUC16 protein fragment after cleavage and CA125 release.

Thus, there remains a need for the identification of antibodies that are directed against sequences in the peptide backbone of MUC16, and that are useful for diagnosis and treatment of cancers in which MUC16 is expressed and/or overexpressed.

SUMMARY OF THE INVENTION

The invention provides an antibody, or an antigen-binding fragment thereof, that specifically binds to a polypeptide, or antigenic portion thereof, wherein the polypeptide is selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19). In one embodiment, the antibody internalizes into a cell. While not intending to limit the invention to a particular sequence of MUC 16 ectodomain, in one embodiment, the MUC16 ectodomain polypeptide comprises a polypeptide selected from the group of Polypeptide 1 NFSPLARRVDRVAIYEE (SEQ ID NO:01) and Polypeptide 2 TLDRSSVLVDGYSPNRNE (SEQ ID NO:02). In another embodiment, the antibody lacks specific binding to a glycosylated MUC16 extracellular domain. In yet a further embodiment, the antibody specifically binds to the Polypeptide 2 (SEQ ID NO:02) of the MUC16 ectodomain polypeptide, and wherein the antibody comprises a variable heavy ($V_H$) chain encoded by SEQ ID NO:06, and a variable light ($V_L$) chain encoded by SEQ ID NO:07. In yet another alternative embodiment, the antibody specifically binds to the Polypeptide 2 (SEQ ID NO:02) of the MUC16 ectodomain polypeptide, and wherein the antibody comprises a variable heavy ($V_H$) chain encoded by SEQ ID NO:04, and a variable light ($V_L$) chain encoded by SEQ ID NO:05. In a further embodiment, the antibody specifically binds to the Polypeptide 1 (SEQ ID NO:01) of the MUC 16 ectodomain polypeptide, and wherein the antibody comprises a variable heavy ($V_H$) chain encoded by SEQ ID NO:08, and a variable light ($V_L$) chain encoded by at least one of SEQ ID NO:09 and SEQ ID NO:10. In one embodiment, the MUC16 cytoplasmic domain polypeptide comprises VTTRR RKKEGEYNVQ QQ (SEQ ID NO:18). More preferably, but without limitation, the MUC16 cytoplasmic domain polypeptide comprises Polypeptide 3 CGVLVTTRRRKKEGEYNVQQQ (SEQ ID NO:03). In an alternative embodiment, the MUC16 extracellular domain polypeptide that contains a cysteine loop polypeptide comprises CQVSTFRSVPNRHHTGVDSLC (SEQ ID NO:19). More preferably, but without limitation, the MUC16 extracellular domain polypeptide comprises Polypeptide 4 KSYF SDCQVSTFRS VPNRHHTGVD SLCNFSPL (SEQ ID NO:15). In yet another alternative embodiment, the antibody specifically binds to the Polypeptide 4 (SEQ ID NO:15) of the MUC16 extracellular domain polypeptide, and wherein the antibody comprises a variable heavy ($V_H$) chain encoded by SEQ ID NO:11, and a variable light ($V_L$) chain encoded by SEQ ID NO:12. In a further alternative embodiment, the antibody is selected from the group of a chimeric antibody, a monoclonal antibody, a recombinant antibody, an antigen-binding fragment of a recombinant antibody, a humanized antibody, and an antibody displayed upon the surface of a phage. In another embodiment, the antigen-binding fragment is selected from the group of a Fab fragment, a F(ab')2 fragment, and a Fv fragment. In an alternative embodiment, the antibody, or antigen-binding fragment thereof, is covalently linked to a cytotoxic agent or a prodrug of a cytotoxic agent. In a preferred embodiment, the antibody is a monoclonal antibody produced by a hybridoma cell line.

The invention also provides an isolated monoclonal antibody, or an antigen-binding fragment thereof, produced by a hybridoma cell line, wherein the antibody specifically binds to a polypeptide, or antigenic portion thereof, wherein the polypeptide is selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19). In one embodiment, the MUC16 ectodomain polypeptide comprises Polypeptide 1 (SEQ ID NO:01) and the antibody is selected from the group of 9B11.20.16, 10A2, 2F4, 23D3, 30B1, and 31B2. In an alternative embodiment, the MUC16 ectodomain polypeptide comprises Polypeptide 2 (SEQ ID NO:02), and wherein the antibody is selected from the group of 4H11.2.5, 13H1, 29G9, 9C9.21.5.13, 28F8, 23G12, 9C7.6, 11B6, 25G4, 5C2.17, 4C7, 26B2, 4A5.37, 4A2, 25H3, and 28F7.18.10. In yet a further embodiment, the MUC16 cytoplasmic domain polypeptide comprises Polypeptide 3 CGVLVTTRRRKKEGEYNVQQQ (SEQ ID NO:03), and wherein the antibody is selected from the group of 31A3.5.1, 19D1, 10F6, 22E10, 22F1, 3H8, 22F11, 4D7, 24G12, 19G4, 9A5, 4C2, 31C8, 27G4, and 6H2. In another alternative embodiment, the MUC16 extracellular domain polypeptide comprises Polypeptide 4 KSYF SDCQVSTFRS VPNRHHTGVD SLCNFSPL (SEQ ID NO:15), and wherein the antibody is selected from the group of 24B3 and 9C7.

The invention additionally provides a composition comprising (a) any one or more of the antibodies, or antigen-binding fragments thereof, that are described herein, and (b) a pharmaceutically acceptable carrier.

Also provided by the invention is a hybridoma cell line that produces a monoclonal antibody that specifically binds to a polypeptide, or antigenic portion thereof, selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19).

The invention additionally provides a method for detecting a disease that comprises overexpression of MUC 16 in a subject, comprising a) providing i) a sample from a subject, and ii) any one or more of the antibodies, or antigen-binding fragments thereof, that are described herein, b) contacting the sample with the antibody under conditions for specific binding of the antibody with its antigen, and c) detecting an increased level of binding of the antibody to the sample compared to a control sample lacking the disease, thereby detecting the disease in the subject. In one embodiment, the disease is cancer. In a preferred embodiment, the cancer is selected from the group of ovarian cancer and breast cancer. While not intending to limit the method of detection, in one embodiment, detecting binding of the antibody to the sample is immunohistochemical, enzyme-linked immunosorbent assay (ELISA), fluorescence-activated cell sorting (FACS), Western blot, immunoprecipitation, and/or radiographic imaging.

Also provided herein is a method for treating a disease that comprises overexpression of MUC16, comprising administering to a subject having the disease a therapeutically effective amount of any one or more of the antibodies, or antigen-binding fragments thereof, that are described herein. In one embodiment, the disease is cancer, as exemplified by ovarian cancer and breast cancer.

The invention also provides an isolated antibody, or an antigen-binding fragment thereof, that specifically binds to a MUC16 polypeptide or to an antigenic portion thereof, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO:30), and e) TLDRSSVLVDGYSQNRDD (SEQ ID NO: 31). In one embodiment, the antibody is selected from the group of a monoclonal antibody, a chimeric antibody, a recombinant antibody, an antigen-binding fragment of a recombinant antibody, a humanized antibody, and an antibody displayed upon the surface of a phage. In a preferred embodiment, the antibody is a monoclonal antibody produced by hybridoma cells selected from the group of 12B10-3G10, 10C4-3H5, 10C4-1F2, 10C4-2H8, 10C4-1G7, 17F2-3G5, 17F2-3F6, 17F2-2F9, 17F2-1E11, 12B10-3F7, 12B10-2F6, 12B10-2F10, 25E9-3, 25E9-5, 25E9-1, 25E9-16, 21B8-1H11, 21B8-3G6, 21B8-3H9, 21B8-1G8, 21E1-1E3, 21E1-1G9, 21E1-2G7, 21E1-3G12, 4H1-2E1, 4H1-2E3, 4H1-3E1, 4H1-3H3, 15A8-2E2, 15A8-2E10, 15A8-2E11, 15A8-3D2, 22B5-1F6, 22B5-3G9, 22B5-2G8, and 22B5-3F11. In a particular embodiment, the MUC16 polypeptide is TLDRKSVFVDGYSQNRDD (SEQ ID NO:21), and the antibody comprises a variable heavy ($V_H$) chain sequence SEQ ID NO:27, and a variable light ($V_L$) chain sequence SEQ ID NO:29, such as the monoclonal antibody produced by hybridoma cell 12B10-3G10. In an alternative embodiment, the antigen-binding fragment is selected from the group of a Fab fragment, a F(ab')2 fragment, and a Fv fragment. In a more preferred embodiment, the antibody, or antigen-binding fragment thereof, is covalently linked to a cytotoxic agent and/or to a prodrug of a cytotoxic agent. In a further embodiment, the antibody specifically binds to human MUC16 (SEQ ID NO:25). In another embodiment, the antibody internalizes into a cell. In an alternative embodiment, the antibody lacks specific binding to a glycosylated MUC16 extracellular domain.

The invention also provides a composition comprising (a) any one or more of the invention's antibodies and/or antigen-binding fragments thereof, and (b) a pharmaceutically acceptable carrier.

The invention further provides a hybridoma cell that produces an antibody, or an antigen-binding fragment thereof, that specifically binds to a MUC16 polypeptide or to an antigenic portion thereof, wherein the MUC16 polypeptide is selected from the group of a) TLDRKSVFVDGYSQNRDD (SEQ ID NO:21), b) KSYFSDCQVLAFRSVSNNNNHTGVDSLCNFSPL, (SEQ ID NO:22), c) SLYSNCRLASLRPKKNGTATGVNAICSYHQN (SEQ ID NO:23), d) KSYFSDCQVNNFRS (SEQ ID NO:30), and e) TLDRSSVLVDGYSQNRDD (SEQ ID NO: 31).

The invention also provides an isolated nucleotide sequence comprising a polynucleotide that encodes at least one of a variable heavy ($V_H$) chain sequence and the variable light ($V_L$) chain sequence of an antibody that specifically binds to a MUC16 polypeptide, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS, and e) TLDRSSVLVDGYSQNRDD (SEQ ID NO: 31). In one embodiment, the MUC16 polypeptide is TLDRKSVFVDGYSQNRDD (SEQ ID NO:21) and the polynucleotide encoding the variable heavy ($V_H$) chain sequence comprises SEQ ID NO:26, and wherein the polynucleotide encoding the variable light ($V_L$) chain sequence comprises SEQ ID NO:28.

The invention also provides a method for producing an antibody that specifically binds to a MUC16 polypeptide or to an antigenic portion thereof, comprising administering to a subject an immunologically effective amount of a MUC16 polypeptide selected from the group of a) TLDRKS VF VDGYS QNRDD (SEQ ID NO:21), b) KSYFSDCQV-LAFRSVSN NNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO:30), and e) TLDRSSVLVDGYSQNRDD (SEQ ID NO: 31).

The invention additionally provides a method for identifying a subject as having disease, comprising determining the level, in a sample from the subject, of specific binding of any one or more of the invention's antibodies and/or antigen-binding fragments thereof, with the MUC16 polypeptide or with the antigenic portion thereof, wherein detecting an altered level of the specific binding relative to a control sample identifies the subject as having disease. In one embodiment, the disease is cancer exemplified by ovarian cancer and breast cancer. In another embodiment, the method further comprises detecting an altered level of binding of the antibody to the sample compared to a control sample. Optionally, the detecting is selected from the group of immunohistochemistry, enzyme-linked immunosorbent assay (ELISA), fluorescence-activated cell sorting (FACS), Western blot, immunoprecipitation, and radiographic imaging.

The invention also provides a method for reducing one or more symptoms of disease comprising administering to a subject in need thereof a therapeutically effective amount of any one or more of the invention's antibodies and/or antigen-binding fragment thereof. In one embodiment, the disease is cancer, exemplified by ovarian cancer and breast cancer. Optionally, the method further comprises detecting a reduction in one or more symptoms of the disease after the administration step.

BRIEF DESCRIPTION OF THE DRAWINGS

FIG. 1: Three MUC1-6 carboxy terminus peptides were synthesized at the MSKCC Microchemistry Core Facility. Polypeptide 1 is near the putative cleavage site, Polypeptide 2 is before the transmembrane, and Polypeptide 3 is the internal peptide, which is inside the transmembrane.

FIG. 3A: OC125 (Score 0); FIG. 3B: OC125 (Score 1); FIG. 3C: OC125 (Score 2); FIG. 3D: OC125 (Score 3); FIG. 3E: OC125 (Score 4); FIG. 3F: OC125 (Score 5); FIG. 3G: 4H11 (Score 0); FIG. 3H: 4H11 (Score 1); FIG. 3I: 4H11 (Score 2); FIG. 3J: 4H11 (Score 3); FIG. 3K: 4H11 (Score 4); FIG. 3L: 4H11 (Score 5).

FIG. 4A: Western blot analysis of GST-ΔMUC16$^{c114}$ fusion protein with monoclonal antibodies 9C9.21.5.13 and 4H11.2.5. FIG. 4B: Western blot analysis of SKOV3-phrGFP-ΔMUC16$^{c114}$ and SKOV3-phrGFP-ΔMUC16$^{c334}$ protein extract and probed with monoclonal antibodies 9C9.21.5.13 and 4H11.2.5.

FIG. 8A-FIG.8I: Nucleotide sequence encoding antibody variable heavy ($V_H$) chain and antibody variable light ($V_L$) chain. FIG. 8A: 4A5 $V_H$ (SEQ ID NO:04), FIG. 8B: 4A5 $V_L$ (SEQ ID NO:05), FIG. 8C: 4H11 $V_H$ (SEQ ID NO:06), FIG. 8D: 4H11 $V_L$ (SEQ ID NO:07), FIG. 8E: 9B11 $V_H$ (SEQ ID NO:08), FIG. 8F: 9B11 $V_{L,A}$ (SEQ ID NO:09), FIG. 8G: 9B11 $V_{L,B}$ (SEQ ID NO:10), FIG. 8H: 24B3 $V_H$ (SEQ ID NO:11), FIG. 8I: 24B3 $V_L$ (SEQ ID NO:12).

FIG. 9A-FIG. 9F: FIG. 9A: *Homo sapiens* MUC16 (GenBank NP_078966) (SEQ ID NO:13), FIG. 9B: Polypeptide 1 (SEQ ID NO:01), FIG. 9C: Polypeptide 2 (SEQ ID NO:02), FIG. 9D: Polypeptide 3 (SEQ ID NO:03), FIG. 9E: Transmembrane domain (SEQ ID NO:14), FIG. 9F: Polypeptide 4 (SEQ ID NO:15) containing a cysteine loop polypeptide (SEQ ID NO:19).

FIG. 17: CD8 leader sequence, CD3 zeta chain intracellular domain sequence, (G4S)₃ serine-glycine linker sequence, CD8 transmembrane domain sequence, and CD28 transmembrane+intracellular domains (—STOP) sequence.

FIG. 18A-FIG.18E: SFG_4H11z sequence.

Figure 19A:
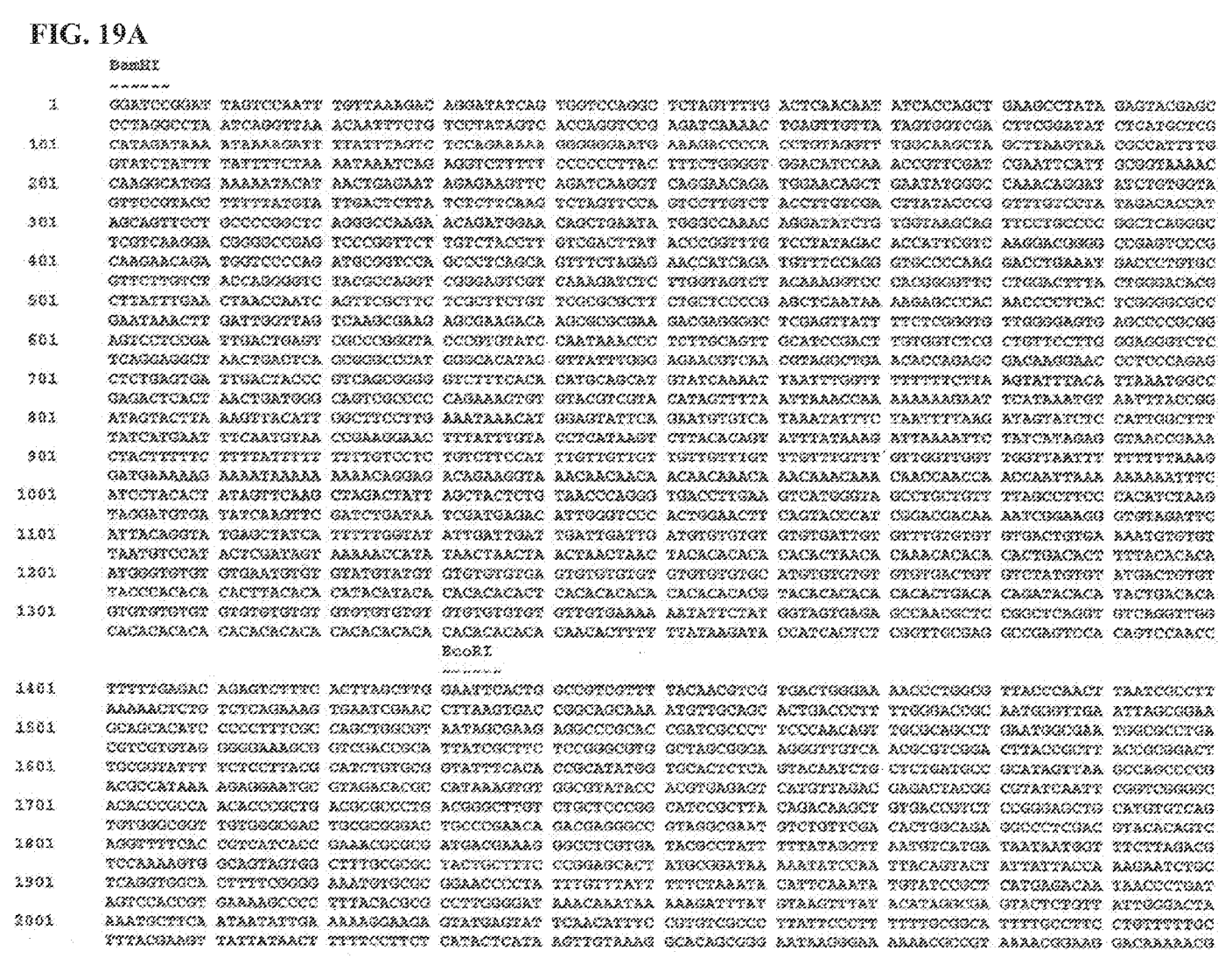
Figure 19B:
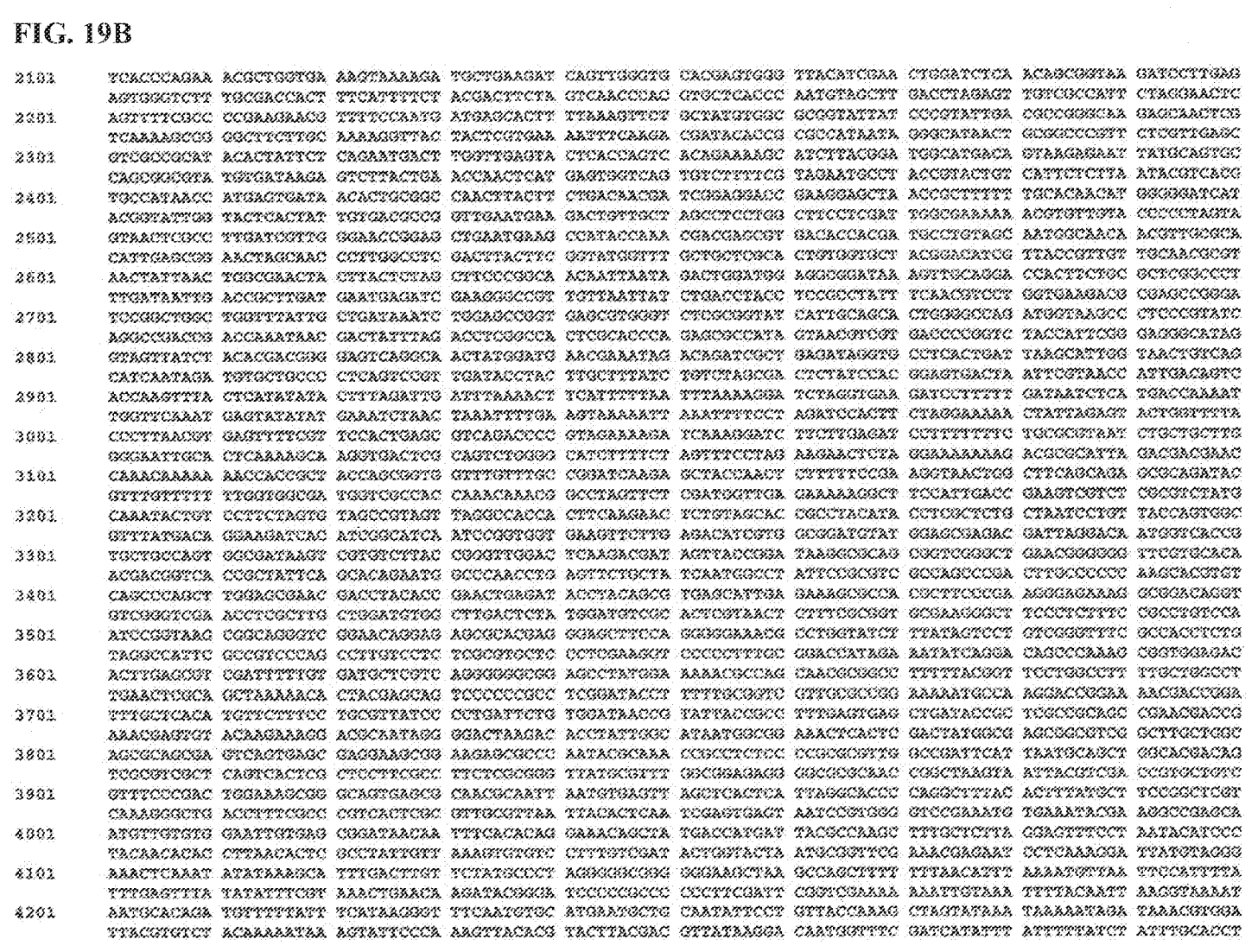
Figure 19C:
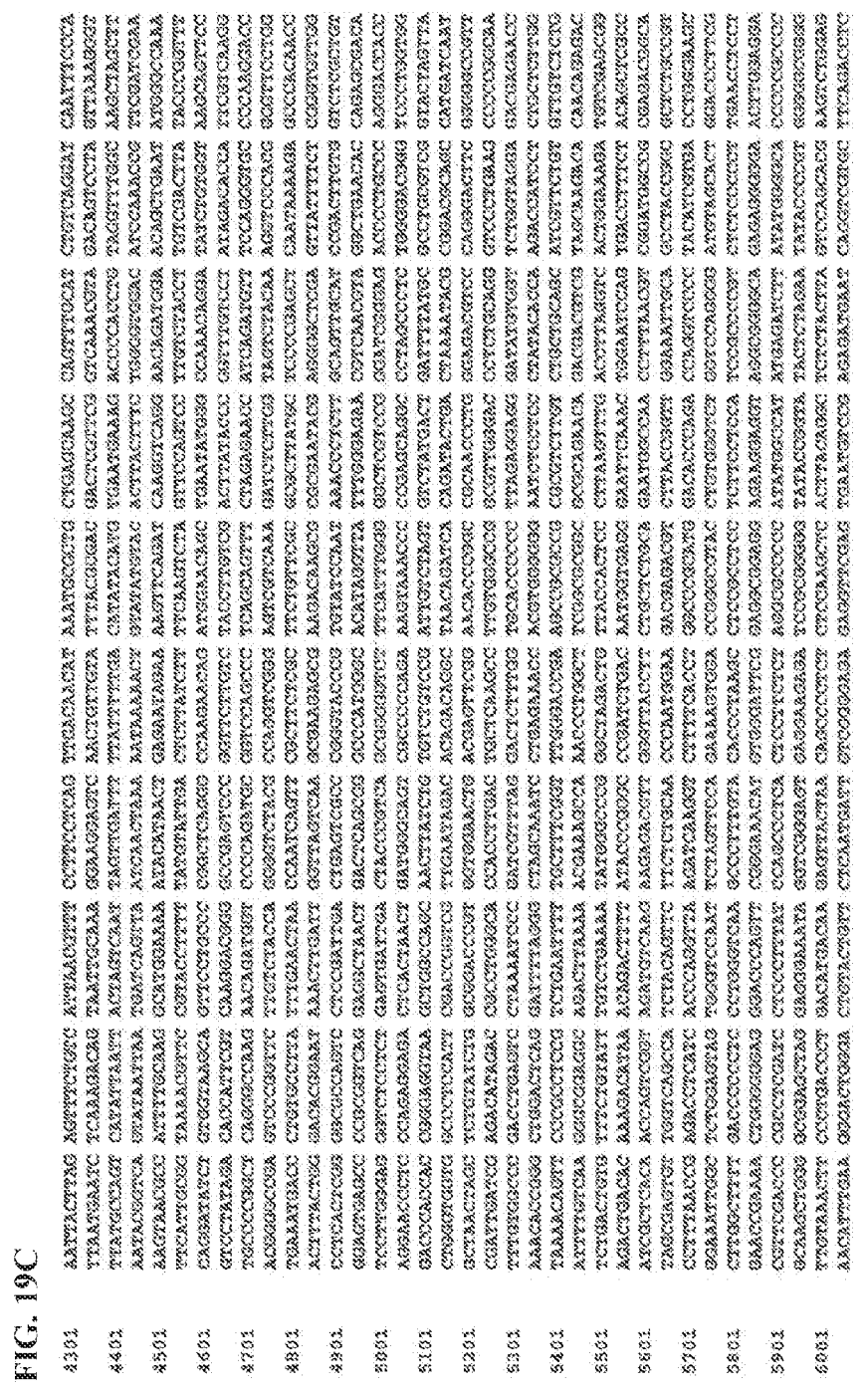

FIG. 19A-FIG. 19F: SFG-4H11-28z sequence.

FIG. 20: (A) Mouse MUC16-CD Peptide 1 (SEQ ID NO:21), Mouse first Cysteine Loop Peptide 2 (SEQ ID NO:22), and Mouse second Cysteine Loop Peptide 3 (SEQ ID NO:23). (B) Alignment of mouse MUC16 (SEQ ID NO:24) and human MUC16 (SEQ ID NO:25) amino acid sequences. A cysteine was added to the peptide sequence at the N terminus of Peptide 1 and Peptide 3 for better conjugation with KLH.

FIG. 21: ID8 extract with 1:10 dilution of Mouse MUC16 monoclonal Primary Supernatants.

FIG. 24 (A) Nucleotide sequence encoding 12B10-3G10-$V_H$ (SEQ ID NO:26), (B) 12B10-3G10-$V_H$ Amino Acid sequence (SEQ ID NO:27), (C) Nucleotide sequence encoding 12B10-3G10-$V_L$ (SEQ ID NO:28) (Note the VL has an optional NotI site added by the primer for cloning, and (D) 12B10-3G10-$V_L$Amino Acid sequence (SEQ ID NO:29).

FIG. 25: FACS Analysis with Purified 12B10-3G10 mAb on ID8 (mouse), OVCAR-3 (human) and BR5—FVB1 (mouse) cell lines.

DEFINITIONS

Figure 2:
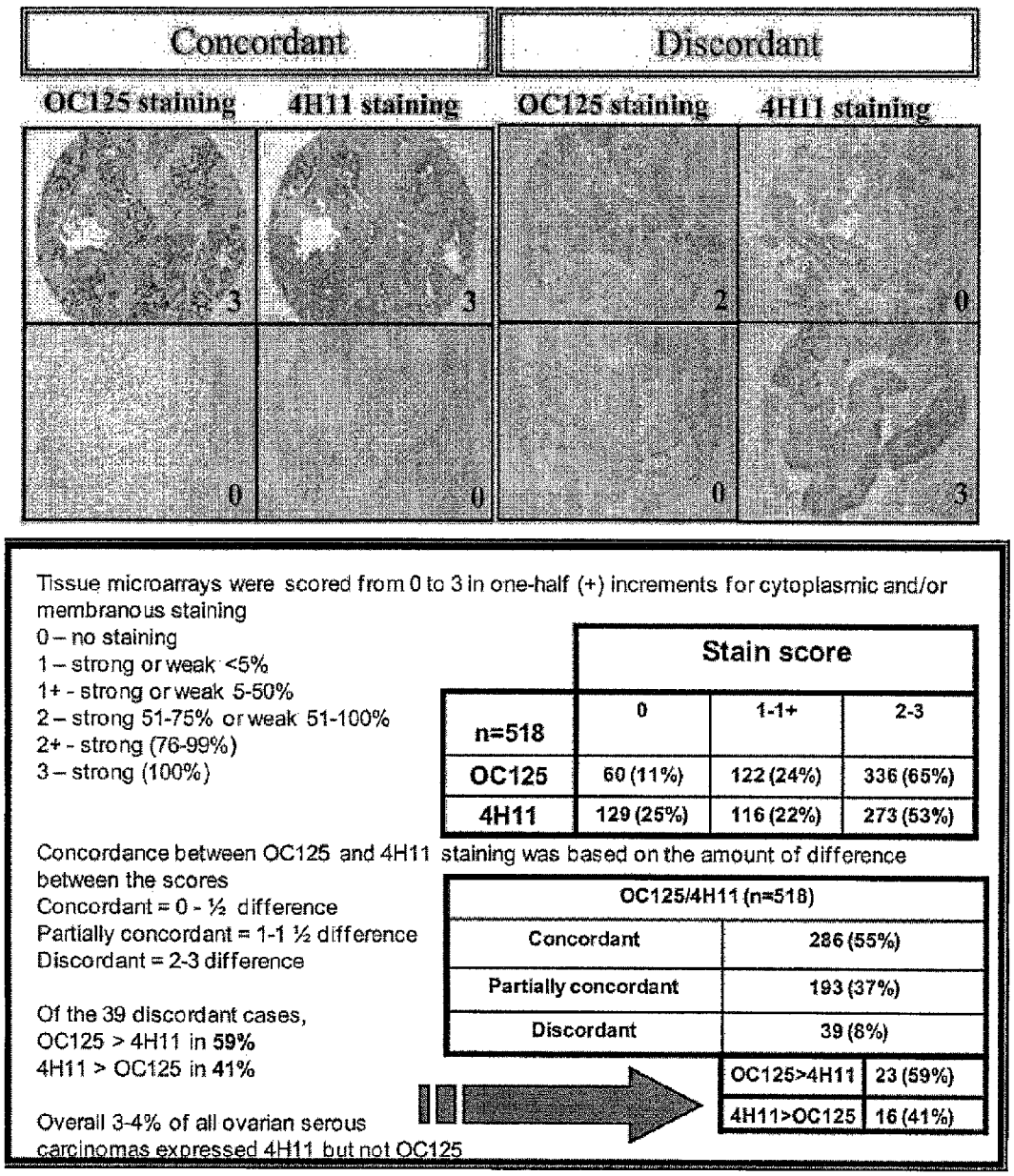
FIG. 2: Comparison staining of high-grade serous ovarian carcinomas using OC125 (left panel) and 4H11 (right panel)
Figure 3A:
FIG. 3A-FIG. 3L: Immunohistochemical scoring of OC125 and 4H11 on tissue microarrays of high-grade ovarian serous carcinoma. Only membranous and/or cytoplasmic staining was considered positive. Score 0: No staining; Score 1: <5% strong or weak; Score 2: 5-50% strong or weak; Score 3: 51-75% strong or 51-100% weak; Score 4: 76-99% strong; Score 5: 100% strong.
Figure 3B:
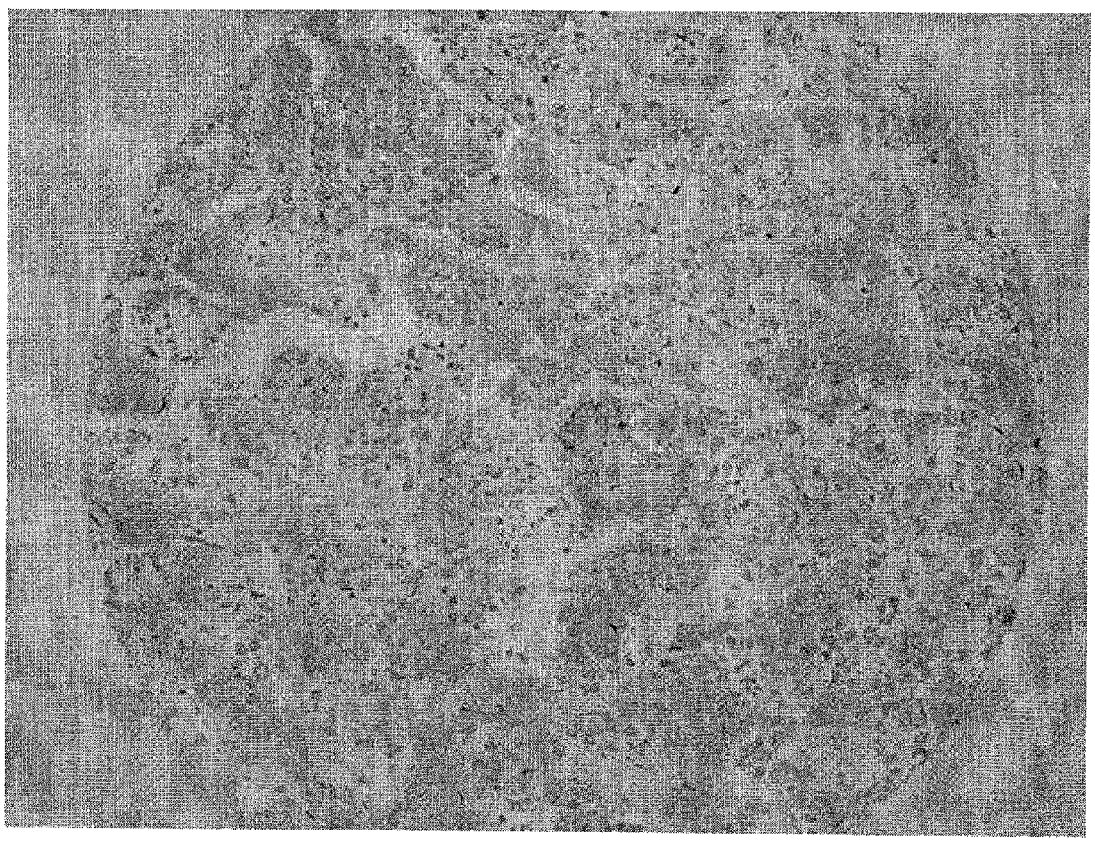
Figure 3C:
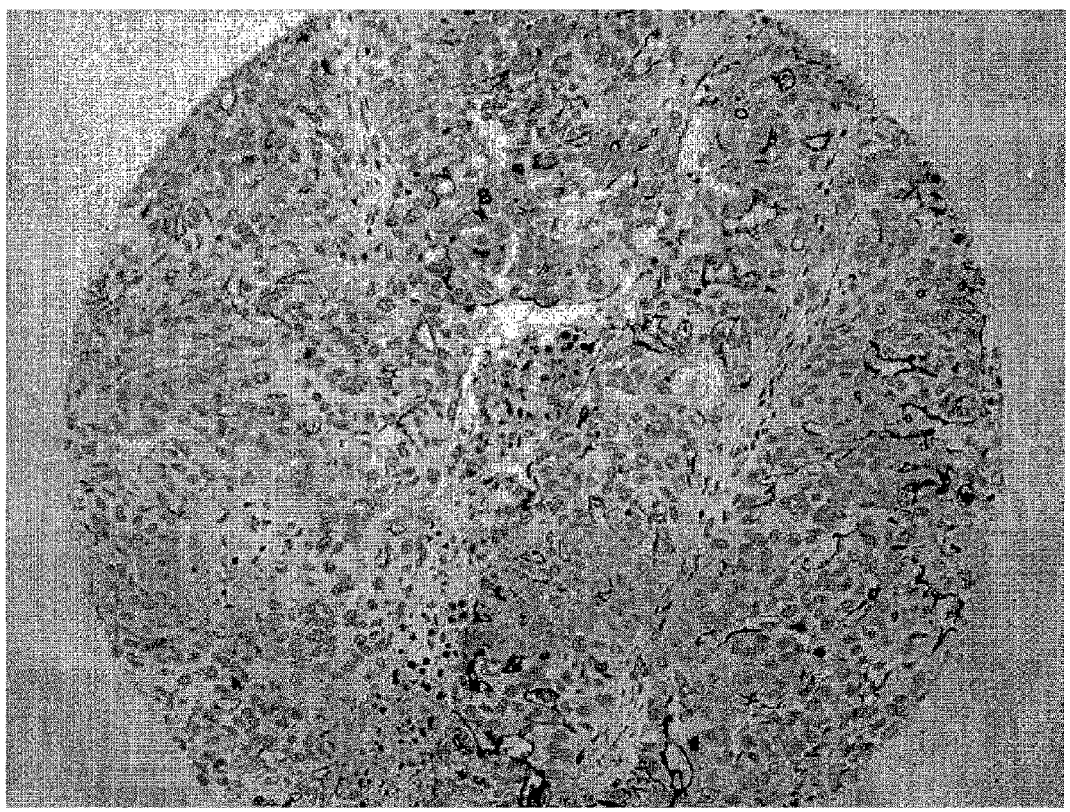
Figure 3D:
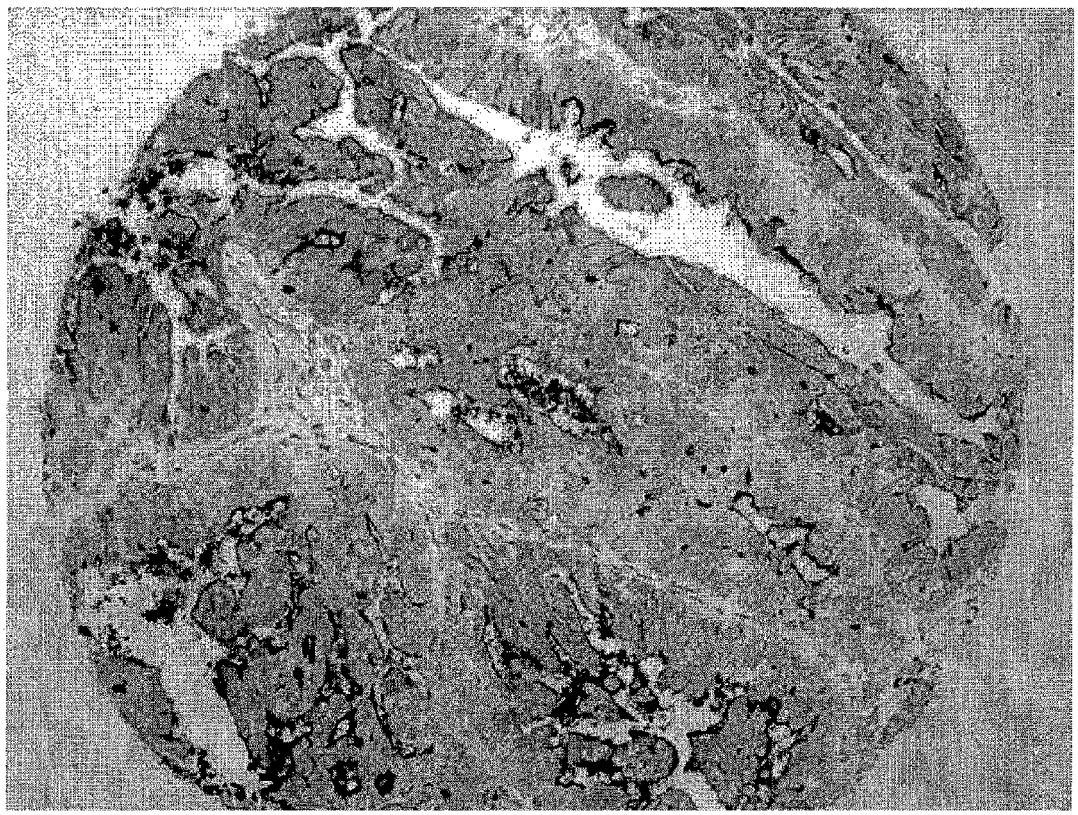
Figure 3E:
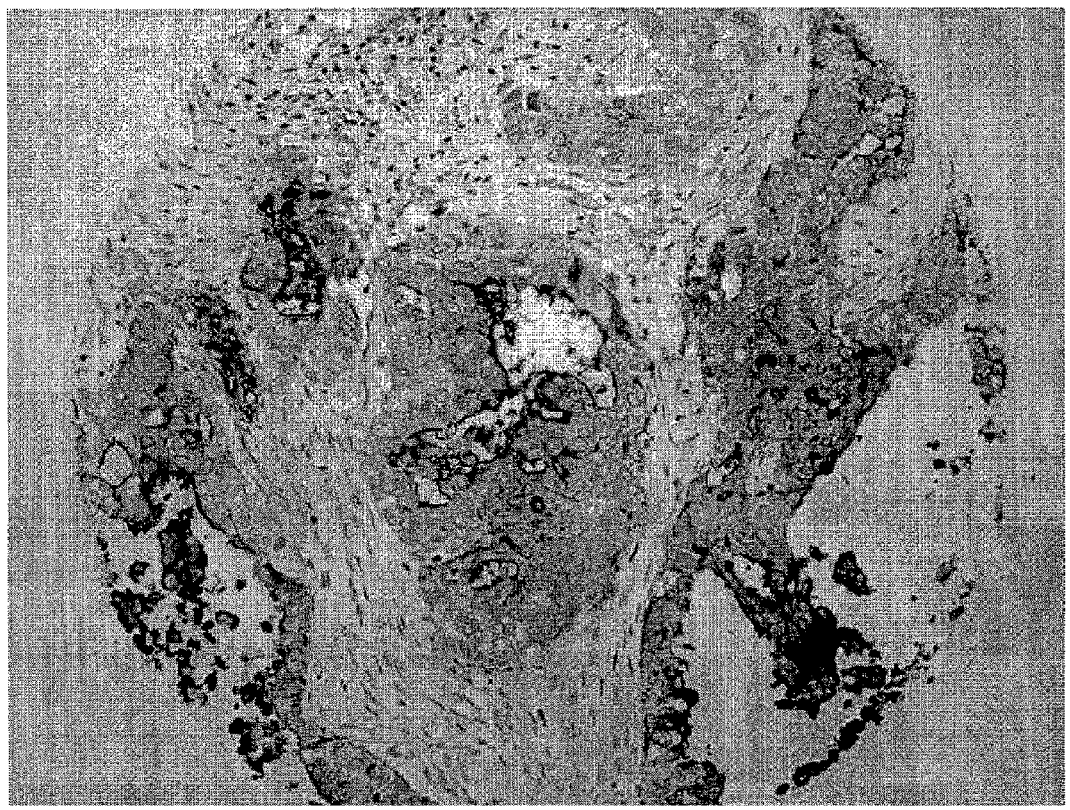
Figure 3F:
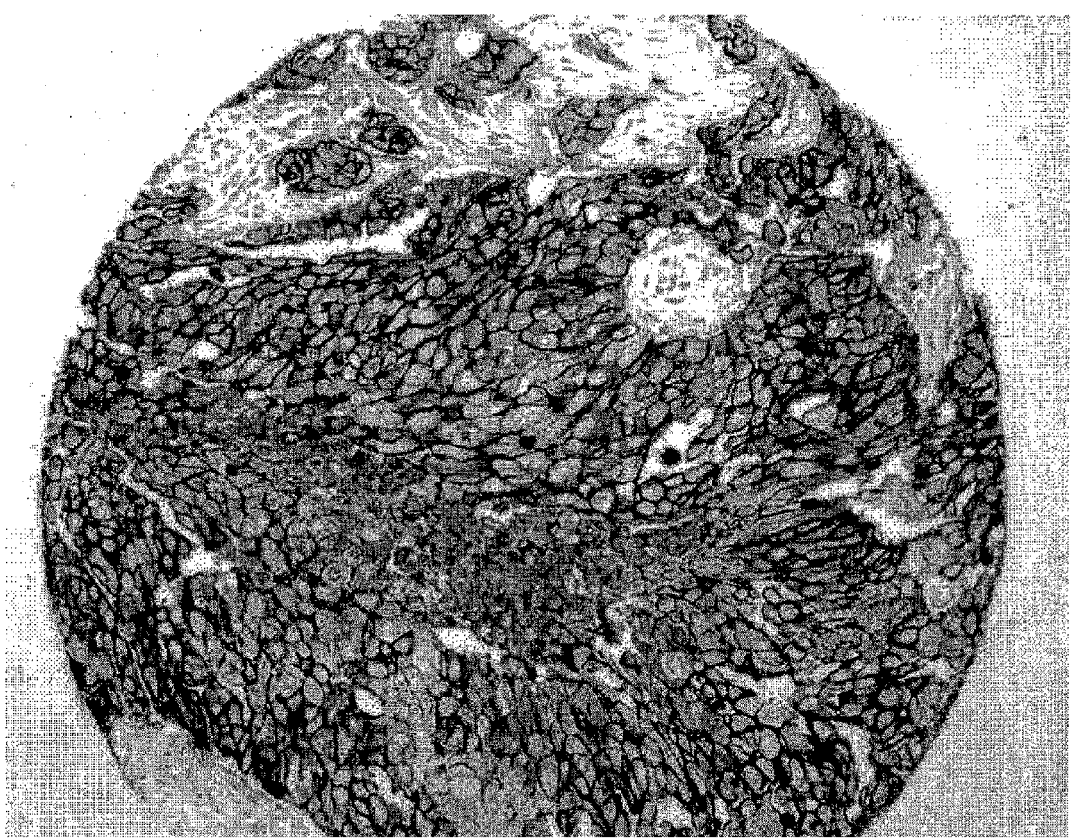
Figure 3G:
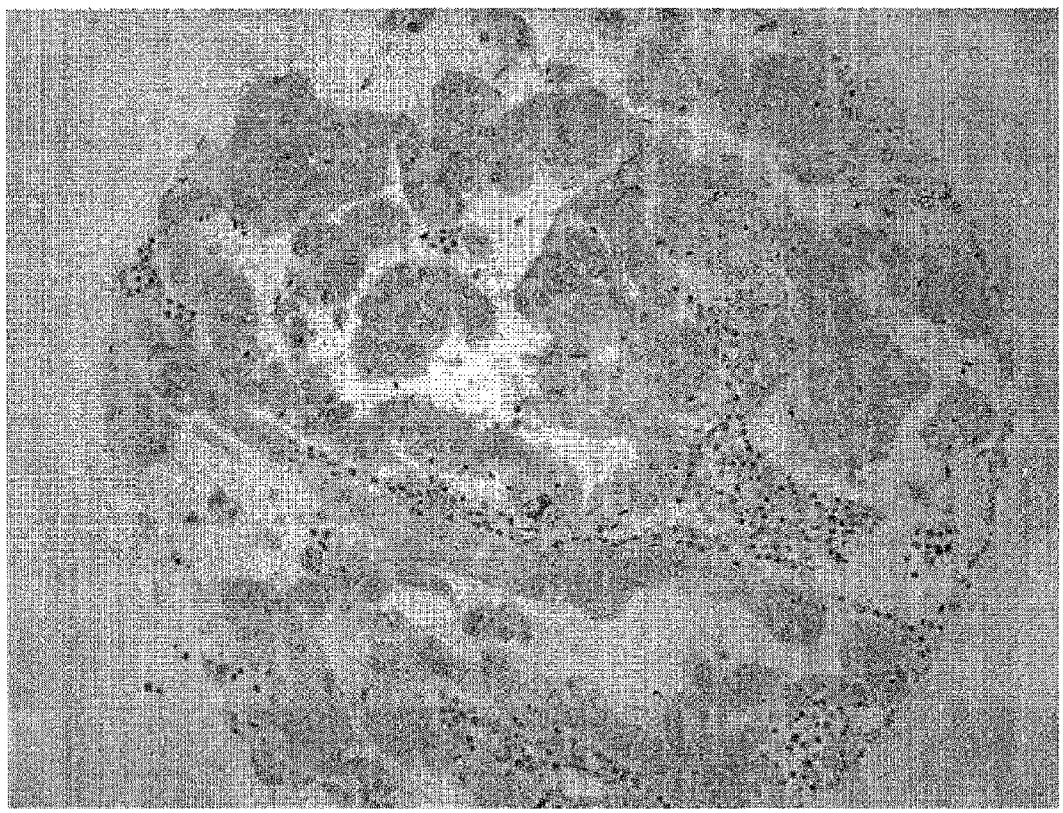
Figure 3H:
Figure 3I:
Figure 3J:
Figure 3K:
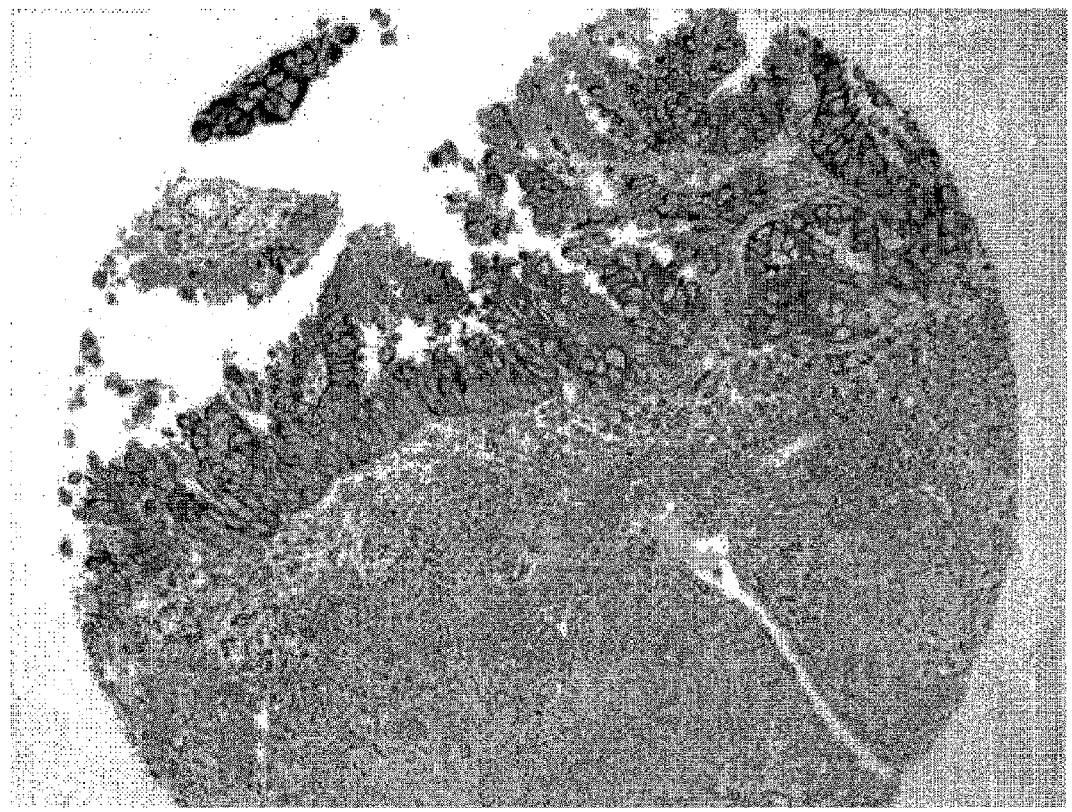
Figure 3L:
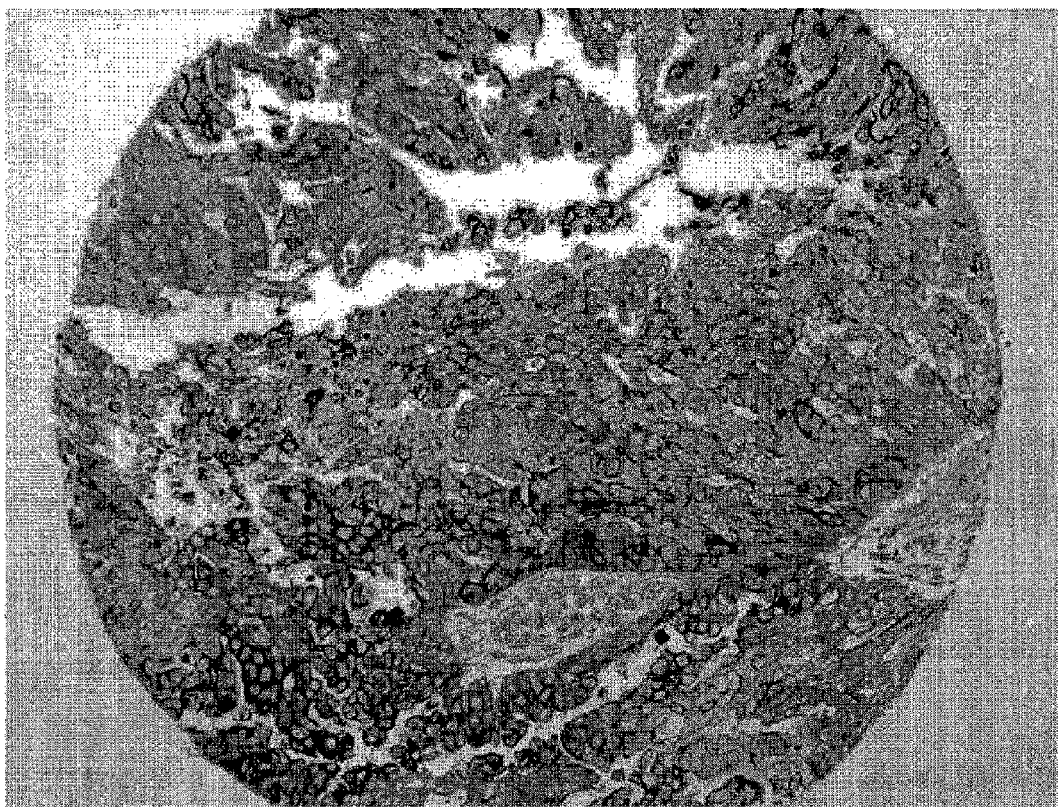

To facilitate understanding of the invention, a number of terms are defined below.

The terms "purified," "isolated," and grammatical equivalents thereof as used herein, refer to the reduction in the amount of at least one undesirable component (such as cell, protein, nucleic acid sequence, carbohydrate, etc.) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in an "enrichment," i.e., an increase in the amount of a desirable component cell, protein, nucleic acid sequence, carbohydrate, etc.).

The term "antibody" refers to an immunoglobulin (e.g., IgG, IgM, IgA, IgE, IgD, etc.). The basic functional unit of each antibody is an immunoglobulin (Ig) mononer (containing only one immunoglobulin ("Ig") unit). Included within this definition are polyclonal antibody, monoclonal antibody, and chimeric antibody.

The variable part of an antibody is its "V domain" (also referred to as "variable region"), and the constant part is its "C domain" (also referred to as "constant region") such as the kappa, lambda, alpha, gamma, delta, epsilon and mu constant regions. The "variable domain" is also referred to as the "$F_V$ region" and is the most important region for binding to antigens. More specifically, variable loops, three each on the light ($V_L$) and heavy ($V_H$) chains are responsible for binding to the antigen. These loops are referred to as the "complementarity determining regions" ("CDRs" and "idiotypes."

The immunoglobulin (Ig) monomer of an antibody is a "Y"-shaped molecule that contains four polypeptide chains: two light chains and two heavy chains, joined by disulfide bridges.

Light chains are classified as either (λ) or kappa (κ). A light chain has two successive domains: one constant domain ("$C_L$") and one variable domain ("$V_L$"). The variable domain, $V_L$, is different in each type of antibody and is the active portion of the molecule that binds with the specific antigen. The approximate length of a light chain is 211 to 217 amino acids.

Each heavy chain has two regions, the constant region and the variable region. The There are five types of mammalian Ig heavy denoted a α, δ, ε, γ, and μ. The type of heavy chain present defines the class of antibody; these chains are found in IgA, IgD, IgE, IgG, and IgM antibodies, respectively. Distinct heavy chains differ in size and composition; α and γ contain approximately 450 amino acids, while μ and ε have approximately 550 amino acids. Each heavy chain has two regions, the constant region ("$C_H$") and the variable ("$V_H$") region. The constant region ($C_H$) is identical in all antibodies of the same isotype, but differs in antibodies of different isotypes. Heavy chains γ, α and δ have a constant region composed of three tandem (in a line) Ig domains, and a hinge region for added flexibility. Heavy chains μ and ε have a constant region composed of four immunoglobulin domains. The variable region ($V_H$) of the heavy chain differs in antibodies produced by different B cells, but is the same for all antibodies produced by a single B cell or B cell clone. The variable region of each heavy chain is approximately 110 amino acids long.

The term "specifically binds" and "specific binding" when made in reference to the binding of two molecules (e.g. antibody to an antigen, etc.) refer to an interaction of the two molecules that is dependent upon the presence of a particular structure on one or both of the molecules. For example, if an antibody is specific for epitope "A" on the molecule, then the presence of a protein containing epitope A (or free, unlabelled A) in a reaction containing labeled "A" and the antibody will reduce the amount of labeled A bound to the antibody.

The teem "capable of binding" when made in reference to the interaction between a first molecule (such as antibody, polypeptide, glycoprotein, nucleic acid sequence, etc.) and a second molecule (such as antigen, polypeptide, glycoprotein, nucleic acid sequence, etc.) means that the first molecule binds to the second molecule in the presence of suitable concentration of salts, and suitable temperature, and pH. The conditions for binding molecules may be determined using routine and/or commercially available methods The terms "antigen," "immunogen," "antigenic," "immunogenic," "antigenically active," "immunologic," and "immunologically active" when made in reference to a molecule, refer to any substance that is capable of inducing a specific humoral immune response (including eliciting a soluble antibody response) and/or cell-mediated immune response (including eliciting a CTL response). Antigenic peptides preferably contain at least 5, at least 6, at least 7, at least 8, at least 9, and more preferably at least 10 amino acids. To elicit antibody production, in one embodiment, antigens may be conjugated to keyhole limpet hemocyanin (KLH) or fused to glutathione-S-transferase (GST).

A "cognate antigen" when in reference to an antigen that binds to an antibody, refers to an antigen that is capable of specifically binding to the antibody.

In one embodiment, the antigen comprises an epitope. The terms "epitope" and "antigenic determinant" refer to a structure on an antigen, which interacts with the binding site of an antibody or T cell receptor as a result of molecular complementarity. An epitope may compete with the intact antigen, from which it is derived, for binding to an antibody.

As used herein the terms "portion" and "fragment" when made in reference to a nucleic acid sequence or protein sequence refer to a piece of that sequence that may range in size from 2 contiguous nucleotides and amino acids, respectively, to the entire sequence minus one nucleotide and amino acid, respectively.

A "subject" that may benefit from the invention's methods includes any multicellular animal, preferably a mammal. Mammalian subjects include humans, non-human primates, murines, ovines, bovines, ruminants, lagomorphs, porcines, caprines, equines, canines, felines, ayes, etc.). Thus, mammalian subjects are exemplified by mouse, rat, guinea pig, hamster, ferret and chinchilla. The invention's compositions and methods are also useful for a subject "in need of reducing one or more symptoms of" a disease, e.g., in need of reducing cancer metastasis and/or in need of reducing one or more symptoms of cancer, includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable). The invention's compositions and methods are also useful for a subject "at risk" for disease (such as cancer) refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

"Cancer cell" refers to a cell undergoing early, intermediate or advanced stages of multi-step neoplastic progression as previously described (Pitot et al., Fundamentals of Oncology, 15-28 (1978)). This includes cells in early, intermediate and advanced stages of neoplastic progression including "pre-neoplastic cells (i.e., "hyperplastic cells and dysplastic cells), and neoplastic cells in advanced stages of neoplastic progression of a dysplastic cell.

"Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

"Cancer" refers to a plurality of cancer cells that may or may not be metastatic, such as ovarian cancer, breast cancer, lung cancer, prostate cancer, cervical cancer, pancreatic cancer, colon cancer, stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia.

"Sample" and "specimen" as used herein are used in their broadest sense to include any composition that is obtained and/or derived from a biological source, as well as sampling devices (e.g., swabs), which are brought into contact with biological or environmental samples. "Biological samples" include those obtained from a subject, including body fluids (such as urine, blood, plasma, fecal matter, cerebrospinal fluid (CSF), semen, sputum, and saliva), as well as solid tissue. Biological samples also include a cell (such as cell lines, cells isolated from tissue whether or not the isolated cells are cultured after isolation from tissue, fixed cells such as cells fixed for histological and/or immunohistochemical analysis), tissue (such as biopsy material), cell extract, tissue extract, and nucleic acid (e.g., DNA and RNA) isolated from a cell and/or tissue, and the like. These examples are illustrative, and are not to be construed as limiting the sample types applicable to the present invention.

"Overexpression of MUC16" by a cell of interest (such as a cancer cell) refers to a higher level of MUC16 protein and/or mRNA that is expressed by the cell of interest compared to a control cell (such as a non-cancerous cell, normal cell, etc.).

"Internalize" when in reference to a cell refers to entry from the extracellular medium into the cell membrane and/or cytoplasm.

"Glycosylated" when in reference to a sequence (e.g., an amino acid sequence or nucleotide sequence) refers to a sequence that is covalently linked to one or more saccharides.

"Pharmaceutical" and "physiologically tolerable" composition refers to a composition that contains pharmaceutical molecules, i.e., molecules that are capable of administration to or upon a subject and that do not substantially produce an undesirable effect such as, for example, adverse or allergic reactions, dizziness, gastric upset, toxicity and the like, when administered to a subject. Preferably also, the pharmaceutical molecule does not substantially reduce the activity of the invention's compositions. Pharmaceutical molecules include "diluent" (i.e., "carrier") molecules and excipients.

"Immunogenically effective" and "antigenically effective" amount of a molecule interchangeably refer to an amount of the molecule that is capable of inducing a specific humoral immune response (including eliciting a soluble antibody response) and/or cell-mediated immune response (including eliciting a cytotoxic T-lymphocyte (CTL) response).

"Treating" a disease refers to reducing one or more symptoms (such as objective, subjective, pathological, clinical, sub-clinical, etc.) of the disease.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, antibody, etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "increase," "elevate," "raise," and grammatical equivalents (including "higher," "greater," etc.) when in reference to the level of any molecule (e.g., amino acid sequence, and nucleic acid sequence, antibody, etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "alter" and "modify" when in reference to the level of any molecule and/or phenomenon refer to an increase or decrease.

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

DESCRIPTION OF THE INVENTION

The invention provides antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

Using synthetic peptides, the inventors raised novel-specific antibodies to the carboxy-terminal portion of MUC16, retained by the cell, proximal to the putative cleavage site. These antibodies were characterized using fluorescence-activated cell-sorting analysis, enzyme-linked immunoassay, Western blot analysis, and immunohistochemistry. Each of the selected monoclonal antibodies was reactive against recombinant GST-$\Delta$MUC16$^{c114}$protein and the MUC16 transfected SKOV3 cell line. Three antibodies, 4H11, 9C9, and 4A5 antibodies demonstrated high affinities by Western blot analysis and saturation-binding studies of transfected SKOV3 cells, and displayed antibody internalization. Immunohistochemical positivity with novel antibody 4H11 was similar to OC125, but with important differences, including diffuse positivity in lobular breast cancer and a small percentage of OC125-negative ovarian carcinomas which showed intense and diffuse 4H11 antibody binding.

The invention's compositions and methods are useful for diagnostic and therapeutic applications, as well as biologic studies such as membrane receptor trafficking and intracellular events. Diagnostic applications include, for example, detection of cancer using immunohistochemical, radiographic imaging, enzyme-linked immunosorbent assay (ELISA), fluorescence-activated cell sorting (FACS), Western blot, and/or immunoprecipitation detection.

The invention is further described under (A) MUC16, (B) Prior Art Antibodies, (C) Invention's Antibodies, (D) Hybridoma Cell Lines, (E) Conjugates Of The Invention's Antibodies Linked To Cytotoxic Agents And/Or Prodrugs, (F) Detecting Muc 16 Portions And Diagnostic Applications, and (G) Therapeutic Applications.

A. MUC16

Figure 10:
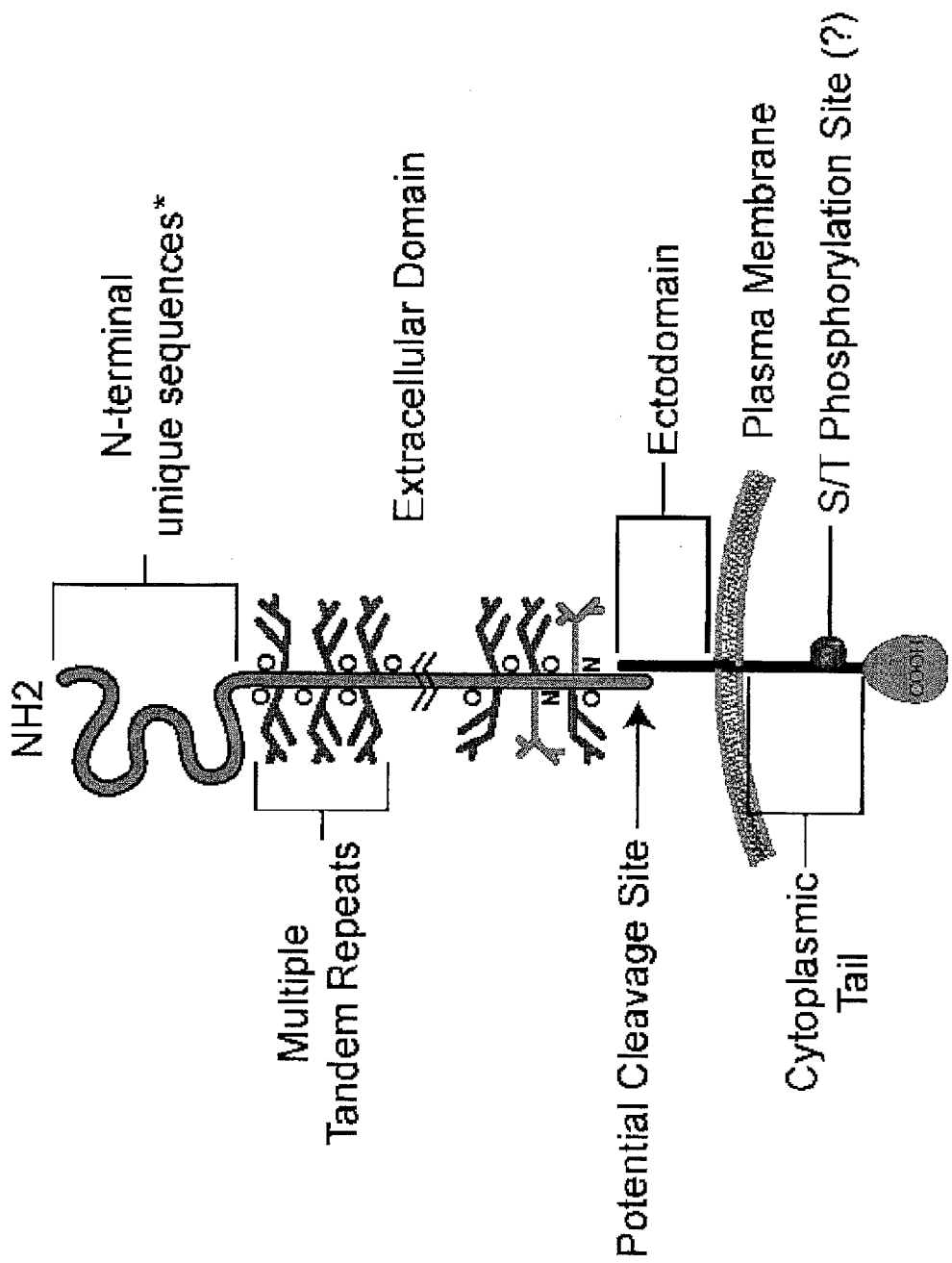
FIG. 10: Schematic of MUC1-6 structure.

"MUC16," "MUC-16" and "Mucin 16" interchangeably refer to a type I membrane protein that is part of a family of tethered mucins. A schematic of Muc16 is in FIG. 10, and an exemplary human Muc16 amino acid sequence (SEQ ID NO:13) is shown in FIG. 9A-FIG.9F. An alignment of mouse MUC16 (SEQ ID NO:24) and human MUC16 (SEQ ID NO:25) amino acid sequences is shown in FIG. 20B. The term "type 1 protein" refers to a "membrane protein" that is at least partially embedded in the lipid bilayer of a cell, virus and the like, and that contains a transmembrane domain (TM) sequence embedded in the lipid bilayer of the cell, virus and the like. The portion of the protein on the $NH_2$-terminal side of the TM domain is exposed on the exterior side of the membrane, and the COOH-terminal portion is exposed on the cytoplasmic side.

Recently, the sequence of the cDNA-encoding MUC16/CA125 was described by Yin and Lloyd in 2001 and completed by O'Brien in 2002 (10-12). The complete MUC16 protein has various components consisting of a cytoplasmic tail with potential phosphorylation sites, a transmembrane domain, and an external domain proximal to an apparent cleavage site. Distal to the cleavage site, the released external domain contains 16-20 tandem repeats of 156 amino acids, each with many potential glycosylation sites (11). The overall repeat structure (FIG. 10) is well conserved across mammals, but the repeats are not completely identical in exact amino acid composition.

The MUC16 protein is part of a family of tethered mucins that includes both MUC1 and MUC4 (13). MUC1 is present in a variety of tissues and appears to signal through a beta catenin pathway, interact with EGF receptor, mediates drug resistance and can act as an oncogene (14-17). The MUC4 protein is also expressed in a variety of tissues but is common on neoplasms of the gastrointestinal track (18-20). In contrast, the CA125 antigen has been more restricted in its distribution and is present primarily in gynecologic tissues and overexpressed in Müllerian neoplasms (21). However, the CA125 antigen, recognized by the OC125 antibody, is a heavily glycosylated antigen expressed in the tandem repeat region of the larger MUC16 protein. This glycoprotein is typically shed from a putative cleavage site in the extracellular domain of the MUC16 peptide backbone.

Thus, "MUC 16" protein contains (a) a "cytoplasmic domain," (b) a "transmembrane domain," and (c) a "extracellular domain." The MUC16 extracellular domain contains a cleavage site between a non-glycosylated ectodomain and a large glycosylated ectodomain of tandem repeats.

The terms "cytoplasmic domain," "cytoplasmic tail," and "CT" are used interchangeably to refer to a protein sequence, and portions thereof, that is on the cytoplasmic side of the lipid bilayer of a cell, virus and the like. Methods for determining the CT of a protein are known in the art Elofsson et al. (2007) Annu. Rev. Biochem. 76:125-140; Bernsel et al. (2005) Protein Science 14:1723-1728).

The terms "transmembrane domain" and "TM" are used interchangeably to refer to a protein sequence, and portions thereof, that spans the lipid bilayer of a cell, virus and the like. Methods for determining the TM of a protein are known in the art (Elofsson et al. (2007) Annu Rev. Biochem. 76:125-140; Bernsel et al. (2005) Protein Science 14:1723-1728).

The terms "ectodomain" and "extracellular domain" are interchangeably used when in reference to a membrane protein to refer to the portion of the protein that is exposed on the extracellular side of a lipid bilayer of a cell, virus and the like. Methods for determining the ectodomain of a protein are known in the art (Singer (1990) Annu. Rev. Cell Biol. 6:247-296 and High et al. (1993) J. Cell Biol. 121:743-750, and McVector software, Oxford Molecular).

The exemplary Muc16 of FIG. 9A-FIG. 9F contains (a) a "MUC16 cytoplasmic domain" from amino acid 14476 to 14507, vttrr rkkegeynvq qqcpgyyqsh ldledlq (SEQ ID NO:16), that interacts with the intracellular signal transduction machinery; (b) a "MUC16 transmembrane domain" from amino acid 14452 to 14475, fwaviligl agllgvitcl icgvl (SEQ ID NO:14) that spans the plasma membrane; and (c) a "MUC16 extracellular domain" amino acid 1 to 14392 (SEQ ID NO:13) that contains a cleavage site between an non-glycosylated ectodomain and a large glycosylated ectodomain of tandem repeats. The "MUC16 ectodomain" is exemplified by nfsplar rvdrvaiyee flrmtrngtq lqnftldrss vlvdgyspnr nepltgnsdl p (SEQ ID NO:17) from amino acid 14394 to 14451 of SEQ ID NO:13 of FIG. 9A-FIG. 9F.

The exemplary MUC16 ectodomain contains both Polypeptide 1 (nfsplar rvdrvaiyee (SEQ ID NO:01), which is from amino acid 14394 to 14410 of SEQ ID NO:13), and Polypeptide 2 (tldrss vlvdgyspnr ne (SEQ ID NO:02), which is from amino acid 14425 to 14442 of SEQ ID NO:13), against which the invention's exemplary antibodies were produced. Polypeptide 3, cgvlvttrr rkkegeynvq qq (SEQ ID NO:03) is from amino acid 14472 to 14492 of SEQ ID NO:13, and contains both a transmembrane domain portion (cgvl) and a cytoplasmic domain portion (vttrr rkkegeynvq qq (SEQ ID NO:18)). Thus, the CGVL is optional in SEQ ID NO:03, as it is part of the transmembrane domain.

Polypeptide 4 (ksyf sdcqvstfts vpnrhhtgvd slcnfspl (SEQ ID NO:15), is located in a non-glycosylated portion of the Muc16 extracellular domain, is from amino acid 14367 to 14398 of SEQ ID NO:13, and contains a cysteine loop polypeptide cqvstfrsvpnrhhtgvdslc (SEQ ID NO:13).

B. Prior Art Antibodies

The expression of the MUC16/CA125 antigen has long been associated with gynecologic tissues. "CA125," "CA-125," "Cleaved CA125," and "cleaved CA-125," interchangeably refer to the glycosylated external domain of the tethered mucin MUC16, that is distal to the cleavage site (Payne et al., U.S. Pat. No. 7,202,346). This released external domain contains 16-20 tandem repeats of 156 amino acids, each with potential glycosylation sites. An apparent cysteine-based disulfide loop of 19 amino acids is present in all repeats and the N-terminal end contains a hairbrush structure that is heavily O-glycosylated (11). The deduced size would be 2.5 MD for the protein part, and with added carbohydrates, this could increase to 5 MD (10, 26). CA125, though it is not sensitive or specific enough to be used as a general screening tool, is routinely used to monitor patients with ovarian carcinoma. The tests used to measure CA125 are antibody based detection methods, as are the immunohistochemical stains routinely performed for diagnostic purposes. The epitope specificity of 26 antibodies to MUC16 was studied in the first report from the International Society of Oncodevelopmental Biology and Medicine (ISOBM) TD-1 Workshop and the application of 22 antibodies to immunohistochemistry was reported in the second report from the TD-1 workshop (7, 21). The existing antibodies were grouped as OC125-like, M11-like, or OV197-like and all of the known antibodies recognized CA125 epitopes in the repeating, glycosylated elements in the external domain of the tethered mucin MUC16, distal to the putative cleavage site.

The vast majority of MUC16-reactive antibodies, including OC125, react with the glycosylation-dependent antigen present exclusively in the cleaved portion of the molecule so the true distribution of MUC16 expression is not known (21). There is currently no antibody available to track the fate of the remaining MUC16 protein fragment after cleavage and CA125 release.

C. Invention's Antibodies

In order to better explore the biology of human MUC16, the inventors have derived monoclonal antibodies against the extracellular portion of the MUC1-6-carboxy terminus, proximal to the putative cleavage site, as well as one monoclonal antibody against the internal cytoplasmic domain. In contrast to prior antibodies, these are derived against the peptide backbone of MUC16 and are not directed at complex glycoprotein epitopes. Since these epitopes are proximal to the cleavage site, they are unlikely to be found in the circulation and provide novel targets for diagnostic methods and therapeutic interventions. Data herein demonstrate the identification and characterization of exemplary antibodies developed against the MUC16 peptide backbone.

The inventors have developed novel antibodies that are directed at the non-cleaved, non-glycosylated peptide backbone of MUC16. These are exemplified by both 4H11 and 9C9 antibodies, which react with peptide sequences in the non-cleaved ectodomain of MUC16 and are detectable on the surface of ovarian cancer cell lines and in paraffin-fixed tissues from human ovarian cancer surgical specimens. The antibodies show high affinity and are readily internalized by ovarian cancer cells when bound to the ectodomain of MUC16. This suggests that the proximal portion of MUC16 has an independent biology from the more distal, cleaved portion of the mucin. It also suggests that the proximal portions of MUC16 could provide convenient targets for diagnostic and therapeutic interventions. Targeting the peptide backbone of MUC16 provides highly specific tissue delivery for genetically engineered cells, liposomes, or antibody conjugates, including conjugates with the invention's antibodies.

The invention's antibodies, exemplified by antibody 4H11, are useful as tools in immunohistochemistry. Date herein show that 4H11 is relatively specific to high-grade ovarian serous carcinoma. Invasive lobular breast carcinoma is the major exception and shows extensive MUC16 protein as detected by 4H11. Lobular carcinoma of the breast has unique biology which is characterized by a propensity to metastasize to serosal surfaces (27). Since MUC16 is the cognate binding partner of mesothelin, this may have important implications for lobular cancer (28). The discordance rates for OC125 and 4H11 also suggest that 4H11 might provide additional, independent information from OC125 in a subset of ovarian carcinomas. Some tumors that are negative with OC125 retain cytoplasmic and extracellular portions of the MUC16 glycoprotein, portions of the molecule that are likely involved in transduction of signals potentially important in the malignant phenotype.

Thus, in one embodiment, the invention provides an isolated antibody, or an antigen-binding fragment thereof, that specifically binds to a polypeptide, or antigenic portion thereof, wherein the polypeptide is exemplified by a) MUC16 ectodomain polypeptide (exemplified by NFSPLAR RVDRVAIYEE FLRMTRNGTQ LQNFTLDRSS VLVDGYSPNR NEPLTGNSDL P (SEQ ID NO:17)), b) MUC16 cytoplasmic domain polypeptide (exemplified by VTTRR RKKEGEYNVQ QQ (SEQ ID NO:18), which is contained within each of CGVLVTTRR RKKEGEYNVQ QQ (SEQ ID NO:03) and LVTTRR RKKEGEYNVQ QQ (SEQ ID NO:20)), and c) MUC16 extracellular domain polypeptide that contains a cysteine loop polypeptide CQVSTFRSVPNRHHTGVDSLC (SEQ ID NO:19).

Figure 5A:
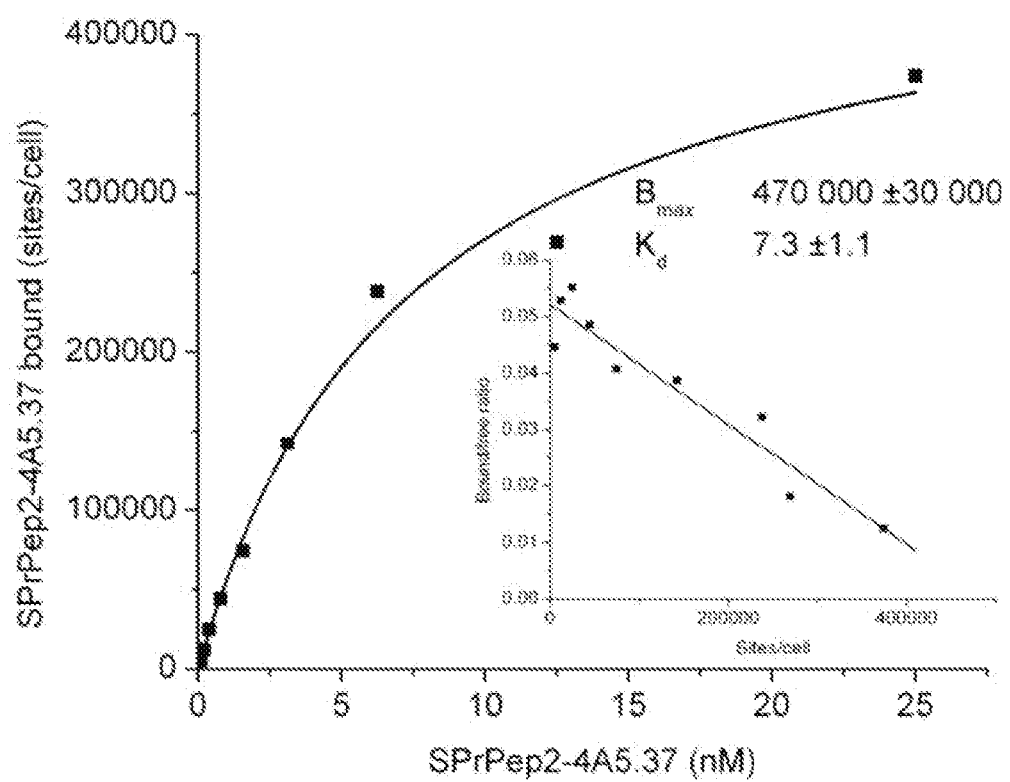
FIG. 5A-5D: MUC1-6 carboxy terminus monoclonal antibodies binding affinity on OVCAR3 cells.
Figure 5B:
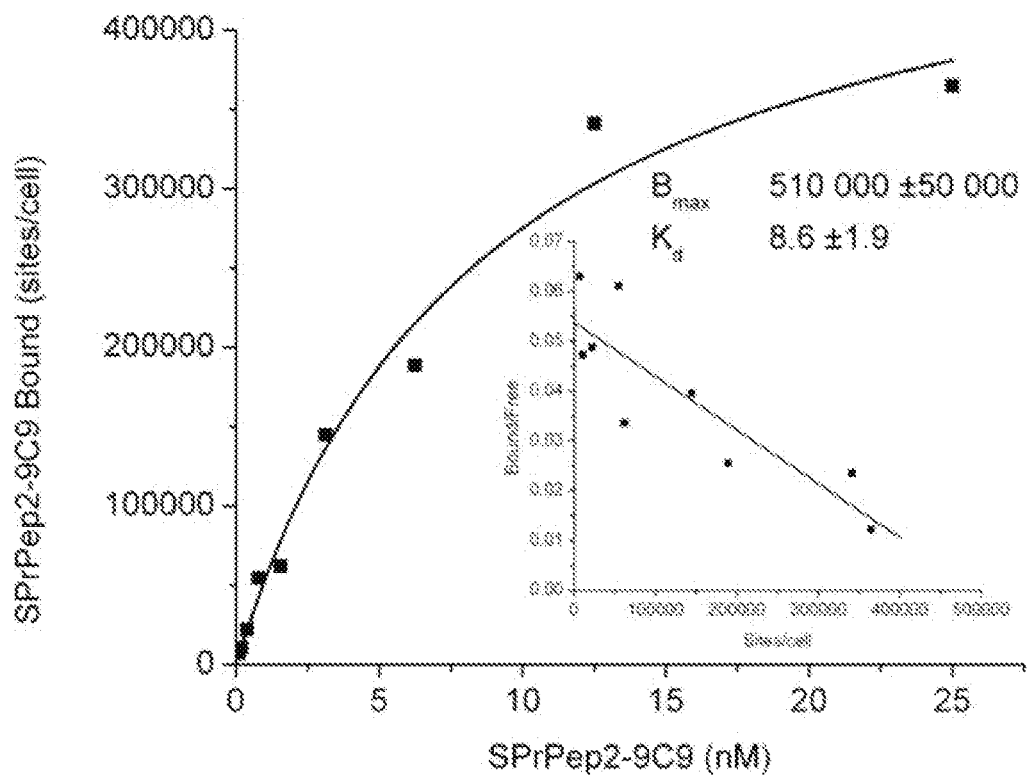
Figure 5C:
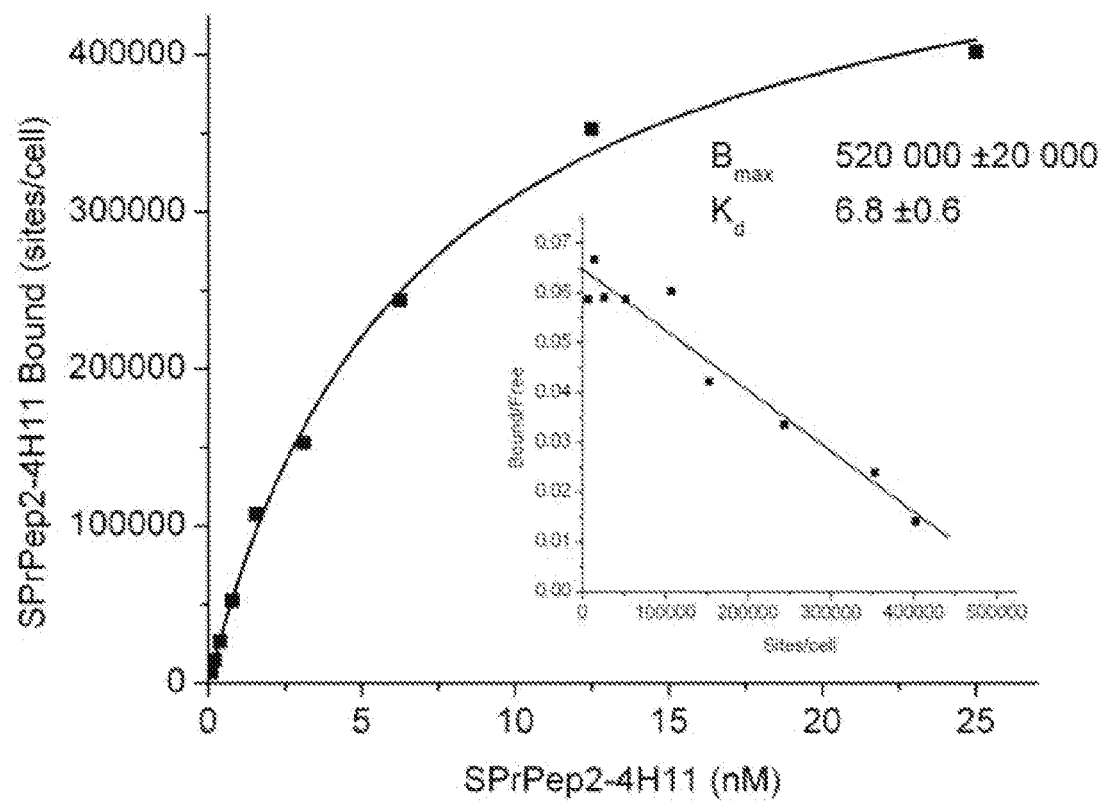
Figure 5D:
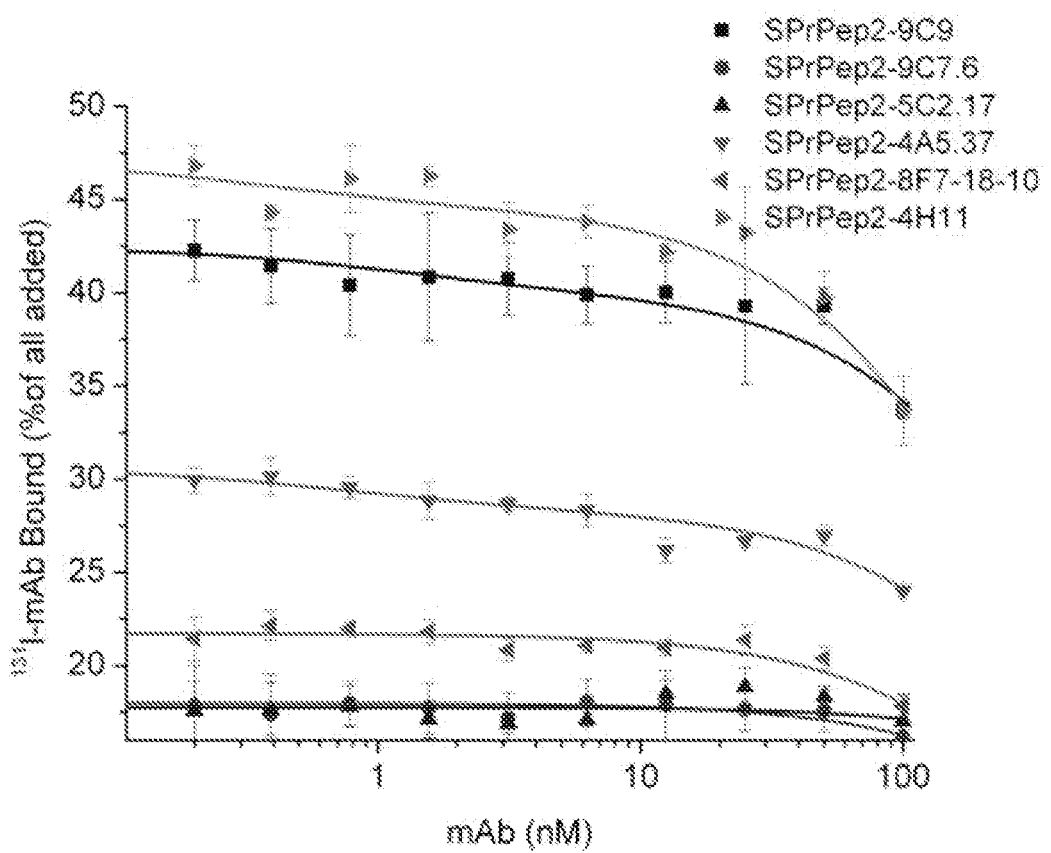
Figure 5E:
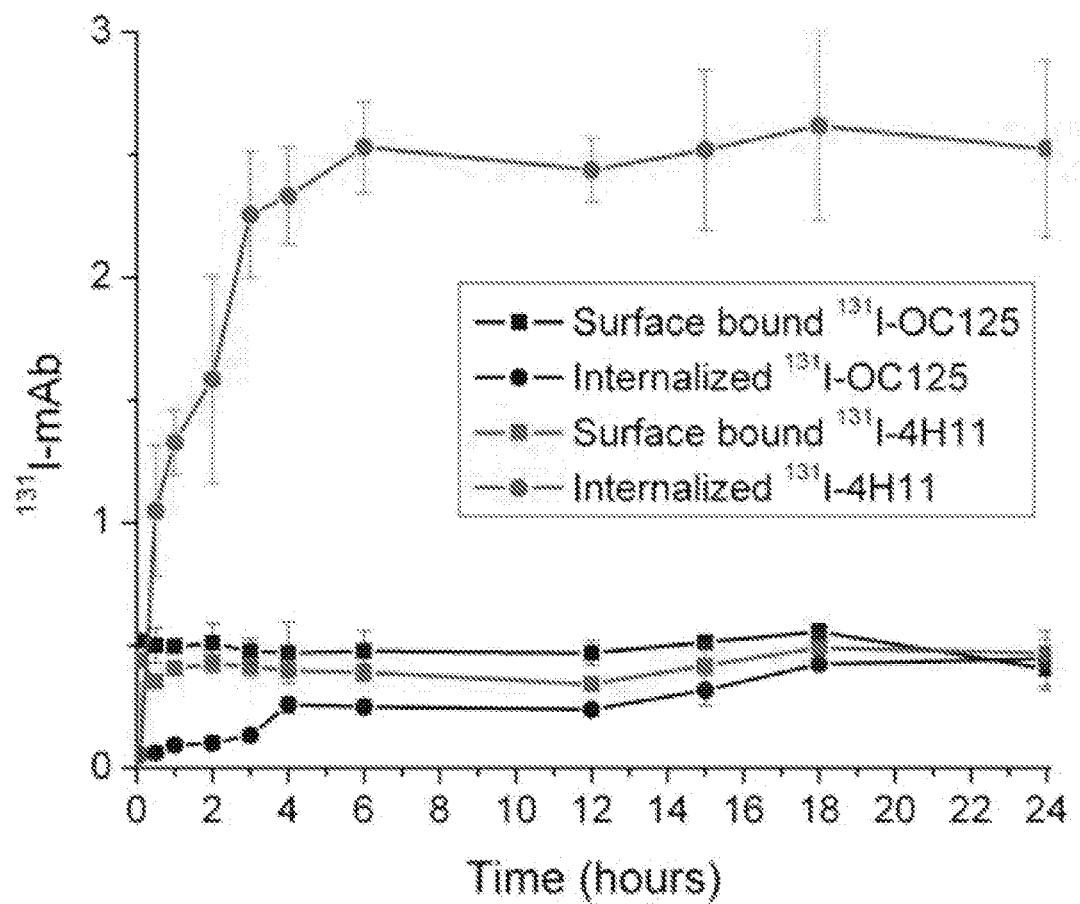
FIG. 5E: Internalization of radio-labeled 4H11 and OC125 monoclonal antibodies on SKOV3-phrGFP-ΔMUC16$^{c334}$ stable transfected cells.
Figure 6A:
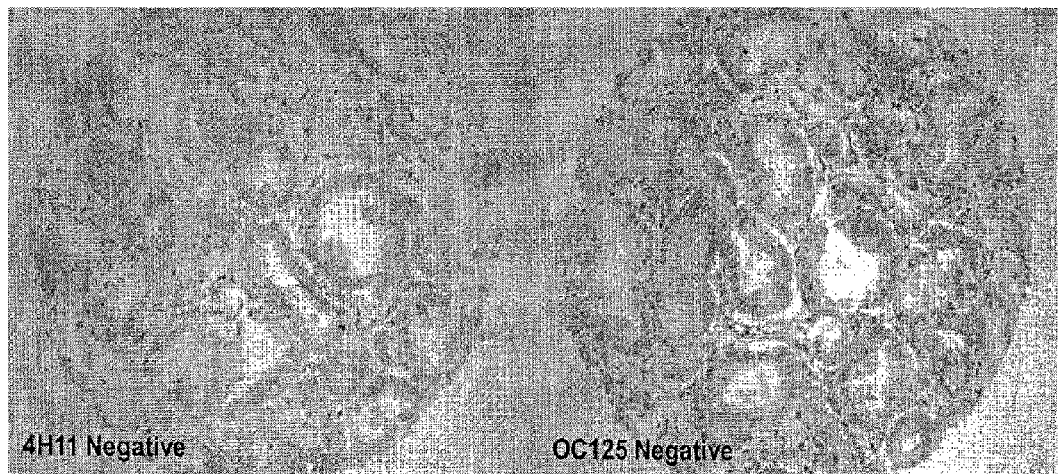
FIG. 6A-D: Comparison staining intensities of OC125 and 4H11 monoclonal antibodies on tissue microarrays containing cancers of the prostate (2A, concordant), lung (2B, discordant), breast (2C, discordant), and pancreas (2D, discordant).
Figure 6B:
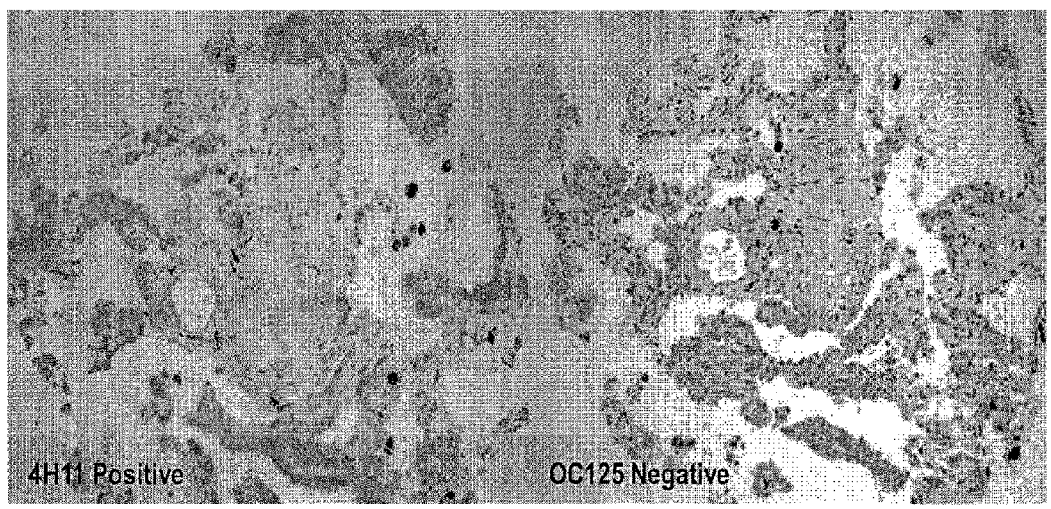
Figure 6C:
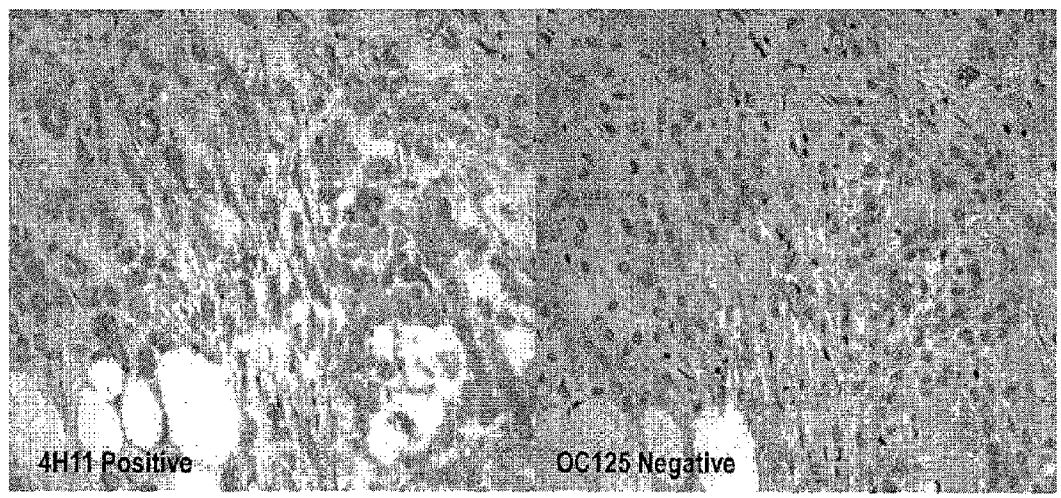
Figure 6D:
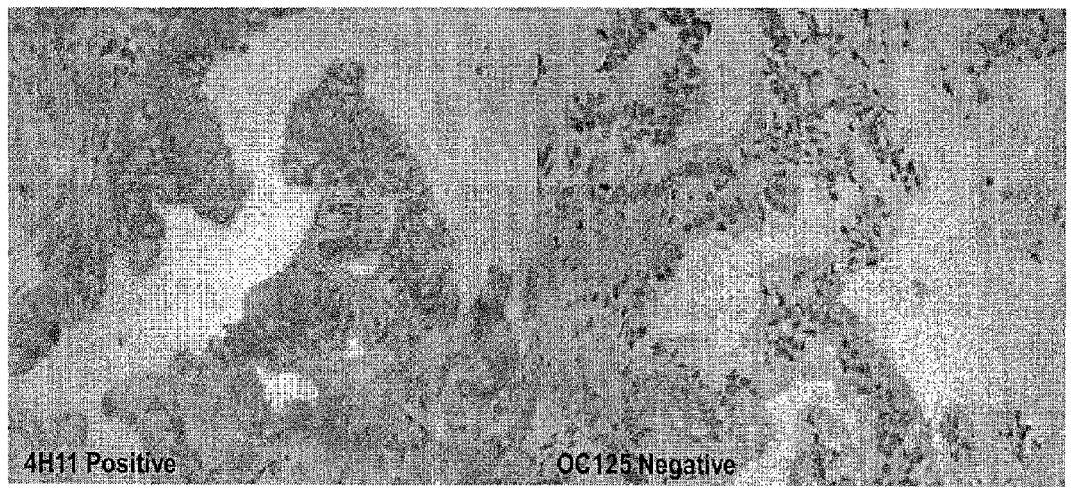

One advantage of the invention's antibodies is that the antibody internalizes into a cell, thereby being useful in applications for delivery inside a cell, such as disease therapy. "Internalized" when in reference to a molecule that is internalized by a cell refers to passage of the molecule that is in contact with the extracellular surface of a cell membrane across the cell membrane to the intracellular surface of the cell membrane and/or into the cell cytoplasm. Methods for determining internalization are disclosed herein, including the detection of radiolabeled molecule inside the cell (FIG. 5E).

In one embodiment, the invention's antibodies specifically bind to MUC16 ectodomain polypeptide that comprises a polypeptide selected from the group consisting of Polypeptide 1 NFSPLARRVDRVAIYEE (SEQ ID NO:01) and Polypeptide 2 TLDRSSVLVDGYSPNRNE (SEQ ID NO:02). Data herein show that the invention's antibodies specifically bind to GST-ΔMUC16$^{c\ 114}$ (Example 2, Table 1A). The specificity of the invention's antibodies is in contrast to prior art antibodies (e.g., VK8, M11 and OC125 antibodies) that did not bind to GST-ΔMUC16$^{c114}$ purified protein or cell lysates of the SKOV3-phrGFP-ΔMUC16$^{c114}$ cell line (Example 2, FIG. 2).

In a further embodiment, the invention's antibodies lack specific binding to a glycosylated MUC16 extracellular domain, exemplified by the cleaved CA-125 described in Payne et al., U.S. Pat. No. 7,202,346.

While not intending to limit the sequence of the $V_L$ and $V_H$ regions of the invention's antibodies, in one embodiment, the antibody specifically binds to the Polypeptide 2 (SEQ ID NO:02) of the MUC16 ectodomain polypeptide, wherein the antibody comprises a variable heavy ($V_H$) chain encoded by SEQ ID NO:06 (i.e., the antibody 4H11 variable heavy (VH) chain amino acid sequence of FIG. 8C), and a variable light ($V_L$) chain encoded by SEQ ID NO:07 (i.e., the antibody 4H11 variable light ($V_L$) chain amino acid sequence of FIG. 8D). In a particular embodiment, the antibody is chimeric, wherein at least one of the $V_L$ and $V_H$ chains is fused to a human immunoglobulin constant region.

Also without intending to limit the sequence of the $V_L$ and $V_H$ regions of the invention's antibodies, in one embodiment, the antibody specifically binds to the Polypeptide 2 (SEQ ID NO:02) of the MUC16 ectodomain polypeptide, wherein the antibody comprises a variable heavy ($V_H$) chain encoded by SEQ ID NO:04 (i.e., the antibody 4A5 variable heavy ($V_H$) chain nucleotide sequence of FIG. 8A), and a variable light ($V_L$) chain encoded by SEQ ID NO:05 (i.e., the antibody 4A5 variable light ($V_L$) chain nucleotide sequence of FIG. 8B). In a particular embodiment, the antibody is chimeric wherein at least one of the $V_L$ and $V_H$ chains is covalently linked to a human immunoglobulin constant region.

Still without intending to limit the sequence of the $V_L$ and $V_H$ regions of the invention's antibodies, in one embodiment, the antibody specifically binds to the Polypeptide 1 (SEQ ID NO:01) of the MUC16 ectodomain polypeptide, wherein the antibody comprises a variable heavy ($V_H$) chain encoded by SEQ ID NO:08 (i.e., the antibody 9B11 variable heavy (VH) chain nucleotide sequence of FIG. 8E), and a variable light (V$_L$) chain encoded by at least one of SEQ ID NO:09 (i.e., antibody 9B11 variable light (V$_{L.A}$) chain nucleotide sequence of FIG. 8F), and SEQ ID NO:10 (i.e., the antibody 9B11 variable light (V$_{L.B}$) chain nucleotide sequence of FIG. 8G). In a particular embodiment, the antibody is chimeric wherein at least one of the V$_L$ and V$_H$ chains is covalently linked to a human immunoglobulin constant region.

While not intending to restrict the source of antigen to which the invention's antibodies bind, in one embodiment, the MUC16 ectodomain polypeptide is expressed by a cell. Data herein show that the invention's exemplary antibodies bind to SKOV3 cells transduced with phrGFP-ΔMUC16$^{c114}$ (Example 2).

While not limiting the sequence of antigen to which the invention's antibodies bind, in a further embodiment, the invention's antibodies specifically bind to a MUC16 cytoplasmic domain polypeptide that comprises VTTRR RKKEGEYNVQ QQ (SEQ ID NO:18). In a particular embodiment, the MUC 16 cytoplasmic domain polypeptide comprises Polypeptide 3 CGVLVTTRRRKKEGEYN-VQQQ (SEQ ID NO:03). In some embodiment, the MUC16 cytoplasmic domain polypeptide is expressed by a cell. For example, data herein show that the invention's exemplary antibody binds to SKOV3 cells transduced with phrGFP-ΔMUC16$^{c114}$ (Example 2). In a particular embodiment, the cell is permeabilized to facilitate internalization of the antibody into the cell so that it comes into contact with its cytoplasmic antigen.

Still without limiting the sequence of antigen to which the invention's antibodies bind, in a further embodiment, the invention's antibodies bind to a MUC16 extracellular domain polypeptide that contains a cysteine loop polypeptide CQVSTFRSVPNRHHTGVDSLC (SEQ ID NO:19). In a more preferred embodiment, the MUC16 extracellular domain polypeptide comprises Polypeptide 4 KSYF SDC-QVSTFRS VPNRHHTGVD SLCNFSPL (SEQ ID NO:15).

Still without intending to limit the sequence of the V$_L$ and V$_H$ regions of the invention's antibodies, in one embodiment, the antibody specifically binds to Polypeptide 4 (SEQ ID NO:15) of the MUC 16 extracellular domain polypeptide, wherein the antibody comprises a variable heavy (V$_H$) chain encoded by SEQ ID NO:11 (i.e., the antibody 24B3 variable heavy (V$_H$) chain amino acid sequence of FIG. 8H), and a variable light (V$_L$) chain encoded by SEQ ID NO:12 (i.e., the antibody 24B3 variable light (V$_L$) chain amino acid sequence of FIG. 8I).

The invention contemplates chimeric antibodies (see U.S. Pat. No. 7,662,387), monoclonal antibodies, recombinant antibodies, an antigen-binding fragment of a recombinant antibody, a humanized antibody, and an antibody displayed upon the surface of a phage (U.S. Pat. No. 7,202,346). In particular, the invention contemplates antibody fragments that contain the idiotype ("antigen-binding region" or "antigen-binding fragment") of the antibody molecule. For example, such antigen-binding fragments include, but are not limited to, the Fab region, F(ab')2 fragment, pFc' fragment, and Fab' fragments.

The "Fab region" and "fragment, antigen binding region," interchangeably refer to portion of the antibody arms of the immunoglobulin "Y" that function in binding antigen. The Fab region is composed of one constant and one variable domain from each heavy and light chain of the antibody. Methods are known in the art for the construction of Fab expression libraries (Huse et al., Science, 246:1275-1281 (1989)) to allow rapid and easy identification of monoclonal Fab fragments with the desired specificity. In another embodiment, Fc and Fab fragments can be generated by using the enzyme papain to cleave an immunoglobulin monomer into two Fab fragments and an Fc fragment. The enzyme pepsin cleaves below the hinge region, so a "F(ab')2 fragment" and a "pFc' fragment" is formed. The F(ab')2 fragment can be split into two "Fab' fragments" by mild reduction.

The invention also contemplates a "single-chain antibody" fragment, i.e., an amino acid sequence having at least one of the variable or complementarity determining regions (CDRs) of the whole antibody, and lacking some or all of the constant domains of the antibody. These constant domains are not necessary for antigen binding, but constitute a major portion of the structure of whole antibodies. Single-chain antibody fragments are smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies. Techniques for the production of single-chain antibodies are known (U.S. Pat. No. 4,946,778). The variable regions of the heavy and light chains can be fused together to form a "single-chain variable fragment" ("scFv fragment"), which is only half the size of the Fab fragment, yet retains the original specificity of the parent immunoglobulin.

The "Fc region" and "Fragment, crystallizable region" interchangeably refer to portion of the base of the immunoglobulin "Y" that function in role in modulating immune cell activity. The Fc region is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils. In an experimental setting, Fc and Fab fragments can be generated in the laboratory by cleaving an immunoglobulin monomer with the enzyme papain into two Fab fragments and an Fc fragment.

The invention contemplates polyclonal antibodies and monoclonal antibodies. "Polyclonal antibody" refers to an immunoglobulin produced from more than a single clone of plasma cells; in contrast "monoclonal antibody" refers to an immunoglobulin produced from a single clone of plasma cells. Generic methods are available for making polyclonal and monoclonal antibodies that are specific to a desirable polypeptide. For the production of monoclonal and polyclonal antibodies, various host animals can be immunized by injection with the peptide corresponding to any molecule of interest in the present invention, including but not limited to hamsters, rabbits, mice, rats, sheep, goats, etc. For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 (1975)), techniques using germ-free animals and utilizing technology such as that described in PCT/US90/02545, as well as the trioma technique, the human B-cell hybridoma technique (See e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)). In some particularly preferred embodiments of the present invention, the present invention provides monoclonal antibodies.

Also contemplated are chimeric antibodies. As used herein, the term "chimeric antibody" contains portions of two different antibodies, typically of two different species. See, e.g.: U.S. Pat. No. 4,816,567 to Cabilly et al.; U.S. Pat. No. 4,978,745 to Shoemaker et al.; U.S. Pat. No. 4,975,369 to Beavers et al.; and U.S. Pat. No. 4,816,397 to Boss et al. Chimeric antibodies include monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a Hc region that aggregates (e.g., IgM H chain).

The invention also contemplates "humanized antibodies," i.e., chimeric antibodies that have constant regions derived substantially or exclusively from human antibody constant regions, and variable regions derived substantially or exclusively from the sequence of the variable region from a mammal other than a human. Humanized antibodies preferably have constant regions and variable regions other than the complement determining regions (CDRs) derived substantially or exclusively from the corresponding human antibody regions and CDRs derived substantially or exclusively from a mammal other than a human. Thus, in one embodiment, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody may also comprise at least a portion of an immunoglobulin constant region (Fc), typically that of a human immunoglobulin. Humanized antibodies may be generated using methods known in the art, e.g., U.S. Pat. No. 5,225,539 to Winter et al., including using human hybridomas (Cote et al., Proc. Natl. Acad. Sci. U.S.A.80:2026-2030 (1983)) or by transforming human B cells with EBV virus in vitro (Cole et al., in *Monoclonal Antibodies and Cancer Therapy*, Alan R. Liss, pp. 77-96 (1985)). Additional methods include, for example, generation of transgenic non-human animals which contain human immunoglobulin chain genes and which are capable of expressing these genes to produce a repertoire of antibodies of various isotypes encoded by the human immunoglobulin genes (U.S. Pat. Nos. 5,545,806; 5,569,825 and 5,625,126). Humanized antibodies may also be made by substituting the complementarity determining regions of, for example, a mouse antibody, into a human framework domain (PCT Pub. No. WO92/22653).

Importantly, early methods for humanizing antibodies often resulted in antibodies with lower affinity than the non-human antibody starting material. More recent approaches to humanizing antibodies address this problem by making changes to the CDRs. See U.S. Patent Application Publication No. 20040162413, hereby incorporated by reference. In some embodiments, the invention's humanized antibodies contain an optimized heteromeric variable region (e.g. that may or may not be part of a full antibody other molecule) having equal or higher antigen binding affinity than a donor heteromeric variable region, wherein the donor heteromeric variable region comprises three light chain donor CDRs, and wherein the optimized heteromeric variable region comprises: a) a light chain altered variable region comprising; i) four unvaried human germline light chain framework regions, and ii) three light chain altered variable region CDRs, wherein at least one of the three light chain altered variable region CDRs is a light chain donor CDR variant, and wherein the light chain donor CDR variant comprises a different amino acid at only one, two, three or four positions compared to one of the three light chain donor CDRs (e.g. the at least one light chain donor CDR variant is identical to one of the light chain donor CDRs except for one, two, three or four amino acid differences).

Chimeric antibodies containing amino acid sequences that are fused to constant regions from human antibodies, or to toxins or to molecules with cytotoxic effect, are known in the art (e.g., U.S. Pat. Nos. 7,585,952; 7,227,002; 7,632,925; 7,501,123; 7,202,346; 6,333,410; 5,475,092; 5,585,499; 5,846,545; 7,202,346; 6,340,701; 6,372,738; 7,202,346; 5,846,545; 5,585,499; 5,475,092; 7,202,346; 7,662,387; 6,429,295; 7,666,425; and 5,057,313).

Antibodies that are specific for a particular antigen may be screened using methods known in the art (e.g., U.S. Pat. No. 7,202,346) and disclosed herein. For example, In the production of antibodies, screening for the desired antibody can be accomplished by radioimmunoassay, ELISA (enzyme-linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In one embodiment, the invention's antibodies are monoclonal antibodies produced by a hybridoma cell line. In a particular embodiment, the monoclonal antibody specifically binds to a MUC16 ectodomain polypeptide that comprises Polypeptide 1 (SEQ ID NO:01), as exemplified by the antibody selected from the group consisting of 9B11.20.16, 10A2, 2F4, 23D3, 30B1, and 31B2 (Tables 1 and 2). In a preferred embodiment, the antibody is 9B11.

In another embodiment, the monoclonal antibody specifically binds to a MUC16 ectodomain polypeptide that comprises Polypeptide 2 (SEQ ID NO:02), wherein the antibody is exemplified by 4H11.2.5, 13H1, 29G9, 9C9.21.5.13, 28F8, 23G12, 9C7.6, 11B6, 25G4, 5C2.17, 4C7, 26B2, 4A5.37, 4A2, 25H3, and 28F7.18.10 (Tables 1 and 2). In a preferred embodiment, the antibody is exemplified by 4H11.2.5, 4A5.37, 9C9.21.5.13, 28F7.18.10, 9C7.6, and 5C2.17.

In a further embodiment, the monoclonal antibody specifically binds to a MUC16 cytoplasmic domain polypeptide that comprises Polypeptide 3 CGVLVTTRRRKKEGEYN-VQQQ (SEQ ID NO:03), wherein the antibody is exemplified by 31A3.5.1, 19D1, 10F6, 22E10, 22F1, 3H8, 22F11, 4D7, 24G12, 19G4, 9A5, 4C2, 31C8, 27G4, and 6H2 (Tables 1 and 2). In a preferred embodiment, the antibody is 31A3.5.1.

In another embodiment, the monoclonal antibody specifically binds to a MUC16 extracellular domain polypeptide that comprises Polypeptide 4 KSYF SDCQVSTFRS VPN-RHHTGVD SLCNFSPL (SEQ ID NO:15), wherein the antibody is exemplified by 24B3 and 9C7 (Table 2).

The invention's antibodies and methods for their use (both diagnostic and therapeutic) are disease specific. "Specificity" of a method and/or molecule for disease, such as "specificity for cancer" which is interchangeably used with "cancer specificity", refers to the proportion (e.g., percentage, fraction, etc.) of negatives (i.e., healthy individuals not having disease) that are correctly identified, i.e., the percentage of healthy subjects who are correctly identified as not having disease. Specificity may be calculated according to the following equation:

Specificity=number of true negatives/(number of true negatives+number of false positives).

Thus, in some embodiments, the invention's compositions and/or methods have a "cancer specificity" greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% specificity is most desirable, i.e., not predicting anyone from the healthy group as having cancer, it is not necessary. Data herein demonstrate the invention's cancer specificity (Table 3).

In alternative embodiments, specificity is expressed (together with sensitivity) as a statistical measure of the performance of a binary classification test, such as using a Receiver Operator Characteristic (ROC) curve". For any test, there is usually a trade-off between specificity and sensitivity. For example: in cancer screening tests of human subjects, it is undesirable to risk falsely identifying healthy people as having cancer (low specificity), due to the high costs. These costs are both physical (unnecessary risky procedures) and financial. This trade-off can be represented graphically using a ROC curve. "Receiver Operator Characteristic curve" and "ROC curve" refer to a plot of the true positive rate (AKA sensitivity) versus true negative rate (AKA 1-specificity). The measured result of the test is represented on the x axis while the y axis represents the number of control (e.g., healthy) or case (e.g., cancer) subjects. For any given cut point (each point along the x axis) a sensitivity and specificity of the assay can be measured. The range of sensitivity and specificity for any given assay can range from 0% to 100%, depending on the selected cut point. For this reason, in some preferred embodiments, the AUC is used as the standard measure of an assay's specificity and/or sensitivity. The "area under the curve" ("AUC") for the ROC curve plot is equal to the probability that a classifier will rank a randomly chosen positive instance higher than a randomly chosen negative one. Thus, AUC is a general measure of a tests ability to successfully discriminate between case (e.g., cancer) and control (e.g., healthy) subjects. Random chance would generate an AUC of 0.5. Therefore, in one embodiment, useful tests preferably have AUC's greater than 0.50, including any value from 0.51 to 1.00, such as from 0.55 to 1.00, from 0.60 to 1.00, from 0.65 to 1.00, from 0.70 to 1.00, from 0.75 to 1.00, from 0.80 to 1.00, from 0.85 to 1.00, from 0.90 to 1.00, from 0.95 to 1.00, and most preferably 1.00. AUC values greater than 0.50 include 0.51, 0.52, 0.52, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, and 0.99.

The invention's antibodies and methods for their use (both diagnostic and therapeutic) are disease sensitive. "Sensitivity" of a method and/or molecule for disease, such as "sensitivity for cancer" which is interchangeably used with "cancer sensitivity," refers to the proportion (e.g., percentage, fraction, etc.) of positives (i.e., individuals having cancer) that are correctly identified as such (e.g. the percentage of people with cancer who are identified as having the condition). Sensitivity may be calculated according to the following equation; Sensitivity=number of true positives/(number of true positives+number of false negatives).

Thus, in some embodiments, the invention's compositions and/or methods have a "disease sensitivity," such as "cancer sensitivity," greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% sensitivity is most desirable (i.e., predicting all subjects from the cancer group as having cancer), it is not necessary.

In alternative embodiments, the invention's compositions and/or methods have a "disease sensitivity," such as "cancer sensitivity," equal to or lower than 50%, including any numerical value from 0% to 50%, such as 1%, 2%, 3%, 4%, 6%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, and 49%.

In some embodiments, sensitivity is expressed (together with specificity) as a statistical measure of the performance of a binary classification test, such as using AUC of a ROC curve, as discussed above with respect to specificity.

D. Hybridoma Cell Lines

In addition to the invention's novel antibodies, the invention also provides hybridoma cell lines that produce these antibodies. "Hybridoma cell" refers to a cell line produced by fusing a specific antibody-producing B cell with a myeloma (B cell cancer) cell that is selected for its ability to grow in tissue culture and for an absence of antibody chain synthesis. The antibodies produced by the hybridoma cell are all of a single specificity and are therefore monoclonal antibodies (in contrast to polyclonal antibodies).

In a particular embodiment, the invention provides hybridoma cell lines that produce a monoclonal antibody that specifically binds to a polypeptide, or antigenic portion thereof, selected from the group consisting of a) MUC16 ectodomain polypeptide (e.g., NFSPLAR RVDRVAIYEE FLRMTRNGTQ LQNFTLDRSS VLVDGYSPNR NEPLT-GNSDL P (SEQ ID NO:17)), b) MUC16 cytoplasmic domain polypeptide (e.g., VTTRR RKKEGEYNVQ QQ (SEQ ID NO:18)), and c) MUC16 extracellular domain polypeptide that contains a cysteine loop polypeptide CQVSTFRSVPN-RHHTGVDSLC (SEQ ID NO:19). The MUC16 polypeptide SEQ ID NO:18 is contained within LVTTRR RKKEGEY-NVQ QQ (SEQ ID NO:20). Thus, SEQ ID NO:20 contains both a transmembrane domain amino acid (L) and a cytoplasmic domain portion VTTRR RKKEGEYNVQ QQ (SEQ ID NO:18), i.e., the L is optional, as it is part of the transmembrane domain. The MUC16 polypeptide SEQ ID NO:18 is also contained within CGVLVTTRR RKKEGEYNVQ QQ (SEQ ID NO:03). Thus, SEQ ID NO:03 contains both a transmembrane domain portion (CGVL) and a cytoplasmic domain portion VTTRR RKKEGEYNVQ QQ (SEQ ID NO:18), i.e., the CGVL is optional, as it is part of the transmembrane domain.

E. Conjugates Of The Invention's Antibodies Linked To Cytotoxic Agents And/Or Prodrugs The invention contemplates conjugate antibodies. A "conjugate" antibody refers to an antibody of the present invention covalently linked to a cytotoxic agent and/or a prodrug of a cytotoxic agent.

"Cytotoxic agent" refers any agent that is capable of reducing the growth of, and/or killing, a target cell. A "prodrug" represents an analog of a cytotoxic agent that substantially lacks cytotoxic activity until subjected to an activation step. Activation steps may include enzymatic cleavage, a chemical activation step such as exposure to a reductant, or a physical activation step such as photolysis.

The covalent linkage between the invention's antibodies and the cytotoxic agent or prodrug can include cleavable linkages such as disulfide bonds, which may advantageously result in cleavage of the covalent linkage within the reducing environment of the target cell. Such conjugates are useful as tumor-cell specific therapeutic agents.

In one embodiment, the cytotoxic agent is a small drug molecule (Payne et al., U.S. Pat. No. 7,202,346). In another embodiment, the cytotoxic agent a maytansinoid, an analog of a maytansinoid, a prodrug of a maytansinoid, or a prodrug of an analog of a maytansinoid (U.S. Pat. Nos. 6,333,410; 5,475,092; 5,585,499; 5,846,545; 7,202,346). In another embodiment, the cytotoxic agent may be a taxane (see U.S. Pat. Nos. 6,340,701 & 6,372,738 & 7,202,346) or CC-1065 analog (see U.S. Pat. Nos. 5,846,545; 5,585,499; 5,475,092 & 7,202,346).

In another embodiment, the cytotoxic agent is exemplified by an auristatin, a DNA minor groove binding agent, a DNA minor groove alkylating agent, an enediyne, a duocarmycin, a maytansinoid, and a vinca alkaloid (U.S. Pat. No. 7,662, 387).

In a further embodiment, the cytotoxic agent is an anti-tubulin agent (U.S. Pat. No. 7,662,387). In yet another embodiment, the cytotoxic agent is exemplified by dimethylvaline-valine-dolaisoleuine-dolaproine-phenylalanine-p-phenylenediamine (AFP), dovaline-valine-dolaisoleunine-dolaproine-phenylalanine (MMAF), and monomethyl auristatin E (MAE) (U.S. Pat. No. 7,662,387).

In an additional embodiment the toxic agent is exemplified by radioisotope emitting radiation, immunomodulator, lectin, and toxin (U.S. Pat. No. 6,429,295). In particular, the radioisotope emitting radiation is an alpha-emitter selected from the group consisting of $^{212}$Bi, $^{213}$Bi, and $^{211}$At, or a beta-emitter selected from the group consisting of $^{186}$Re and $^{90}$Y, or a gamma-emitter $^{131}$I (U.S. Pat. No. 7,666,425).

In an alternative embodiment, the toxin is exemplified by ricin, the A-chain of ricin, and pokeweed antiviral protein (U.S. Pat. No. 5,057,313).

In yet another embodiment, the cytotoxic agent is an anti-cancer drug selected from the group consisting of methotrexate, 5-fluorouracil, cycloheximide, daunomycin, doxorubicin, chlorambucil, trenimon, phenylenediamine mustard, adriamycin, bleomycin, cytosine arabinoside or Cyclophosphamide (U.S. Pat. No. 5,057,13).

F. Detecting Muc16 Portions And Diagnostic Applications

The invention provides a method for detecting a disease that comprises overexpression of MUC16 in a subject, wherein the method comprises a) providing i) a sample from a subject, and ii) any one or more of the invention's antibodies, b) contacting the sample with the antibody under conditions for specific binding of the antibody with its cognate antigen, and c) detecting an increased level of binding of the antibody to the sample compared to a control sample lacking the disease, thereby detecting the disease in the subject. Generic methods for detecting disease using antibodies are known in the art (Payne et al., U.S. Pat. No. 7,202,346). The invention's methods are particularly useful in detecting cancer, such as ovarian cancer and breast cancer.

The invention's methods are not limited to a particular approach to detecting binding of the invention's antibodies to their antigens. In one embodiment, detecting binding to the invention's antibodies typically involves using antibodies that are labeled with a detectable moiety, such as radioisotope (e.g., 3H, $^{14}$C, $^{32}$P, $^{35}$S, and/or $^{125}$I), fluorescent or chemiluminescent compound (e.g., fluorescein isothiocyanate, rhodamine, and/or luciferin) and/or an enzyme (e.g., alkaline phosphatase, beta-galactosidase and/or horseradish peroxidase).

Methods for conjugating antibodies to a detectable moiety are known in the art (e.g., Hunter, et al., Nature 144:945 (1962); David, e at., Biochemistry 13:1014 (1974); Pain, et al., J. Immunol. Meth. 40:219 (1981); and Nygren, J. Histochem. and Cytochem. 30:407 (1982).

Thus, the invention's antibodies may be employed in immunoassays, such as competitive binding assays, direct and indirect sandwich assays, and immunoprecipitation assays, including immunohistochemistry, enzyme-linked immunosorbent assay (ELISA), fluorescence-activated cell sorting (FACS), and Western blots.

For example, with respect to immunohistochemical detection, data herein demonstrate that antibody 4H11 is useful in detecting high-grade ovarian serous carcinoma, lobular cancer (28), and a subset of ovarian carcinomas that are negative with OC125 and that retain cytoplasmic and extracellular portions of the MUC16 glycoprotein.

The antibodies of the invention also are useful for radiographic in vivo imaging, wherein an antibody labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies.

The invention's antibodies are additionally useful as affinity purification agents. In this process, the antibodies are immobilized on a suitable support, such a Sephadex resin or filter paper, using methods well known in the art, to capture and purify molecules that contain antigens that specifically bind to the invention's antibodies.

G. Therapeutic Applications

The invention provides methods for treating a disease that comprises overexpression of MUC16, comprising administering to a subject having the disease a therapeutically effective amount of any one or more of the invention's antibodies. Generic methods for treating disease with antibodies are known in the art (Payne et al., U.S. Pat. No. 7,202,346). The invention's methods are particularly useful in treating cancer, such as ovarian cancer and breast cancer. These methods are also applicable to primary cancer, metastatic cancer, and recurrent cancer.

The term "administering" to a subject means providing a molecule to a subject. This may be done using methods known in the art (e.g., Erickson et al., U.S. Pat. No. 6,632,979; Furuta et al., U.S. Pat. No. 6,905,839; Jackobsen et al., U.S. Pat. No. 6,238,878; Simon et al., U.S. Pat. No. 5,851,789). The invention's compositions may be administered prophylactically (i.e., before the observation of disease symptoms) and/or therapeutically (i.e., after the observation of disease symptoms). Administration also may be concomitant with (i.e., at the same time as, or during) manifestation of one or more disease symptoms. Also, the invention's compositions may be administered before, concomitantly with, and/or after administration of another type of drug or therapeutic procedure (e.g., surgery). Methods of administering the invention's compositions include, without limitation, administration in parenteral, oral, intraperitoneal, intranasal, topical and sublingual forms. Parenteral routes of administration include, for example, subcutaneous, intravenous, intramuscular, intrastemal injection, and infusion routes.

In one embodiment, the invention's compositions comprise a lipid for delivery as liposomes. Methods for generating such compositions are known in the art (Borghouts et al. (2005). J Pept Sci 11, 713-726; Chang et al. (2009) PLoS One 4, e4171; Faisal et al. (2009) Vaccine 27, 6537-6545; Huwyler et al. (2008) Int J Nanomedicine 3, 21-29; Song et al. (2008) Int J Pharm 363, 155-161; Voinea et al. J Cell Mol Med 6, 465-474).

Antibody treatment of human beings with cancer is known in the art, for example in U.S. Pat. Nos. 5,736,137; 6,333,410; 5,475,092; 5,585,499; 5,846,545; 7,202,346; 6,340,701; 6,372,738; 7,202,346; 5,846,545; 5,585,499; 5,475,092; 7,202,346; 7,662,387; 7,662,387; 6,429,295; 7,666,425; 5,057,313.

The invention's antibodies may be administered with pharmaceutically acceptable carriers, diluents, and/or excipients. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The invention's antibodies are typically administered in a therapeutic amount. The terms "therapeutic amount," "pharmaceutically effective amount," "therapeutically effective amount," and "biologically effective amount," are used interchangeably herein to refer to an amount that is sufficient to achieve a desired result, whether quantitative or qualitative. In particular, a pharmaceutically effective amount is that amount that results in the reduction, delay, and/or elimination of undesirable effects (such as pathological, clinical, biochemical and the like) that are associated with disease. For example, a "therapeutic amount that reduces cancer" is an amount that reduces, delays, and/or eliminates one or more symptoms of cancer.

For example, specific "dosages" of a ""therapeutic amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors, which those skilled in the art will recognize. The dosage amount and frequency are selected to create an effective level of the compound without substantially harmful effects.

When present in an aqueous dosage form, rather than being lyophilized, the antibody typically will be formulated at a concentration of about 0.1 mg/ml to 100 mg/ml.

Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs.

The methods of the present invention can be practiced in vitro, in vivo, or ex vivo.

EXPERIMENTAL

The following examples serve to illustrate certain preferred embodiments and aspects of the present invention and are not to be construed as limiting the scope thereof.

Example 1

Materials And Methods

The following is a brief description of the exemplary materials and methods used in the subsequent Examples.
Cell Cultures:

OVCAR3, SKOV3, and A2780 cell lines were obtained through the American Type Culture Collection (ATCC, Manassas, Va.) and sustained in culture according to the ATCC literature. For the creation of MUC16+ transfected cell lines, the carboxyterminus portion of the MUC16 cDNA was introduced as green fluorescent protein fusion proteins using the Vitality phrGFP vector expression system (Stratagene, La Jolla, Calif.). Stable cell lines were selected using geneticin (G418, Invitrogen, Grand Island, N.Y.) in their respective culture media and isolated by expression of Green Fluorescence Protein. Stable transfectants were routinely maintained in G418 in their culture media respectively. The $\Delta MUC16^{c114}$ transfectants have cell surface expression of MUC16 protein from the putative cleavage site to the carboxyterminus (AA 1776 to 1890) (12).
Monoclonal Preparation:

Using the MUC16 sequence, peptide sequences encoding elements of the $\Delta MUC16^{c114}$ amino acid sequence were synthesized at the Memorial Sloan-Kettering Cancer Center (MSKCC) Microchemistry Core Facility. The inventors synthesized 3 polypeptides (FIG. 1) and modified Polypeptide 1 and Polypeptide 2 with a cysteine at the N-terminus for better conjugation to KLH. Equal concentrations of the KLH-conjugated peptides were mixed and then used as the immunogen for 5 BALB/c mice. The inventors selected 1 of the 5 mice whose serum showed the highest reactivity to individual peptides by ELISA, and the MSKCC Monoclonal Antibody Core Facility performed the fusion and selected the antibodies using standard protocols. After 10 days of fusion, supernatants were selected and screened for reactivity by ELISA against the individual synthetic peptides.
ELISA:

Sandwich ELISA was performed to see the positivity of the antibodies to individual peptides and GST-$\Delta MUC16^{c114}$ fusion protein following routine core facility protocol for ELISA assay.

FACS Analyses:

Adherent target cells were removed by 0.05% Trypsin and 0.1% EDTA, washed, and counted by a hemocytometer. Cells were distributed into multiple Eppendorf tubes with at least $0.5-1\times10^6$ cells per tube. Cells were washed with phosphate buffered saline (PBS) containing 1% FCS and 0.025% Sodium Azide (FACS buffer). For internal FACS staining, cells in the Eppendorf tubes were permeabilized with 1:10 diluted FACS Permeabilizing Solution 2 (BD BioSciences, San Jose, Calif.) for 10 minutes at room temperature and then washed twice with ice cold FACS buffer. Then they were incubated either without (for second antibody control) or with 1 μg/tube of bioreactive supernatants of mouse MUC16 monoclonals for 30 minutes on ice. For surface FACS staining, cells were incubated either without (for second antibody control) or with 1 μg/tube of bioreactive supernatants of MUC16 monoclonals (9B11.20.16, 9C9.21.5.13 and 4H11.2.5), Mouse anti-human OC125 (M3519), Mouse anti-human Mil (M3520) (DakoCytomation, Dako North America Inc., Carpinteria, Calif.) or VK8 (kindly provided by Dr. Beatrice Yin and Dr. Ken Lloyd, MSKCC, New York, N.Y.) for 30 minutes on ice. Cells in Eppendorf tubes were also surface stained with 1 μg/tube of non-specific isotype matched control mouse antibodies (13C4 for IgG1 and 4E11 for IgG2b monoclonals obtained from MSKCC Monoclonal Core Facility) and incubated on ice for 30 minutes. All cells were washed three times with FACS buffer. Cells were incubated with 1 μg/tube of second antibody Goat anti-mouse IgG1-PE or IgG2b-PE for 30 minutes on ice and then washed three times with FACS buffer. The cells were analyzed by a FACS Calibur machine at the MSKCC Flow Cytometry Core Facility.

Western Blot Analysis:

Stable cell lines were cultured in 10 cm dishes in their respective culture media and incubated with 5% $CO_2$ at 37° C. for 3 days. They were washed twice with ice cold PBS to remove the serum-containing media. Adherent cells were scraped with 1-2 ml of ice cold PBS, and the cells were spun down in an Eppendorf tube at 4° C. in an Eppendorf centrifuge. Supernatant was discarded, and the cells were lysed with 0.2 ml of modified Ripa lysis buffer (20 mM Tris-HCL; pH 7.4; 150 mM NaCl; 1% NP-40; 1 mM Na3VO4; 1 mM PMSF; 1 mM DTT; 10 m/ml leupeptin; and 10 μg/ml aprotinin) for 30 minutes on ice and spun at 4° C. for 10 minutes. The soluble solution was separated into a tube and the debris pellet was discarded. Protein concentration was measured using the Bio-Rad Protein Assay (BioRaD Laboratories, Hercules, Calif.). Equal amounts of proteins (GST-MUC16-CD-fusion protein or stable cell line extracts) were separated by sodium dodecyl sulfate polyacrylamide gel electrophoresis (SDS-PAGE) and transferred to nitrocellulose membrane using a BioRad transfer apparatus in a cold room at 4° C. The membranes were blocked with 3% bovine serum albumin (BSA) in PBS with 0.1% Tween-20 (PBST) at 4° C. overnight. Membranes were probed with primary antibody (1:1000 dilution) for 1 hr at room temperature and then washed three times with PBST. Then the membranes were stained with corresponding second antibody, anti-Mouse IgG Horse Radish Peroxidase (HRP) linked whole antibody from sheep (GE Healthcare, UK) (1:5000 dilution), for 1 hr at room temperature. Membranes were washed three times with PBST and developed with a Western Lightning® chemiluminescence reagent (ECL, Perkin Elmer, Waltham, Mass.) for 1-5 minutes at room temperature, and the signals were developed on Kodak BioMax Film.

Binding and internalization studies with monoclonal antibodies and OVCAR3 and SKOV3 stable transfectants:

Purified monoclonal antibodies were labeled with $^{131}I$ using the iodogen method and purified by size exclusion chromatography (22). Saturation binding studies were performed with radiolabeled antibodies using substrates of intact OVCAR-3 cells. Briefly, 10 test solutions were prepared (in triplicate) and they contained increasing amounts of the radioiodinated antibodies, 3-500 000 cells in a total volume of 500 μL of PBS (0.2% BSA; pH 7.4). The cells were isolated by rapid filtration through a glass fiber membrane and washed with ice cold tris buffered saline. Cells were counted in a gamma counter with standards of total activity added. For each concentration of radiolabeled antibody, non-specific binding was determined in the presence of 100 nM of the unmodified antibody. The data were analyzed with a least squares regression method (Origin, Microcal, Software Inc., Northampton, Mass.) to determine the $K_d$ and $B_{max}$ values, and a Scatchard transformation was performed.

Antibody cell internalization studies were performed with $^{131}I$-4H11 and $^{131}I$-OC125 monoclonal antibodies and SKOV3-phrGFP-ΔMUC16$^{c334}$ stable transfected cells. Briefly, radiolabeled antibody (370 MBq/mg, 100 kcpm) in 2 mL of medium was added to SKOV3 cells plated in a 6-well plate. The plates were incubated at 37° C. for up to 24 hours. At various time points, the medium was removed from three wells and the cells washed with 2×2 mL PBS. Cell surface bound activity was then stripped and collected with 2×2 mL of an ice cold acid wash (100 mM acetic acid 100 mM glycine; pH 3.0). The cells were then dissolved with 2×1 ml 1 M NaOH and collected. At the end of the study all samples were counted with a gamma counter together with standards, representing the initial amount of radioactivity added. All the media samples were analyzed by ITLC-SG with mobile phases of 5% TCA to determine unbound $^{131}I$.

Tissue Microarray (TMA):

Tissue microarrays were either constructed within our institution or bought from a commercial laboratory if not available internally. Briefly, core-needle biopsies of pre-existing paraffin-embedded tissue were obtained from the so-called donor blocks and then relocated into a recipient paraffin-arrayed "master" block by using the techniques by Kononen et al. and subsequently modified by Hedvat et al (23-24). A manually operated Tissue Arrayer MTA-1 from Beecher Instruments Inc. (Sun Prairie, Wis.) was used to produce sample circular spots (cores) that measured 0.6 to 1.0 mm in diameter. The cores were arrayed 0.3 to 0.4 mm apart from each other. A layer of control tissues was strategically laid around the actual tissue microarrays in order to avoid edging effects. The specific composition of each tissue microarray is delineated below. Slides of tissue microarrays for ovarian cancer, prostate cancer, adenocarcinoma of the lung, mucinous neoplasms of the pancreas, and invasive ductal and invasive lobular breast carcinoma were prepared by cutting 4 um sections from formalin-fixed paraffin-embedded tissue. Normal adult and fetal tissue microarrays were obtained from a commercial source (Biomax, US). OVCAR3 cells were used as positive controls.

Immunohistochemistry:

Immunohistochemistry was performed on the tissue microarrays with both standard OC125 (Ventana, Tuscon, Ariz.) and the novel monoclonal antibodies. Sections of the tissue microarrays were cut at 4 microns, placed on Superfrost/Plus microscope slides (Fisher brand) and baked in a 60° oven for at least 60 minutes. The slides were then deparaffinized and hydrated to distilled water, soaked in citrate buffer at pH 6.00 for 30 minutes at 97° C., washed in running water for 2-5 minutes, incubated for 5 minutes in 3% hydrogen peroxide diluted in distilled water. Slides were washed in distilled water for 1 minute, transferred to a bath of phosphate buffered saline (PBS), pH 7.2, for two changes of 5 minutes each and placed in 0.05% BSA diluted in PBS for a minimum of 1 minute. After drying around tissue sections, normal serum was applied at a 1:20 dilution in 2% BSA/PBS and incubated for a minimum of 10 minutes at room temperature in a humidity chamber. The serum was then suctioned off without allowing the sections to dry, and approximately 150 lambda of novel antibody at a dilution of 1:1000 was placed on the tissue. The slide was incubated overnight (approximately 15-18 hours) at 4° C. in a humidity chamber. Primary antibody was washed off using three changes of PBS for 10 minutes each. Secondary antibody, biotinylated α-mouse from Vector laboratories (Burlingame, Calif.), was applied at 1:500 dilution in 1% BSA/PBS and incubated for 45-60 minutes at room temperature in humidity chamber. The antibody was washed off again using three changes of PBS as above. Slides were then transferred to a bath of diaminobenzidine (DAB), diluted in PBS for 5-15 minutes. The slides were then washed in tap water for 1 minute, counterstained using Harris modified hematoxylin (Fisher), decolorized with 1% acid alcohol and blue in ammonia water, dehydrated with 3 changes each of 95% ethanol, 100% ethanol and xylene for 2 minutes each and coverslipped with permanent mounting medium.

Immunohistochemistry Scoring:

Commercially available antibodies, such as OC125 and M11, target complex glycosylation-dependent epitopes. Our hypothesis is that glycosylation may be tissue specific; therefore, it was important to examine the utility of the peptide-directed antibodies in paraffin-fixed tissues and survey the prevalence of MUC16 expression. The three candidate antibodies, 4H11, 9C9 and 4A5, were characterized using OVCAR3 cell line pellets. Of the three, the 4H11 antibody showed the strongest, most diffuse and consistent staining pattern at multiple dilutions, with the least amount of background staining and, therefore, was optimized for use in human tissues in the pathology core facility.

Using 4H11, the inventors stained and scored positivity using tissue microarrays from high-stage, high-grade ovarian serous carcinomas (FIG. 2), these tumors being the most common type of ovarian cancer, representing approximately 80-85% of all ovarian carcinomas in Western industrialized nations (25). To test the specificity of the novel antibody, the inventors also stained tissue microarrays of cancers of the prostate, lung, breast, and pancreas and compared their staining intensities with that of OC125 monoclonal antibody (FIG. 6A-D). To determine whether there would be any cross-reactivity with normal human tissues, the antibodies were also tested on normal human adult and fetal TMAs.

All of the stained sections were reviewed by a reference pathologist (KJP). A subset of cores for which there was equivocal staining was also independently scored by a second pathologist (RAS) to ensure consistency in scoring methods. Only cytoplasmic and/or membranous staining was considered positive. If a portion of the cell showed membranous staining, that was considered partial staining. A scoring system was devised to provide a semiquantitative assessment of staining distribution and intensity in individual cores. At the same time, it was designed to be useful for comparing the staining distribution and intensity between OC125 and the novel antibodies. The score incorporated the percentage of cells, the intensity and pattern of the staining according to the following standards: score 0: no staining; score 1: <5% strong or weak; score 2: 5-50% strong or weak; score 3: 51-75% strong or 51-100% weak; score 4: 76-99% strong; and score 5: 100% strong staining (FIG. 3A-FIG. 3L). The pathologist first reviewed all tissue microarrays stained with OC125 and scored each core. Then the same cores stained with the novel antibodies were scored 1 to several days after OC125 without reference to the previous results. Direct comparison of the scoring between the stains for each core was made only after all of the scoring was completed. The same process was used for all non-ovarian tissue microarrays. After comparison, core staining was determined to be concordant, equivocal, or discordant based on the point differentials. Concordant cores differed by 0 to 1 point, equivocal cores differed by 2 points, and discordant cores differed by 3 to 5 points. The one exception to this rule was when the difference of 1 point was between a score of 0 and 1, in which case, the differences were considered equivocal. This was in order to truly separate negative cases from even focally positive ones.

Example 2

Generation and Characterization of Anti-MUC16 Monoclonal Antibodies

MUC16-directed monoclonal antibodies were isolated by ELISA-based screening using both the individual peptides and recombinant GST-ΔMUC16$^{c114}$ protein followed by sequential subcloning for single cell clones.

Tables 1A and 1B:

MUC1-6-carboxyterminus monoclonal antibodies showing their reactivity to GST-ΔMUC16$^{c114}$ western, FACS analysis on OVCAR3 wild type cells

TABLE 1A

| | Peptide 1 | | | | Peptide 2 | | | | Peptide 3 | | |
|---|---|---|---|---|---|---|---|---|---|---|---|
| ELISA Hybridoma Sups (1:1) | (1:10) GST-MucCD Western +/− | (1:1) OVCAR3 FACS +/− | Isotype | ELISA Hybridoma Sups (1:1) | (1:10) GST-MucCD Western +/− | (1:1) OVCAR3 FACS +/− | Isotype | ELISA Hybridoma Sups (1:1) | (1:10) GST MucCD Western +/− | (1:1) OVCAR3 FACS +/− | Isotype |
| 10A2 | + | − | IgG1, IgM | 13H1 | Weak | − | IgG1 | 22E10 | + | − | IgG2b |
| 23D4 | − | − | missing | 28F8 | + | + | IgG1, IgM | 22F11 | Weak | − | IgM |
| 2F4 | Weak | − | IgG1, IgM | 11B6 | − | − | IgM | 19G4 | Weak | − | IgG1, IgM |
| 9B11 | Weak | +/− | IgG1 | 4C7 | + | − | IgG1 | 31A3 | Weak | − | IgG1 |
| 23D3 | Weak | + | IgG1, IgG2b | 28F7 | + | + | IgG1 | 4C2 | + | − | IgG1, IgM |
| 30B1 | − | − | IgG1 | 9C7 | + | + | IgG1 | 27G4 | + | − | IgM |
| 31B2 | + | − | IgM | 9C9 | + | + | IgG1, IgG2b | 19D1 | + | − | IgG2b |
| | | | | 4H11 | + | + | IgG2b, IgM | 22F1 | + | − | IgG2b, IgM |
| | | | | 4A2 | − | − | IgG1 | 4D7 | + | − | IgG3 |
| | | | | 4A5 | + | + | IgG1 | 9A5 | − | − | IgM |

TABLE 1A-continued

| Peptide 1 | | | | Peptide 2 | | | | Peptide 3 | | | |
|---|---|---|---|---|---|---|---|---|---|---|---|
| ELISA Hybridoma Sups (1:1) | (1:10) GST-MucCD Western +/− | OVCAR3 FACS +/− | Isotype | ELISA Hybridoma Sups (1:1) | (1:10) GST-MucCD Western +/− | OVCAR3 FACS +/− | Isotype | ELISA Hybridoma Sups (1:1) | (1:10) GST MucCD Western +/− | OVCAR3 FACS +/− | Isotype |
| | | | | 29G9 | + | − | IgG1 | 31C8 | − | − | IgG2b |
| | | | | 5C2 | + | + | IgG1 | 6H2 | Weak | − | IgG1, IgM |
| | | | | 23G12 | − | − | IgG1, IgG2a | 10F6 | − | − | IgG1 |
| | | | | 25G4 | − | − | IgG1, IgM | 3H8 | + | − | IgG1, IgM |
| | | | | 26B2 | + | + | IgG1, IgG2b, IgM | 24G12 | − | − | IgG1, IgM |
| | | | | 25H3 | − | − | IgG1, IgM | | | | |

TABLE 1B

| Peptide 1 | | | Peptide 2 | | | Peptide 3 | | |
|---|---|---|---|---|---|---|---|---|
| | OVCAR3 FACS +/− | Isotype | | OVCAR3 FACS +/− | Isotype | | OVCAR3 FACS +/− | Isotype |
| 9B11.20.16 | +/− | IgG1 | 9C9.21.5.13 | + | IgG2b | 31A3.5.1 | − | IgG1 |
| | | | 4H11.2.5 | + | IgG2b | | | |
| | | | 9C7.6 | + | IgG1 | | | |
| | | | 5C2.17 | + | IgG1 | | | |
| | | | 4A5.37 | + | IgG1 | | | |
| | | | 28F7.18.10 | + | IgG1 | | | |

TABLE 2

Antibodies specific for exemplary portions of MUC16

1. Muc16 Polypeptide 1:

```
14394                 14410                         (MUC16 sequence)
NFSPLARRVDRVAIYEE (SEQ ID NO: 01)                          17 aa
```

Mouse monoclonals which are specific to this peptide are:
9B11.20.16 (IgG1)
10A2 (IgG1, IgM)
2F4 (IgG1, IgM)
23D3 (IgG1, IgG2b)
30B1 (IgG1)
31B2 (IgM)

2. Muc16 Polypeptide 2:

```
14425                 14442                         (MUC16 sequence)
TLDRSSVLVDGYSPNRNE (SEQ ID NO: 02)                         18 aa
```

Mouse monoclonals which are specific to this peptide are:
4H11.2.5 (IgG2b)       13H1 (IgG1)          29G9 (IgG1)
9C9.21.5.13 (IgG2b)    28F8 (IgG1, IgM)     23G12 (IgG1, IgG2a)
9C7.6 (IgG1)           11B6 (IgM)           25G4 (IgG1, IgM)
5C2.17 (IgG1)          4C7 (IgG1)           26B2 (IgG1, IgG2b, IgM)
4A5.37 (IgG1)          4A2 (IgG1)           25H3 (IgG1, IgM)
28F7.18.10 (IgG1)

3. Muc16 Polypeptide 3 (SEQ ID NO: 03)

```
14472                 14492                         (MUC16 sequence)
CGVLVTTRRRKKEGEYNVQQQ                                      21 aa
```

Mouse monoclonals which are specific to this peptide are:
31A3.5.1 (IgG1)        19D1 (IgG2b)         10F6 (IgG1)
22E10 (IgG2b)          22F1 (IgG2b, IgM)    3H8 (IgG1, IgM)
22F11 (IgM)            4D7 (IgG3)           24G12 (IgG1, IgM)
19G4 (IgG1, IgM)       9A5 (IgM)
4C2 (IgG1, IgM)        31C8 (IgG2b)
27G4 (IgM)             6H2 (IgG1, IgM)
14452                 14475
FWAVILIGLAGLLGLITCLICGVL (SEQ ID NO: 14) is Transmembrane region      24 aa TABLE 2-continued Antibodies specific for exemplary portions of MUC16

4. Muc16 Polypeptide 4 (SEQ ID NO: 15) containing a
cysteine loop polypeptide (SEQ ID NO: 19):

```
14367                           14398                    (MUC16 sequence)
KSYFSDCQVSTFRSVPNRHHTGVDSLCNFSPL (SEQ ID NO:15)               32 aa
      |————S-S————————|
```

Mouse monoclonals which are specific to this peptide are:

| Clone | Isotype |
|---|---|
| 24B3 | (IgM) |
| 9C7 | (IgM) |
| 4F12 | IgM kappa |
| 6H6 | IgM kappa |
| 25C2 | IgM kappa |
| 6E8 | IgM kappa |
| 2A3 | IgM, IgG1, IgG2b, kappa |
| 2G4 | IgM, IgG1, kappa |
| 4C8 | IgM, kappa |
| 2A6 | IgG1 kappa |
| 24G12 | IgG1 kappa |
| 15D5 | IgG1 kappa |
| 6E2 | IgM, IgG1, IgG3, IgG2a, kappa |
| 7E6 | IgM, kappa, lambda |
| 7G11 | IgM kappa |
| 20C3 | IgG1, IgG2b |
| 9A3 | IgM kappa |
| 15B6 | IgM kappa |
| 19D3 | IgM kappa |
| 5H8 | IgM, IgG1, IgG2b, kappa |
| 24A12 | IgM kappa |
| 2D10 | IgG3, IgM kappa |
| 5B2 | IgM, IgG3, IgG2b, IgG2a, IgG1, kappa |
| 8B6 | IgG2a, IgG3, kappa |
| 5A11 | IgM, kappa |
| 7D11 | light kappa only |
| 9F10 | IgM, kappa |
| 15D10 | IgM, kappa |
| 18D2 | IgM, kappa |
| 13A11 | IgM, kappa |
| 1A9 | IgM, kappa |
| 3B2 | IgM, kappa |
| 24F6 | IgM, kappa |
| 24E4 | IgM, kappa |
| 5A1 | IgG2a, IgM, kappa |
| 7B9 | IgM, kappa |
| 22F4 | IgM, kappa |

The identified monoclonal antibodies are listed in Table 1A and Table 2. Each of the selected monoclonal antibodies was reactive against GST-ΔMUC16$^{c114}$. The commercial MUC16-directed antibodies (OC125, M11, or VK8) did not bind to GST-ΔMUC16$^{c114}$ in ELISA or Western blotting. The clones were tested in FACS against OVCAR3 ovarian cancer cells and in Western blot analysis against GST-ΔMUC16$^{c114}$ (Table 1B), and selected purified monoclonal antibodies were isolated.

Figure 7A:
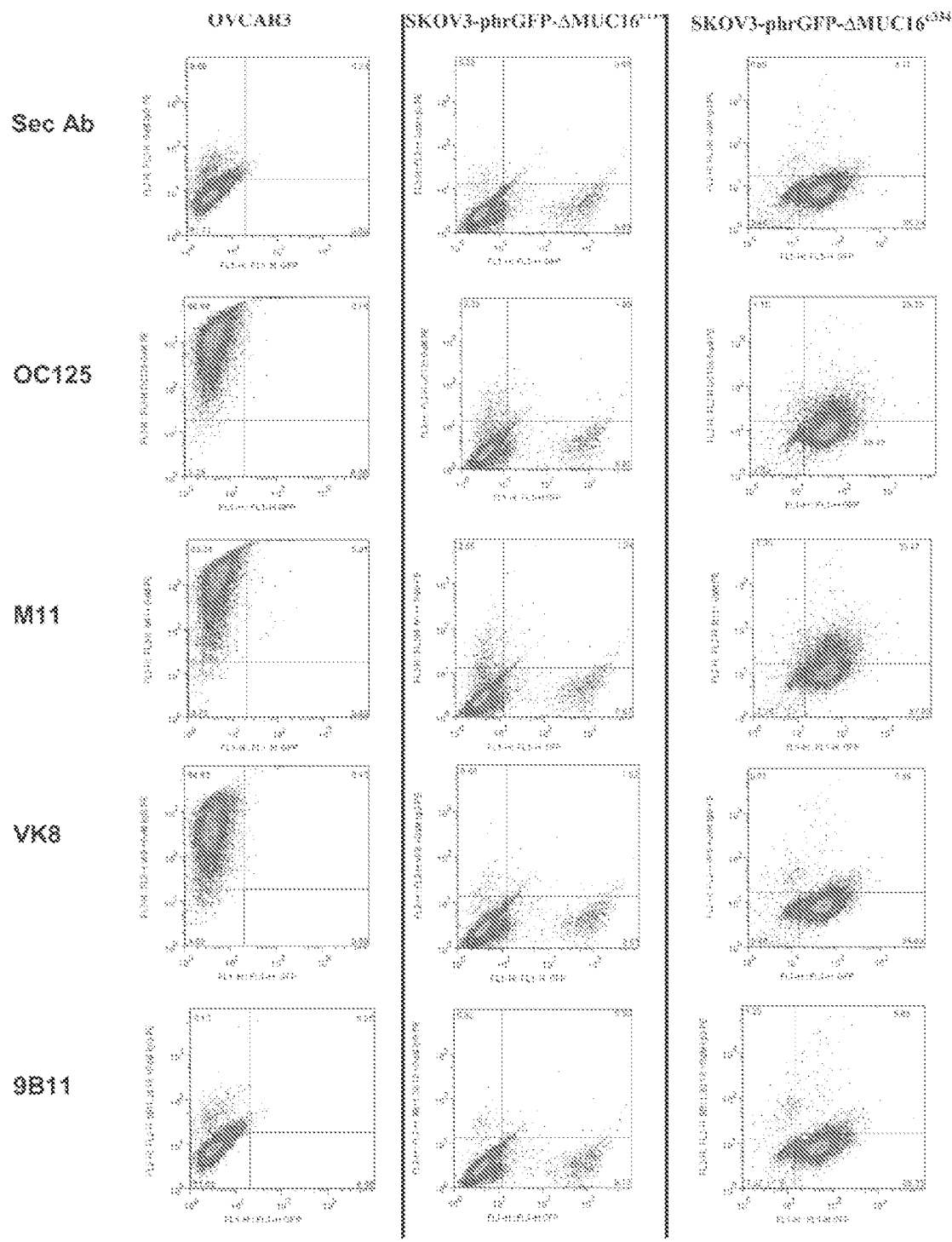
FIGS. 7A and 7B: FACS analysis as described in the Material and Methods section was performed with commercial antibodies and MUC1-6 carboxy terminus monoclonal antibodies on OVCAR3 wt, SKOV3-phrGFP-ΔMUC16$^{c114}$ and SKOV3-phrGFP-ΔMUC16$^{c334}$ stable transfected cell lines.
Figure 7B:
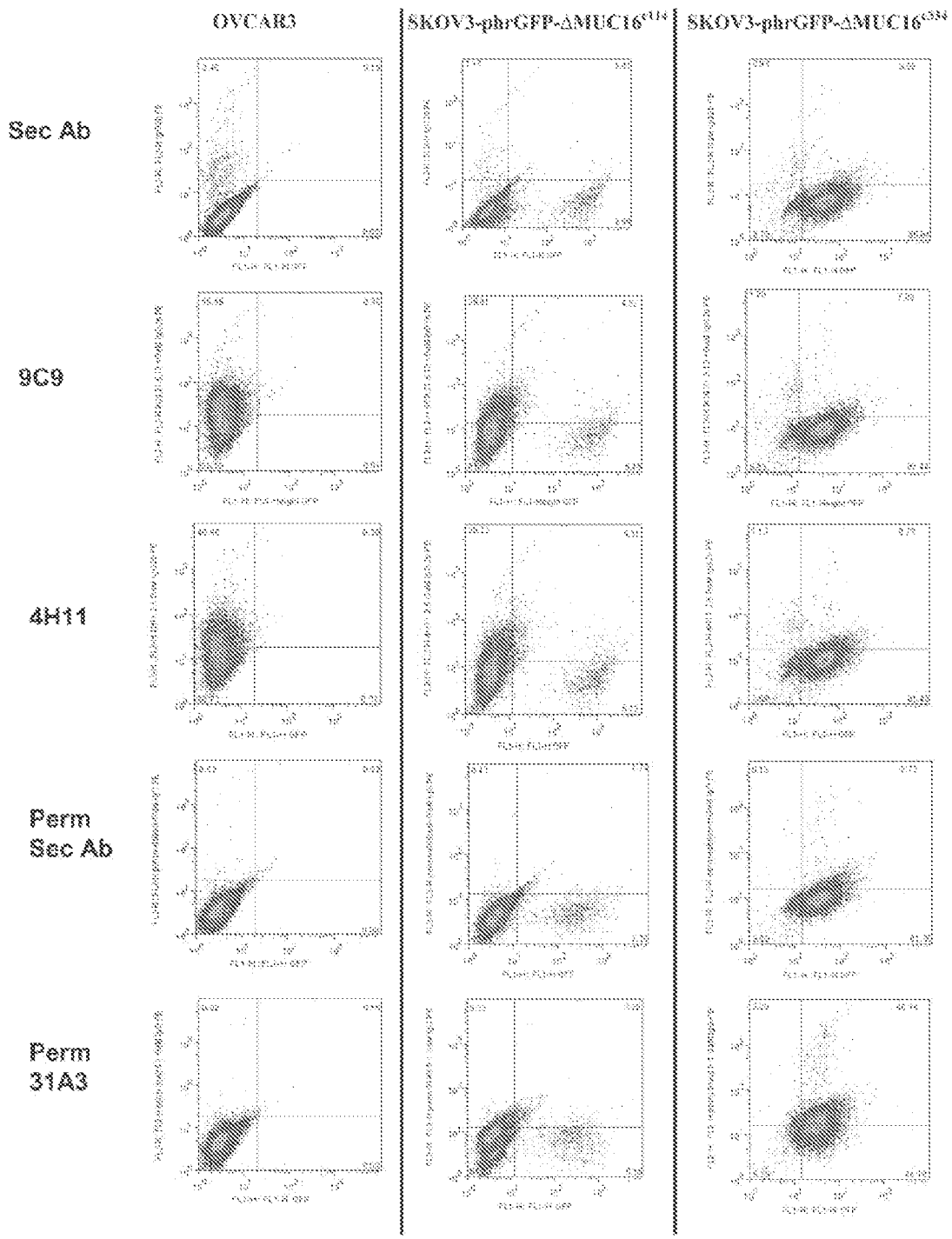

The inventors used the OVCAR3 wild type and the SKOV3 cells transduced with phrGFP-ΔMUC16$^{c114}$ to characterize the selected antibodies by FACS analysis. All of the selected monoclonal antibodies bound to both cell lines while commercial VK8, M11 and OC125 antibodies bound to the OVCAR3 cells but not to the SKOV3-phrGFP-ΔMUC16$^{c114}$ cell line. The antibodies against Polypeptide 3 required permeabilization since it is an internal epitope (FIG. 7A and FIG. 7B).

Figure 4A:
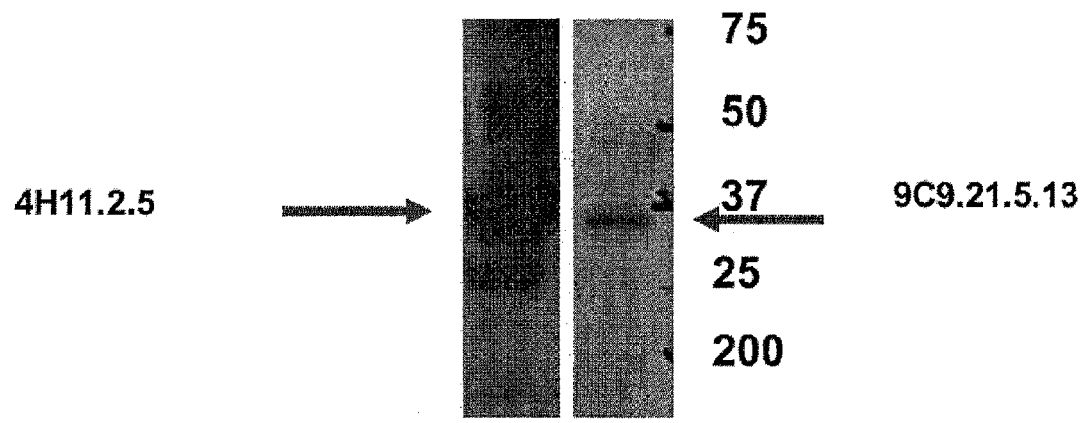
FIGS. 4A and 4B: Western blot analysis.
Figure 4B:
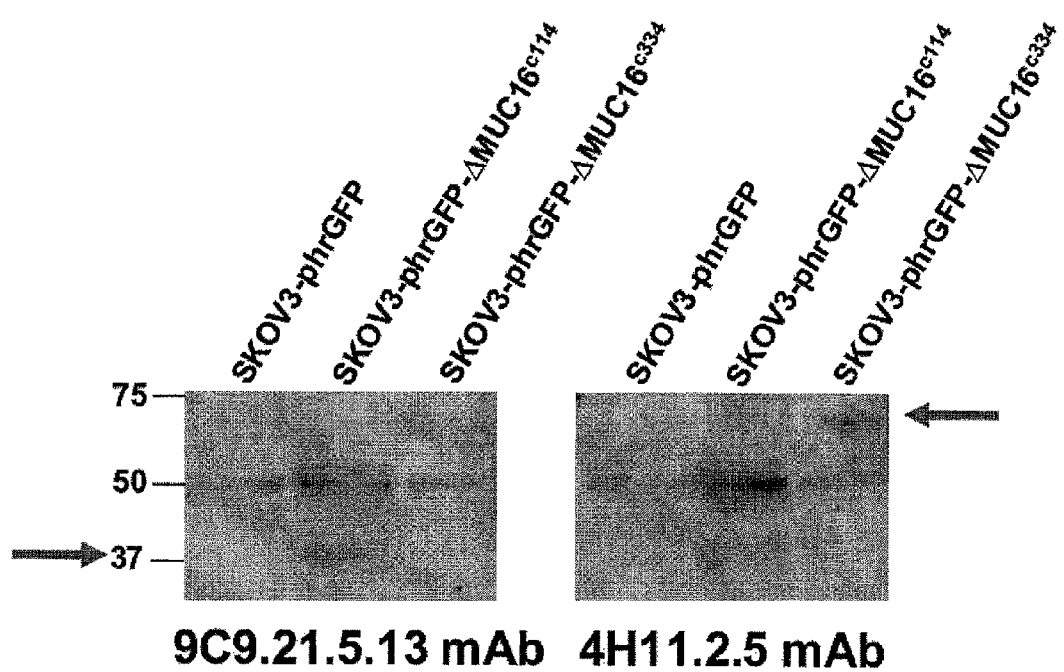

Western blot analysis using the GST-ΔMUC16$^{c114}$ purified protein showed strong binding with 4H11 and 9C9 antibodies (FIG. 4A), while the other selected antibodies showed less binding. The SKOV3-phrGFP-ΔMUC16$^{c114}$ transfectant was also positive by Western blot analysis using 4H11 and 9C9 antibodies (FIG. 4B). As before, the commercial antibodies did not interact with the GST-ΔMUC16$^{c114}$ purified protein or cell lysates of the SKOV3-phrGFP-ΔMUC16$^{c114}$ cell line.

The binding of six monoclonal antibodies against OVCAR3MUC16 were examined in affinity binding studies. Three antibodies-9C7, 5C2 and 28F7—showed only modest levels of binding compared to the nonspecific binding of these antibodies to the OVCAR3 cells, which carry large numbers of MUC16 binding sites. In contrast, 4H11, 9C9, and 4A5 monoclonal antibodies showed highly specific binding affinity, as shown in FIG. 5A-FIG. 5D, with binding affinities of 6.8-8.6 nM against the cell surface epitopes of OVCAR3 cells. The inventors also examined the internalization of antibody bound to cell surface MUC16 protein. The inventors examined internalization in the transfected SKOV3-phrGFP-ΔMUC16$^{c334}$ cell line which bears the carboxy terminus of MUC16, including the 4H11 epitope and a single degenerate tandem repeat sequence to interact with the OC125 antibody. The commercial antibodies OC125, M11, and VK8 all bind to the cell surface of this transduced cell line. The $^{131}$I-labeled 4H11 showed rapid internalization at a high level, whereas $^{131}$I-labeled OC125 antibody was internalized at a much lower rate (FIG. 5E).

Example 3

Immunohistochemistry Results:

Given their highly specific binding affinities, the antibodies 9C9, 4A5, and 4H11 were characterized for utility in immunohistochemistry using OVCAR3 cell lines. Of the three, the 4H11 antibody was selected to be optimized for use in human tissues based on its robust, sensitive and specific staining pattern as compared to the other two antibodies.

A. Ovary

Two high-stage, high-grade ovarian serous carcinoma tissue microarray slides composed of 419 cores, representing primary, metastatic and recurrent tumors from 40 patients were stained with both OC125 and 4H11 monoclonal antibodies (FIG. 2). The OC125 tissue microarrays showed 279 (66%) cores with 3-5 staining, 99 (24%) with 1-2 staining, and 41 (10%) with no staining. The 4H11 tissue microarrays showed 236 (56%) with 3-5 staining, 91 (22%) with 1-2 staining, and 92 (22%) with no staining. The two antibodies were concordant in 233 (56%) cores, equivocal in 161 (38%), and discordant in 25 (6%). Of the 25 discordant cores, 12 (48% of discordant cases, 3% of all cases) showed greater 4H11 positivity than OC125. Nine were discordant by a difference of 4 points, and 3 were discordant by a difference of 5 points. There was a total of 186 discordant and equivocal cores together, 48 (26%) of which showed greater staining with 4H11 than OC125. The staining pattern of both 4H11 and OC125 was cytoplasmic and membranous, although the membranous pattern of OC125 was stronger and better defined than 4H11 in the majority of cases. Discordant cases demonstrated higher levels of 4H11 than other cases.

B. Breast Cancer

A variety of other tissues were also examined for 4H11 staining to test the antibody's specificity. Of the 50 cores of invasive ductal carcinomas of the breast (number of patients unavailable), only 2 (4%) showed a score of 4 or greater 4H11 staining and none had scores of 3-5 for OC125 staining. The staining pattern with OC125 was mostly apical/luminal with some granular cytoplasmic staining. Some tumors with intracytoplasmic lumina also picked up the OC125 stain. 4H11 showed a more diffuse cytoplasmic blush without membranous accentuation.

In contrast, the invasive lobular breast carcinoma tissue microarray (composed of 179 cores with viable tumor, number of patients unavailable) had frequent MUC16 staining with 4H11. In this tissue microarray, 168 cores (94%) showed no staining for OC125, 5 (3%) showed 1-2 staining, and only 6 (3%) showed a staining intensity of 3. 4H11 staining was different in its distribution pattern, with 49 (27%) showing no staining, 81 (45%) showing 1-2 staining, and 49 (27%) showing 3-4 staining. Neither OC125 nor 4H11 had cores with a staining intensity of 5. The staining pattern was of cytoplasmic, luminal/membranous, or intraluminal for both OC125 and 4H11. The intraluminal pattern was strong and intense for both stains and highlighted the intracytoplasmic lumen that is commonly present in lobular carcinomas. The concordance rates were 34% concordant, 43% equivocal, and 23% discordant. Of the equivocal and discordant cases, there was none in which the OC125 was greater than the 4H11. All 42 discordant cases and 76 of 77 equivocal cases had 4H11 greater than OC125. There was also focal luminal staining with 4H11 in benign breast ducts and lobular carcinoma in situ.

C. Lung, Pancreatic and Prostatic Adenocarcinomas

Tumors from other organs were not reactive with either antibody. The lung adenocarcinoma TMA had 237 cores from 86 patients containing viable tumor. In the pancreatic TMA there were 92 cores from 21 patients containing pancreatic mucinous tumors, including intraductal papillary mucinous neoplasms (IPMN) and invasive ductal carcinomas. In the prostate cancer TMA there were 169 cores (number of patients not available). None of these cancer tissue microarrays had significant binding to either OC125 or 4H11. This information is summarized in Table 3.

TABLE 3

Staining intensity of OC125 as compared to 4H11 in tissue microarrays

| | OC125 vs. 4H11 staining intensity score (%) | | | | | |
| | 0 | | 1-2 | | 3-5 | |
| Site | OC125 | 4H11 | OC125 | 4H11 | OC125 | 4H11 |
|---|---|---|---|---|---|---|
| Ovary high grade serous | 10 | 28 | 24 | 22 | 66 | 56 |
| Breast invasive ductal | 68 | 78 | 32 | 18 | 0 | 4 |
| Breast invasive lobular | 94 | 27 | 3 | 45 | 3 | 27 |
| Lung adenocarcinoma | 63 | 77 | 24 | 18 | 13 | 5 |
| Pancreas mucinous neoplasms | 98 | 88 | 2 | 10 | 0 | 2 |
| Prostate adenocarcinoma | 0 | 0 | 0 | 0 | 0 | 0 |

Score
0: 0% staining;
1: <5% strong or weak;
2: 5-50% strong or weak;
3: 51-75% strong or 51-100% weak;
4: 76-99% strong
5: 100% strong D. Normal Tissues There was no staining with OC125 or 4H11 in normal adult colon, rectum, ectocervix, small intestine, ovary, liver, pancreatic ducts, spleen, kidney, and skin. OC125 and 4H11 both stained endocervical glands (OC125 luminal, 4H11 weak cytoplasmic), esophageal glands (luminal), bronchial epithelium (OC125 luminal, 4H11 intracytoplasmic granules), and thymic corpuscles (cytoplasmic). 4H11 demonstrated weak to moderate staining of the gastric glands, particularly at the crypts, with an intracytoplasmic granular pattern. Other organs that showed punctuate intracytoplasmic staining with 4H11 only were prostate, seminiferous tubules of the testes, and the islet cells of the pancreas. The staining in the pancreatic islets cells was particularly strong and consistent. There was also nonspecific staining of liver, kidney and brain with 4H11. There were no cases that stained with OC125 and not 4H11.

Similarly, there was no staining with either OC125 or 4H11 in fetal heart, gallbladder, colon, small intestine, liver, rectum, adrenal, thyroid, spleen, skin, bone, epididymis, brain, lung, muscle, smooth muscle, kidney, eye, umbilical cord, and placenta. OC125 only stained thymic corpuscles in a pattern similar to that in adult tissue. 4H11 stained both fetal pancreatic endocrine cells and endocervical glands in a similar pattern to that of their adult counterparts. Islet cells showed a granular cytoplasmic pattern, and endocervical glands showed a linear luminal pattern, which was more similar to the OC125 pattern in the adult tissue.

Example 4

Successful Eradication of Established Peritoneal Ovarian Tumors in SCID-Beige Mice Following Adoptive Transfer of T Cells Genetically Targeted to the MUC16 Antigen.

Purpose:

Most patients diagnosed with ovarian cancer will ultimately die from their disease. For this reason, novel approaches to the treatment of this malignancy are needed. Adoptive transfer of a patients own T cells, genetically modified ex vivo through the introduction of a gene encoding an chimeric antigen receptor (CAR), an artificial T cell receptor, targeted to a tumor associated antigen, is a novel and promising approach to cancer therapy applicable to the treatment of ovarian cancer.

Experimental Design:

We have generated several CARs targeted to the retained extracellular domain of MUC16, termed MUC-CD, an antigen highly expressed on a majority of ovarian carcinomas. We investigate the in vitro biology of human T cells retrovirally transduced to express these CARs by co-culture assays on artificial antigen presenting cells (AAPCs) generated from NIH3T3 fibroblasts genetically modified to express the target MUC-CD antigen, as well as by cytotoxicity assays utilizing the human OV-CAR3(MUC-CD) ovarian tumor cell line and primary patient tumor cells. Finally, we assess the in vivo anti-tumor efficacy of MUC-CD targeted T cells in a SCID-Beige orthotopic, xenogeneic OV-CAR3(MUC-CD) murine tumor model.

Exemplary sequences used in this work are in FIG. 17, FIG. 18A-FIG. 18E, and FIG. 19A-FIG. 19F.

Results:

CAR modified MUC-CD targeted T cells derived from both healthy donors and ovarian cancer patients exhibited efficient in vitro cytolytic activity against both human ovarian cell lines as well as primary ovarian carcinoma cells. MUC-CD targeted T cells may be further expanded ex vivo through multiple cycles of co-culture on 3T3(MUC-CD/B7.1) AAPCs. Expanded MUC-CD targeted T cells infused into SCID-Beige mice bearing intraperitoneal human OV-CAR3 (MUC-CD) tumors either delayed progression or fully eradicated tumor even in the setting of advanced disease.

Conclusion:

These promising pre-clinical studies justify further investigation of MUC-CD targeted T cells as a potential therapeutic approach in the clinical setting treating patients with high risk MUC-16$^+$ ovarian carcinomas.

Introduction

Ovarian cancer is the sixth most common cancer worldwide and the seventh leading cause of cancer-related deaths in women (1, 2). Despite multimodality therapy with surgery and chemotherapy, most patients with ovarian carcinomas have a poor prognosis. For this reason, alternative approaches to treating this disease are urgently needed.

Infusion of a patient's own T cells genetically targeted ex vivo to antigens expressed on the surface of tumor cells is a promising novel approach to the adoptive immunotherapy of cancer, and one which has only recently been explored in earnest in the clinical setting. T cells may be genetically modified to target tumor associated antigens through the retroviral introduction of genes encoding artificial T cell receptors termed chimeric antigen receptors (CARs). Genetic engineering of T cells to express artificial T cell receptors that direct cytotoxicity toward a tumor cell presents a means to enhance immune recognition and elimination of cancer cells. CARs are most commonly composed of a single chain fragment length antibody (scFv), derived from a murine monoclonal antibody targeting a given tumor associated antigen, fused to a transmembrane domain (typically CD8, CD28, OX-40, and 4-1BB), fused to the TCR chain cytoplasmic signaling domain (3-13). When used to reprogram T-cell specificity, these fusion receptors permit recognition of native antigen. When expressed by the T cells, the resulting construct, upon engagement with the targeted antigen, induces T cell activation, proliferation, and lysis of targeted cells. These fusion receptors transduce a functional antigen-dependent co-stimulatory signal in primary T cells, permitting sustained T-cell proliferation when both endogenous TCR and a chimeric receptor for stimulatory signaling are engaged. To date, preclinical studies utilizing CAR-modified T cells have demonstrated promising results in a wide variety of malignancies (3, 4, 11, 14-18). More recently this approach been investigated clinically in the form of phase I trials (6, 19-21). These genetic approaches offer a means to enhance immune recognition and elimination of cancer cells.

Ovarian carcinomas appear to be relatively immunogenic tumors capable of inducing an endogenous immune response based on the fact that long-term prognosis of patients is markedly influenced by the degree and quality of the endogenous immune response to the tumor. Specifically, it has been well documented that the presence of endogenous effector T cells within the ovarian cancer tumor microenvironment directly correlates to prolonged patient survival (22-25). In contrast, increasing numbers of immune suppressive CD4$^+$ CD25$^{hi}$ regulatory T cells (Tregs) within the tumor, which in turn presumably abrogate the anti-tumor activity of infiltrating effector T cells, correlates with shorter patient survival (26-29). In fact, it appears that it is the ratio of Tregs to effector T cells within the tumor microenvironment which ultimately dictates whether the endogenous immune response to the cancer is of benefit or detriment to the patient (24, 28). In this setting, the ability to generate and subsequently expand a population of tumor targeted effector T cells ex vivo which are subsequently infused back into the patient, may in turn skew the Treg to effector T cell ratio to one more favorable to eradicating the disease.

Mucins are important biomolecules for cellular homeostasis and protection of epithelial surfaces. Changes to expression of mucins in ovarian cancer might be exploited in diagnosis, prognosis and treatment (1). MUC16 is one such mucin which is over expressed on most ovarian carcinomas and is an established surrogate serum marker (CA-125) for the detection and progression of ovarian cancers (30-33). MUC16 is a high-glycosylated mucin composed of a large cleaved and released domain, termed CA-125, consisting of multiple repeat sequences, and a retained domain (MUC-CD) which includes a residual non-repeating extracellular fragment, a transmembrane domain, and a cytoplasmic tail (34). Since the antigen is otherwise only expressed at low levels in the uterus, endometrium, fallopian tubes, ovaries, and serosa of the abdominal and thoracic cavities, MUC16 is a potentially attractive target for immune-based therapies.

However, the fact that most of the extracellular domain of MUC16 is cleaved and secreted limits the utility of MUC 16 as a target antigen on ovarian carcinomas. In fact, to date, all reported MAbs to MUC16 bind to epitopes present on the large secreted CA-125 fraction of the glycoprotein, with none known to bind to the retained extra-cellular fraction (MUC-CD) of the antigen (35-37). Since the MUC-CD fraction of the antigen is retained on cell surface, generating T cells specific to this portion of MUC16 may largely overcome the limitation of MUC16 as a target for adoptive cellular immunotherapy. To this end, we have previously generated a series of murine MAbs specific to the retained MUC-CD extracellular domain (38). Utilizing a hybridoma which expresses one such MAb, 4H11, we have successfully constructed several CARs specific to the MUC-CD antigen. This invention provides a nucleic acid encoding a chimeric T cell receptor, composed of, at least a zeta chain, a signaling region and a binding element that specifically interacts with a selected target as well as the chimeric T cell receptor comprising a zeta chain portion, a signaling region and a binding element.

In this report, we demonstrate highly efficient retroviral transduction of these MUC-CD targeted CARs into human T cells with resulting T cells able to specifically target and lyse MUC-CD$^+$ tumor cells in vitro. Furthermore, we demonstrate efficient MUC-CD targeted T cell expansion in vitro through repeated co-culture on NIH (3T3) fibroblasts genetically modified to express MUC-CD and the co-stimulatory ligand B7.1 (CD80). Successful expansion of modified T cells allowed us to subsequently generate sufficient T cell numbers to conduct in vivo studies in immune compromised SCID-Beige mice bearing established intraperitoneal MUC-CD$^+$ human ovarian tumors. Significantly, in these studies we demonstrate marked anti-tumor efficacy of MUC-CD targeted T cells, both following direct intraperitoneal as well as intravenous injection when compared to either untreated mice, or mice treated with T cells bearing a CAR targeted to an irrelevant antigen. In addition, we demonstrate significant cytotoxicity of 4H11-28z$^+$ patient's T cells and healthy donor's T cells targeting primary ascites-derived ovarian carcinoma cells from cancer patients.

To our knowledge this is the first report wherein T cells genetically targeted to the MUC16 antigen demonstrate marked anti-tumor efficacy against MUC16$^+$ tumors either in vitro or in vivo. These data serve as a rationale for proposing future clinical trials utilizing this approach in patients with high risk ovarian carcinomas.

Materials and Methods

Cell Lines and T Cells

The OV-CAR3 tumor cell line was cultured in RPMI 1640 (Invitrogen, Grand Island, N.Y.) supplemented with 10% heat-inactivated FBS, nonessential amino acids, HEPES buffer, pyruvate, and BME (Invitrogen). The PG13 and gpg29 retroviral producer cell lines were cultured in DMEM (Invitrogen) supplemented with 10% FCS, and NIH-3T3 artificial antigen-presenting cells (AAPC), described previously (3), were cultured in DMEM supplemented with 10% heat-inactivated donor calf serum. T cells were obtained from peripheral blood of healthy donors under IRB approved protocol #95-054, in BD Vacutainer CPT tubes (Becton Dickinson, Franklin Lakes, N.J.) as per the manufacturers instructions. All media were supplemented with 2 mmol/L L-glutamine (Invitrogen), 100 units/mL penicillin, and 100 µg/mL streptomycin (Invitrogen). T cells were cultured RPMI 1640 media as above supplemented with 20 IU/ml IL-2 (Novartis Pharmaceuticals, East Hanover, N.J.) and where indicated, medium was supplemented with 10 ng/mL interleukin 15 (R&D Systems, Minneapolis, Minn.).

Isolation of Patients Ascites-Derived Cancer Cells

Primary human ascites-derived cancer cells were obtained from ovarian cancer patients undergoing surgery for newly diagnosed advanced serous ovarian carcinoma under IRB approved protocol #97-134. The tumor cells were isolated from ascitic fluid of patients by centrifugation at 600 g for 10 min at room temperature. Cells were washed once with 1×PBS and cultured in RPMI 1640 media supplemented with 10% FBS for future analysis.

Generation of the MUC-CD Targeted 4H11z and 4H11-28z CARs

The heavy and light chain variable regions of the 4H11 monoclonal antibody were derived from the hybridoma cell line 4H11. Utilizing cDNA generated from 4H11 RNA we isolated the $V_H$ coding region by RACE PCR utilizing modified primers as described elsewhere (39, 40). The $V_L$ chain variable region was cloned by standard PCR utilizing modified primers as described by Orlandi et al (41, 42). The resulting $V_H$ and $V_L$ fragments were subcloned into the TopoTA PCR 2.1 cloning vector (Invitrogen) and sequenced. The $V_H$ and $V_L$ fragments were subsequently ligated to a (Gly$_4$Ser)$_3$ spacer domain, generating the 4H11 scFv and fused to the human CD8 leader peptide (CD8L) by overlapping PCR (9, 41). In order to construct the MUC-CD targeted 4H$_{11}$CARs, the coding region of the CD8L-4H11 scFv was fused to the human CD8 hinge and transmembrane domains (to generate the 4H11z CAR), or alternatively to the CD28 transmembrane and cytoplasmic signaling domains (to generate the 4H11-28z CAR), fused to the T cell receptor CD3-signaling domain (3, 9, 43). The resulting CAR constructs were subsequently sub-cloned into the modified MMLV retroviral vector SFG (44). VSV-G preudotyped retroviral supernatants derived from transduced gpg29 fibroblasts were used to construct stable PG13 gibbon ape leukemia virus (GaLV) envelope-pseudotyped retroviral producing cell lines (41).

Retroviral Gene Transfer

Isolated healthy donor peripheral blood mononuclear cells (PBMCs) were activated with phytohemagglutinin (PHA) at 2 µg/ml (Sigma. St. Louis, Mo.) and retrovirally transduced on retronectin coated non-tissue culture plates (45). Briefly, six-well non-tissue culture plates (BD Biosciences, San Jose, Calif.) were coated with RetroNectin (RN) (Takara Biomedicals, Otsu, Japan) as per manufacturer's instructions. Forty-eight hours after PHA activation, aliquots of 1×10$^6$ T cells in 1 ml of supplemented RPMI medium were placed in each well of the RN-coated plates, along with 1 ml of SFG retroviral supernatant. T cells were centrifuged daily for 3 consecutive days with fresh retroviral supernatant added daily at 2000 g at 30° C. for 1 hr (45). Gene transfer was assessed on day 7 by FACS.

In order to generate the relevant NIH-3T3 murine fibroblast artificial antigen presenting cells, a MUC-CD construct encoding the retained extracellular, transmembrane and cytoplasmic domains of the MUC-16 antigen was initially sub-cloned into SFG retroviral vector, SFG(MUC-CD). 3T3 (MUC-CD) AAPCs were generated by retroviral transduction of SFG(MUC-CD) into wild-type NIH-3T3 fibroblasts, while 3T3(MUC-CD/B7.1) AAPCs were generated by retroviral transduction of previously established 3T3 (B7.1) fibroblasts (41, 46). Highly enriched cell lines were isolated by FACS.

To generate the OV-CAR3(MUC-CD) and OV-CAR3 (MUC-CD/GFP-FFLuc) cell lines, we retrovirally transduced the WT OV-CAR3 human ovarian cancer cell line with SFG(GFP—FFLuc) as described previously (47) and/or SFG (MUC-CD) VSV-G pseudotyped retroviral supernatants derived from gpg29 fibroblasts as described elsewhere (44). Resulting tumor cells were sorted by FACS for either MUC-CD expression alone for the OVCAR3(MUC-CD) cell line, or dual MUC-CD and GFP expression for the OVCAR3 (MUC-CD/GFP-FFLuc) cell line. MUC-CD expression by FACS was assessed using the 4H11 MAb.

In Vitro Analyses of CAR$^+$ Human T Cells

To assess in vitro expansion and cytokine release upon stimulation, transduced T cells were co-cultured for 7 days after retroviral transduction in 6-well tissue culture plates (BD Biosciences) on confluent NIH 3T3 AAPCs in RPMI medium supplemented with 10% FBS in the absence of supplemented cytokines. In order to generate sufficient numbers of CAR-modified T cells for in vivo studies, transduced T cells were co-cultured on B7.1$^+$ AAPCs (3T3(MUC-CD/B7.1)) in RPMI medium supplemented with 20 IU IL-2/mL and 10 ng/mL IL-15 as described previously (3, 43). Patients T cells were activated and expanded with human CD3/CD28 beads (DYNAL®, Invitrogen, Carlsbad, Calif.) following manufacturer's recommendations.

Western Blot Analysis of CAR Expression

Western blot analysis of T-cell lysates under reducing conditions with 0.1 mol/L DTT (Sigma) was performed as previously described (46). Briefly, transduced T cells were washed in PBS and resuspended in radioimmunoprecipitation assay (RIPA) buffer (Boston BioProducts, Worcester, Mass.) with mini complete protease inhibitor as per the manufacturer's instructions (Roche Diagnostics, Indianapolis, Ind.). Resulting proteins were separated on 12% SDS-PAGE mini gels (Bio-Rad, Hercules, Calif.) after the addition of 6× reducing loading buffer (Boston BioProducts, Worcester, Mass.) and heating at 100° C. for 10 min. Separated proteins were subsequently transferred to Immobilon membranes and probed using an anti-human CD3ζ chain monoclonal antibody (BD Biosciences). Antibody binding was detected by probing the blot with goat anti-mouse horse radish peroxidase-conjugated antibody followed by luminescent detection using Western Lighting Chemiluminescence Reagent Plus (Perkin-Elmer Life Sciences, Boston, Mass.) as per the manufacturer's instructions.

Cytotoxicity Assays

In vitro modified T cell cytotoxicity was assessed using the DELFIA® EuTDA assay (PerkinElmer LAS, Inc, Boston, Mass.) following manufacturer's recommendations. Cytotoxocity was assessed at 2 hours at effector T cell to target OV-CAR3(MUC-CD) or primary tumor cells (E:T) at indicated ratios. Effector T cells in these assays represent the number of CD8$^+$ CAR$^+$ T cells.

Cytokine Detection Assays

Cytokine assays were performed as per manufacturer's specifications using a multiplex Human Cytokine Detection assay to detect IL-2 and IFNγ (Millipore Corporation, Billerica, Mass.) utilizing the Luminex IS 100 system. Cytokine concentrations were assessed using IS 2.3 software (Luminex Corp., Austin, Tex.).

In Vivo SCID-Beige Mouse Tumor Models

In all in vivo studies, 8-12 week-old FOX CHASE C.B.-17 (SCID-Beige mice) (Taconic, Hudson, N.Y.) were initially injected ip with either $3\times10^{60}$V-CAR$^3$(MUC-CD), or for bioluminescent imaging (BLI) studies $3\times10^{60}$V-CAR$^3$ (MUC-CD/GFP-FFLuc) tumor cells. Subsequently, $3\times10^7$ CAR$^+$ T cells were injected ip or iv on day 1 or 7 following tumor injection as indicated. Mice were monitored for distress as assessed by increasing abdominal girth, ruffled fur, and decreased response to stimuli. Distressed mice were euthanized. All murine studies were done in context of an Institutional Animal Care and Use Committee-approved protocol (#00-05-065).

Bioluminescent imaging (BLI) of OVCAR3(MUC-CD/GFP-FFLuc) tumor cells in SCID-Beige mice BLI was performed using Xenogen IVIS imaging system with Living Image software (Xenogen; Alameda, Calif.). Briefly, OVCAR3(MUC-CD/GFP-FFLuc) tumor bearing mice were injected by ip with D-luciferin (150 mg/kg; Xenogen) suspended in 200 μl PBS and imaged under 2% isoflurane anesthesia after 10 min. Image acquisition was done on a 25-cm field of view at medium binning level for 0.5-min exposure time (3, 43).

Flow Cytometry

All flow cytometric analyses of T cells and tumor cells was performed using a FACScan cytometer with Cellquest software (BD Biosciences). T cells were analyzed using CAR-specific polyclonal goat Alexa Fluor 647 antibody (Molecular probes, Eugene, Oreg.) phycoerythrin-labeled anti-human CD4, CD8, B7.1 (Caltag Laboratories, Burlingame, Calif.), B7.2 (Invitrogen, Camarillo, Calif.), 4-1BBL, and OX40 antibodies (Ancell Corporation, Bayport, Minn.). 3T3(MUC-CD) and OV-CAR3(MUC-CD) cells were stained with Alexa Fluor 647 labeled 4H11 antibody (generated and labeled in the MSKCC monoclonal antibody core facility).

CFSE labeling of CAR$^+$ T cells

CAR$^+$ T cells were stained with CFSE using the CellTrace™ CFSE cell proliferation kit following manufacturer's recommendations (Molecular Probes, Eugene, Oreg.). Proliferation of CFSE labeled T cells was analyzed by FACS. For detection of CFSE labeling T cells in vivo, ovarian tumors were macerated through 40 μm cell strainer (BD Falcon, Franklin Lakes, N.J.) and washed twice with 2% FBS/PBS before antibody staining and FACS analysis.

Statistics

Survival data assessed by log-rank analysis using Graph-Pad Prism software (GraphPad Prism software, San Diego, Calif.). Cytokine data were analyzed by Student's one-tailed t-test.

Results

Figure 11:
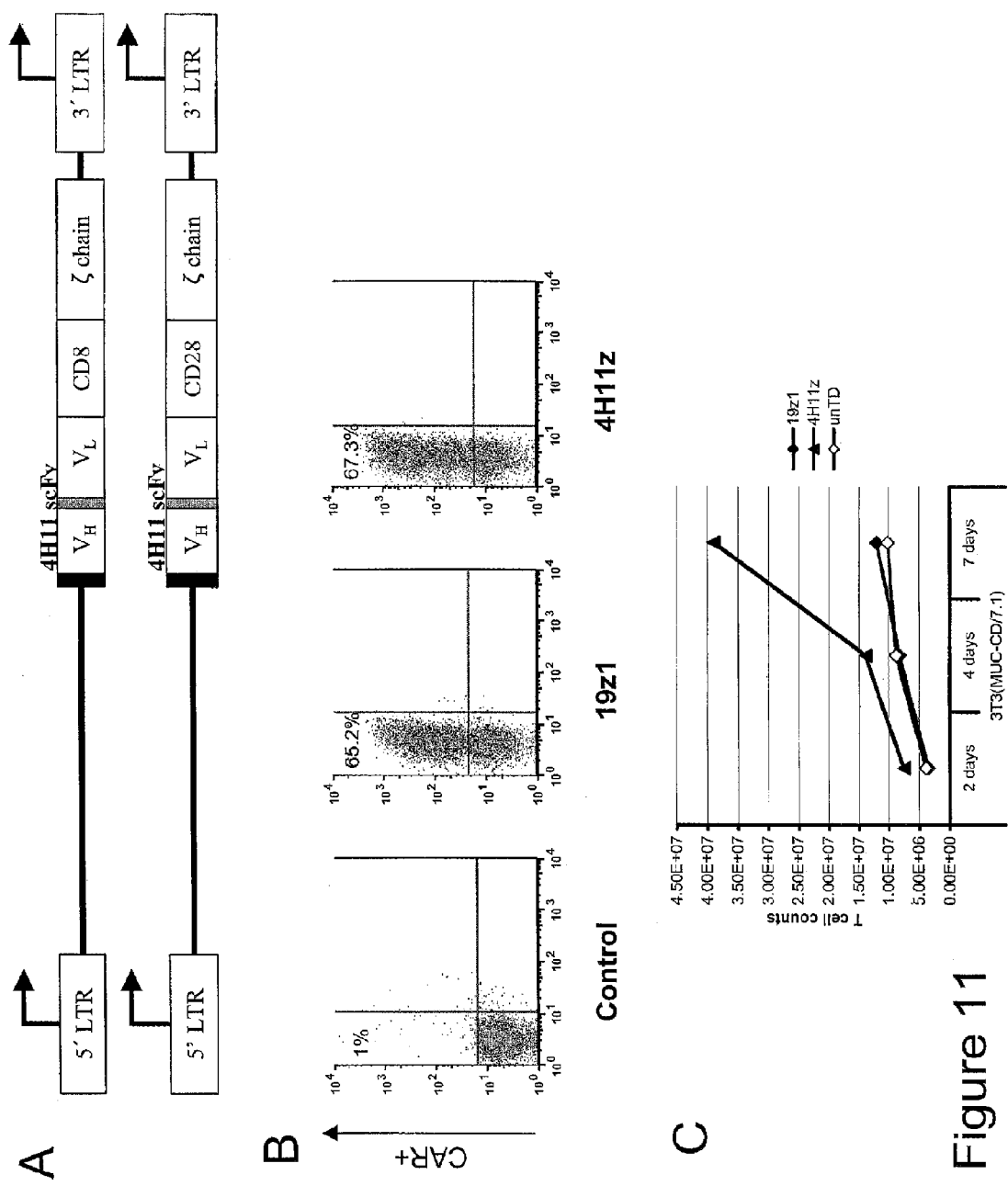
FIG. 11. Design and in vitro analysis of MUC-CD targeted CARs. (A) Schematic diagram of the first generation 4H11z and second generation 4H11-28z retroviral vectors. 4H11scFv: MUC16 specific scFv derived from the heavy ($V_H$) and light ($V_L$) chain variable regions of the monoclonal antibody 4H11; CD8: CD8 hinge and transmembrane domains; CD28: CD28 transmembrane and cytoplasmic signaling domains; ζ chain: T cell receptor ζ chain cytoplasmic signaling domain; LTR: long terminal repeat; black box: CD8 leader sequence; grey box: (Gly$_4$Ser)$_3$ linker; arrows indicate start of transcription. (B) FACS analysis of human T cells retrovirally transduced to express either the 4H11z or 19z1 CAR. (C) 4H11z$^+$ but not 19z1$^+$ T cells expand on 3T3(MUC-CD/B7.1) AAPC. CAR$^+$ were co-cultured on 3T3(MUC-CD/B7.1) AAPC monolayers at 3×10$^6$ CAR$^+$ T cells/well of a 6 well plate. Proliferation of CAR$^+$ T cells, normalized to the CAR$^+$ T cell fraction as assessed by FACS for the CAR$^+$ fraction in combination with viable T cell counts obtained on days 2, 4 and 7, as assessed by trypan blue exclusion assays.

We have constructed SFG retroviral vectors encoding first (4H11z) and second generation (4H11-28z) CARs targeted to the MUC-CD antigen using the 4H11 hybridoma which generates a MAb specific to the MUC-CD antigen (FIG. 11A). We confirmed expression of appropriately sized CAR proteins by Western blot analysis of resulting PG-13 retroviral producer cells (SFG-4H11z and SFG-4H11-28z) probed with a ζ-chain specific antibody (data not shown).

In order to assess the function of the first generation 4H11z CAR, healthy donor T cells isolated from peripheral blood were retrovirally transduced to express the 4H11z and control 19z1 CARs (FIG. 11B). Function of the 4H11z CAR was assessed by proliferation of 4H11z transduced T cells following co-culture on 3T3(MUC-CD/B7.1) AAPCs. Results demonstrate specific proliferation of 4H11z transduced T cells, when compared to 19z1 modified T cells (FIG. 11C). These data are consistent 4H11z CAR mediated specific binding to the MUC-CD antigen and subsequent T cell activation.

Figure 12:
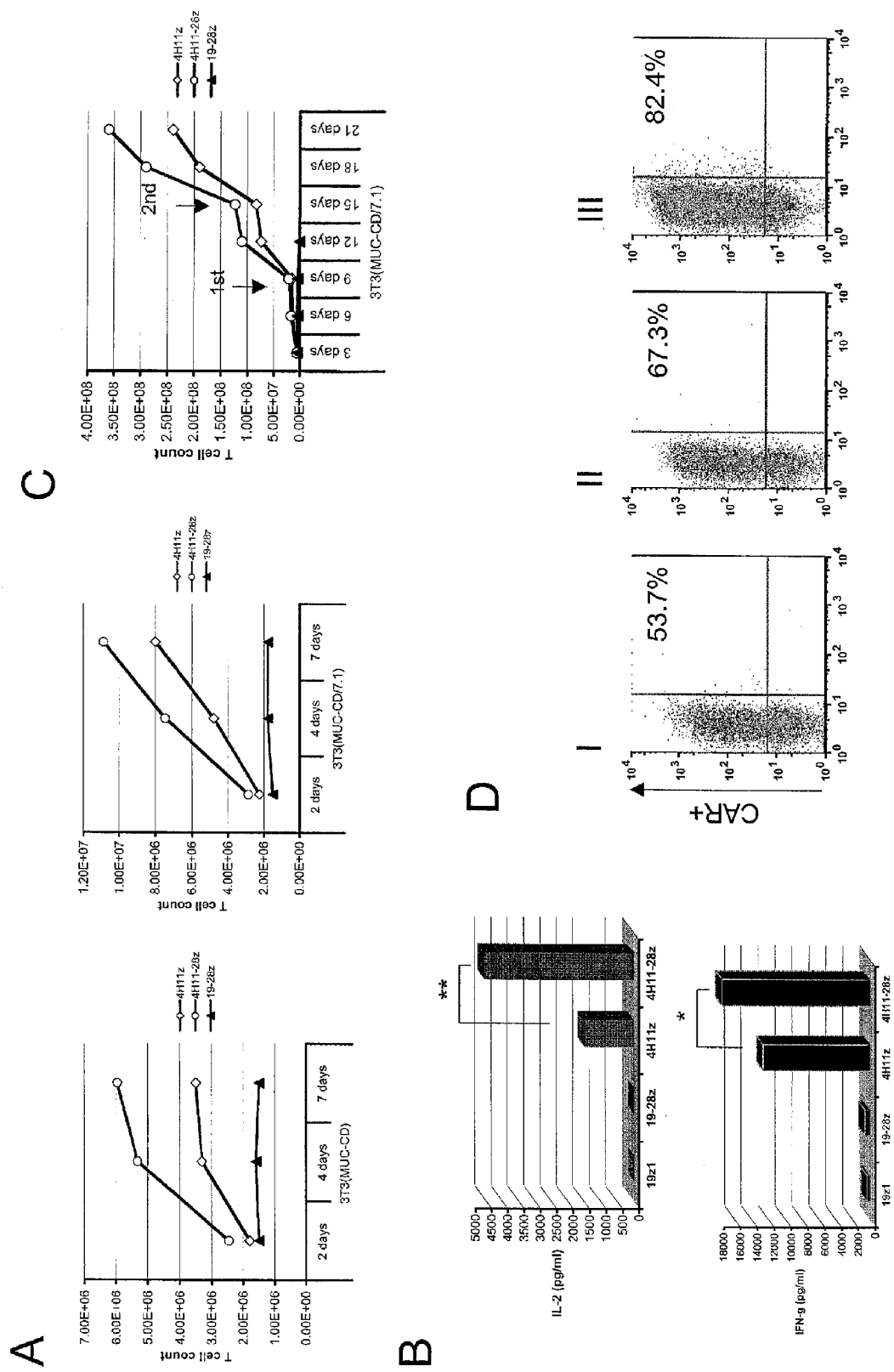
FIG. 12. In vitro comparison of T cells modified to express the first generation 4H11z CAR to T cells modified to express the second generation co-stimulatory 4H11-28z CAR. (A) CAR$^+$ T cells were co-cultured on MUC-CD monolayers with (right panel) or without B7.1 (left panel). 3×10$^6$ CAR$^+$ T cells were co-cultured on AAPC monolayers in 6 well tissue culture plates in cytokine-free medium. Total viable T cell counts were assessed on days 2, 4 and 7, by trypan blue exclusion assays. 4H11-28z$^+$ T cells markedly expanded when compared to 4H11z$^+$ T cells upon co-culture with 3T3 (MUC-CD) AAPCs, p=0.0023 (4H11z compared to 4H11-28z). In contrast, both 4H11z$^+$ and 4H11-28z$^+$ T cells expanded similarly on 3T3(MUC-CD/B7.1) AAPCs, p=0.09, (4H11z compared to 4H11-28z). Control 19-28z$^+$ T cells did not proliferate on 3T3(MUC-CD), p=0.0056 (19-28z compared to 4H11z), p=0.0011 (19-28z compared to 4H11-28z), or on 3T3(MUC-CD/B7.1), p=0.0026 (19-28z compared to 4H11z), p=0.0087 (19-28z compared to 4H11-28z). (B) 4H11-28z$^+$ but not 4H11z$^+$ T cells secrete IL-2 upon co-culture with 3T3(MUC-CD) AAPCs. Tissue culture supernatants at day 2 following activation on 3T3(MUC-CD) AAPCs were analyzed for cytokine secretion. 4H11-28z$^+$ T cells, in contrast to 4H11z$^+$ T cells, demonstrated enhanced secretion of IL-2 consistent with T cell co-stimulation mediated through the 4H11-28z CAR. *p=0.0008 (19z1 or 19-28z compared to 4H11z), p=0.0026 (19z1 or 19-28z compared to 4H11-28z), p=0.0046 (4H11z compared to 4H11-28z). Furthermore, both 4H11-28z$^+$ and 4H11z$^+$ T cells secreted IFNγ. *p=0.011 (4H11z compared to 4H11-28z). Control 19z1 and 1928z transduced T cells failed to secrete either IL-2 or IFNγ. p=0.0034 (19z1 compared to 4H11z), p=0.036 (19-28z compared to 4H11z), ***p=0.0008 (19-28z compared to 4H11-28z). (C) Expansion of CAR$^+$ T cells following 3 cycles of stimulation on 3T3(MUC-CD/B7.1). Human T cells transduced to express either 4H11z or 4H11-28z CARs demonstrated a>2 log expansion over 2 cycles of stimulation on 3T3(MUC-CD/B7.1) AAPCs. Arrows indicate 1st and 2nd cycles of restimulation on AAPCs. (D) FACS analysis of the CAR$^+$ T cell fraction of 4H11-28z$^+$ T cells increased following each weekly cycle of stimulation. (I) FACS following initial transduction, (II) FACS at 7 days following first stimulation on AAPCs, (III) FACS at 7 days following second stimulation on AAPCs. These data are representative of one of three different experiments using three different healthy donor T cell populations, all of which demonstrated similar proliferation and cytokine secretion patterns.

Since most malignancies fail to express co-stimulatory ligands, we further modified the 4H11z CAR to express the CD28 transmembrane and cytoplasmic co-stimulatory signaling domains, constructing the second generation 4H11-28z CAR (FIG. 11A). To assess whether the 4H11-28z CAR, when expressed by human T cells, was capable of generating both a primary activating signal (termed "signal 1") through the ζ chain, as well as a co-stimulatory signal (termed "signal 2") through the CD28 cytoplasmic domain, which in turn allows for efficient T cell proliferation in the absence of exogenous co-stimulatory ligands, we compared T cell proliferation following co-culture on either 3T3(MUC-CD) or 3T3(MUC-CD/B7.1) AAPCs in the absence of exogenous cytokines. As expected, the second generation 4H11-28z$^+$ T cells markedly expanded when compared to 4H11z$^+$ T cells upon co-culture with 3T3(MUC-CD) AAPCs. In contrast, both 4H11z$^+$ and 4H11-28z$^+$ T cells expanded similarly on 3T3(MUC-CD/B7.1) AAPCs (FIG. 12A). Co-stimulation mediated by the 4H11-28z CAR was further verified by analysis of day 2 tissue culture supernatants from co-culture experiments on 3T3(MUC-CD) AAPCs demonstrating enhanced IL-2 secretion, a cytokine typically secreted in the context of T cell co-stimulation, when compared to control 19z1$^+$ and 19-28z$^+$ T cells and first generation 4H11z$^+$ T cells (FIG. 12B). Secretion of IFNγ was comparable between 4H11z$^+$ and 4H11-28z$^+$ activated T cells.

We next assessed the ability of MUC-CD targeted T cells to expand following weekly re-stimulations through co-culture on 3T3(MUC-CD/B7.1) AAPCs in the context of exogenous IL-2 and IL-15 (3). Both 4H11z$^+$ and 4H11-28z$^+$ T cells expanded greater than 2 logs over 3 weeks (FIG. 12C). T cells transduced with the 4H11-28z were further analyzed by FACS for CAR expression 7 days after initial activation on AAPCs and following two subsequent co-stimulations on AAPCs demonstrating an expected enrichment of the CAR$^+$ T cell fraction (FIG. 12D). Similar data was generated with expanded 4H11z$^+$ T cells (data not shown).

In Vitro Cytotoxicity and Proliferation of MUC-CD Targeted T Cells Following Co-Culture with OV-CAR3(MUC-CD) and Freshly Isolated Ascites Derived Ovarian Tumor Cells.

Figure 13:
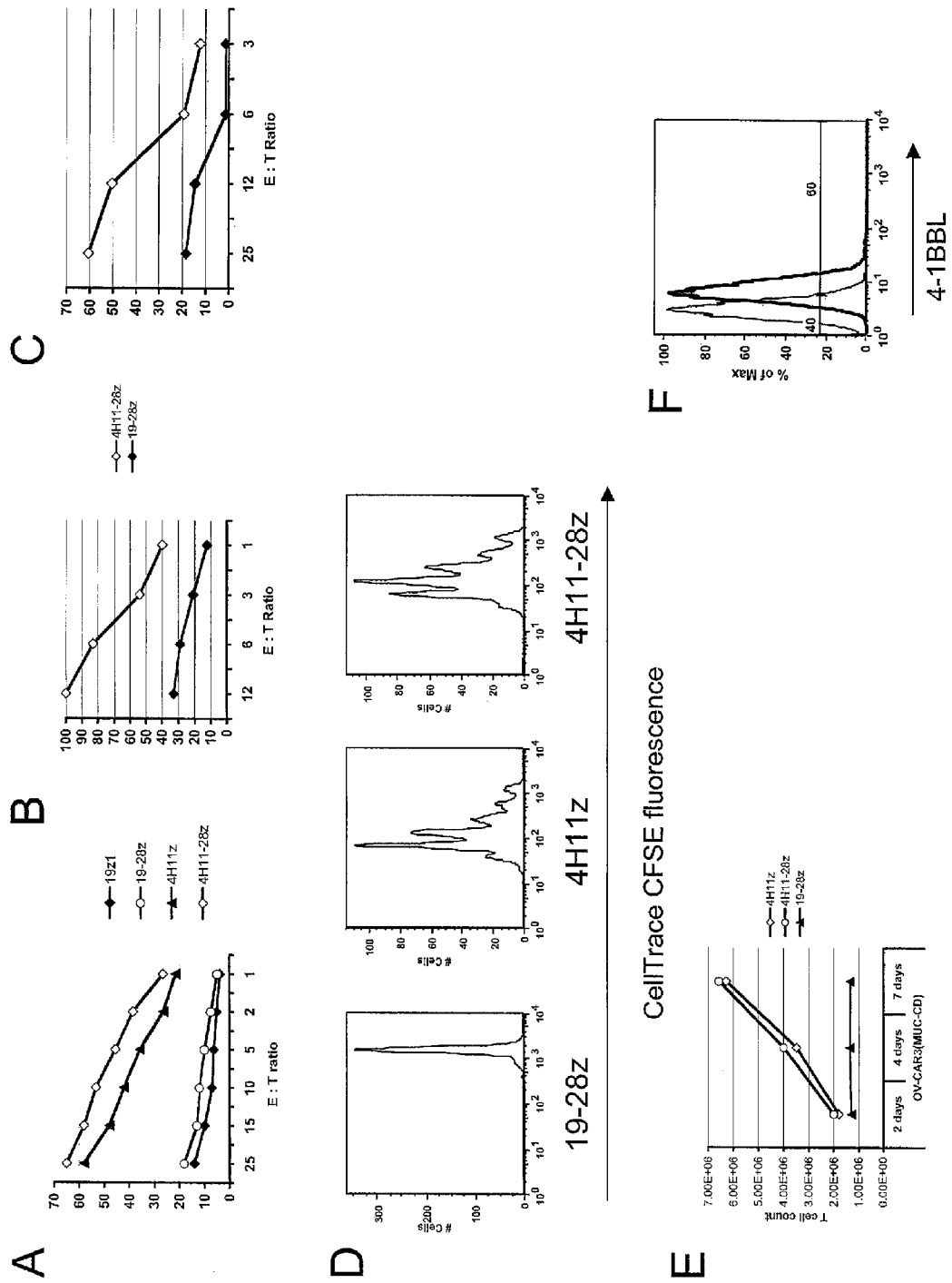
FIG. 13. MUC-CD targeted T cells specifically expand and lyse MUC-CD$^+$ tumor cells. (A) Cytotoxicity assay of 4H11z$^+$ and 4H11-28z' T cells targeting OV-CAR(MUC-CD) tumor cells demonstrates efficient cytotoxicity mediated by T cells from healthy donors modified to express the first and second generation MUC-CD targeted CARs. Control T cells modified to express the first and second generation CD19-targeted 19z1 and 19-28z CARs failed to demonstrate significant lysis of target tumor cells. (B) Healthy donor T cells modified to express the 4H11-28z CAR equally lyse primary patient ascites-derived MUC-CD$^+$ tumor cells when compared to T cells modified to express the control 19-28z CAR. This data represents 1 or 3 experiments targeting primary tumor cells from 3 ovarian carcinoma patients with similar results. (C) Autologous T cells isolated from peripheral blood, when modified with the 4H11-28z CAR, exhibit significant lysis of autologous MUC-CD$^+$ ascites-derived tumor cells when compared to control 19-28z$^+$ autologous T cells. These data represent 1 of 3 experiments utilizing T cells and autologous tumor cells from 3 different ovarian carcinoma patients with similar results. (D) Antigen specific proliferation of MUC-CD targeted CFSE labeled T cells after co-culture with OV-CAR$^3$(MUC-CD) tumor cells. CFSE labeled CAR$^+$ T cells were co-cultured with MUC-CD expressing OV-CAR$^3$ tumor cells at 1:1 ratio for 5 days. Proliferation of CFSE labeled T cells was assessed by FACS demonstrating efficient proliferation of both 4H11z$^+$ and 4H11-28z$^+$ T cells but not control 19-28z' T cells. (E) CFSE results were further confirmed by absolute T cell numbers assessed on days 2, 4 and 7 following co-culture with OV-CAR3(MUC-CD) tumor cells. (F) FACS analysis of the expression of 4-1BBL on OVCAR3(MUC-CD) cells. OV-CAR3(MUC-CD) cells were stained with anti-human 4-1BBL antibody (thick line) or with isotype control (thin line). FACS analysis demonstrated expression of 4-1BBL on OV-CAR3(MUC-CD) tumor cells. Further FACS analyses failed to reveal expression of the co-stimulatory ligands B7.1, B7.2, or OX-40L.

In order to assess the ability of 4H11z$^+$ and 4H11-28z$^+$ T cells to target and lyse human ovarian carcinoma tumors, we utilized the human OV-CAR3 cell line which was genetically modified to express the MUC-CD antigen thereby better reflecting the majority of clinical ovarian tumor samples which express the 4H11-targeted MUC-CD antigen (48). We initially verified specific lysis by MUC-CD targeted T cells demonstrating similar significant cytotoxic activity of 4H11z and 4H11-28z CAR modified T cells targeting OV-CAR3 (MUC-CD) tumor cells when compared control T cells expressing the irrelevant first and second generation CD19-targeted 19z1 and 1928z CARs (FIG. 13A). Healthy donor T cells modified to express the 4H11-28z CAR similarly exhibited lysis of freshly isolated ascites derived MUC-CD$^+$ ovarian carcinoma cells when compared to 19-28z transduced T cells (FIG. 13B). Moreover, patient's peripheral blood T cells modified to express the 4H11-28z CAR similarly lysed autologous primary MUC-CD$^+$ tumor cells derived from the same ascites sample when compared to T cells modified to express the control 19-28z CAR (FIG. 13C).

We further assessed the ability of 4H11z$^+$ and 4H11-28z$^+$ T cells from healthy donors to proliferate following co-culture on OV-CAR3(MUC-CD) as assessed by FACS of CFSE labeled T cells, as well as absolute T cells numbers over 7 days following co-culture with tumor (FIGS. 13D and E). Surprisingly, we found that both 4H11z$^+$ and 4H11-28z$^+$ T cells expanded equally well following co-culture with OV-CAR3(MUC-CD) tumor cells suggesting the ability of this tumor cell line to co-stimulate T cells through expression of a co-stimulatory ligand. To address this possibility, we conducted further FACS analyses of OV-CAR3(MUC-CD) tumor cells demonstrating expression of the co-stimulatory 4-1BBL ligand (FIG. 13F), but not the B7.1, B7.2, or OX-40L co-stimulatory ligands (data not shown).

In Vivo Anti-Tumor Activity of MUC-CD Targeted T Cells in SCID-Beige Mice.

Figure 14:
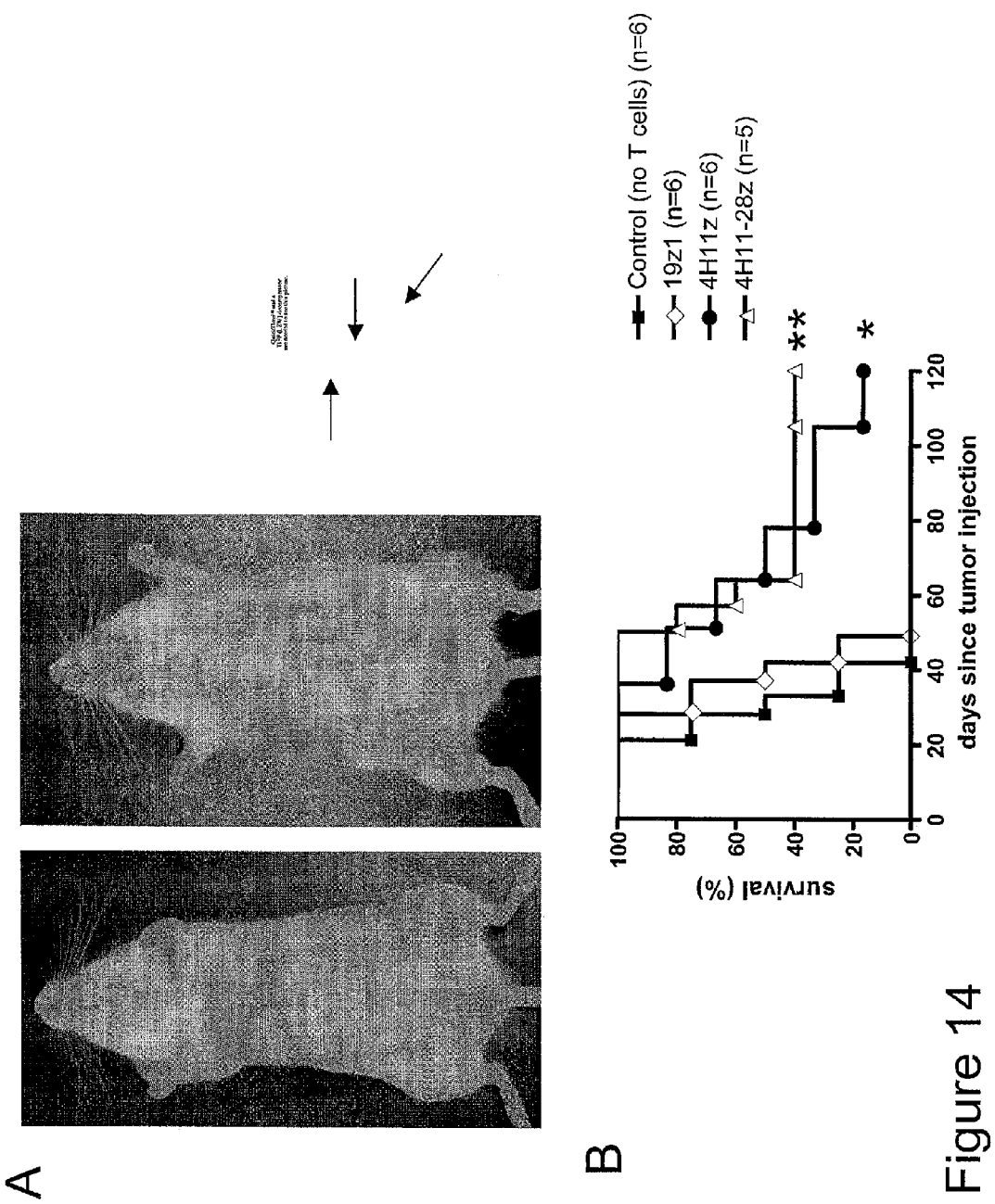
FIG. 14. Eradication of OV-CAR3(MUC-CD) tumors after intra-peritoneal treatment with first and second generation of MUC-CD targeted T cells. (A) Intraperitoneal injection of OV-CAR3(MUC-CD) tumors in untreated SCID-Beige mice results in abdominal distension and nodular peritoneal tumors. SCID-Beige mice were injected intraperitoneally with $3\times10^6$ OV-CAR3(MUC-CD) cells. At 5 weeks post intraperitoneal injection of OV-CAR3(MUC-CD) tumor cells mice developed ascities as evidenced by a distended abdomen (center panel) when compared to a tumor free mouse (left panel). Post mortem visualization of the peritoneum demonstrates nodular tumor masses (arrows) within the abdominal cavity (right panel). (B) Intraperitoneal injection of 4H11z$^+$ and 4H11-28z$^+$ T cells either delay tumor progression or fully eradicate disease. Kaplan-Meier survival curve of SCID-Beige mice treated with first or second generation of MUC-CD targeted T cells. SCID-Beige mice were infused ip with $3\times10^6$ OV-CAR3(MUC-CD) tumor cells on day 1 followed by $3\times10^7$ 4H11z$^+$ or 4H11-28z$^+$ T cells on day 2. All untreated mice or mice treated with control 19z1$^+$ T cells developed established tumors and were sacrificed by day 50. In contrast, 27% of mice treated with either 4H11z$^+$ or 4H11-28z$^+$ T cells remained without clinical evidence of disease by day 120. *p=0.01 (4H11z compared to 19z1), **p=0.0023 (4H11-28z compared to 19z1), p=0.63 (4H11z compared to 4H11-28z).

To assess the in vivo anti-tumor activity of 4H11z$^+$ and 4H11-28z$^+$ T cells, we next generated an orthotopic xenotransplant ovarian cancer tumor model by ip injection of OV-CAR3(MUC-CD) tumor cells into SCID-Beige mice. If left untreated, these mice developed marked ascites and multiple nodular peritoneal tumors by 3 weeks following tumor cell injection (FIG. 14A). All untreated tumor bearing mice had to be euthanized by 7 weeks following tumor cell injection due to evidence of distress.

To assess the in vivo anti-tumor efficacy of MUC-CD-targeted T cells, SCID-Beige mice were injected ip with OV-CAR3(MUC-CD/GFP-FFLuc) tumor cells on day 1 followed by ip injection of 4H11z' or 4H11-28z$^+$ T cells on day 2. For negative controls, tumor bearing mice were either untreated or treated with T cells modified to express the irrelevant CD 19-targeted CAR. Collectively, we found that 27% of all mice treated with MUC-CD targeted T cells (3/11 mice) remained alive without clinical evidence of disease 120 days out from tumor injection with no statistically significant difference in survival when comparing the 4H11z$^+$ and 4H11-28z$^+$ T cell treated cohorts (FIG. 14B). In contrast, both MUC-CD-targeted T cell treated cohorts demonstrated statistically significant enhanced survival when compared to untreated and 19z1$^+$ T cell treated control cohorts.

Figure 15:
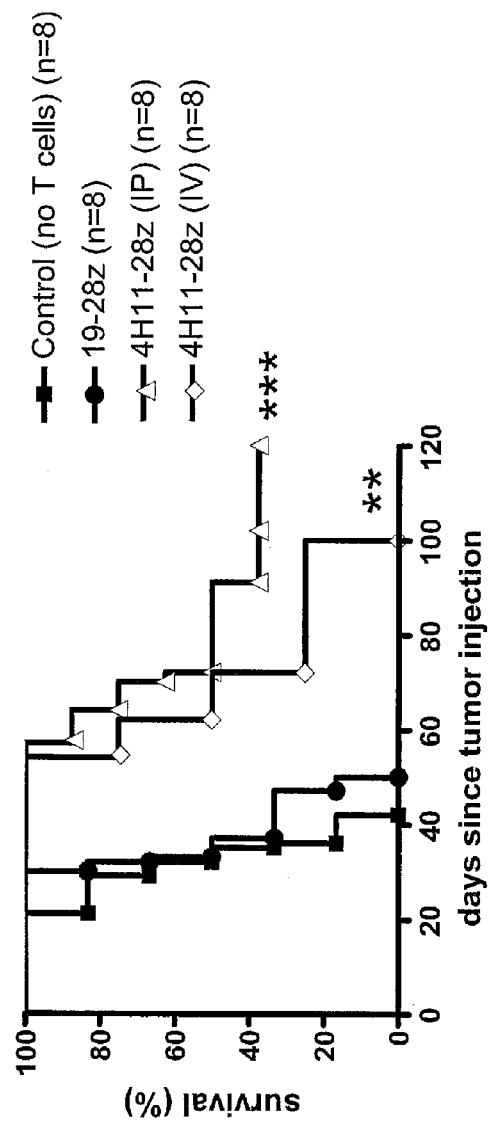
FIG. 15. MUC-CD targeted 4H11-28z$^+$ T cells successfully traffic to ip OV-CAR3(MUC-CD/GFP-FFLuc) tumors following systemic intravenous infusion resulting in equally efficient anti-tumor efficacy when compared to ip 4H11-28z$^+$ treated tumor bearing mice. (A) Kaplan-Meier survival curve of SCID-Beige mice treated ip or iv with 4H11-28z$^+$ T cells. SCID-Beige mice were injected intraperitoneally with $3\times10^{6}$OV-CAR3(MUC-CD/GFP-FFLuc) tumor cells followed by either iv or ip infusion of $3\times10^7$ 4H11-28z$^+$ T cells. Tumor eradication is enhanced after either ip or iv infusion of 4H11-28z$^+$ T cells when compared to control treated mice. Both ip and iv 4H11-28z$^+$ T cell treated mice exhibited statistically enhanced survival (*p<0.0001 and p=0.0038, respectively) when compared to 19-28z$^+$ T cell treated control cohorts. Conversely, difference in survival between the ip and iv 4H11-28z$^+$ T cell cohorts was not statistically significant (p=0.22). (B) BLI of tumor progression of representative ip and iv 4H11-28z$^+$ T cell treated mice with ultimately progressive disease following treatment compared to BLI of tumor progression in a representative control 19-28z$^+$ T cell treated mouse. (C) Systemically injected CFSE stained 4H11-28z$^+$ T cells traffic to advanced ip OV-CAR(MUC-CD) tumors. Presence of iv injected CFSE labeled 19-28z$^+$ control T cells (left panel) and 4H11-28z$^+$ T cells (right panel) 1 day following infusion into SCID-Beige mice with advanced OV-CAR (MUC-CD) tumors (injected 7 days earlier), as assessed by FACS analysis of single cell OV-CAR3(MUC-CD) tumor suspensions, reveals a marked population of 4H11-28z$^+$ but not control 19-28z$^+$ T cells within peritoneal OV-CAR3 (MUC-CD) tumors.
Figure 15:
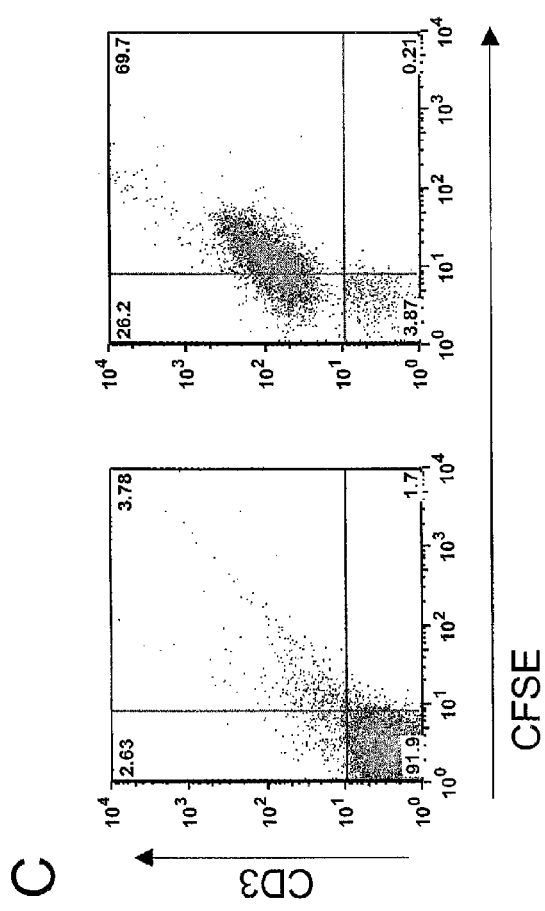

To assess whether systemically infused MUC-CD-targeted T cells successfully traffic to ip tumors, we next compared ip to iv infusion of 4H11-28z$^+$ T cells in SCID-Beige mice bearing ip OV-CAR3(MUC-CD/GFP-FFLuc) tumors. Both ip and iv 4H11-28z$^+$ T cell treated mice exhibited statistically enhanced survival when compared to untreated or 19-28z$^+$ T cell treated control cohorts as assessed by overall survival (FIG. 15A) as well as by BLI of tumor progression (FIG. 15B). Furthermore, we found overall survival between the ip and iv treated groups to be statistically equivalent by log rank analysis. These data imply successful trafficking of iv infused 4H11-28z$^+$ T cells to peritoneal tumors. We further confirmed trafficking of iv infused CFSE labeled 4H11-28z$^+$ T cells to the peritoneum by FACS analysis of single cell suspensions of macerated OV-CAR3(MUC-CD) tumors (FIG. 15C).

In Vivo Anti-Tumor Activity of MUC-CD Targeted T Cells in SCID-Beige Mice Bearing Well Established OV-CAR3 (MUC-CD/GFP-FFLuc) Tumors.

Figure 16:
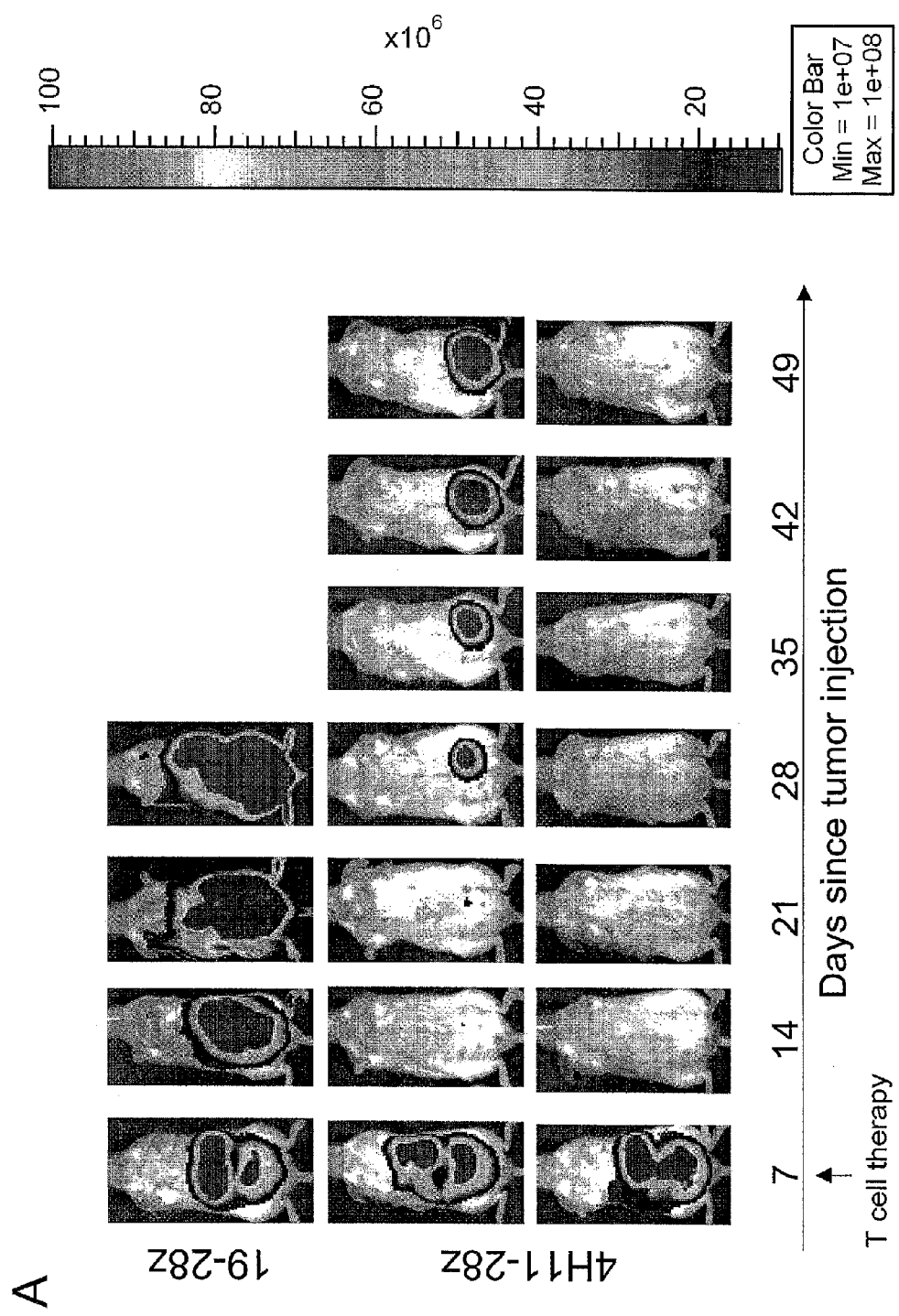
FIG. 16. Eradication of advanced OV-CAR3(MUC-CD) tumors in SCID-Beige mice by ip infusion of 4H11-28z$^+$ T cells. SCID-Beige mice were injected ip with $3\times10^{6}$OV-CAR3(MUC-CD/GFP-FFLuc) tumor cells 7 days prior to ip treatment with $3\times10^7$ 4H11-28z$^+$ T cells. (A) BLI of 4H11-28z$^+$ T cell treated mice with either relapsed disease (middle row) or eradicated disease (bottom row) compared to a representative 19-28z$^+$ T cell treated control mouse. (B) Kaplan-Meier survival curve of SCID-Beige mice with advanced OV-CAR3(MUC-CD/GFP-FFLuc) tumors treated ip with 4H11-28z$^+$ T cells. All 4H11-28z$^+$ T cell treated mice demonstrated enhanced survival when compared to control 19-28z$^+$ T cell treated mice (**p=0.0011), with an overall long-term survival of 25% at day 120.
Figure 16:
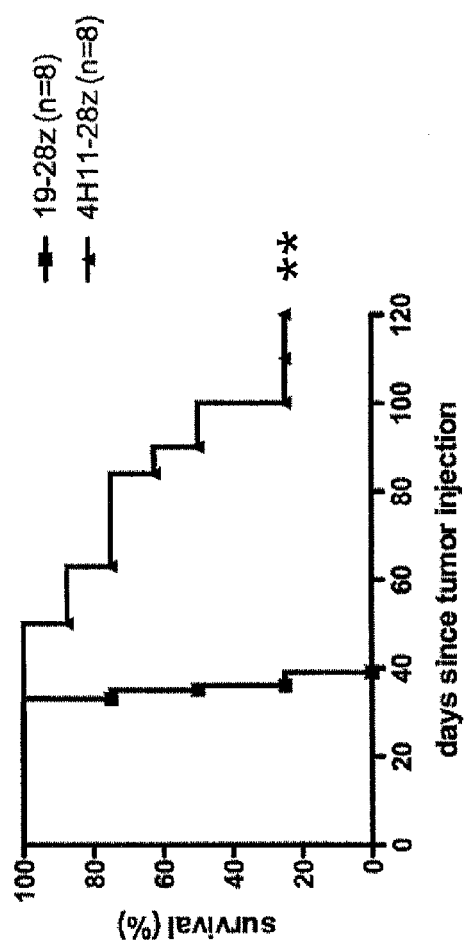

To further assess whether 4H11-28z$^+$ T cells were able to eradicate more clinically relevant tumor burdens, we next treated SCID-Beige mice bearing well established ip OV-CAR3(MUC-CD/GFP-FFLuc) tumor injected 7 days prior to adoptive T cell therapy. Once more, we found that therapy with MUC-CD targeted T cells markedly eradicated BLI evident disease in all treated mice (FIG. 16A) with 5 of 8 treated mice eventually developing relapsed progressive disease, and 3 mice remaining disease free as assessed by BLI imaging (not shown) out to 120 days post-tumor cell infusion (FIG. 16B). These data demonstrate potent in vivo anti-tumor activity mediated by MUC-CD targeted T cells even in the setting of advanced disease.

Discussion

Based on extensive analyses of patient tumor samples, ovarian carcinomas appear to be relatively immunogenic tumors. Specifically, researchers have found there to be a direct correlation between prognosis following surgery and chemotherapy and the quantity of tumor infiltrating effector T cells (TILs) in pretreatment tumor samples (25, 49, 50). Furthermore, others have described an inverse correlation between prognosis following therapy and pre-treatment levels of Tregs within the tumor, which in turn presumably inhibit the anti-tumor function of tumor specific effector TILs (26, 28, 51). Both of these findings imply a role for an endogenous effector T cell response to tumor in controlling disease progression both prior to and following initial therapy and strongly support the contention that ovarian carcinomas may be susceptible to killing by adoptive infusion of autologous T cells targeted to ovarian tumor cell antigens.

While endogenous effector TILs are one source for pre-sumably tumor specific T cells, an alternative approach to adoptive T cell therapy is to isolate autologous peripheral blood T cells which in turn may be genetically modified ex vivo to target tumor cell antigens. One such genetic approach is to retrovirally transduce patient T cells with CARs targeted to surface exposed antigens either unique to or over-expressed by the tumor. To this end, promising preclinical studies utilizing this approach in other malignancies have recently been translated into the clinical setting (6, 16, 19, 52). Similarly, we have previously generated CARs targeted to the CD 19 antigen expressed on normal B cells as well as most B cell malignancies and are currently conducting clinical trials treating patients with relapsed B cell chronic lymphocytic leukemia and acute lymphoblastic leukemias with autologous T cell modified to express a CD19 specific CAR (53).

Application of this approach to ovarian carcinomas requires the identification to suitable target antigens expressed on the tumor cell surface. Significantly, other investigators have studied this approach in both the pre-clinical and clinical setting (4, 11, 54-57). Specifically, several groups have demonstrated significant anti-tumor responses to subcutaneous human ovarian carcinoma cell line tumors in immune compromised mice following intratumoral and/or intravenous infusion of T cells expressing CARs specific to the mesothelin and Lewis-Y antigens overexpressed on these tumor cell lines (56, 58, 59). Furthermore, Kershaw et al recently published the results of a phase I clinical trial treating patients with relapsed ovarian carcinomas with autologous T cells modified to express a CAR specific to the alpha-folate receptor (6). The authors of this study found that therapy with targeted T cells was well tolerated, but noted a lack of anti-tumor response in these studies related to poor persistence of modified T cells over time as well as a yet undefined T cell inhibitory factor in the serum of several treated patients.

In our studies, we have chosen to target the MUC-16 glycoprotein which is over-expressed on a majority of ovarian carcinomas (1, 30, 32, 33). The utility of MUC-16 as a target antigen for adoptive T cell therapy is compromised by the fact that most of the extracellular portion of this molecule is cleaved by the tumor cell, secreted, and may be detected in the serum as the CA-125 tumor marker. However, following cleavage of this secreted fraction of MUC-16, there remains a residual extracellular fraction of the glycoprotein, termed MUC-CD, which is retained on the tumor surface and is therefore an attractive target for immune-based therapies. To this end, we utilized a series of murine hybridomas generated to the MUC-CD antigen to construct CARs specific to MUC-CD. Of these CARs, we identified a CAR generated from the 4H11 murine hybridoma termed 4H11z, which, when expressed in human T cells, following co-culture on 3T3 (MUC-CD/B7.1) AAPCs, resulted in rapid destruction of AAPC monolayers as well as marked modified T cell expansion. Significantly, the antigen to the 4H11 antibody is highly expressed on a majority of pre-treatment ovarian carcinoma surgical tumor samples obtained from patients treated at our institution as assessed by immuno-histochemistry (48).

Optimal T cell activation requires both a primary T cell receptor mediated signal, "signal 1," along with a co-stimulatory "signal 2." Classically, this co-stimulatory signal may be provided by ligation of either B7.1 (CD80) or B7.2 (CD86) on the target cell with the T cell co-stimulatory receptor CD28. Alternatively, co-stimulation may be generated by ligation of 4-1BBL or OX-40L on the target cell with the respective 4-1BB or OX40 co-stimulatory receptors on the T cell (12, 60, 61). Since most tumor cells fail to express co-stimulatory ligands, we and others have previously demonstrated that second generation CARs further incorporating the cytoplasmic signaling domains the co-stimulatory receptors CD28, 4-1BB, and/or OX40 resulted in CARs capable of providing both signal 1 and signal 2 to the T cell upon binding to cognate antigen in the absence of exogenous co-stimulatory ligands (7-10, 12, 13, 15, 16, 62-65). To this end, we constructed a second generation CAR from the 4H11z CAR incorporating the transmembrane and cytoplasmic signaling domain of CD28 as described elsewhere (3, 9, 43). Consistent with previous studies, we found that T cells transduced to express the resulting 4H11-28z CAR, but not the first generation 4H11z CAR, efficiently expanded upon co-culture with 3T3(MUC-CD) fibroblasts in the absence of exogenous co-stimulation consistent with the ability of the 4H11-28z CAR to deliver both signal 1 and signal 2 to the T cell. This conclusion is further supported by the finding that 4H11-28z$^+$ T cells secreted significantly higher levels of IL-2, a cytokine indicative of T cell co-stimulation, upon co-culture on 3T3 (MUC-CD) fibroblasts when compared to T cells transduced to express the first generation 4H11z CAR.

We next assessed the ability of 4H11z$^+$ and 4H11-28z$^+$ T cells to target and lyse human ovarian carcinoma tumor cells. To this end, we initially utilized the OV-CAR3 human ovarian cancer cell line. Since the OV-CAR3 tumor cell line binds the 4H11 antibody weakly, we further genetically modified the cell line to express MUC-CD (OV-CAR3(MUC-CD)) to better mimic the clinical setting wherein a majority of clinical ovarian carcinoma tumor specimens highly express the 4H11 MUC-CD antigen (48). We demonstrated that human T cells modified to express either 4H11z or 4H11-28z eradicated OV-CAR3(MUC-CD) tumor cells in vitro, and surprisingly observed that both 4H11z$^+$ and 4H11-28z$^+$ T cells expanded following co-culture with tumor in vitro. To define the etiology of this unanticipated 4H11z$^+$ T cell expansion, we further assessed whether OV-CAR3(MUC-CD) tumor cells expressed co-stimulatory ligands, and found that this tumor cell line expressed 4-1BBL, consistent with our experimental findings as well as with previously published reports demonstrating 4-1BBL expression by a variety of carcinoma cell lines (66-68). In order to further validate the clinical relevance of these findings, we subsequently demonstrated specific in vitro lysis of primary ascites-derived tumor cells isolated from untreated ovarian carcinoma patients by both healthy donor allogeneic 4H11-28z$^+$ T cells as well as more significantly autologous 4H11-28z$^+$ patient peripheral blood T cells. These data strongly support the contention that treatment with autologous 4H11-based CAR$^+$ T cells have promise in future clinical applications.

In order to assess the in vivo relevance of our in vitro findings, we next generated a murine orthotopic OV-CAR3 (MUC-CD) tumor model in SCID-Beige mice. We injected mice i.p. with OV-CAR3(MUC-CD) tumor cells and the following day infused 4H11z$^+$, 4H11-28z$^+$, and control 19z1$^+$ T cells i.p. This treatment approach resulted in a significant but similar delay to tumor progression and long-term survival in both the 4H11z$^+$ and 4H11-28z$^+$ T cell treated cohorts when compared to untreated mice or mice treated with control T cells targeted to the irrelevant CD19 antigen. We next compared ip to iv treatment with 4H11-28z$^+$ T cells of orthotopic OV-CAR3(MUC-CD/GFP-FFLuc) bearing mice, and found similar statistically significant survivals of mice over time with either direct ip infusion of T cells or systemic iv infusion of targeted T cells. Significantly, iv treated mice by day 1 following treatment, exhibited successful trafficking of targeted T cells to the peritoneum. These data suggests that adoptive therapy with targeted T cells may be equally efficacious following either a direct infusion into the peritoneum or through systemic iv infusion. These findings further support the future clinical potential of this approach in treating patients both with local relapse of disease as well as metastatic relapse to sites outside of the peritoneum.

Finally, we assessed the ability of 4H11-28z$^+$ T cells to eradicate more established disease by delaying modified T cell ip infusion by 7 days, when mice had greater established tumor burdens as assessed by bioluminescent imaging. This experimental setting better reflects the initial clinical setting wherein this adoptive T cell approach would be utilized. Significantly, despite the setting of markedly established disease, 4H11-28z$^+$ T cells retained the ability to lyse larger tumor burdens, delay relapse of tumor, and in a significant percentage of mice, fully eradicate disease.

In the studies presented here, we have consistently utilized mixed populations of CD4$^+$ and CD8$^+$ CAR$^+$ T cells to assess both in vitro and in vivo anti-tumor activity. To this end, ongoing studies will address the role of isolated CD4$^+$ and CD8+ CAR+ T cell subsets in the successful eradication of disease in this SCID-Beige OV-CAR³(MUC-CD) tumor model. The results of these studies may have implications to translating this therapeutic approach to the clinical setting. Furthermore, we acknowledge the limitations associated with the presented SCID-Beige tumor model. Namely, this is a xenotransplant model in an immune compromised mouse. To this end, ongoing studies in or laboratory are focused on generating a more clinically relevant syngeneic immune competent tumor model to better define the biology and antitumor efficacy of MUC-CD targeted CAR-modified T cells in the context of an intact immune system.

In conclusion, herein we present the first published data demonstrating the feasibility of targeting MUC-16, an antigen over-expressed on a majority of ovarian carcinomas, through adoptive therapy with genetically modified T cells targeted to the retained MUC-CD portion of the MUC-16 antigen. Further, this report is the first to demonstrate efficient targeting of T cells in an orthotopic, clinically relevant, murine model of ovarian cancer, demonstrating efficacy both by ip and iv infusion of modified T cells. Finally, these data support the further translation of this approach to the clinical setting in the form of a phase I clinical trial in patients with persistent or relapsed ovarian carcinomas following initial therapy with surgery and chemotherapy. [jf1]

Example 5

Raising Mouse MUC16 Monoclonal Antibodies in Mice and Hamsters.

We selected 3 different regions of mouse MUC16 genome for which monoclonal antibodies were generated in mouse and hamster. The selected regions of the mouse MUC16 are Peptide 1 (SEQ ID NO:21, ecto region of cytoplasmic domain), Peptide 2 (SEQ ID NO:22, first cysteine loop) and Peptide 3 (SEQ ID NO:23, second cysteine loop) (FIG. 20A) and its comparison with human MUC16 is shown in FIG. 20B. A cysteine was added to the peptide sequence at the N terminus of Peptide 1 (SEQ ID NO:21) and Peptide 3 (SEQ ID NO:23) for better conjugation with KLH. Individual peptides were conjugated to KLH using Promega kit. These 3 conjugated peptides were pooled and immunized into 5 mice and 4 hamsters. 5 immunizations with a 3 week interval for each immunization were administered. Sera from these animals were tested by ELISA for their specific reactivity with individual peptides (SEQ ID NO:21, 22 and 23). Positive selected animals were allowed to rest for a month and then i.v. boosted with pooled peptides immunogen (SEQ ID NO:21, 22 and 23) and harvested the spleens after 4 days. Splenocytes were mixed with hybridoma partners and plated into microtiter plates at various clonal densities. Plates were cultured at 37° C. 5% $CO_2$ for 10 days and then selected the clones. Supernatants from these selected clones were tested by ELISA for their specific reactivity with individual peptides (SEQ ID NO:21, 22 and 23). Positive clonal sups were tested by FACS, western blot and imaging using 2 mouse cell lines (ID8 and BR5—FVB1) and a human cell line (OVCAR-3).

Table 4 shows the summary of mouse and hamster monoclonal antibodies against mouse MUC16 peptide antigens Peptide 1 (SEQ ID NO:21), Peptide 2 (SEQ ID NO:22), and Peptide 3 (SEQ ID NO:23). A very strong antigenic response was seen with Peptide 1 (SEQ ID NO:21).

TABLE 4

| Mouse MUC16 | Mouse mAbs | Frozen Mouse mAb | |
|---|---|---|---|
| Peptide 1 | 46 | 16 (3-IgG1; 8-IgG2b; 1-IgM; 4-Unkown isotype) | |
| Peptide 2 | 0 | 0 | Animals not iv boosted with peptide 2 |
| Peptide 3 | 6 | 6 (4-IgG1; 2-IgM) | |
| Peptide 1, 2, 3 | 0 | 0 | |
| Peptide 1, 2 | 0 | 0 | |
| Peptide 2, 3 | 0 | 0 | |
| No Peptide | 0 | 0 | |

| Mouse MUC16 | Hamster mAbs | Frozen Hamster mAb |
|---|---|---|
| Peptide 1 | 69 | 21 |
| Peptide 2 | 6 | 6 |
| Peptide 3 | 7 | 7 |
| Peptide 1, 2, 3 | 2 | 1 |
| Peptide 1, 2 | 1 | 1 |
| Peptide 2, 3 | 1 | 0 |
| No Peptide | 10 | 2 |

Details of mouse and hamster mAbs against Peptide 1 (SEQ ID NO:21), Peptide 2 (SEQ ID NO:22), and Peptide 3 (SEQ ID NO:23 are listed in Table 5 and Table 6 respectively.

TABLE 5

| isotype | PEPTIDE | Fusion Well | Cloned | Clones | | | |
|---|---|---|---|---|---|---|---|
| — | 1 | 01D01 | | | | | |
| — | 1 | 09F07 | | | | | |
| IgG 1 | 1 | 16A09 | no success | | | | |
| — | 1 | 21A07 | | | | | |
| — | 1 | 24G10 | | | | | |
| IgG 1 | 1 | 10C04 | yes | 10C4-3H5 | 10C4-1F2 | 10C4-2H8 | 10C4-1G7 |
| IgG 1 | 1 | 17F02 | yes | 17F2-3G5 | 17F2-3F6 | 17F2-2F9 | 17F2-1E11 |
| IgG 2b | 1 | 01A08 | | | | | |
| IgG 2b | 1 | 01F08 | | | | | |
| IgG 2b | 1 | 12B10 | yes | 12B10-3F7 | 12B10-3G10 | 12B10-2F6 | 12B10-2F10 |
| IgG 2b | 1 | 17H10 | | | | | |
| IgG 2b | 1 | 18D05 | | | | | |
| IgG 2b | 1 | 23B12 | | | | | |
| IgG 2b | 1 | 25E09 | | 25E9-3 | 25E9-5 | 25E9-13 | 25E9-16 |
| IgM | 1 | 16F12 | | | | | |
| IgG 1 | 3 | 04A06 | no success | | | | |
| IgG 1 | 3 | 05D01 | no success | | | | |

TABLE 5-continued

| isotype | PEPTIDE | Fusion Well | Cloned | Clones | | | |
|---|---|---|---|---|---|---|---|
| IgG 1 | 3 | 21B08 | yes | 21B8-1H11 | 21B8-3G6 | 21B8-3H9 | 21B8-1G8 |
| IgG 1 | 3 | 21E01 | yes | 21E1-1E3 | 21E1-1G9 | 21E1-2G7 | 21E1-3G12 |
| IgM | 3 | 08A02 | | | | | |
| IgM | 3 | 13E05 | | | | | |

TABLE 6

| Hamster mAb | Peptide | Cloned | | | |
|---|---|---|---|---|---|
| 01H03 | | | | | |
| 02F02 | 1 | | | | |
| 04E 4 | | | | | |
| 04G07 | 1 | | | | |
| 04H01 | 3 | 4H1-2E1 | 4H1-2E3 | 4H1-3E1 | 4H1-3H3 |
| 06A08 | 1 | | | | |
| 06F02 | 1 | | | | |
| 07F08 | 3 | | | | |
| 07H05 | 2 | | | | |
| 09A05 | | | | | |
| 09E 1 | 3 | | | | |
| 09F08 | 1 | | | | |
| 09H10 | | | | | |
| 10G06 | 1 | | | | |
| 10H11 | 1 | | | | |
| 11B10 | 1 | | | | |
| 12F09 | 2 | | | | |
| 15A08 | 1 | 15A8-2E2 | 15A8-2E10 | 15A8-2E11 | 15A8-3D2 |
| 15H08 | 3 | | | | |
| 19B05 | 1 | | | | |
| 21H04 | 3 | | | | |
| 22B05 | 2 | 22B5-1F6 | 22B5-3G9 | 22B5-2G8 | 22B5-3F11 |
| 22D11 | 3 | | | | |
| 23G12 | 1 | | | | |
| 25E 8 | 1 | | | | |
| 27H09 | 3 | | | | |
| 28B12 | 1&2&3 | | | | |
| 28C12 | 2 | | | | |
| 30H02 | 1 | | | | |
| 31A11 | 2 | | | | |
| 31C01 | 2 | | | | |
| 33H06 | 1&2 | | | | |
| 34F10 | 1 | | | | |
| 34H05 | 1 | | | | |
| 36C01 | 1 | | | | |
| 36C11 | | | | | |
| 36E 4 | 1 | | | | |
| 37E 10 | 1 | | | | |
| 10H11 | 1 | | | | |

Hamster antibody 22B05 recognizes mouse (SEQ ID NO:22) and also the corresponding human sequence (SEQ ID NO:15).

Figure 22:
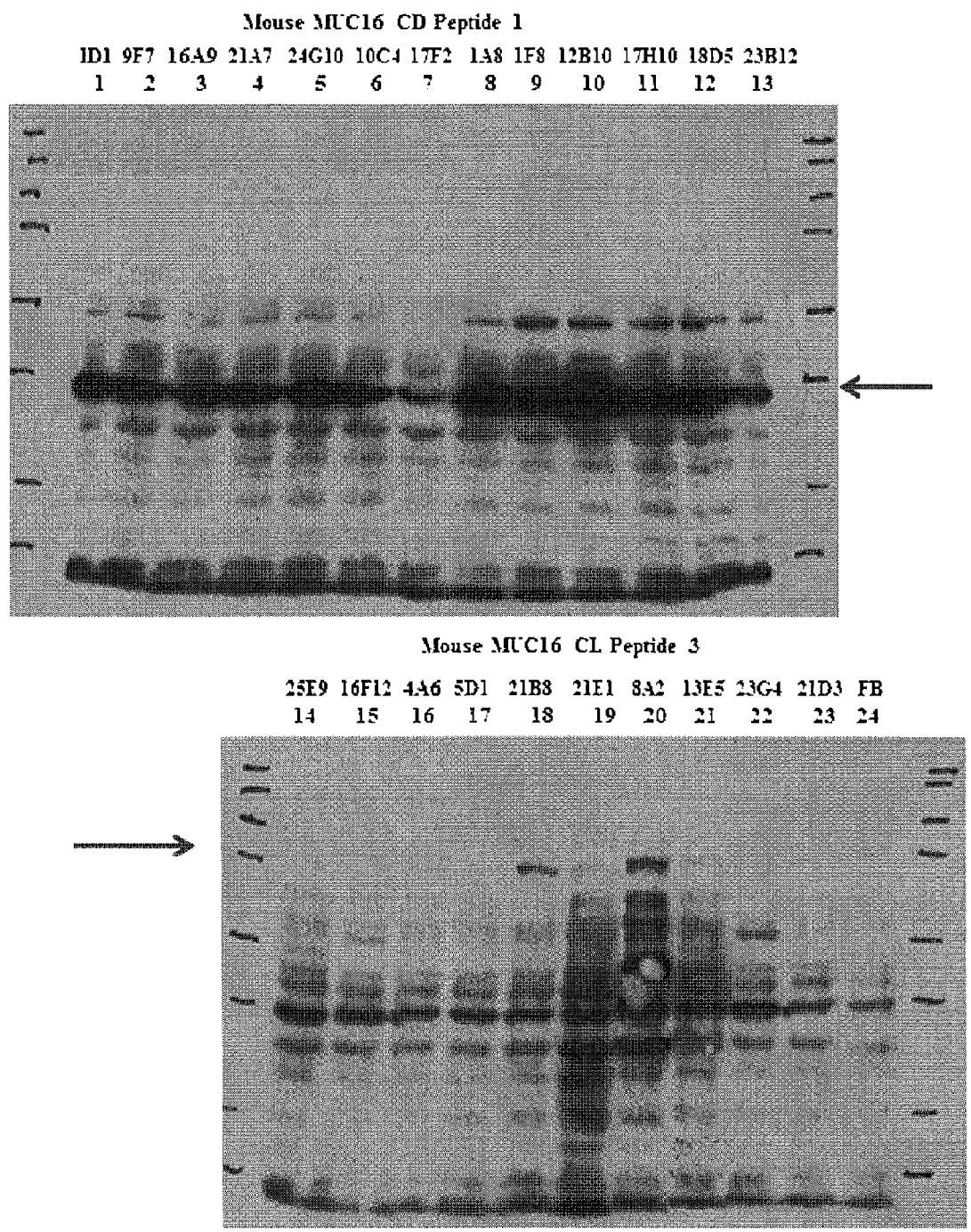
FIG. 22: BR5—FVB 1 extract with 1:10 dilution of Mouse MUC 16 monoclonal Primary Supernatants

Western blot analysis using mouse ID8 and BR5—FVB1 cell extracts were also performed for all the selected monoclonal antibodies as shown in FIG. 21 and FIG. 22 respectively.

Among the mouse MUC16 monoclonal antibodies, we selected 12B10-3G10 subclone mouse mAb for further screening. Similarly, hamster monoclonal antibodies, 15A8-2E10, 22B5-2G8 and 4H1-2E1 subclones were selected for further screening.

Figure 23A:
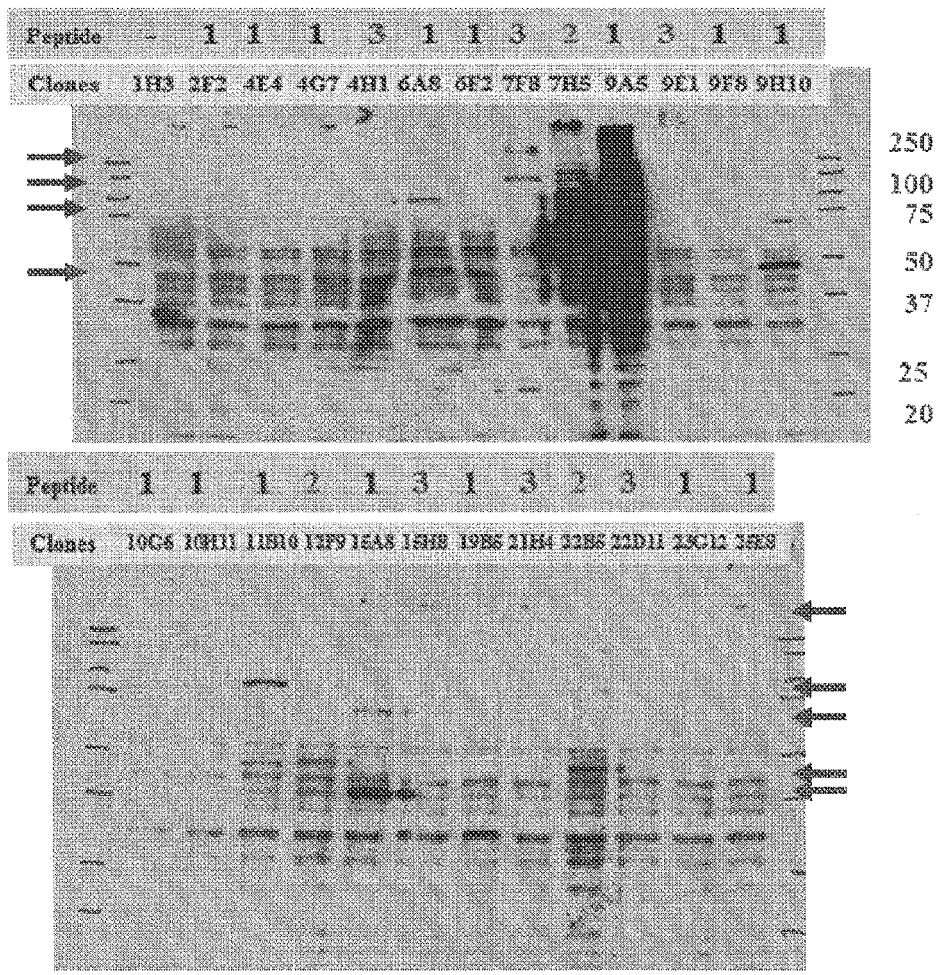
FIG. 23A and FIG. 23B: Western Blot showing 38 hamster's monoclonal antibody Supernatants on ID8 cell extracts.
Figure 23B:
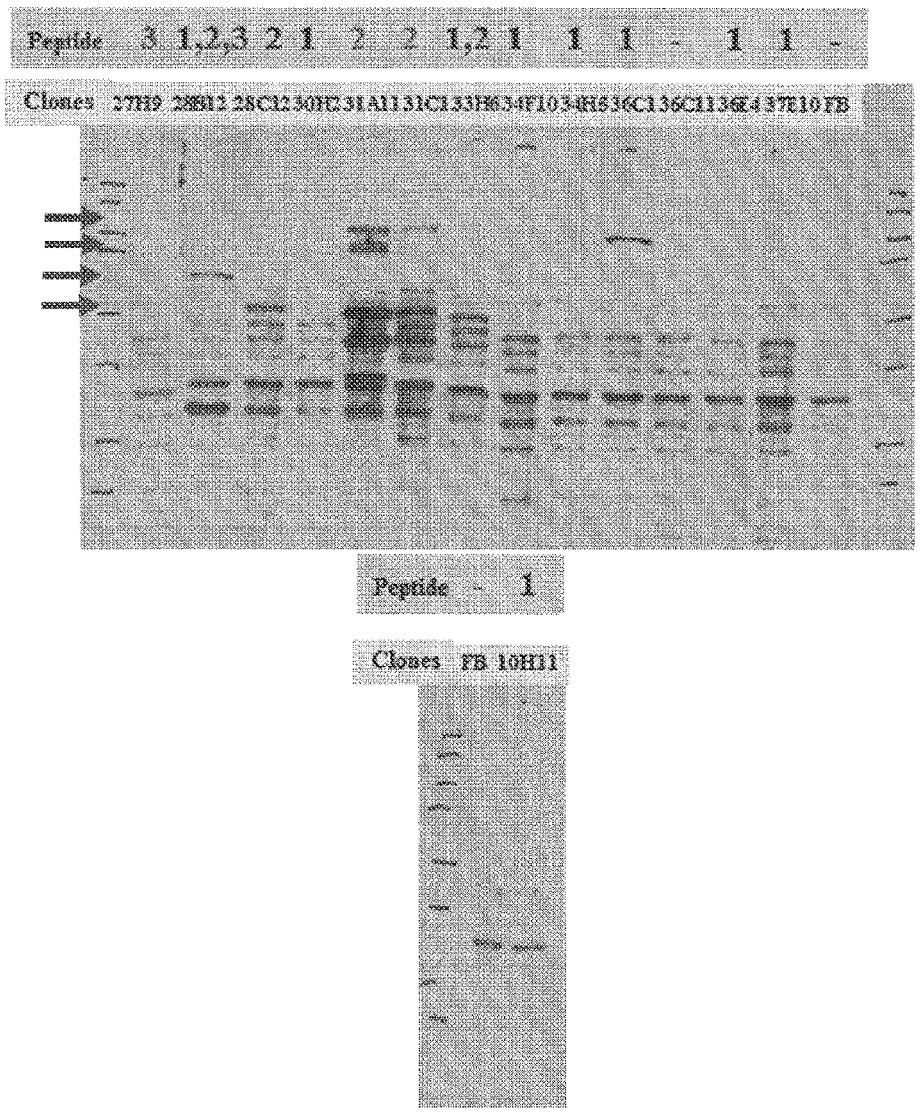

Immunohistochemical analysis was performed with paraffin and cryosections of ID8 (mouse), OVCAR-3 (human), BR5—FVB1 (mouse) cell lines and 13.5 days of Embryo. Paraffin or cryosections were probed with mouse 12B10 mAb, hamster 15A8, hamster 22B5 and hamster 4E1 mAbs to see the early development of mouse MUC16 (FIG. 23A and FIG. 23B)

12B10-3G10 sub clone were further analyzed for single chain Fv fragments. FIG. 24 shows 12B10-3G10 $V_H$ and $V_L$ DNA and Amino Acids sequences. Bioreactive supernatants and purified 12B10-3G10 were generated for animal studies and other characterization studies. FACS analysis was performed with purified 12B10-3G10 on ID8, OVCAR3 and BR5—FVB1 cells showing over 90% positivity to both mouse and human MUC16 ecto-domain fragment (FIG. 25).

References Cited In The Specification And Examples 1-3

1. Bast R C, Jr., Feeney M, Lazarus H, Nadler L M, Colvin R B, Knapp R C. Reactivity of a monoclonal antibody with human ovarian carcinoma. J Clin Invest 1981; 68(5):1331-7.

2. Bast R C, Jr., Klug T L, St John E, Jenison E, Niloff J M, Lazarus H, et al. A radioimmunoassay using a monoclonal antibody to monitor the course of epithelial ovarian cancer. N Engl J Med 1983; 309(15):883-7.

3. Rustin G J, Bast R C, Jr., Kelloff G J, Barrett J C, Carter S K, Nisen P D, et al. Use of CA-125 in clinical trial evaluation of new therapeutic drugs for ovarian cancer. Clin Cancer Res 2004; 10(11):3919-26.

4. Rosen D G, Wang L, Atkinson J N, Yu Y, Lu K H, Diamandis E P, et al. Potential markers that complement expression of CA125 in epithelial ovarian cancer. Gynecol Oncol 2005; 99(2):267-77.
5. Bast R C, Jr., Badgwell D, Lu Z, Marquez R, Rosen D, Liu J, et al. New tumor markers: CA125 and beyond. Int J Gynecol Cancer 2005; 15 Suppl 3:274-81.
6. Moore R G, Maclaughlan S, Bast R C, Jr. Current state of biomarker development for clinical application in epithelial ovarian cancer. Gynecol Oncol 2009.
7. Nustad K, Lebedin Y, Lloyd K O, Shigemasa K, de Bruijn H W, Jansson B, et al. Epitopes on CA 125 from cervical mucus and ascites fluid and characterization of six new antibodies. Third report from the ISOBM TD-1 workshop. Tumour Biol 2002; 23(5):303-14.
8. Fendrick J L, Konishi I, Geary S M, Parmley T H, Quirk J G, Jr., O'Brien T J. CA125 phosphorylation is associated with its secretion from the WISH human amnion cell line. Tumour Biol 1997; 18(5):278-89.
9. Fendrick J L, Staley K A, Gee M K, McDougald S R, Quirk J G, Jr., O'Brien T J. Characterization of CA 125 synthesized by the human epithelial amnion WISH cell line. Tumour Biol 1993; 14(5):310-8.
10. O'Brien T J, Beard J B, Underwood L J, Shigemasa K. The CA 125 gene: a newly discovered extension of the glycosylated N-terminal domain doubles the size of this extracellular superstructure. Tumour Biol 2002; 23(3):154-69.
11. Yin B W, Dnistrian A, Lloyd K O. Ovarian cancer antigen CA125 is encoded by the MUC16 mucin gene. Int J Cancer 2002; 98(5):737-40.
12. Yin B W, Lloyd K O. Molecular cloning of the CA125 ovarian cancer antigen: identification as a new mucin, MUC16. J Biol Chem 2001; 276(29):27371-5.
13. Hollingsworth M, Swanson B. Mucins in Cancer: protection and control of the cell surface. Nature Reviews: Cancer 2004; 4(1):45-60.
14. Huang L, Ren J, Chen D, Li Y, Kharbanda S, Kufe D. MUC1 cytoplasmic domain coactivates Wnt target gene transcription and confers transformation. Cancer Biol Ther 2003; 2(6):702-6.
15. Li Q, Ren J, Kufe D. Interaction of human MUC1 and beta-catenin is regulated by Lck and ZAP-70 in activated Jurkat T cells. Biochem Biophys Res Commun 2004; 315 (2):471-6.
16. Ren J, Agata N, Chen D, Li Y, Yu W H, Huang L, et al. Human MUC1 carcinoma-associated protein confers resistance to genotoxic anticancer agents. Cancer Cell 2004; 5(2):163-75.
17. Ren J, Bharti A, Raina D, Chen W, Ahmad R, Kufe D. MUC1 oncoprotein is targeted to mitochondria by heregulin-induced activation of c-Src and the molecular chaperone HSP90. Oncogene 2006; 25(1):20-31.
18. Ramsauer V P, Pino V, Farooq A, Carothers Carraway C A, Salas P J, Carraway K L. Muc4-ErbB2 Complex Formation and Signaling in Polarized CACO-2 Epithelial Cells Indicate That Muc4 Acts as an Unorthodox Ligand for ErbB2. Mol Biol Cell 2006.
19. Bafna S, Singh A P, Moniaux N, Eudy J D, Meza J L, Batra S K. MUC4, a multifunctional transmembrane glycoprotein, induces oncogenic transformation of NIH3T3 mouse fibroblast cells. Cancer Res 2008; 68(22):9231-8.
20. Ponnusamy M P, Singh A P, Jain M, Chakraborty S, Moniaux N, Batra S K. MUC4 activates HER2 signalling and enhances the motility of human ovarian cancer cells. Br J Cancer 2008; 99(3):520-6.
21. Nap M, Vitali A, Nustad K, Bast R C, Jr., O'Brien T J, Nilsson O, et al. Immunohistochemical characterization of 22 monoclonal antibodies against the CA125 antigen: 2nd report from the ISOBM TD-1 Workshop. Tumour Biol 1996; 17(6):325-31.
22. Markwell M A, Fox C F. Surface—specific iodination of membrane proteins of viruses and eucarytic cells using 1,3,4,6-tetrachloro-3alpha,6alpha-diphenylglycouril. Biochemistry 1978; 17:4807-4817.
23. Kononen J, Bubendorf L, Kallioniemi A, Barlund M, Schraml P, Leighton S, et al. Tissue microarrays for high-throughput molecular profiling of tumor specimens. Nat Med 1998; 4(7):844-7.
24. Hedvat C V, Hegde A, Chaganti R S, Chen B, Qin J, Filippa D A, et al. Application of tissue microarray technology to the study of non-Hodgkin's and Hodgkin's lymphoma. Hum Pathol 2002; 33(10):968-74.
25. Soslow R A. Histologic subtypes of ovarian carcinoma: an overview. Int J Gynecol Pathol 2008; 27(2):161-74.
26. O'Brien T J, Beard J B, Underwood L J, Dennis R A, Santin A D, York L. The CA 125 gene: an extracellular superstructure dominated by repeat sequences. Tumour Biol 2001; 22(6):348-66.
27. Harris M, Howell A, Chrissohou M, Swindell R I, Hudson M, Sellwood R A. A comparison of the metastatic pattern of infiltrating lobular carcinoma and infiltrating duct carcinoma of the breast. Br J Cancer 1984; 50(1):23-30.
28. Kaneko O, Gong L, Zhang J, Hansen J K, Hassan R, Lee B, et al. A binding domain on mesothelin for CA125/MUC16. J Biol Chem 2009; 284(6):3739-49.

References Cited In Example 4

1. Singh A P, Senapati S, Ponnusamy M P, et al. Clinical potential of mucins in diagnosis, prognosis, and therapy of ovarian cancer. Lancet Oncol 2008; 9(11):1076-85.
2. Sun C C, Ramirez P T, Bodurka D C. Quality of life for patients with epithelial ovarian cancer. Nat Clin Pract Oncol 2007; 4(1):18-29.
3. Brentjens R J, Latouche J B, Santos E, et al. Eradication of systemic B-cell tumors by genetically targeted human T lymphocytes co-stimulated by CD80 and interleukin-15. Nat Med 2003; 9(3):279-86.
4. Hwu P, Yang J C, Cowherd R, et al. In vivo antitumor activity of T cells redirected with chimeric antibody/T-cell receptor genes. Cancer Res 1995; 55(15):3369-73.
5. Imai C, Mihara K, Andreansky M, et al. Chimeric receptors with 4-1BB signaling capacity provoke potent cytotoxicity against acute lymphoblastic leukemia. Leukemia 2004; 18(4):676-84.
6. Kershaw M H, Westwood J A, Parker L L, et al. A phase I study on adoptive immunotherapy using gene-modified T cells for ovarian cancer. Clin Cancer Res 2006; 12(20 Pt 0:6106-15.
7. Kochenderfer J N, Feldman S A, Zhao Y, et al. Construction and preclinical evaluation of an anti-CD19 chimeric antigen receptor. J Immunother 2009; 32(7):689-702.
8. Loskog A, Giandomenico V, Rossig C, Pule M, Dotti G, Brenner M K. Addition of the CD28 signaling domain to chimeric T-cell receptors enhances chimeric T-cell resistance to T regulatory cells. Leukemia 2006; 20(10):1819-28.
9. Maher J, Brentjens R J, Gunset G, Riviere I, Sadelain M. Human T-lymphocyte cytotoxicity and proliferation directed by a single chimeric TCRzeta/CD28 receptor. Nat Biotechnol 2002; 20(1):70-5.

10. Moeller M, Haynes N M, Trapani J A, et al. A functional role for CD28 costimulation in tumor recognition by single-chain receptor-modified T cells. Cancer Gene Ther 2004; 11(5):371-9.
11. Parker L L, Do M T, Westwood J A, et al. Expansion and characterization of T cells transduced with a chimeric receptor against ovarian cancer. Hum Gene Ther 2000; 11(17):2377-87.
12. Sadelain M, Brentjens R, Riviere I. The promise and potential pitfalls of chimeric antigen receptors. Curr Opin Immunol 2009; 21(2):215-23.
13. Stephan M T, Ponomarev V, Brentjens R J, et al. T cell-encoded CD80 and 4-1BBL induce auto- and transcostimulation, resulting in potent tumor rejection. Nat Med 2007; 13(12):1440-9.
14. Daly T, Royal R E, Kershaw M H, et al. Recognition of human colon cancer by T cells transduced with a chimeric receptor gene. Cancer Gene Ther 2000; 7(2):284-91.
15. Jensen M C, Cooper L J, Wu A M, Forman S J, Raubitschek A. Engineered CD20-specific primary human cytotoxic T lymphocytes for targeting B-cell malignancy. Cytotherapy 2003; 5(2):131-8.
16. Pule M A, Savoldo B, Myers G D, et al. Virus-specific T cells engineered to coexpress tumor-specific receptors: persistence and antitumor activity in individuals with neuroblastoma. Nat Med 2008; 14(11):1264-70.
17. Savoldo B, Rooney C M, Di Stasi A, et al. Epstein Barr virus specific cytotoxic T lymphocytes expressing the anti-CD30zeta artificial chimeric T-cell receptor for immunotherapy of Hodgkin disease. Blood 2007; 110(7):2620-30.
18. Wang G, Chopra R K, Royal R E, Yang J C, Rosenberg S A, Hwu P. A T cell-independent antitumor response in mice with bone marrow cells retrovirally transduced with an antibody/Fc-gamma chain chimeric receptor gene recognizing a human ovarian cancer antigen. Nat Med 1998; 4(2):168-72.
19. Hollyman D, Stefanski J, Przybylowski M, et al. Manufacturing validation of biologically functional T cells targeted to CD19 antigen for autologous adoptive cell therapy. J Immunother 2009; 32(2):169-80.
20. Lamers C H, Sleijfer S, Vulto A G, et al. Treatment of metastatic renal cell carcinoma with autologous T-lymphocytes genetically retargeted against carbonic anhydrase IX: first clinical experience. J Clin Oncol 2006; 24(13):e20-2.
21. Till B G, Jensen M C, Wang J, et al. Adoptive immunotherapy for indolent non-Hodgkin lymphoma and mantle cell lymphoma using genetically modified autologous CD20-specific T cells. Blood 2008; 112(6):2261-71.
22. Hamanishi J, Mandai M, Iwasaki M, et al. Programmed cell death 1 ligand 1 and tumor-infiltrating CD8+ T lymphocytes are prognostic factors of human ovarian cancer. Proc Natl Acad Sci USA 2007; 104(9):3360-5.
23. Leffers N, Gooden M J, de Jong R A, et al. Prognostic significance of tumor-infiltrating T-lymphocytes in primary and metastatic lesions of advanced stage ovarian cancer. Cancer Immunol Immunother 2009; 58(3):449-59.
24. Sato E, Olson S H, Aim J, et al. Intraepithelial C D8+ tumor-infiltrating lymphocytes and a high CD8+/regulatory T cell ratio are associated with favorable prognosis in ovarian cancer. Proc Natl Acad Sci USA 2005; 102(51): 18538-43.
25. Zhang L, Conejo-Garcia J R, Katsaros D, et al. Intratumoral T cells, recurrence, and survival in epithelial ovarian cancer. N Engl J Med 2003; 348(3):203-13.
26. Curiel T J, Coukos G, Zou L, et al. Specific recruitment of regulatory T cells in ovarian carcinoma fosters immune privilege and predicts reduced survival. Nat Med 2004; 10(9):942-9.
27. Leffers N, Lambeck A J, de Graeff P, et al. Survival of ovarian cancer patients overexpressing the tumour antigen p53 is diminished in case of MHC class I down-regulation. Gynecol Oncol 2008; 110(3):365-73.
28. Nelson B H. The impact of T-cell immunity on ovarian cancer outcomes Immunol Rev 2008; 222:101-16.
29. Wolf D, Wolf A M, Rumpold H, et al. The expression of the regulatory T cell-specific forkhead box transcription factor FoxP3 is associated with poor prognosis in ovarian cancer. Clin Cancer Res 2005; 11(23):8326-31.
30. Badgwell D, Bast R C, Jr. Early detection of ovarian cancer. Dis Markers 2007; 23(5-6):397-410.
31. Bast R C, Jr., Badgwell D, Lu Z, et al. New tumor markers: CA125 and beyond. Int J Gynecol Cancer 2005; 15 Suppl 3:274-81.
32. Fritsche H A, Bast R C. CA 125 in ovarian cancer: advances and controversy. Clin Chem 1998; 44(7):1379-80.
33. Krivak T C, Tian C, Rose G S, Armstrong D K, Maxwell G L. A Gynecologic Oncology Group Study of serum CA-125 levels in patients with stage III optimally debulked ovarian cancer treated with intraperitoneal compared to intravenous chemotherapy: an analysis of patients enrolled in GOG 172. Gynecol Oncol 2009; 115(1):81-5.
34. O'Brien T J, Beard J B, Underwood L J, Dennis R A, Santin A D, York L. The CA 125 gene: an extracellular superstructure dominated by repeat sequences. Tumour Biol 2001; 22(6):348-66.
35. Bellone S, Anfossi S, O'Brien T J, et al. Generation of CA125-specific cytotoxic T lymphocytes in human leukocyte antigen-A2.1-positive healthy donors and patients with advanced ovarian cancer. Am J Obstet Gynecol 2009; 200(1):75 el-10.
36. Berek J S. Immunotherapy of ovarian cancer with antibodies: a focus on oregovomab. Expert Opin Biol Ther 2004; 4(7):1159-65.
37. O'Brien T J, Tanimoto H, Konishi I, Gee M. More than 15 years of CA 125: what is known about the antigen, its structure and its function. Int J Biol Markers 1998; 13(4): 188-95.
38. Rao T D, Park K J, Smith-Jones P, et al. Novel monoclonal antibodies against proximal (carboxy-terminal) portions of MUC16 (submitted to Applied Immunohistochemistry and Molecular Morphometry).
39. Wang Z, Raifu M, Howard M, et al. Universal PCR amplification of mouse immunoglobulin gene variable regions: the design of degenerate primers and an assessment of the effect of DNA polymerase 3' to 5' exonuclease activity. J Immunol Methods 2000; 233(1-2):167-77.
40. Doenecke A, Winnacker E L, Hallek M. Rapid amplification of cDNA ends (RACE) improves the PCR-based isolation of immunoglobulin variable region genes from murine and human lymphoma cells and cell lines. Leukemia 1997; 11(10):1787-92.
41. Gong M C, Latouche J B, Krause A, Heston W D, Bander N H, Sadelain M. Cancer patient T cells genetically targeted to prostate-specific membrane antigen specifically lyse prostate cancer cells and release cytokines in response to prostate-specific membrane antigen. Neoplasia 1999; 1(2):123-7.

42. Orlandi R, Gussow D H, Jones P T, Winter G. Cloning immunoglobulin variable domains for expression by the polymerase chain reaction. Proc Natl Acad Sci USA 1989; 86(10):3833-7.
43. Brentjens R J, Santos E, Nikhamin Y, et al. Genetically targeted T cells eradicate systemic acute lymphoblastic leukemia xenografts. Clin Cancer Res 2007; 13(18 Pt 1):5426-35.
44. Riviere I, Brose K, Mulligan R C. Effects of retroviral vector design on expression of human adenosine deaminase in murine bone marrow transplant recipients engrafted with genetically modified cells. Proc Natl Acad Sci USA 1995; 92(15):6733-7.
45. Quintas-Cardama A, Yeh R K, Hollyman D, et al. Multifactorial optimization of gammaretroviral gene transfer into human T lymphocytes for clinical application. Hum Gene Ther 2007; 18(12):1253-60.
46. Latouche J B, Sadelain M. Induction of human cytotoxic T lymphocytes by artificial antigen-presenting cells. Nat Biotechnol 2000; 18(4):405-9.
47. Santos E B, Yeh R, Lee J, et al. Sensitive in vivo imaging of T cells using a membrane-bound Gaussia princeps luciferase. Nat Med 2009; 15(3):338-44.
48. Park K J, Soslow R, Linkov I, Rao T D, D S. The extracellular portion of the MUC16 cytoplasmic domain is detectable in ovarian carcinomas using novel monoclonal antibody, 4H11. Mod Pathol, 2008; 21(1s):217A-218A.
49. Raspollini M R, Castiglione F, Rossi Degl'innocenti D, et al. Tumour-infiltrating gamma/delta T-lymphocytes are correlated with a brief disease-free interval in advanced ovarian serous carcinoma. Ann Oncol 2005; 16(4):590-6.
50. Tomsova M, Melichar B, Sedlakova I, Steiner I. Prognostic significance of CD3+ tumor-infiltrating lymphocytes in ovarian carcinoma. Gynecol Oncol 2008; 108(2):415-20.
51. Woo E Y, Chu C S, Goletz T J, et al. Regulatory CD4(+) CD25(+) T cells in tumors from patients with early-stage non-small cell lung cancer and late-stage ovarian cancer. Cancer Res 2001; 61(12):4766-72.
52. Lamers C H, Langeveld S C, Groot-van Ruijven C M, Debets R, Sleijfer S, Gratama J W. Gene-modified T cells for adoptive immunotherapy of renal cell cancer maintain transgene-specific immune functions in vivo. Cancer Immunol Immunother 2007; 56(12):1875-83.
53. Brentjens R, Hollyman D, Weiss M, et al. A Phase I trial for the treatment of chemo-refractory chronic lymphocytic leukemia with CD19-targeted autologous T cells. Molecular Therapy 2008; 16:S15.
54. Barber A, Zhang T, DeMars L R, Conejo-Garcia J, Roby K F, Sentman C L Chimeric NKG2D receptor-bearing T cells as immunotherapy for ovarian cancer. Cancer Res 2007; 67(10):5003-8.
55. Barber A, Zhang T, Sentman C L. Immunotherapy with chimeric NKG2D receptors leads to long-term tumor-free survival and development of host antitumor immunity in murine ovarian cancer. J Immunol 2008; 180(1):72-8.
56. Carpenito C, Milone M C, Hassan R, et al. Control of large, established tumor xenografts with genetically retargeted human T cells containing CD28 and CD137 domains. Proc Natl Acad Sci USA 2009; 106(9):3360-5.
57. Kershaw M H, Westwood J A, Hwu P. Dual-specific T cells combine proliferation and antitumor activity. Nat Biotechnol 2002; 20(12):1221-7.
58. Hung C F, Wu T C, Monie A, Roden R. Antigen-specific immunotherapy of cervical and ovarian cancer. Immunol Rev 2008; 222:43-69.
59. Westwood J A, Smyth M J, Teng M W, et al. Adoptive transfer of T cells modified with a humanized chimeric receptor gene inhibits growth of Lewis-Y-expressing tumors in mice. Proc Natl Acad Sci USA 2005; 102(52): 19051-6.
60. Habib-Agahi M, Jaberipour M, Searle P F. 4-1BBL costimulation retrieves CD28 expression in activated T cells. Cell Immunol 2009; 256(1-2):39-46.
61. Habib-Agahi M, Phan T T, Searle P F. Co-stimulation with 4-1BB ligand allows extended T-cell proliferation, synergizes with CD80/CD86 and can reactivate anergic T cells. Int Immunol 2007; 19(12):1383-94.
62. Brentjens R J, Sadelain M. Somatic cell engineering and the immunotherapy of leukemias and lymphomas. Adv Pharmacol 2004; 51:347-70.
63. Finney H M, Akbar A N, Lawson A D. Activation of resting human primary T cells with chimeric receptors: costimulation from CD28, inducible costimulator, CD134, and CD137 in series with signals from the TCR zeta chain. J Immunol 2004; 172(1):104-13.
64. Sadelain M, Riviere I, Brentjens R. Targeting tumours with genetically enhanced T lymphocytes. Nat Rev Cancer 2003; 3(1):35-45.
65. Wilkie S, Picco G, Foster J, et al. Retargeting of human T cells to tumor-associated MUC1: the evolution of a chimeric antigen receptor. J Immunol 2008; 180(7):4901-9.
66. Li Q, Ai J, Song Z, Liu J, Shan B. 4-1BB (CD137) ligand enhanced anti-tumor immune response against mouse forestomach carcinoma in vivo. Cell Mol Immunol 2008; 5(5):379-84.
67. Salih H R, Kosowski S G, Haluska V F, et al. Constitutive expression of functional 4-1BB (CD137) ligand on carcinoma cells. J Immunol 2000; 165(5):2903-10.
68. Wan Y L, Zheng S S, Zhao Z C, Li M W, Jia C K, Zhang H. Expression of co-stimulator 4-1BB molecule in hepatocellular carcinoma and adjacent non-tumor liver tissue, and its possible role in tumor immunity. World J Gastroenterol 2004; 10(2):195-9.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. An isolated antibody, or an antigen-binding fragment thereof, that specifically binds to a MUC16 polypeptide or to an antigenic portion thereof, wherein the MUC16 polypeptide is
TLDRSSVLVDGYSPNRNE (SEQ ID NO:02),
   wherein the antibody comprises a variable heavy ("VH") chain encoded by SEQ ID NO:06 and a variable light ("VL") chain encoded by SEQ ID NO:07.

2. The antibody or antigen-binding fragment thereof of claim 1, wherein the antibody is a monoclonal antibody.

3. The antibody or antigen-binding fragment thereof of claim 1, wherein the antibody is a chimeric antibody.

4. A humanized antibody or antigen-binding fragment thereof made by substituting, the complementarity determining regions of a first antibody into a human framework domain, wherein the humanized antibody or antigen-binding fragment thereof specifically binds to a MUC16 polypeptide or to an antigenic portion thereof, wherein the first antibody specifically binds to the MUC16 polypeptide or the antigenic portion thereof, wherein the MUC16 polypeptide is TLDRSSVLVDGYSPNRNE (SEQ ID NO:02), and wherein the first antibody comprises a VH chain encoded by SEQ ID NO:06 and a VL chain encoded by SEQ ID NO:07.

5. The antibody of claim 4, wherein substantially all of framework domain residues of the humanized antibody are those of a human immunoglobulin sequence, and wherein one or more of the framework domain residues are replaced by corresponding nonhuman residues.

6. The antibody or antigen-binding fragment of claim 1, wherein the antigen-binding fragment is selected from the group consisting of a Fab fragment, a F(ab')$_2$ fragment, and a Fv fragment.

7. The antibody or antigen-binding fragment of claim 1, wherein the antibody, or antigen-binding fragment thereof, is covalently linked to a cytotoxic agent or a prodrug of a cytotoxic agent.

8. The antibody or antigen-binding fragment of claim 4, wherein the antibody internalizes into a cell.

9. The antibody or antigen-binding fragment of claim 4, wherein the antibody lacks specific binding to a glycosylated MUC16 extracellular domain.

10. A composition comprising (a) the antibody, or antigen-binding fragment thereof, of claim 1 and (b) a pharmaceutically acceptable carrier.

11. A composition comprising (a) the antibody, or antigen-binding fragment thereof, of claim 4 and (b) a pharmaceutically acceptable carrier.

12. A hybridoma cell that produces an antibody of claim 1.

13. A method for identifying a subject as having a cancer in which MUC16 is expressed, wherein said method comprises administering the antibody of claim 1 to the subject, and determining the presence and location of the antibody in the subject, wherein said antibody is labeled.

14. A method for identifying a subject as having a cancer in which MUC16 is expressed, wherein said method comprises administering the antibody of claim 4 to the subject, and determining the presence and location of the antibody in the subject, wherein said antibody is labeled.

15. The method of claim 13, wherein the cancer is selected from the group consisting of ovarian cancer and breast cancer.

16. The method of claim 14, wherein the cancer is selected from the group consisting of ovarian cancer and breast cancer.

17. An ex vivo method for identifying a subject as having a cancer in which MUC16 is expressed, wherein said method comprises
   (a) obtaining a first sample front a first subject;
   (b) contacting the first sample with the antibody of claim 1; and
   (c) determining whether the antibody has an increased level of binding to the first sample as compared to a control sample lacking the disease.

18. The ex vivo method of claim 17, wherein the cancer is selected from the group consisting of ovarian cancer and breast cancer.

19. An ex vivo method for identifying a subject as having a cancer in which MUC16 is expressed, wherein said method comprises
   (a) obtaining a first sample from a first subject;
   (b) contacting the first sample with the antibody of claim 4; and
   (c) determining whether the antibody has an increased level of binding to the first sample as compared to a control sample lacking the disease.

20. The ex vivo method of claim 19, wherein the cancer is selected from the group consisting of ovarian cancer and breast cancer.

21. A single chain variable fragment (scFv) comprising a VH chain sequence encoded by SEQ ID NO:06 and a VL chain sequence encoded by SEQ ID NO:07.

22. A chimeric antigen receptor (CAR) comprising the scFv of claim 21.

23. The CAR of claim 22, comprising in amino- to carboxy-terminal order: a human CD8 leader peptide, the scFv comprising the VH chain sequence encoded by SEQ ID NO:06 and the VL chain sequence encoded by SEQ ID NO:07, a human CD8 hinge domain, a human CD8 transmembrane domain, and a CD3-zeta signaling domain.

24. The CAR of claim 22, consisting essentially of, in amino- to carboxy-terminal order: a human CD8 leader peptide, the scFv comprising the VH chain sequence encoded by SEQ ID NO:06 and the VL chain sequence encoded by SEQ ID NO:07, a human CD8 hinge domain, a human CD8 transmembrane domain, and a CD3-zeta signaling domain.

25. The CAR of claim 22, comprising in amino- to carboxy-terminal order: a human CD8 leader peptide, the scFv comprising the VH chain sequence encoded by SEQ ID NO:06 and the VL chain sequence encoded by SEQ ID NO:07, a human CD28 transmembrane domain, a human CD28 intracellular domain, and a CD3-zeta signaling domain.

26. A T cell expressing the CAR of claim 22.

27. A T cell expressing the CAR of claim 23.

28. A T cell expressing the CAR of claim 24.

29. A T cell expressing the CAR of claim 25.

30. A method fir treating a cancer in which MUC16 is expressed, comprising administering to a subject the antibody or antigen binding fragment thereof of claim 1.

31. A method for treating a cancer in which MUC16 is expressed, comprising administering to a subject the T cell of claim 26.

32. A method for treating a cancer in which MUC16 is expressed, comprising administering to a subject the T cell of claim 27.

33. A method for treating a cancer in which MUC16 is expressed, comprising administering to a subject the T cell of claim 28.

34. A method for treating a cancer in which MUC16 is expressed, comprising administering to a subject the T cell of claim 29.

35. The method of claim 31, wherein the administering is intraperitoneally or intravenously.

36. The method of claim 32, wherein the administering is intraperitoneally or intravenously.

37. The method of claim 33, wherein the administering is intraperitoneally or intravenously.

38. The method of claim 34, wherein the administering is intraperitoneally or intravenousiy.

39. The method of claim 30, wherein the cancer is selected from the group consisting of ovarian cancer and breast cancer.

40. The method of claim 31, wherein the cancer is ovarian cancer.

41. The method of claim 32, wherein the cancer is ovarian cancer.

42. The method of claim 33, wherein the cancer is ovarian cancer.

43. The method of claim 34, wherein the cancer is ovarian cancer.

44. The method of claim 30, which further comprises detecting a reduction in one or more symptoms of the disease after the administering step.

45. A method for treating a cancer in which MUC16 is expressed, comprising administering to a subject the antibody or antigen binding fragment thereof of claim 2.

46. A method for treating a cancer in which MUC16 is expressed, comprising administering to a subject the antibody or antigen binding fragment thereof of claim 3.

47. A method for treating a cancer in which MUC16 is expressed, comprising administering to a subject the antibody or antigen binding fragment thereof of claim 4.

48. A method for treating a cancer in which MUC16 is expressed, comprising administering to a subject the antibody or antigen binding fragment thereof of claim 5.

49. A method for treating a cancer in which MUC16 is expressed, comprising administering to a subject the antibody or antigen binding fragment thereof of claim 6.

50. A method for treating a cancer in which MUC16 is expressed, comprising administering to a subject the antibody or antigen binding fragment thereof of claim 7.

51. A method for treating a cancer in which MUC16 is expressed, comprising administering to a subject the antibody or antigen binding fragment thereof of claim 8.

52. A method for treating a cancer in which MUC16 is expressed, comprising administering to a subject the antibody or antigen binding fragment thereof of claim 9.

53. The method of claim 45, wherein the cancer is selected from the group consisting of ovarian cancer and breast cancer.

54. The method of claim 46, wherein the cancer is selected from the group consisting of ovarian cancer and breast cancer.

55. The method of claim 47, wherein the cancer is selected fro the group consisting of ovarian cancer and breast cancer.

56. The method of claim 48, wherein the cancer is selected from the group consisting of ovarian cancer and breast cancer.

57. The method of claim 49, wherein the cancer is selected from the group consisting of ovarian cancer and breast cancer.

58. The method of claim 50, wherein the cancer is selected from the group consisting of ovarian cancer and breast cancer.

59. The method of claim 51, wherein the cancer is selected from the group consisting of ovarian cancer and breast cancer.

60. The method of claim 52, wherein the cancer is selected from the group consisting of ovarian cancer and breast cancer.

61. The CAR of claim 22, consisting essentially of, in amino- to carboxy-terminal order: a human CD8 leader peptide, the scFv comprising the VH chain sequence encoded by SEQ ID NO:06 and the VL chain sequence encoded by SEQ ID NO:07, a human CD28 transmembrane domain, a human CD28 intracellular domain, and a CD3-zeta signaling domain.

62. A T cell expressing the CAR of claim 61.

63. A method for treating a cancer in which MUC16 is expressed, comprising administering to a subject the T cell of claim 62.

64. The method of claim 63, wherein the administering is intraperitoneally or intravenously.

65. The method of claim 63, wherein the cancer is ovarian cancer.

66. The CAR of claim 22, comprising in amino- to carboxy-terminal order: a human CD8 leader peptide, a VH chain sequence encoded by SEQ ID NO:06, a spacer encoded by SEQ ID NO:34, a VL chain sequence encoded by SEQ ID NO:07, a human CD8 hinge domain, a human CD8 transmembrane domain, and a CD3-zeta signaling domain.

67. The CAR of claim 22, comprising in amino- to carboxy-terminal order: a human CD8 leader peptide, a VH chain sequence encoded by SEQ ID NO:06, a spacer encoded by SEQ ID NO:34, a VL chain sequence encoded by SEQ ID NO:07, a human CD28 transmembrane domain, a human CD28 intracellular domain, and a CD3-zeta signaling domain.

68. A T cell expressing the CAR of claim 66.

69. A T cell expressing the CAR of claim 67.

70. A method for treating a cancer in which MUC16 is expressed, comprising administering to a subject the T cell of claim 68.

71. A method for treating a cancer in which MUC16 is expressed, comprising administering to a subject the T cell of claim 69.

72. The method of claim 70, wherein the administering is intraperitoneally or intravenously.

73. The method of claim 71, wherein the administering is intraperitoneally or intravenously.

74. The method of claim 70, wherein the cancer is ovarian cancer.

75. The method of claim 71, wherein the cancer is ovarian cancer.

* * * * *